US012653805B2

(12) United States Patent
Raman et al.

(10) Patent No.: US 12,653,805 B2
(45) Date of Patent: Jun. 16, 2026

(54) TARGETING LASP1, eIF4A1, eIF4B AND CXC4 WITH MODULATORS AND COMBINATIONS THEREOF FOR CANCER THERAPY

(71) Applicant: The University of Toledo, Toledo, OH (US)

(72) Inventors: Dayanidhi Raman, Toledo, OH (US); Cory M. Howard, Toledo, OH (US); John Nemunaitis, Toledo, OH (US); Francis Charles Brunicardi, Toledo, OH (US); Shi-He Liu, Toledo, OH (US); Amit K. Tiwari, Toledo, OH (US)

(73) Assignee: The University of Toledo, Toledo, OH (US)

( * ) Notice: Subject to any disclaimer, the term of this patent is extended or adjusted under 35 U.S.C. 154(b) by 861 days.

(21) Appl. No.: 17/431,418

(22) PCT Filed: Feb. 17, 2020

(86) PCT No.: PCT/US2020/018485
§ 371 (c)(1),
(2) Date: Aug. 16, 2021

(87) PCT Pub. No.: WO2020/172086
PCT Pub. Date: Aug. 27, 2020

(65) Prior Publication Data

US 2022/0151976 A1 May 19, 2022

Related U.S. Application Data

(60) Provisional application No. 62/807,075, filed on Feb. 18, 2019.

(51) Int. Cl.

| | |
|---|---|
| ***A61K 31/343*** | (2006.01) |
| ***A61K 31/337*** | (2006.01) |
| ***A61K 31/4985*** | (2006.01) |
| ***A61K 31/7048*** | (2006.01) |
| ***A61P 35/00*** | (2006.01) |

(52) U.S. Cl.
CPC .......... *A61K 31/343* (2013.01); *A61K 31/337* (2013.01); *A61K 31/4985* (2013.01); *A61K 31/7048* (2013.01); *A61P 35/00* (2018.01)

(58) Field of Classification Search
CPC ................ A61K 31/343; A61K 31/337; A61K 31/4985; A61K 31/7048; A61K 31/444; A61K 31/4425; A61K 45/06; A61P 35/00
See application file for complete search history.

(56) References Cited

U.S. PATENT DOCUMENTS

2017/0145026 A1 5/2017 Ernst et al.

FOREIGN PATENT DOCUMENTS

WO WO-2016187046 A1 * 11/2016 ......... A61K 31/4985
WO 2018218072 A1 11/2018

OTHER PUBLICATIONS

Feoktistova, K., Tuvshintogs, E., Do, A., & Fraser, C. S. Human eIF4E promotes mRNA restructuring by stimulating eIF4A helicase activity. Proceedings of the National Academy of Sciences, 110(33), 13339-13344. https://doi.org/10.1073/pnas.1303781110 (Year: 2013).*

Malka-Mahieu, H., Newman, M., Désaubry, L., Robert, C., & Vagner, S. Molecular Pathways: The eIF4F Translation Initiation Complex—New Opportunities for Cancer Treatment. Clinical Cancer Research, 23(1), 21-25. https://doi.org/10.1158/1078-0432.ccr-14-2362 (Year: 2016).*

Wang, X., Liu, Y., Zhou, K., Zhang, G., Wang, F., & Ren, J. Isolation and characterization of CD105+/CD90+ subpopulation in breast cancer MDA-MB-231 cell line. PubMed, 8(5), 5105-5112. (Year: 2015).*

Zhou et al.. Knockdown of eIF4E suppresses cell growth and migration, enhances chemosensitivity and correlates with increase in Bax/Bcl-2 ratio in triple-negative breast cancer cells. Medical Oncology, 28(4), 1302-1307. https://doi.org/10.1007/s12032-010-9630-0 (Year: 2010).*

Schettini, F., Giuliano, M., De Placido, S., & Arpino, G. Nab-paclitaxel for the treatment of triple-negative breast cancer: Rationale, clinical data and future perspectives. Cancer Treatment Reviews, 50, 129-141. https://doi.org/10.1016/j.ctrv.2016.09.004 (Year: 2016).*

Zlobine, I. Host Immunity Determines Outcome of Eukaryotic Initiation Factor-4A Inhibition in Breast Cancer. McGill University (Year: 2018).*

McGill Library Thesis Catalog Entry for Zlobine, "Host immunity determines outcome of eukaryotic initiation factor-4A inhibition in breast cancer," (https://library-archives.canada.ca/eng/services/services-libraries/theses/Pages/item.aspx?idNumber=1086267217) (Year: 2018).*

Lin et al., "c-Myc and eIF4F Are Components of a Feedforward Loop that Links Transcription and Translation", American Association for Cancer Research, Cancer Research, 2008, vol. 68, No. 13, pp. 5326-5334.

"High Throughput Screen of 100,000 compound library to Identify Inhibitors of *Mycobacterium tuberculosis* H3Rv", PubChem, BioAssay Record, 2009, pp. 1-9. Retrieved from the Internet: <https://pubchem.ncbi.nlm.nih.gov/bioassay/1949> Apr. 15, 2020.

(Continued)

*Primary Examiner* — Scarlett Y Goon
*Assistant Examiner* — Hoi Yan Lee
(74) *Attorney, Agent, or Firm* — MacMillan, Sobanski & Todd, LLC

(57) ABSTRACT

Described herein are compositions, formulations, and methods useful for sensitizing cancer cells to chemotherapeutic agents, for inhibiting expression or translation of oncogenic proteins, for inhibiting eIF4A, for inhibiting c-MYC, for reducing sternness of breast cancer cells, for treating breast cancer, for overcoming drug resistance of drug-resistant cancer cells, and for reducing tumor cell viability, involving one or more inhibitors of eIF4A, LASP1, CXCR4, CXCL8, CXCL12, ROCK1, BIRC5, MDM2, CCND1, and c-MYC.

2 Claims, 110 Drawing Sheets
(49 of 110 Drawing Sheet(s) Filed in Color)
Specification includes a Sequence Listing.

(56) References Cited

OTHER PUBLICATIONS

Rahimi et al., "CXCR4 supprssion attenuates EGFRvIII-mediated invasion and induces p38 MAPK-dependent protein trafficking and degradation of EGFRvIII in breast cancer cells", Elsevier, Cancer Letters, 2011, vol. 306, pp. 43-51.
Ananthan et al., "High-throughput screening for inhibitors of *Mycobacterium tuberculosis* H37Rv", Elsevier, Tuberculosis, 2009, vol. 89, pp. 334-353.
Yang, et al., "Digitoxin induces apoptosis in cancer cells by inhibiting nuclear factor of activated T-cells-driven c-MYC expression", Journal of Carcinogenesis, 2013, vol. 12, No. 8, pp. 1-16.
Rubio et al., "Transcripome-wide characterization of the eIF4A signature highlights plasticity in translation regulation", Genome Biology, 2014, vol. 15, No. 10, pp. 1-19.
Qi et al., "Effective Targeting of the Survivin Dimerization Interface with Small-Molecule Inhibitors", American Association for Cancer Research, Cancer Research, 2016, vol. 76, No. 2, pp. 453-462.
Iwasaki et al., "The Translation Inhibitor Rocaglamide Targets a Bimolecular Cavity between eIF4A and Polypurine RNA", Molecular Cell, 2018, vol. 73, No. 4, pp. 738-748.
Lyu et al., "Survivin-targeting miR-542-3p overcomes HER3 signaling-induced chemoresistance and enhances the antitumor activity of paclitaxel against HER2-overexpressing breast cancer", Elsevier, Cancer Letters, 2018, vol. 420, pp. 97-108.
PCT International Search Report and Written Opinion, Application No. PCT/US2020/018485, dated May 15, 2020.

* cited by examiner

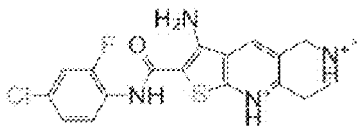

IDNUMBER: AM-807/42860436
NAME: 3-amino-N-(4-chloro-2-fluorophenyl)-6-methyl-5,6,7,8-tetrahydrothieno[2,3-b][1,6]naphthyridine-2-carboxamide
XP GScore: -9.705

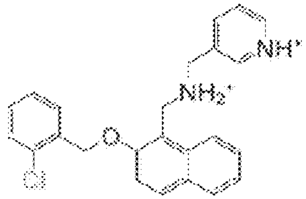

IDNUMBER: AN-465/41673523
NAME: N-({2-[(2-chlorobenzyl)oxy]-1-naphthyl}methyl)-N-(3-pyridinylmethyl)amine
XP GScore: -8.966

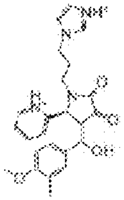

IDNUMBER: AO-022/42019573
NAME: 3-hydroxy-1-[3-(1H-imidazol-1-yl)propyl]-4-(4-methoxy-3-methylbenzoyl)-5-(2-pyridinyl)-1,5-dihydro-2H-pyrrol-2-one
XP GScore: -8.704

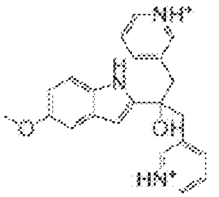

IDNUMBER: AQ-776/42801608
NAME: 2-(5-methoxy-1H-indol-2-yl)-1,3-di(3-pyridinyl)-2-propanol
XP GScore: -8.603

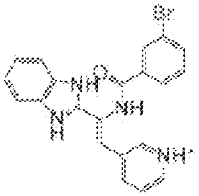

IDNUMBER: AE-848/14270010
NAME: N-[1-(1H-benzimidazol-2-yl)-2-(3-pyridinyl)vinyl]-3-bromobenzamide
XP GScore: -8.1

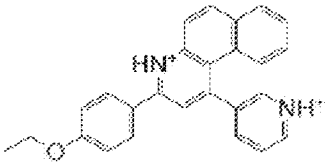

IDNUMBER: AG-205/15157976
NAME: 3-(4-ethoxyphenyl)-1-pyridin-3-ylbenzo[f]quinoline
XP GScore: -7.77

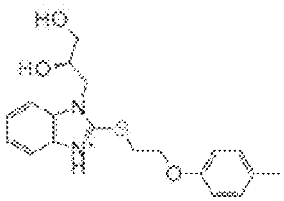

IDNUMBER: AG-670/11899363
NAME: 3-(2-{[2-(4-methylphenoxy)ethyl]sulfanyl}-1H-benzimidazol-1-yl)-1,2-propanediol
XP GScore: -7.665

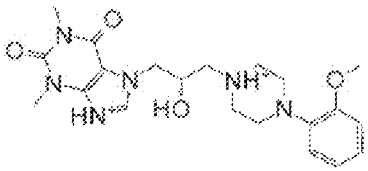

IDNUMBER: AF-833/11253003
NAME: 7-{2-hydroxy-3-[4-(2-methoxyphenyl)-1-piperazinyl]propyl}-1,3-dimethyl-3,7-dihydro-1H-purine-2,6-dione
XP GScore: -7.537

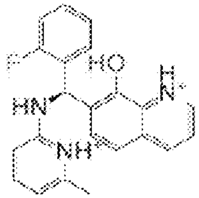

IDNUMBER: AK-968/12862052
NAME: 7-{(2-fluorophenyl)[(6-methyl-2-pyridinyl)amino]methyl}-8-quinolinol
XP GScore: -7.523

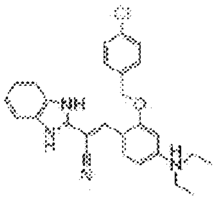

IDNUMBER: AG-205/37049107
NAME: 2-(1H-benzimidazol-2-yl)-3-[2-[(4-chlorobenzyl)oxy]-4-(diethylamino)phenyl]acrylonitrile XP GScore: -7.267

FIG. 10A

Figure 10B:
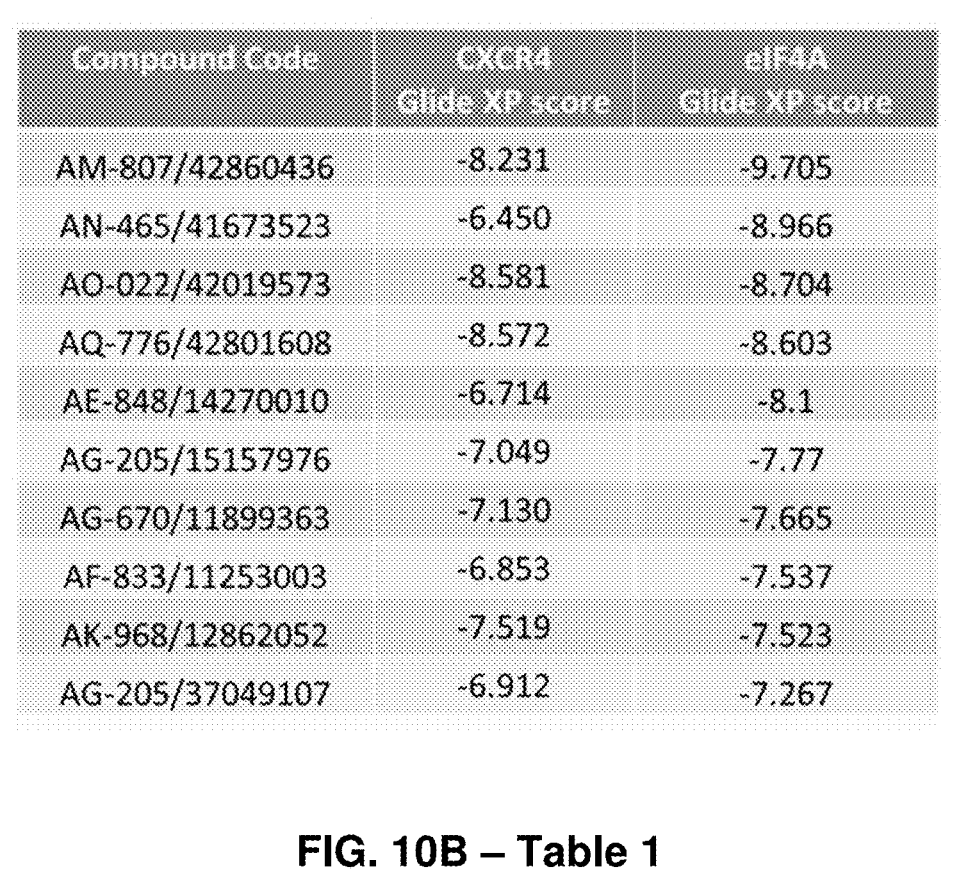

| Compound Code | CXCR4 Glide XP score | eIF4A Glide XP score |
|---|---|---|
| AM-807/42860436 | -8.231 | -9.705 |
| AN-465/41673523 | -6.450 | -8.966 |
| AO-022/42019573 | -8.581 | -8.704 |
| AQ-776/42801608 | -8.572 | -8.603 |
| AE-848/14270010 | -6.714 | -8.1 |
| AG-205/15157976 | -7.049 | -7.77 |
| AG-670/11899363 | -7.130 | -7.665 |
| AF-833/11253003 | -6.853 | -7.537 |
| AK-968/12862052 | -7.519 | -7.523 |
| AG-205/37049107 | -6.912 | -7.267 |

FIG. 10B – Table 1

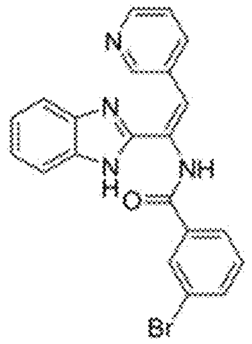
AE-848/14270010
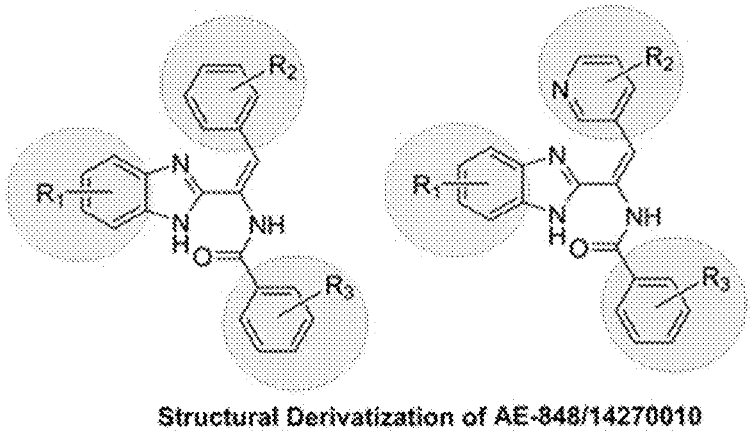
Structural Derivatization of AE-848/14270010
FIG. 15A

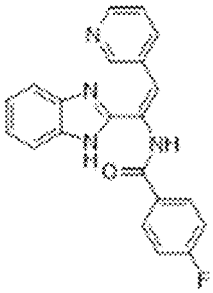
CAST-1901
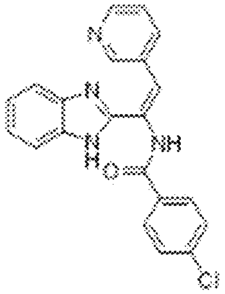
CAST-1902
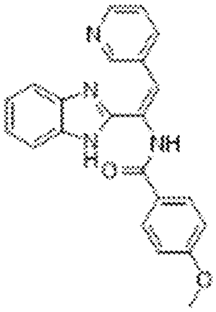
CAST-1903
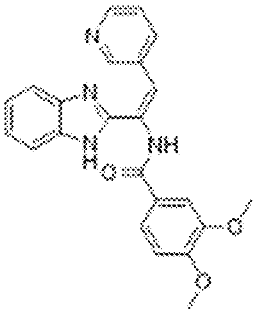
CAST-1904
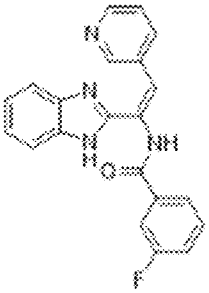
CAST-1905
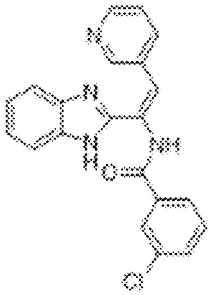
CAST-1906
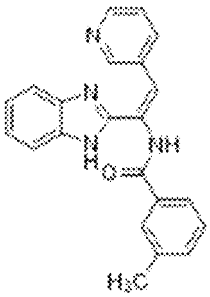
CAST-1907
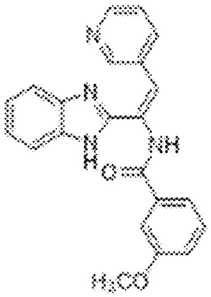
CAST-1908
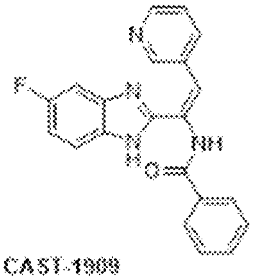
CAST-1909
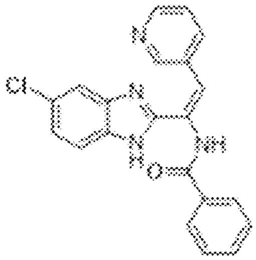
CAST-1910
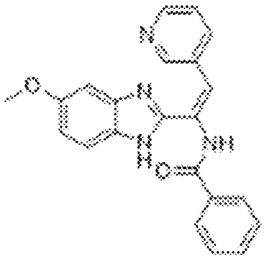
CAST-1911
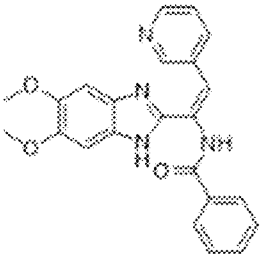
CAST-1912
FIG. 15B

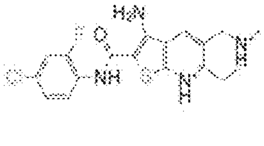

IDNUMBER: AM-807/42860436
NAME: 3-amino-N-(4-chloro-2-fluorophenyl)-6-methyl-5,6,7,8-tetrahydrothieno[2,3-b][1,6]naphthyridine-2-carboxamide
XP GScore: -9.705

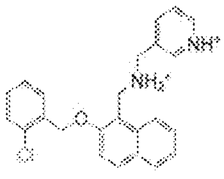

IDNUMBER: AN-465/41673523
NAME: N-({2-[(2-chlorobenzyl)oxy]-1-naphthyl}methyl)-N-(3-pyridinylmethyl)amine
XP GScore: -8.966

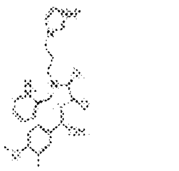

IDNUMBER: AO-022/42019573
NAME: 3-hydroxy-1-[3-(1H-imidazol-1-yl)propyl]-4-(4-methoxy-3-methylbenzoyl)-5-(2-pyridinyl)-1,5-dihydro-2H-pyrrol-2-one
XP GScore: -8.704

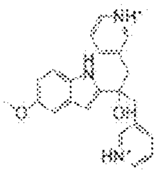

IDNUMBER: AQ-776/42801608
NAME: 2-(5-methoxy-1H-indol-2-yl)-1,3-di(3-pyridinyl)-2-propanol
XP GScore: -8.603

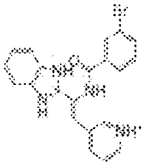

IDNUMBER: AE-848/14270010
NAME: N-[1-(1H-benzimidazol-2-yl)-2-(3-pyridinyl)vinyl]-3-bromobenzamide
XP GScore: -8.1

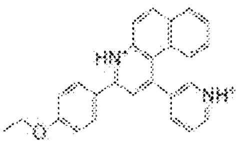

IDNUMBER: AG-205/15157976
NAME: 3-(4-ethoxyphenyl)-1-pyridin-3-ylbenzo[f]quinoline
XP GScore: -7.77

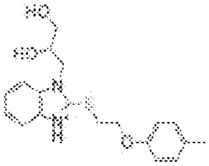

IDNUMBER: AG-670/11899363
NAME: 3-(2-{[2-(4-methylphenoxy)ethyl]sulfanyl}-1H-benzimidazol-1-yl)-1,2-propanediol
XP GScore: -7.665

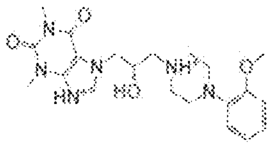

IDNUMBER: AF-833/11253003
NAME: 7-{2-hydroxy-3-[4-(2-methoxyphenyl)-1-piperazinyl]propyl}-1,3-dimethyl-3,7-dihydro-1H-purine-2,6-dione
XP GScore: -7.537

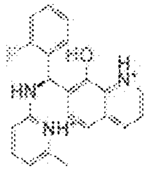

IDNUMBER: AK-968/12862052
NAME: 7-{(2-fluorophenyl)[(6-methyl-2-pyridinyl)amino]methyl}-8-quinolinol
XP GScore: -7.523

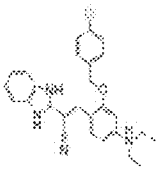

IDNUMBER: AG-205/37049107
NAME: 2-(1H-benzimidazol-2-yl)-3-[2-[(4-chlorobenzyl)oxy]-4-(diethylamino)phenyl]acrylonitrile XP GScore: -7.267

FIG. 15C

AN-465/41673523
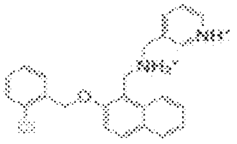
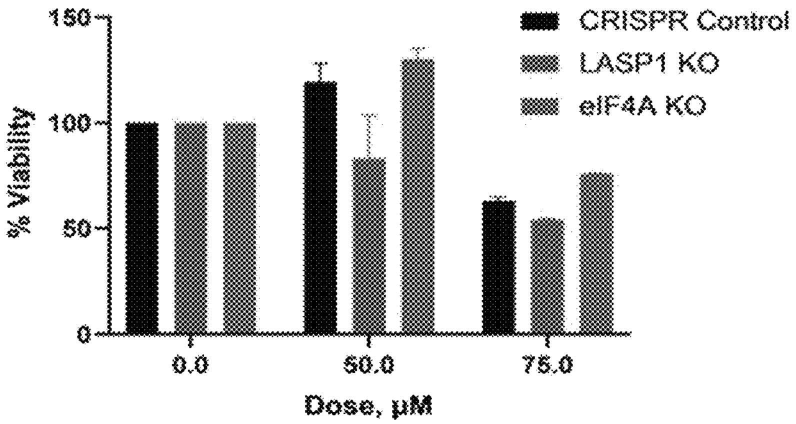
AE-848/14270010
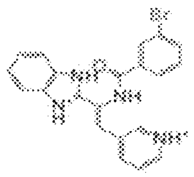
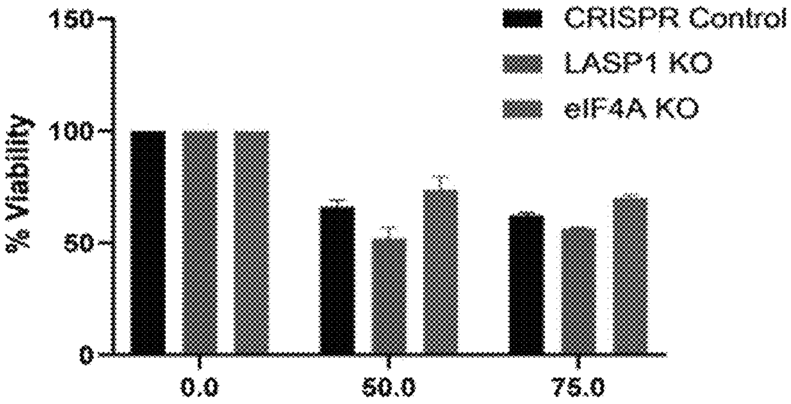
AT-2
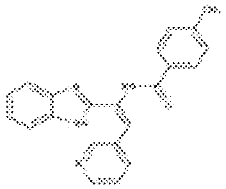
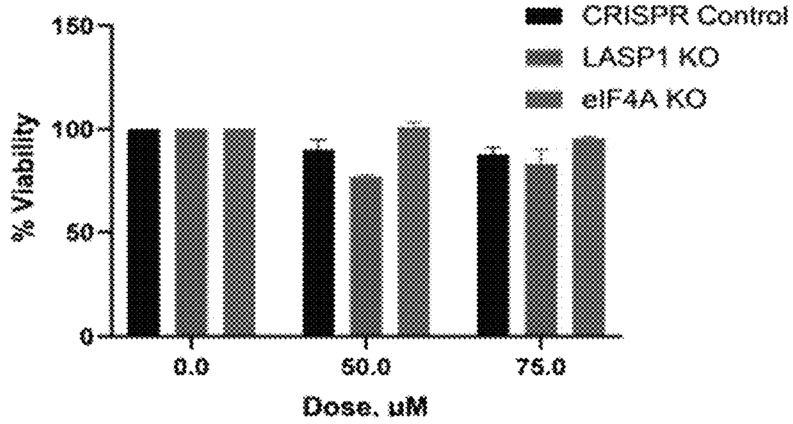
FIG. 15D

AN-465/41673523

CAST-2110 (AT-2) and AE-848/14270010

TARGETING LASP1, eIF4A1, eIF4B AND CXC4 WITH MODULATORS AND COMBINATIONS THEREOF FOR CANCER THERAPY

CROSS-REFERENCE TO RELATED APPLICATIONS

This application is the national phase entry of international application PCT/US2020/018485, filed under the authority of the Patent Cooperation Treaty on Feb. 17, 2020, published; which claims priority to U.S. Provisional Application No. 62/807,075, filed under 35 U.S.C. § 111 (b) on Feb. 18, 2019. The entire disclosure of each of the aforementioned applications is expressly incorporated herein by reference for all purposes.

STATEMENT REGARDING FEDERALLY SPONSORED RESEARCH

This invention was not made with any government support. The government has no rights in this invention.

BACKGROUND

Breast cancer is the second leading cause of death due to cancer in women. One out of eight women (13%) will develop breast cancer in her lifetime and 1 in 36 will succumb to it. Mortality in breast cancer patients is mainly due to metastasis to the lungs, bone, and the brain. More specifically, triple-negative breast cancer (TNBC) is a devastating subtype with a low survival rate. Heterogeneity and plasticity observed in TNBC often results in chemoresistance, tumor relapse, and poor patient outcome. Therefore, it is imperative to find new and effective targets for patients diagnosed with TNBC. In spite of considerable research into therapies to treat this disease, it remains difficult to treat effectively, and the mortality observed in patients indicates that improvements are needed in the diagnosis, treatment, and prevention of this disease.

SEQUENCE LISTING

The instant application contains a Sequence Listing which has been submitted via EFS-web and is hereby incorporated by reference in its entirety. The ASCII copy, created on Feb. 13, 2020, is named 60755-WO-PCT_SL.txt, and is 4,977 bytes in size.

SUMMARY

Triple negative breast cancer (TNBC) remains clinically challenging as effective targeted therapies are lacking. In addition, patient mortality mainly results from the metastasized lesions. CXCR4 has been identified to be one of the major chemokine receptors involved in breast cancer metastasis. LIM and SH3 Protein 1 (LASP1) are key mediators in CXCR4-driven invasion.

Described herein is the identification of an interaction between LASP1 and the components of eukaryotic initiation 4F complex (eIF4F). Activation of the CXCR4-LASP1-eIF4F axis contributes to the preferential translation of oncogenic mRNAs leading to breast cancer progression and metastasis.

It is further shown herein that the expression of CXCR4, LASP1, and eIF4A is upregulated in invasive breast cancer. Moreover, it is demonstrated herein that LASP1 associates with eIF4A in a CXCL12-dependent manner via proximity ligation assay. LASP1 can interact with eIF4A and eIF4B through a GST-pulldown approach. Activation of CXCR4 signaling increased the translation of oncoproteins downstream of eIF4A. Interestingly, genetic silencing of LASP1 interrupted the ability of eIF4A to translate oncogenic mRNAs into oncoproteins. It is also shown herein that a lack of LASP1 sensitizes 231S cells to pharmacological inhibition of eIF4A by rocaglamide A as evident through BIRC5 expression.

It is further shown herein that CXCR4 and LASP1 are mediators for specific components in the protein translational machinery.

Sustained protein synthesis is one of the hallmarks of cancer. A dysregulation in translational control rewires the proteome through preferential translation of oncogenic mRNAs. The resultant oncoproteins are critical for cancer survival, tumor progression, local invasion, and metastasis. Protein synthesis is a tightly regulated process. To date, translational initiation has been identified as the rate limiting step. Translation initiation factor eIF4A1 catalyzes the ATP-dependent unwinding of RNA duplexes and requires the direct binding of its co-factor, eIF4B, along with eIF4G1, for its optimal activity; such complex favors the translation of oncogenic mRNAs.

LASP1 can be incorporated into eIF4F complex in a CXCL12-dependent manner. LASPI plays a role in oncogenic protein synthesis facilitated by eIF4A1 and eIF4B.

In some embodiments, described herein are compositions, formulations, and methods for the treatment of cancer by knockdown of LASP1 or/and eIF4A1/eIF4B expression, and/or in combination with eIF4A1 or CXCR4 or survivin inhibitors and/or pharmacophores or RNA aptamers targeting CXCL12 and CXCL8, and/or humanized antibodies against eIF4A or CXCR4 or eIF4B or CXCL12 or CXCL8.

Provided herein is a method for reducing translation of oncogenic proteins in cancer cells, the method comprising contacting cancer cells with a first agent, wherein the first agent is an inhibitor of a first target selected from the group consisting of: eIF4A, LASP1, CXCR4, CXCL8, CXCL12, ROCK1, BIRC5, MDM2, CCND1, and c-MYC; and contacting the cancer cells with a second agent, wherein the second agent is an inhibitor of a second target selected from the group consisting of: eIF4A, LASP1, CXCR4, CXCL8, CXCL12, ROCK1, BIRC5, MDM2, CCND1, and c-MYC; wherein the first agent and the second agent are administered in amounts effective to reduce translation of oncogenic proteins in the cancer cells. In certain embodiments, the first target is different from the second target.

In certain embodiments, one of the first agent and the second agent comprises an inhibitor of eIF4A. In particular embodiments, the inhibitor of eIF4A is rocaglamide A. In certain embodiments, one of the first agent and the second agent comprises a flavagline. In certain embodiments, one of the first agent and the second agent comprises a cardiac glycoside. In certain embodiments, the first agent comprises an eIF4A inhibitor and the second agent comprises a survivin inhibitor. In certain embodiments, the first agent comprises an eIF4A inhibitor and the second agent comprises a c-MYC inhibitor. In certain embodiments, the first agent comprises a flavagline and the second agent comprises a cardiac glycoside. In certain embodiments, the first agent comprises rocaglamide A and the second agent comprises a cardiac glycoside. In certain embodiments, the first agent comprises rocaglamide A and the second agent comprises digoxin. In certain embodiments, one of the first agent and the second agent comprises LQZ-7F. In certain embodiments, the first agent comprises rocaglamide A and the second agent comprises a survivin inhibitor. In certain embodiments, the first agent comprises rocaglamide A and the second agent comprises LQZ-7F. In certain embodiments, the cancer is breast cancer. In certain embodiments, the cancer is triple negative breast cancer.

In certain embodiments, the first agent and the second agent are administered simultaneously. In certain embodiments, the first agent and the second agent are administered sequentially.

Further provided is a method to sensitize triple negative breast cancer cells to a chemotherapeutic agent, the method comprising administering to triple negative breast cancer cells an effective amount of an eIF4A inhibitor to sensitive the triple negative breast cancer cells to a chemotherapeutic agent. In certain embodiments, the chemotherapeutic agent comprises a taxane. In certain embodiments, the chemotherapeutic agent comprises paclitaxel. In certain embodiments, the eIF4A inhibitor comprises a flavagline. In certain embodiments, the eIF4A inhibitor comprises a rocaglamide A. In certain embodiments, the eIF4A inhibitor comprises a cardiac glycoside. In certain embodiments, the eIF4A inhibitor comprises digoxin.

Further provided is a method for reducing breast cancer stemness, the method comprising administering an effective amount of a eIF4A inhibitor to breast cancer cells to reduce stemness in the breast cancer cells. In certain embodiments, the method further comprises administering a chemotherapeutic agent to the breast cancer cells. In particular embodiments, the chemotherapeutic agent comprises a taxane. In particular embodiments, the chemotherapeutic agent comprises paclitaxel. In certain embodiments, the eIF4A inhibitor comprises a flavagline. In certain embodiments, the eIF4A inhibitor comprises a rocaglamide A. In certain embodiments, the eIF4A inhibitor comprises a cardiac glycoside. In certain embodiments, the eIF4A inhibitor comprises a digoxin.

In certain embodiments, the method further comprises administering a survivin inhibitor to the breast cancer cells in combination with the eIF4A inhibitor. In particular embodiments, the survivin inhibitor comprises LQZ-7F. In particular embodiments, breast cancer stem cells are killed by the combination of the eIF4A inhibitor and survivin inhibitor.

Further provided is a method for inhibiting eIF4A1 in cells, the method comprising contacting cells with an effective amount of a cardiac glycoside to inhibit eIF4A1 in the cells. In certain embodiments, the cardiac glycoside comprises digoxin. In certain embodiments, the cells are breast cancer cells.

Further provided is a method for inhibiting c-MYC in cells, the method comprising treating cells with an effective amount of a cardiac glycoside to inhibit c-MYC in the cells. In certain embodiments, the cardiac glycoside comprises digoxin. In certain embodiments, the cells are breast cancer cells.

Further provided is a method for treating a cancer, the method comprising administering to a subject a first agent, wherein the first agent is an inhibitor of a first target selected from the group consisting of: eIF4A, LASP1, CXCR4, CXCL8, CXCL12, ROCK1, BIRC5, MDM2, CCND1, and c-MYC; and administering to the subject a second agent, wherein the second agent is an inhibitor of a second target selected from the group consisting of: eIF4A, LASP1, CXCR4, CXCL8, CXCL12, ROCK1, BIRC5, MDM2, CCND1, and c-MYC; wherein the first agent and the second agent are administered in amounts effective to treat a cancer in the subject. In certain embodiments, the first target is different from the second target. In certain embodiments, the subject has breast cancer. In certain embodiments, the subject has triple negative breast cancer.

Further provided is a method of overcoming drug resistance in cancer cells, the method comprising administering to drug resistant cancer cells an effective amount of a combination of two or more inhibitors of LASP1, CXCR4, and eIF4A to overcome the drug resistance of the cancer cells. In certain embodiments, the two or more inhibitors comprise a flavagline or a cardiac glycoside. In certain embodiments, the cancer cells are breast cancer cells. In certain embodiments, the cancer cells are triple negative breast cancer cells. In certain embodiments, the drug resistance is paclitaxel resistance.

Further provided is a pharmaceutical composition comprising a first agent comprising an inhibitor of a first target selected from the group consisting of: eIF4A, LASP1, CXCR4, CXCL8, CXCL12, ROCK1, BIRC5, MDM2, CCND1, and c-MYC; a second agent comprising an inhibitor of a second target selected from the group consisting of: eIF4A, LASP1, CXCR4, CXCL8, CXCL12, ROCK1, BIRC5, MDM2, CCND1, and c-MYC; and a pharmaceutically acceptable carrier, diluent, or adjuvant. In certain embodiments, the first target is different from the second target. In certain embodiments, the first agent comprises a flavagline and the second agent comprises a cardiac glycoside. In certain embodiments, the first agent comprises rocaglamide A and the second agent comprises digoxin. In certain embodiments, the first agent comprises a flavagline and the second agent comprises a survivin inhibitor.

Further provided is a kit comprising a first container housing a first agent, wherein the first agent is an inhibitor of a first target selected from the group consisting of eIF4A, LASP1, CXCR4, CXCL8, CXCL12, ROCK1, BIRC5, MDM2, CCND1, and c-MYC; and a second container housing a second agent, wherein the second agent is an inhibitor of a second target selected from the group consisting of eIF4A, LASP1, CXCR4, CXCL8, CXCL12, ROCK1, BIRC5, MDM2, CCND1, and c-MYC.

Further provided is the use of a composition comprising AN-465-41673523, AE-848/14270010, AT-2, or an analogue or derivative thereof, as (i) a probe to understand cell biology or cell cancer; or (ii) a chemoadjuvant in combination with other anticancer agents used in the treatment of triple negative breast cancer, colon cancer, prostate cancer, ovarian cancer, or lung cancer.

Although specific advantages have been enumerated herein, various embodiments may include some, none, or all of the enumerated advantages. Additionally, other technical advantages may become readily apparent to one of ordinary skill in the art after review of the following figures and description.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A shows Radvanyi Breast Invasive Ductal Carcinoma (n=31 for CXCR4, LASP1, eIF4A, and CCND1; n=28 for BIRC5 and ROCK1; n=27 for MDM2) vs. Breast Tissue (n=9 for CXCR4, LASP1, eIF4A, and CCND1; n=2 for BIRC5. n=5 for MDM2 and ROCK1). FIG. 1B shows Radvanyi Breast Invasive Lobular Carcinoma (n=7 for CXCR4, LASP1, eIF4A, and CCND1; n=2 for BIRC5. n=6 for MDM2 and ROCK1) vs. Breast Tissue (n=9 for CXCR4, LASP1, eIF4A, and CCND1; n=2 for BIRC5; n=5 for MDM2 and ROCK1). FIG. 1C shows TCGA Breast Invasive Ductal Carcinoma (n=389) vs. Breast Tissue (n=61). FIG. 1D shows TCGA Breast Invasive Lobular Carcinoma (n=36) vs. Breast Tissue (n=61). * Indicates $p<0.05$ as evaluated by student's t-tests.

FIG. 3A shows co-immunoprecipitation assay of eIF4A and LASP1 in 231S cells following stimulation with 20 nM CXCL12 (n=2). FIG. 3B shows co-immunoprecipitation assay of eIF4B and LASP1 in 231S cells following stimulation with 10 nM CXCL12 (n=3). FIG. 3C shows co-immunoprecipitation assay of LASP1 and eIF4A/B following stimulation with 20 nM CXCL12 in 231S cells (n=2). Fold change was calculated based off the densitometry ratio of co-immunoprecipitated/immunoprecipitated protein signal with 0 min. set to 1. FIGS. 3D-3E show m7GTP pulldown assay in 231S cells following stimulation with 20 nM CXCL12 and 100 nM AMD3465 examining the interaction between: LASP1-eIF4E (n=3) (FIG. 3D) and eIF4G-eIF4E (n=3) (FIG. 3E). Fold change was calculated based off the densitometry ratio of co-precipitate (LASP1 or eIF4G)/precipitate (eIF4E) protein signal with 0 min. set to 1.

FIGS. 4A-4C show 1 mg of 231S lysate was incubated with 1.5 nmoles of GST or GST-LASP1. FIG. 4A shows the presence of eIF4A was detected by Western blotting (n=3). FIG. 4B shows 2 mM ATP and 3 mM $MgCl_2$ exogenously added to the 231S lysate. The presence of eIF4A was then detected by Western blotting (n=3). FIG. 4C shows the presence of eIF4B detected by Western blotting (n=3). FIGS. 4D-4E show purified eIF4A or eIF4B incubated with 1.5 nmoles GST or GST-LASP1. Amounts of purified proteins are indicated in parenthesis. FIG. 4D shows the presence of eIF4B detected by Western blotting (n=3). FIG. 4E shows the presence of eIF4A detected by Western blotting (n=3). Ponceau S stains of each blot are shown below to confirm loading of GST or GST-LASP1 following the elution from glutathione agarose beads. FIG. 4F shows purified eIF4A and eIF4B mixed with purified GST or GST-LASP1 in an equimolar ratio and in solution. Proteins complexes were then captured with glutathione beads and detected for by Western blotting (n=1).

FIG. 5D shows the status of p-eIF4B, p-PDCD4 S67, and p-4E-BP1 Thr70 in MCF7 vector, wild-type CXCR4, and CXCR4 1CTD cells (n=3). Fold change indicates the densitometry ratio of (phospho-protein/total protein)/b-tubulin signal with MCF7 vector cells set to 1. FIG. 5E shows a model of CXCR4 signaling and its effects on the eIF4F complex.

FIG. 6A shows 231S LASP1 NS and KD cells stimulated with 10-20 nM CXCL12. Expression levels of eIF4A-dependent genes were then determined by Western blotting (n=3). Fold change indicates the densitometry ratio of protein signal/b-tubulin with 0 min. set to 1. FIG. 6B shows stable knockdown of LASP1 leads to a reduced expression of eIF4A-dependent genes (n=3). Fold change indicates the densitometry ratio of protein signal/b-tubulin with 231S LASP1 NS cells set to 1. FIG. 6C shows knockdown of LASP1 does not significantly affect CCND1, MDM2, BIRC5, and ROCK1 mRNA levels (n=3). Data was analyzed using the 11Ct method with b-tubulin primers as the control. Fold change was calculated with the 231S LASP1 NS cells set to 1. FIG. 6D shows endogenous expression levels of BIRC5, MDM2, and ROCK1 in MCF7 Vector, Wild-type CXCR4, and CXCR4 1CTD cells (n=3). Fold change indicates the densitometry ratio of protein signal/b-tubulin with MCF7 vector cells set to 1. FIG. 6E shows 231S LASP1 KD cells have a reduced capacity to translate genes harboring a complex 5'UTR as indicated by the GQ 5'UTR luciferase assay (n=3). FIG. 6F shows GQ 5'UTR luciferase assay in 293-HA-CXCR4 CRISPR Control and LASP1 KO cells (n=3). Fold change indicates the luminescent ratio of luciferase/renilla (transfection control) with CMV set to 1. FIG. 6G shows a Western blot analysis of LASP1 protein levels in 293-HA-CXCR4 CRISPR Control and LASP1 KO cells (n=3). * indicates $p<0.05$ as evaluated by unpaired student's t-tests.

FIG. 7A shows representative images of 231S LASP1 NS and KD cells incubated with various concentrations of rocaglamide A at 0 and 36-h time points. FIG. 7B shows percent inhibition of 231S LASP1 NS and KD cells following 36-h RocA drug treatment (n=3). Percent inhibition was calculated in reference to the fold difference of percent confluence between rocaglamide A treated cells and the DMSO control for each cell type at 36 h. FIG. 7C shows percent viability in 231S LASP1 NS and KD cells following rocaglamide A drug treatment. Data is reflective of absorbance at 450 nm with the DMSO condition set to 100% for each cell type. FIG. 7D shows Western blotting of BIRC5 in LASP1 NS/KD cells following 24 h of rocaglamide A incubation (n=3). Fold change indicates the densitometry ratio of BIRC5 signal/b-tubulin with the 231S LASP1 NS DMSO condition set to 1. * indicates $p<0.05$ as evaluated by student's t-tests.

FIGS. 10A-10B: Structures of non-limiting example dual inhibitors of CXCR4 & eIF4A (FIG. 10A), and Table 1, displaying compound codes and glide XP scores for the dual inhibitors (FIG. 10B).

In FIG. 11A, important amino acids are depicted as sticks with the atoms colored as carbon—green, hydrogen—white, nitrogen—blue, oxygen—red, sulfur—yellow, whereas the ligand is shown with the same color scheme as above except for carbon atoms which are represented in yellow. The red dotted lines represent hydrogen bond. In FIG. 11B, blue circles code polar amino acids, hydrophobic amino acids are coded by green circles, the purple arrows depict side chain donor/acceptor interactions, the green lines depict pi-pi stacking interactions, and the blue-red lines represent salt bridge.

In FIG. 12A, important amino acids are depicted as sticks with the atoms colored as carbon—green, hydrogen—white, nitrogen—blue, oxygen—red, sulfur—yellow, whereas the ligand is shown with the same color scheme as above except for carbon atoms which are represented in yellow. The red dotted lines represent hydrogen bond. In FIG. 12B, blue circles code polar amino acids, hydrophobic amino acids are coded by green circles, dark blue circles codes for nucleotides of RNA, the purple arrows depict side chain donor/acceptor interactions, the green lines depict pi-pi stacking interactions, and the blue-red lines represent salt bridge.

In FIG. 13A, important amino acids are depicted as sticks with the atoms colored as carbon—green, hydrogen—white, nitrogen—blue, oxygen—red, sulfur—yellow, whereas the ligand is shown with the same color scheme as above except for carbon atoms which are represented in red. The red dotted lines represent hydrogen bond. In FIG. 13B, blue circles code polar amino acids, hydrophobic amino acids are coded by green circles, the purple arrows depict side chain donor/acceptor interactions, the green lines depict pi-pi stacking interactions, and the blue-red lines represent salt bridge.

In FIG. 14A, important amino acids are depicted as sticks with the atoms colored as carbon—green, hydrogen—white, nitrogen—blue, oxygen—red, sulfur—yellow, whereas the ligand is shown with the same color scheme as above except for carbon atoms which are represented in red. The red dotted lines represent hydrogen bond. In FIG. 14B, blue circles code polar amino acids, hydrophobic amino acids are coded by green circles, dark blue circles codes for nucleotides of RNA, the purple arrows depict side chain donor/acceptor interactions, the green lines depict pi-pi stacking interactions, and the blue-red lines represent salt bridge.

FIGS. 15A-15E: FIG. 15A shows structure (left) and structural derivation (right) of a molecule referred to as AE-848-/14270010. FIGS. 158-15C show structures of additional non-limiting example dual inhibitors of CXCR4 & eIF4A. FIG. 15D shows the CAST compound AE-848/14270010 is efficacious in affecting tumor cell viability. The top panel in FIG. 15D shows CAST compound AN-465/41673523 showed efficacy at 75 μM level. The middle panel in FIG. 15D shows CAST compound AE-848/14270010 demonstrated highest efficacy even at a lower 50 μM level. Added benefit was observed when LASP1 is genetically knocked out (loss of 50% viability). The bottom panel in FIG. 15D shows CAST compound AT-2 (CAST-2110), which is a derivative or variant of AE-848/14270010, a loss in its efficacy compared to AE-848/14270010. FIG. 15E shows an evaluation of paclitaxel-resistant SUM-159-PT TNBC cells. The top panel in FIG. 15E shows resistance of therapy-naïve parental cells compared to paclitaxel-resistant SUM-159-PT TNBC cells. The bottom panel in FIG. 15E shows an evaluation of cross-resistance to doxorubicin in paclitaxel-resistant SUM-159-PT cells.

FIG. 16A shows micrographs depicting the morphology of the therapy naïve (par.) and the paclitaxel-resistant SUM-159PT (Pac 200) cells. Scale bar—400 μm. FIG. 16B shows the total proteins in the lysates from the paclitaxel-resistant SUM-159PT cells were separated by 10-12% SDS-PAGE and probed for the level of eIF4A and its downstream targets along with the key proteins involved in pluripotency, breast cancer stem-cell markers, and drug resistance by immunoblotting with specific antibodies. Fold change in the levels of proteins is indicated above the blots with the therapy naïve (par.) being normalized to 1. β-actin served as the loading control for proteins ABCC1 and OCT4 and β-tubulin served as the loading control for rest of them; (n=3). The graph (FIG. 16C) shows the spread of the data points along with its statistical significance, obtained by normalizing the densitometry intensity value with their corresponding loading controls. $*p<0.05$, $p<0.01$, $*p<0.001$, $**p<0.0001$, ns—not significant. FIG. 16**D shows the levels of key drug transporters were independently tested by immunoblotting and quantitated by densitometry and plotted (n=3).

FIG. 16E shows the total proteins from parental SUM-159PT cells paclitaxel-resistant SUM-159PT cells were separated by 10-12% SDS-PAGE and the expression level of E-cadherin and Snail1 (EMT markers) was analyzed and quantified. The mean expression values from n=3 is represented as a bar diagram where the values are normalized to b-tubulin and indicated as "mean fold change." FIG. 16F shows the viability of parental SUM-159PT cells and paclitaxel-resistant SUM-159PT cells was assessed following RocA treatment for 48 h under adherent conditions (n=3). FIG. 16G shows the viability of parental SUM-159PT cells and paclitaxel-resistant SUM-159PT cells was assessed following RocA treatment for 48 h under non-adherent, low attachment conditions (n=3). FIG. 16H shows the assessment of the eIF4A knockout in paclitaxel-resistant SUM-159PT cells (n=2). FIG. 16I shows the chemosensitivity of CRISPR Control and eIF4A knockout cells derived from paclitaxel-resistant SUM-159PT cells was assessed following their exposure to escalating doses of paclitaxel (n=3).

FIG. 18A shows micrographs depicting the morphology in the CRISPR-control and the eIF4A knockout MDA-Bone-Un cells. Scale bar—100 μm. FIG. 18B shows the viability of MDA-Bone-Un CRISPR Control and eIF4A knockout cells was assessed following treatment with RocA for 48 h under low attachment conditions (n=3). FIG. 18C shows the total proteins in total lysates from CRISPR-control and the eIF4A knockout MDA-Bone-Un cells were separated by 10-12% SDS-PAGE and probed for expression levels of proteins downstream of eIF4A, pluripotency, BCSC markers, ABCC1 by immunoblotting with specific antibodies. β-tubulin served as the loading control (n=3). Fold change in the levels of proteins is indicated above the blots with the CRISPR-Control being normalized to 1. FIG. 18D shows immunoblot representing the differential expression of key ABC drug transporters ABCG2 and ABCB1 in the whole cell lysates from CRISPR-control and the eIF4A knockout MDA-Bone-Un cells. Fold change in the levels of proteins is indicated above the blots with the CRISPR-Control being normalized to 1 (n=3). The graph (FIG. 18E) shows the spread of the data along with its statistical significance. The indicated values are obtained by normalizing the densitometry intensity value with their corresponding loading controls. *p<0.05, ns—not significant.

FIG. 20A show an immunoblot analysis showing the protein levels of ALDH1A1, SOX2, and OCT4 in the isolated $ALDH^+$ population versus the $ALDH^-$ population in MDA-Bone-Un cells. FIG. 20B shows $ALDH^-$ and $ALDH^+$ population from MDA-Bone-Un were compared for their self-renewal potential by assessment of primary and secondary mammosphere formation efficiency. (n=3). FIG. 20C shows a pictorial representation of the primary and secondary mammospheres formed by the $ALDH^-$ and $ALDH^+$ population isolated from MDA-Bone-un. Scale bar—primary mammospheres—800 μm, secondary mammospheres—800 μm. FIG. 20D shows an immunoblot showing the levels of expression for ALDH1A1, SOX2, NANOG in the sorted $ALDH^+$ population versus its $ALDH^-$ counterpart in SUM-159PT cells. FIG. 20E shows SUM-159PT derived $ALDH^-$ and $ALDH^+$ population were compared for their self-renewal potential by assessment of primary and secondary (left and right, respectively) mammosphere formation efficiency. (n=3). FIG. 20F represents the primary and secondary mammospheres formed by the $ALDH^-$ and $ALDH^+$ population sorted from SUM-159PT. Scale bar—primary and secondary mammospheres—800 μm. Data are presented as mean±S.E.M.

FIG. 22A shows an immunoblot showing expression levels of eIF4A between the ALDH− and ALDH+ and the unsorted, parental MDA-Bone-Un cell populations. FIG. 22B shows RocA-induced cell death in the BCSCs was assessed by DRAQ7 staining and images were captured by light microscopy. DRAQ7 staining is carried out on day 7 following the treatment; scale bar—400 μm. FIG. 22C shows the viability of cells following RocA treatment was measured by employing CellTiter-Glo assay. FIGS. 22D-22E represent the reduction in the primary and the secondary MFE following treatment. Data are presented as mean±S.E.M. (n=3). p<0.01, *p<0.001, ****p<0.0001.

FIG. 23A shows eIF4A levels analyzed between the ALDH+ and ALDH− and the unsorted, parental SUM-159PT cells by immunoblotting (n=3). FIG. 23B shows cell death visualized via DRAQ7 staining following RocA treatment on day 7. Scale bar—400 μm (n=3). FIG. 23C shows the cell viability analysis using CellTiter-Glo assay in SUM-159PT cells following RocA treatment (n=3). FIGS. 23D-23E show the self-renewal ability measured by the primary and the secondary MFE following RocA treatment (n=3). Data are presented as mean±S.E.M. *p<0.05, p<0.01, *p<0.001, ****p<0.0001.

FIG. 24A shows representative immunoblots showing the dose-dependent effects of RocA on the levels of eIF4A, molecular targets downstream of eIF4A, pluripotency transcription factors, and BCSC markers ALDH1A1 and CD44 (n=3). FIG. 24B shows the immunoblot obtained following RocA treatment of MDA-Bone-Un derived BCSCs at 45 nM for a period of 72 h. The lysates from three biological replicates were pooled and assessed for the expression of SOX2, OCT4, and ABCB1. Fold change in the levels of proteins is indicated above the blots with DMSO control being normalized to 1. FIG. 24C shows a graph representing the densitometry values normalized to their respective loading controls. The graph shows the spread of the data along with its statistical significance. The indicated values are obtained by normalizing the densitometry intensity value with their corresponding loading controls. *p<0.05, p<0.01, *p<0.001 ns—not significant. The graph shows the trend of SOX2, OCT4, and ABCB1 from 3 biological replicates pooled and analyzed.

FIG. 25A shows an illustration depicting the outcome when eIF4A is targeted in the breast tumor. The illustration depicts the growth factor receptor and GPCR pathways impinging on the key signaling node eIF4A through a common upstream effector mTORC in breast cancer. The significance of targeting eIF4A pharmacologically is brought about by the selective blockade of oncogenic targets downstream of eIF4A. FIG. 25B shows a depiction of the impact of eIF4A in the heterogeneous breast tumor and the modulation of breast cancer stemness, levels of key oncoproteins, and drug transporters.

FIG. 26A shows a map of the tomato-luciferase lentiviral reporter construct. FIG. 26B shows a schematic of the GQ-5'-UTR assay. FIG. 26C shows a characterization of GQ-5'-UTR construct with RocA in 3 cell lines. FIG. 26D shows the Prestwick chemical library screen with Z-scores. Digoxin had a score below −5.

FIG. 29A shows downregulation of the levels of eIF4A1 (50%), c-MYC (60%) upon treatment with 30 nM digoxin (low dose) in triple-negative SUM-159-PT cells. FIG. 29B shows dose-dependent inhibition of downstream effectors of eIF4A1 activity such as BIRC5, or survivin, and Rho Kinase 1 (ROCK1) in triple-negative MDA-MB-231 cells. FIG. 29C shows synergistic inhibition of tumor cellular viability by rocaglamide A and digoxin tested in breast cancer stem cells (BCSCs) which are a subset of tumor cells highly resistant to chemotherapy. Even in inherently chemoresistant BCSCs, the combination of rocaglamide A and digoxin is highly effective in reducing the viability as tested by CellTiter-Glo assay. FIG. 29D shows a plot depicting the synergy (at low concentration) as well as additivity (at high concentrations) between rocaglamide A and digoxin. FIG. 29E shows a schematic of the eIF4A1-C-Myc vicious feedback loop which can be disrupted by rocaglamide A and digoxin.

FIG. 32A shows stable knockdown of LASP1 enhanced the inhibition of cellular proliferation in triple-negative MDA-MB-231 breast cancer cells demonstrated even at a low concentration of 30 nM rocaglamide A. FIG. 32B shows CRISPR-Cas9 mediated knockout of LASP1 (KO) abolished CXCL12-CXCR4-mediated cellular invasion into the Matrigel.

FIG. 36A shows the XP-Glide predicted binding mode of AN-465/41673523 in the active site of Eukaryotic initiation factor 4A-I (Pdb id: 5ZC9, 2 Å). Important amino acids are depicted as sticks with the atoms colored as carbon—gray, hydrogen—white, nitrogen—blue, oxygen—red, sulfur—yellow, whereas the ligand is shown with the same color scheme as above except for carbon atoms which are represented in yellow. The red dotted lines represent hydrogen bond. FIG. 36B shows a schematic diagram of the protein-ligand interaction for ligand. Blue circles code polar amino acids, hydrophobic amino acids are coded by green circles, dark blue circles codes for nucleotides of RNA, the purple arrows depict side chain donor/acceptor interactions, the green lines depict pi-pi stacking interactions, and the blue-red lines represent salt bridge.

FIG. 37A shows the XP-Glide predicted binding mode of AN-465/41673523 in the active site of CXCR4 (Pdb id: 3ODU, 2.5 Å). Important amino acids are depicted as sticks with the atoms colored as carbon—gray, hydrogen—white, nitrogen—blue, oxygen—red, sulfur—yellow, whereas the ligand is shown with the same color scheme as above except for carbon atoms which are represented in yellow. The red dotted lines represent hydrogen bond. FIG. 37B shows a schematic diagram of the protein-ligand interaction is shown for ligand. Blue circles code polar amino acids, hydrophobic amino acids are coded by green circles, the purple arrows depict side chain donor/acceptor interactions, the green lines depict pi-pi stacking interactions, and the blue-red lines represent salt bridge.

DETAILED DESCRIPTION

Figure 1A:
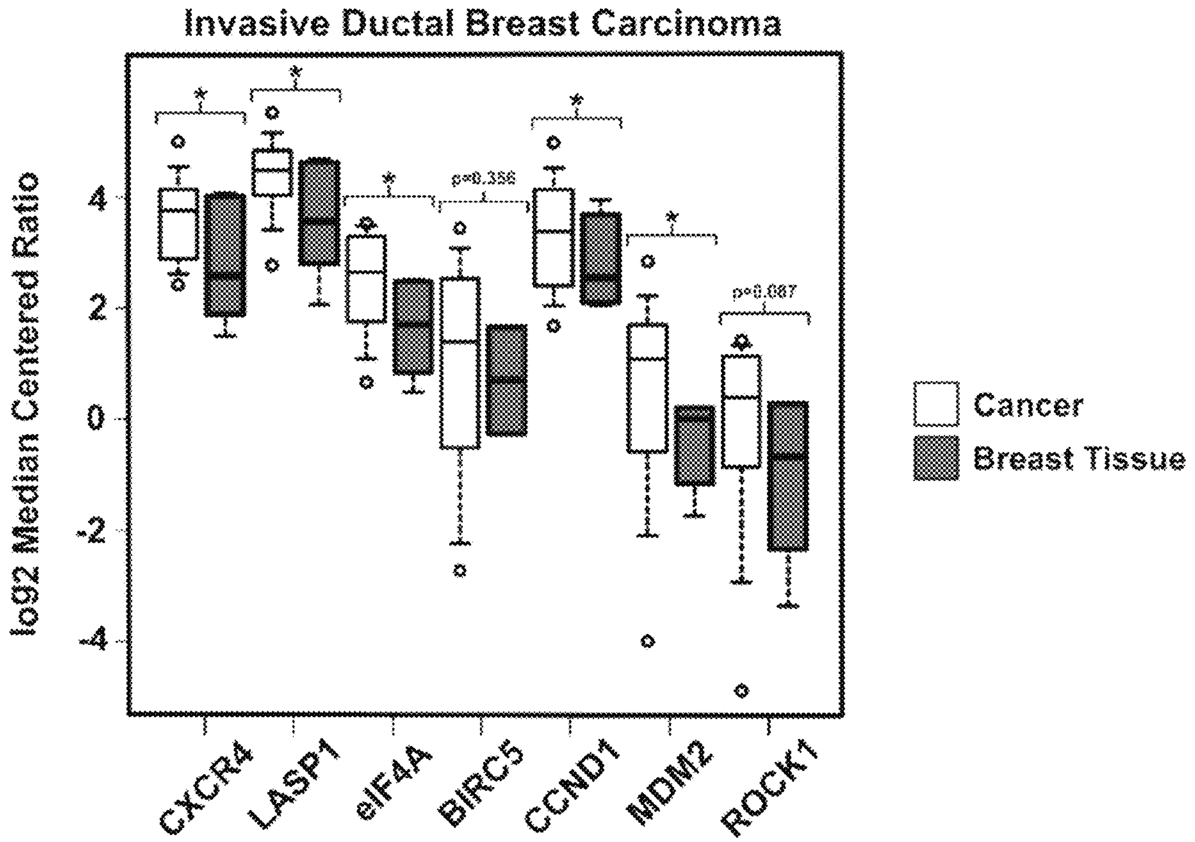
FIGS. 1A-1D: The CXCR4-LASP1-eIF4A/B axis is upregulated in breast carcinoma patients. Gene expression data was obtained and analyzed using the Oncomine website. Two representative datasets were selected. Box and whisker plots of the log 2 median centered ratio (fold change) are shown for each.
Figure 1B:
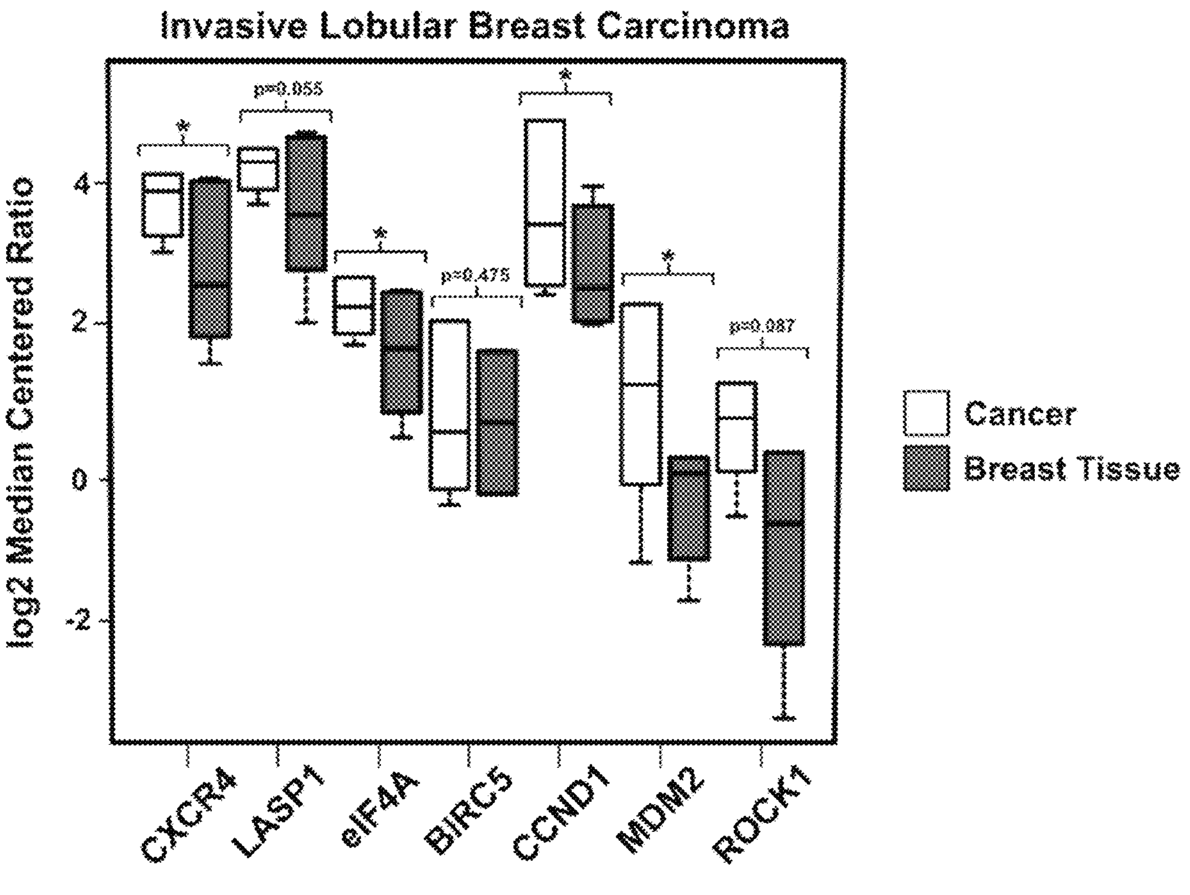
Figure 1C:
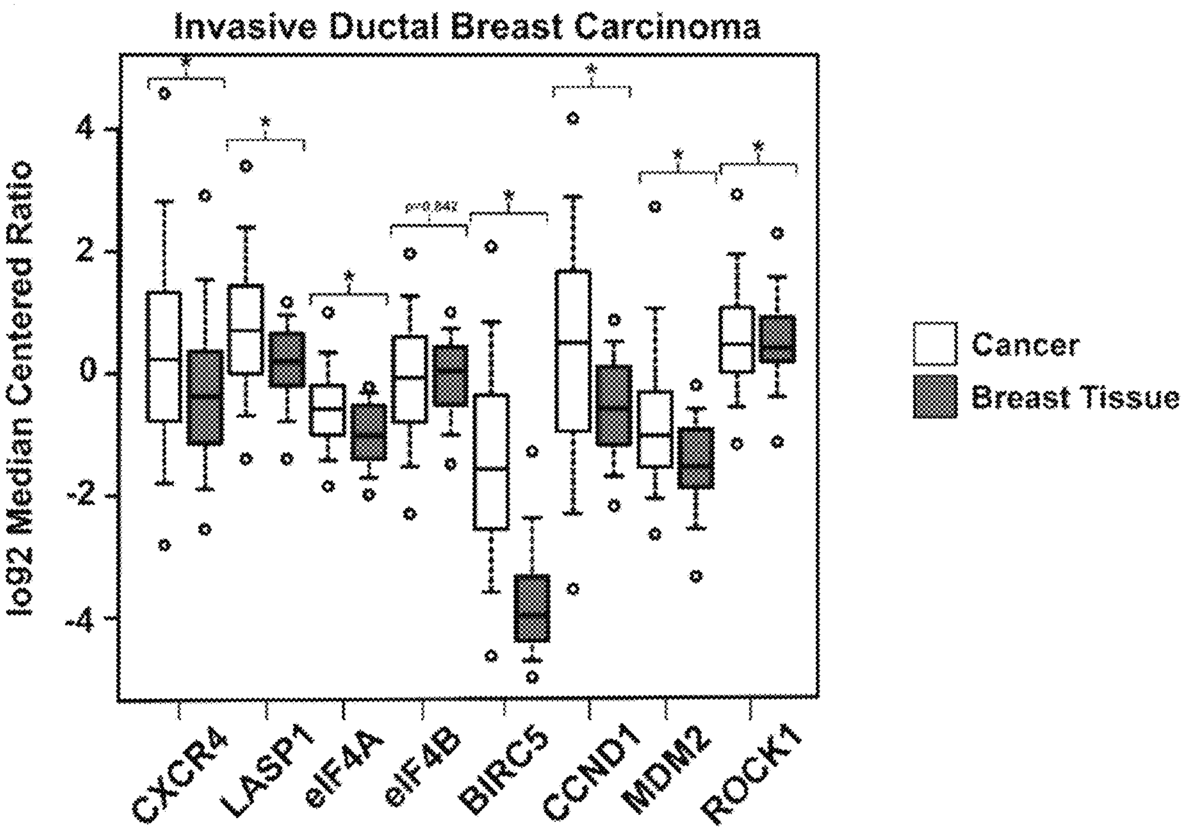
Figure 1D:
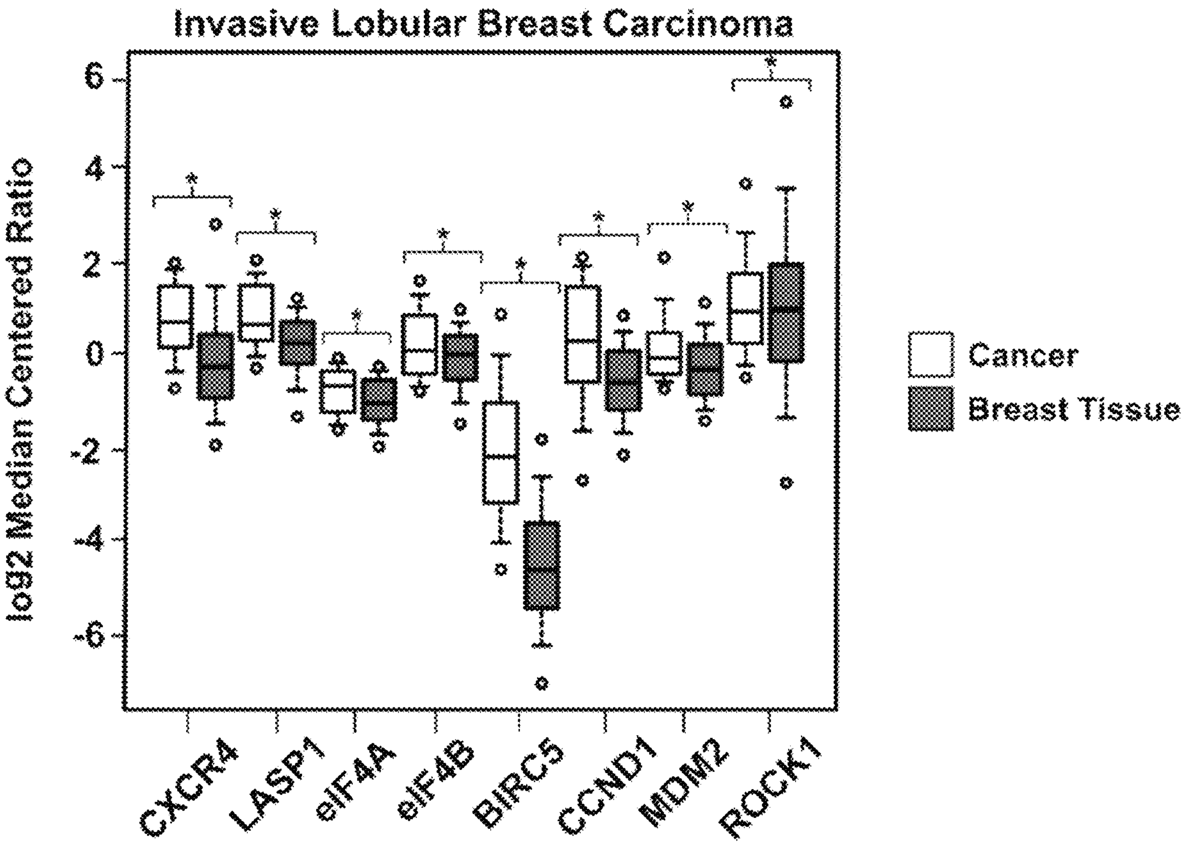

It should be understood that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below. Throughout this disclosure, various publications, patents, and published patent specifications may be referenced by an identifying citation. Such disclosures of these publications, patents, and published patent specifications are hereby incorporated by reference into the present disclosure for all purposes.

In accordance with the present disclosure, the CXCR4-LASP1-eIF4F axis and the eIF4A1-C-MYC feedback loop may be targeted so as to achieve desirable therapeutic effects such as kill cancer cells, reduce the stemness of cancer cells, sensitize cancer cells to chemotherapeutic agents, or inhibit expression of oncogenic proteins. Targeting the CXCR4-LASP1-eIF4F axis or the eIF4A1-c-MYC feedback loop involves inhibiting any one or more of eIF4A, LASP1, CXCR4, CXCL8, CXCL12, ROCK1, BIRC5, MDM2, CCND1, and c-MYC. In certain embodiments, two or more of eIF4A, LASP1, CXCR4, CXCL8, CXCL12, ROCK1, BIRC5, MDM2, CCND1, and c-MYC are inhibited. In certain embodiments, three or more of eIF4A, LASP1, CXCR4, CXCL8, CXCL12, ROCK1, BIRC5, MDM2, CCND1, and c-MYC are inhibited. In certain embodiments, four or more of eIF4A, LASP1, CXCR4, CXCL8, CXCL12, ROCK1, BIRC5, MDM2, CCND1, and c-MYC are inhibited. In certain embodiments, five or more of eIF4A, LASP1, CXCR4, CXCL8, CXCL12, ROCK1, BIRC5, MDM2, CCND1, and c-MYC are inhibited. Various combinations of inhibitors of these targets are described herein. In some embodiments, the combination of inhibitors includes an eIF4A inhibitor and an inhibitor of one or more of LASP1, CXCR4, CXCL8, CXCL12, ROCK1, BIRC5, MDM2, CCND1, and c-MYC. In some embodiments, the combination of inhibitors includes two inhibitors of the same target, such as two eIF4A inhibitors.

Eukaryotic initiation factor-4A (eIF4A) is a member of a family of ATP-dependent helicases that are characterized by seven highly conserved amino acid motifs implicated in RNA remodeling. eIF4A acts as an RNA-dependent ATPase and ATP-dependent RNA helicase to facilitate mRNA binding to the ribosome as part of the eIF4F complex that recognizes and initiates translation of most cellular mRNAs to synthesize specific proteins. A functional eIF4F complex consisting of eIF4A, eIF4E, and eIF4G is involved in translation of mRNAs that contain highly structured 5'-UTRs. In particular, eIF4F recognizes the cap structure at the 5'-end of mRNA through eIF4E, unwinds the secondary structure of the 5'-UTR region through the helicase activity of eIF4A, and binds the 43S complex through interactions between eIF4G and eIF3. eIF4A selectively regulates the translation of a subset of mRNAs. This selectivity is believed to be a result of structural elements and sequence recognition motifs found within the 5'-UTR of the mRNA. Overexpression of eIF4A has been associated with poor prognosis in various cancers, including lymphoma, lung cancer, colon cancer, liver cancer, ovarian cancer, and breast cancer.

An "eIF4A inhibitor", as used herein, refers to an agent or compound that directly interacts with eIF4A, either alone or in a complex (e.g., a ternary complex of an eIF4A inhibitor, an eIF4A, and a mRNA) and may block, inactivate, reduce, or minimize eIF4A activity (e.g., helicase activity or translational effects), or reduce activity by promoting degradation of eIF4A, by about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more as compared to untreated eIF4A. In certain embodiments, an eIF4A inhibitor is a catalytic inhibitor that directly inhibits eIF4A helicase activity. An example of an eIF4A catalytic inhibitor is BPSL1549, a bacterial toxin from *Burkholderia pseudomallei* that deamidates Gln339 of eIF4A and converts it into a dominant-negative mutant.

In some embodiments, an eIF4A inhibitor is an allosteric inhibitor. An allosteric eIF4A inhibitor binds to eIF4A at a site other than the active site, wherein its binding induces a conformational change in eIF4A so that a substrate can no longer bind eIF4A or eIF4A activity is reduced. In certain embodiments, an allosteric eIF4A inhibitor includes hippuristanol and derivatives or analogs thereof. Hippuristanol, which binds the C-terminal domain of both free eIF4A (eIF4Af) and eIF4A bound in an eIF4F complex (eIF4Ac), inhibits eIF4A helicase and ATPase activities.

In some embodiments, an eIF4A inhibitor is a chemical inducer of dimerization. An eIF4A chemical inducer of dimerization causes a non-sequence-specific interaction between eIF4Af and RNA and stimulates the ATP hydrolysis activity of eIF4A, resulting in sequestering of eIF4Af and depletion of eIF4Ac. Examples of eIF4A inhibitors that are chemical inducers of dimerization include pateamine A, and analogs, derivatives, or precursors thereof. Examples of pateamine A derivatives have been described in, for example, U.S. Pat. No. 7,230,021; PCT Publication WO 2016/161168 (a-amino derivatives that lack the C5-methyl group); and U.S. Pat. No. 7,737,134 (desmethyl, desamino-pateamine A derivatives), each derivative of which is incorporated by reference in its entirety.

In some embodiments, an eIF4A inhibitor is a site-directed eIF4A inhibitor. A "site-directed eIF4A inhibitor", as used herein, is an agent or compound that interacts with a specific nucleotide sequence of a mRNA molecule, such as a non-coding nucleotide sequence (e.g., located in the 5'-UTR of a target mRNA), and is capable of forming a stable ternary complex comprising the site-directed eIF4A inhibitor, an eIF4A, and a target mRNA. Exemplary site-directed eIF4A inhibitors include silvestrol, and rocaglamide compounds such as rocaglamide A, as well as analogs, derivatives, or precursors thereof.

Representative silvestrol derivatives and analogs include CR-1-31-B, hydroxamate derivative of silvestrol, episilvestrol, silvestrol dioxane, episilvesterol dioxane, flavagline 61, (−)-4-desmethoxyepisilvestrol, and 1-O-formylaglafoline (FA). Examples of rocaglates and precursors include aglapervirisin A and aglapervirisins B-J. Further examples of silvestrol and rocaglamide derivatives and analogs are described in, for example, U.S. Patent Publication US 2014/0255432, which is incorporated herein by reference in its entirety.

Further examples of site-directed eIF4A inhibitors include compounds as disclosed in PCT Application No. PCT/US2016/063353, which is incorporated herein by reference in its entirety.

In accordance with the present disclosure, another class of example eIF4A inhibitors is cardiac glycosides. As shown in the examples herein, cardiac glycosides directly bind to eIF4A and inhibit its activity. Non-limiting example cardiac glycosides include digoxin, digoxigenin, digitoxigenin, and lanotoside C.

In some embodiments, the combination of inhibitors includes a c-MYC inhibitor. In accordance with the present disclosure, a non-limiting example class of c-MYC inhibitors is cardiac glycosides. As shown in the examples herein, cardiac glycosides can act upstream of eIF4A4 by inhibiting c-MYC. Non-limiting example cardiac glycosides include digoxin, digoxigenin, digitoxigenin, and lanotoside C.

In some embodiments, the combination of inhibitors includes a survivin inhibitor. Survivin, also known as BIRC5, is a downstream effector of eIF4A1. A non-limiting example survivin inhibitor compound is LQZ-7F. LQZ-7F is also known as 3-(5-((2-(6-((2,3-dimethylphenyl)amino)-[1,2,5]oxadiazolo[3,4-b]pyrazin-5-yl)hydrazineylidene)methyl)furan-2-yl)benzoic acid, and has the following chemical structure:

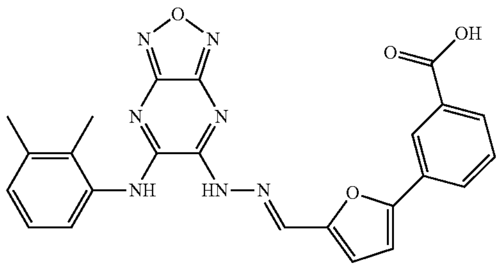 [SMILES: Cc1cccc(Nc2nc3nonc3nc2N/N=C/c2ccc(-c3cccc(C(=O)O)c3)o2)c1C]

In some embodiments, the combination of inhibitors includes CXCR4 inhibitor. One non-limiting example of a CXCR4 inhibitor is the compound referred to herein as AE-848/14270010, which has the following structure:

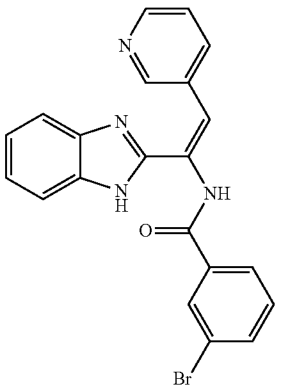

AE-848/14270010

Notably, AE-848/14270010 is a dual inhibitor of CXCR4 and eIF4A, as shown by the examples herein. In some embodiments, one or more dual inhibitors (i.e., inhibitor agents that inhibit two more) of eIF4A, LASP1, CXCR4, CXCL8, CXCL12, ROCK1, BIRC5, MDM2, CCND1, and c-MYC are utilized.

In some embodiments, the combination of inhibitors includes the molecules referred to herein as AN-465/41673523 or CAST-2110 (also referred to as AT-2), the structures of which are shown in FIG. 15D, or an analog or derivative thereof.

Figure 35:
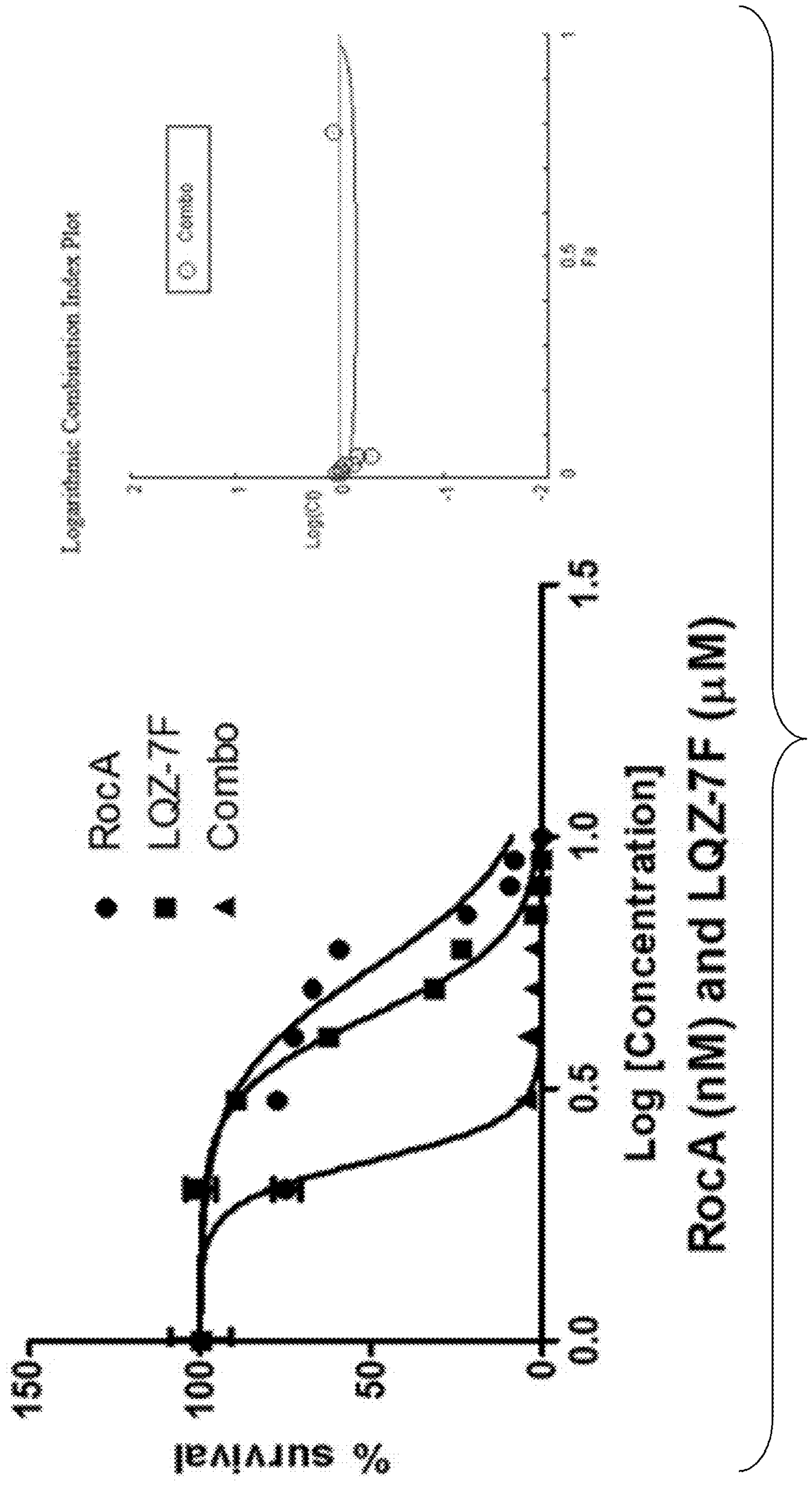
FIG. 35: Dual combination of LQZ-7F and rocaglamide A is synergistically effective against breast cancer stem cells. Breast cancer stem cells isolated from the tumor cells were highly susceptible to cell death when eIF4A1 and survivin were inhibited pharmacologically by rocaglamide A and LQZ-7F, respectively.

In some embodiments, a eIF4a inhibitor is combined with a survivin inhibitor, as discussed in more detail below. One non-limiting example is the combination of rocaglamide A and LQZ-7F. The examples in the present application demonstrate a synergistic benefit from the combination of rocaglamide A with LQZ-7F. (FIG. 35.)

Figure 29A:
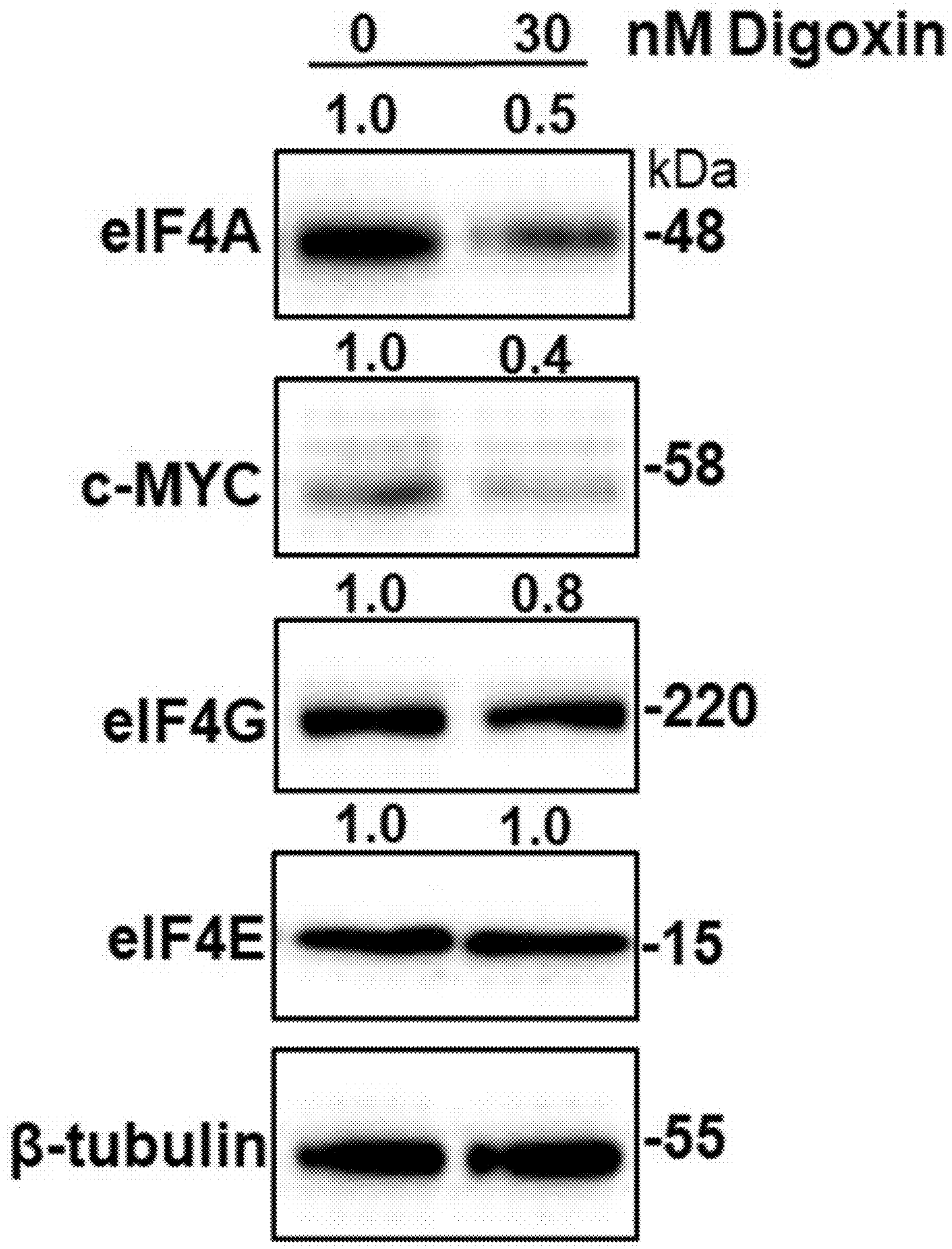
FIGS. 29A-29E: Digoxin in combination with rocaglamide A is efficacious in affecting tumor cell viability.
Figure 29B:
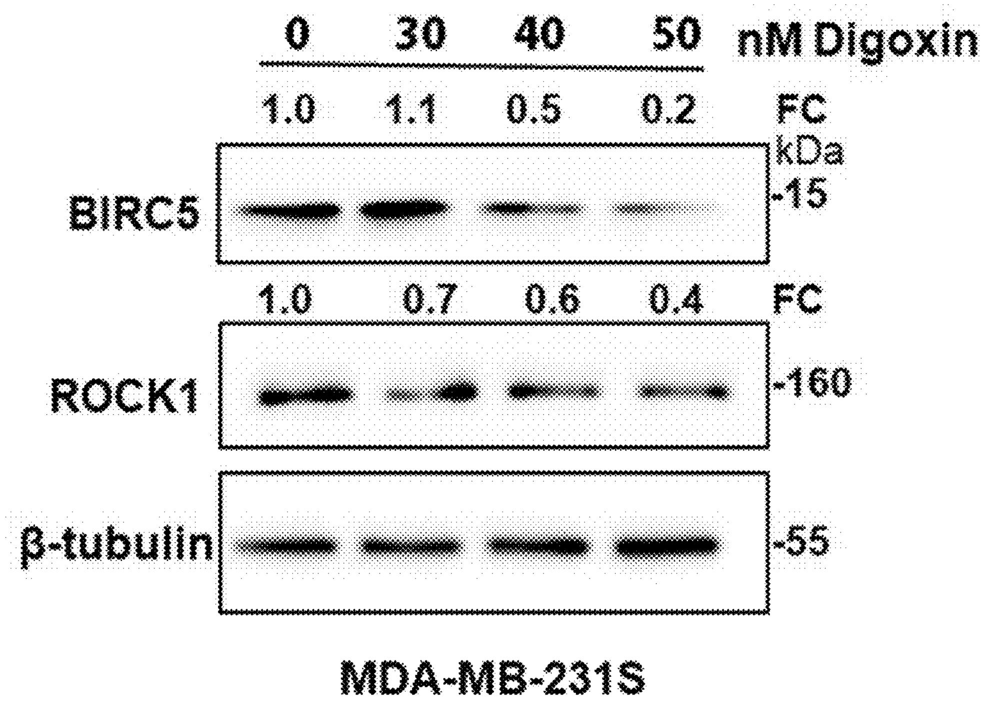
Figure 29C:
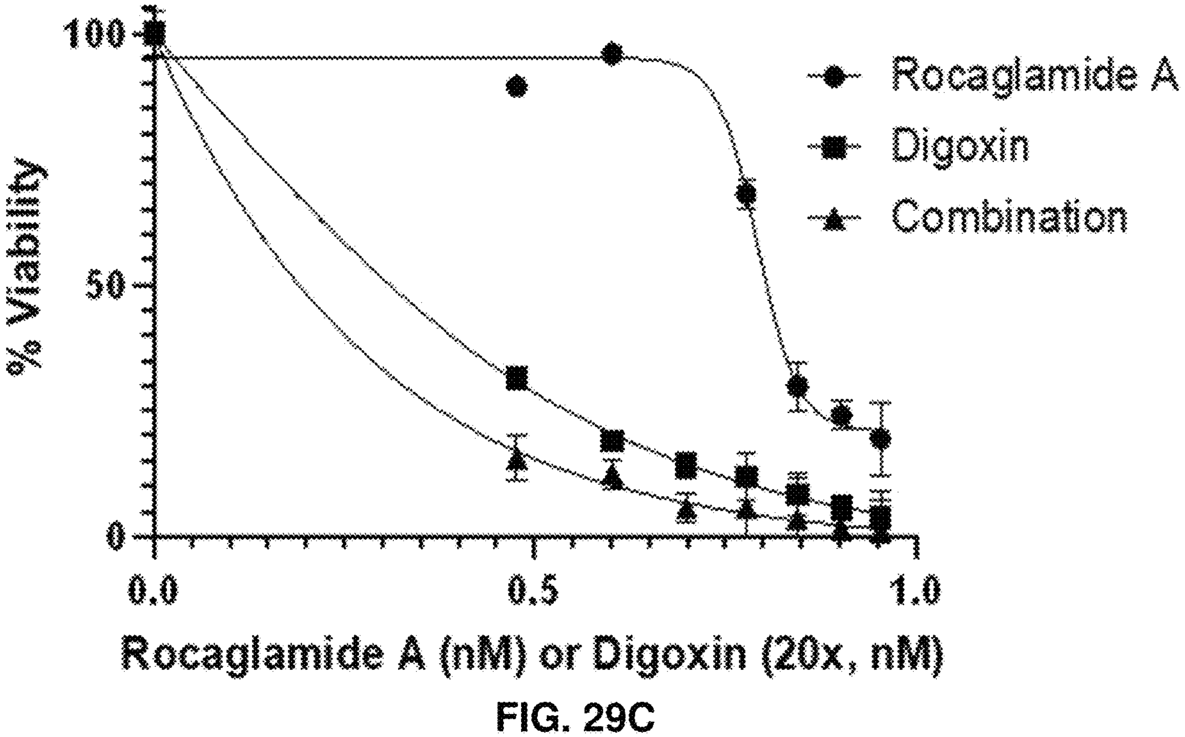
Figure 29D:
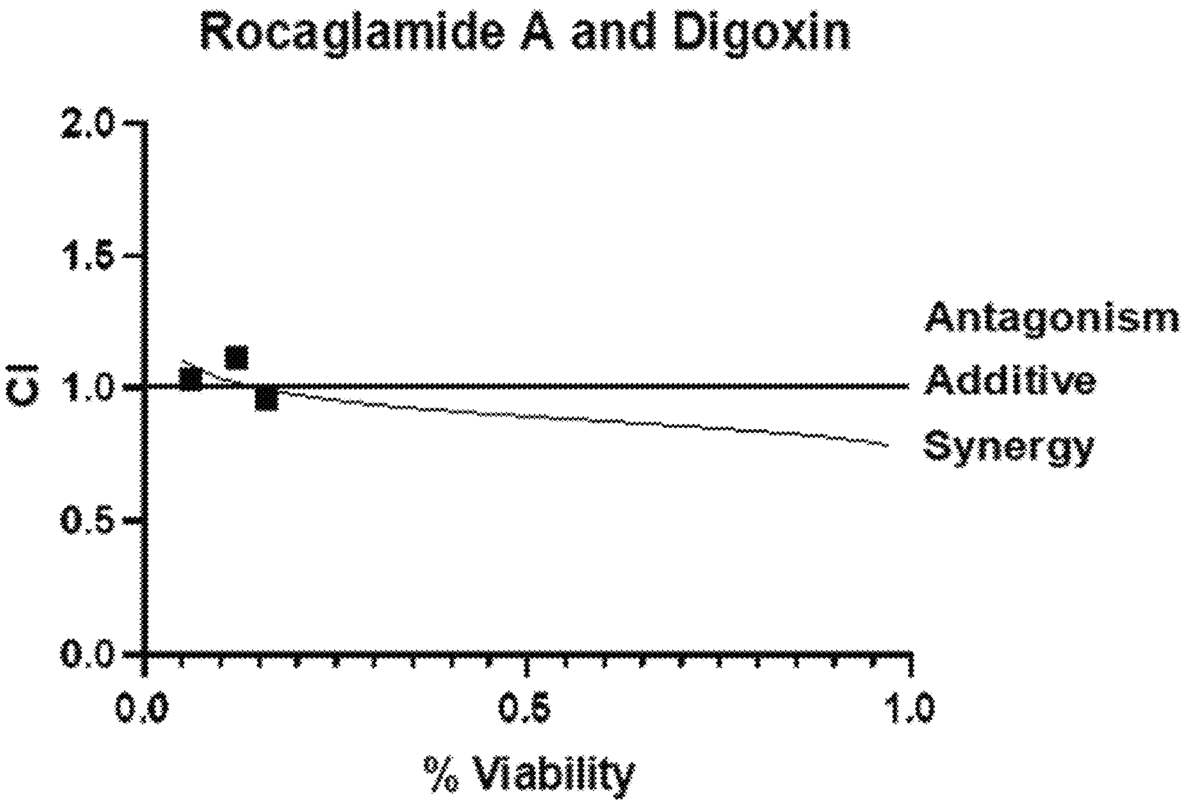

In some embodiments, a eIF4A inhibitor is combined with a c-MYC inhibitor. An example of this is the combination of a flavagline and a cardiac glycoside, such as rocaglamide A and digoxin. The examples in the present application demonstrate synergistic benefit from the combination of rocaglamide A with digoxin. (FIG. 29D.)

Many other combinations of specific inhibitors of eIF4A, LASP1, CXCR4, CXCL8, CXCL12, ROCK1, BIRC5, MDM2, CCND1, and c-MYC are possible and encompassed within the scope of the present application.

In certain embodiments, methods disclosed herein also encompass use or activity of in vivo metabolic products of inhibitor compounds. Such products may result from, for example, the oxidation, reduction, hydrolysis, amidation, esterification, and like processes primarily due to enzymatic activity upon administration of an inhibitor compound. Accordingly, in certain embodiments, the presently disclosed methods include use of compounds that are produced as byproducts of enzymatic or non-enzymatic activity on an inhibitor compound following the administration of such a compound to a mammal for a period of time sufficient to yield a metabolic product. Metabolic products, particularly pharmaceutically active metabolites, are typically identified by administering a radiolabeled compound of the present disclosure in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabeled compound.

In some embodiments, the methods disclosed herein also provide use of pharmaceutically acceptable salt forms of inhibitor compounds. Encompassed within the scope of this disclosure are uses of both acid and base addition salts that are formed by contacting a pharmaceutically suitable acid or a pharmaceutically suitable base with an inhibitor of eIF4A, LASP1, CXCR4, CXCL8, CXCL12, ROCK1, BIRC5, MDM2, CCND1, or c-MYC.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins, and the like. Particularly preferred organic bases are isopropylamine, diethylamine, ethanolamine, trimethylamine, dicyclohexylamine, choline, and caffeine.

Crystallizations may produce a solvate of the compound for use in the disclosed methods. As used herein, the term "solvate" refers to an aggregate that comprises one or more molecules of a compound of the present disclosure with one or more molecules of solvent. The solvent may be water, in which case the solvate may be a hydrate. Alternatively, the solvent may be an organic solvent. Thus, an inhibitor of eIF4A, LASP1, CXCR4, CXCL8, CXCL12, ROCK1, BIRC5, MDM2, CCND1, or c-MYC for use in the presently disclosed compositions or methods may exist as a hydrate, including a monohydrate, dihydrate, hemihydrate, sesquihydrate, trihydrate, tetrahydrate, and the like, as well as the corresponding solvated forms. A compound for use in methods of the present disclosure may be a true solvate, may merely retain adventitious water, or may be a mixture of water plus some adventitious solvent. A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposeable mirror images of one another.

Compounds or their pharmaceutically acceptable salts for use in the presently disclosed compositions and methods may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using, for example, chromatography, and fractional crystallization. Techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When compounds described herein contain olefinic double bonds or other centers of geometric asymmetry, and unless specified otherwise, it is intended that the compounds include both E and Z geometric isomers. Likewise, all tautomeric forms are also intended to be included. The term "tautomer" refers to a proton shift from one atom of a molecule to another atom of the same molecule.

It will also be appreciated by those of skill in the art, although such protected derivatives of compounds of this disclosure may not possess pharmacological activity as such, they may be administered to a mammal and thereafter metabolized in the body to form compounds of this disclosure that are pharmacologically active. Such protected derivatives may, therefore, be described as "prodrugs". In certain embodiments, inhibitor compounds of this disclosure are in the form of a prodrug.

Pharmaceutical compositions of the present disclosure may comprise an effective amount of one or more inhibitors of eIF4A, LASP1, CXCR4, CXCL8, CXCL12, ROCK1, BIRC5, MDM2, CCND1, or c-MYC (an "active" ingredient), and/or additional agents, dissolved or dispersed in a pharmaceutically acceptable carrier. The pharmaceutically acceptable composition may be prepared by combining the solid or liquid of a pharmaceutically acceptable carrier and optionally with pharmaceutically acceptable adjuvants and excipients by using standard and conventional techniques. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid, or aerosol form, and whether it needs to be sterile for such routes of administration as injection. Compositions disclosed herein can be administered orally, intravenously, intranasally, intradermally, transdermally, intrathecally, intraarterially, intraperitoneally, intravaginally, intrarectally, intraosseously, periprosthetically, topically, intramuscularly, subcutaneously, mucosally, intraosseosly, periprosthetically, in utero, topically, locally, via inhalation (e.g., aerosol inhalation), by injection, by infusion, by continuous infusion, by localized perfusion bathing target cells directly, via a catheter, via a lavage, in creams, in lipid compositions (e.g., liposomes), or by other method or any combination of the foregoing as would be known to one of ordinary skill in the art (see, for example, Remington's Pharmaceutical Sciences, 2003, incorporated herein by reference).

For oral administration, one or more inhibitor agents and its (their) salts can be formulated as solids as well as liquids. Solid medications include pills, tablets, dispersible granules, capsules, powder, cachets, and suppositories. A solid carrier which can be at least one substance of which may also function as flavoring agent, solubilizer, lubricant, suspending agent, binder, tablet disintegrating agent, and encapsulating agent, which includes lactose, sucrose, cornstarch, gelatin, magnesium carbonate, magnesium stearate, sugar, pectin, dextrin, cellulosic materials, low melting wax, cocoa butter, and the like. For liquid medicaments, the composition may include aqueous solutions such as syrups, flavored syrups, aqueous or suspensions, emulsions with edible oils, and elixirs. In one non-limiting example, an inhibitor compound is suspended or dispersed in synthetic agents such as tragacanth, acacia, dextran, sodium carboxymethylcellouse, methylcellouse, and gelatin.

For intravenous-administered medicaments, the active ingredient(s) is formulated with suitable liquid injection vehicle, which includes water, saline, dextrose, water-miscible solvents such as ethanol, polyethylene glycol and propylene glycol, and non-aqueous vehicles such as animal and plant oil. The buffer, such as citrate, acetate, or phosphate, can be present to maintain pH, optionally between 6-8, and preferably between pH 6.5-7.5. Antioxidants such as ascorbic acid and sodium bisulphite can be present. The solubilizing agents and stabilizers such as cyclodextrin, lysolectin, oleic acid, stearic acid, and dextrin can be present.

The composition may be administrated in unit dosage form which contains an appropriate amount of active ingredient(s). The quantity of active ingredient(s) in a dose, is varied or adjusted depending upon its potency and its particular application. In some embodiments, quantity ranges between 0.5% to 90% composition weight. In some embodiments, the suitable dosage of compound ranges about 0.1 to 5000 mg per human patient per day, for example from 50 to 2000 mg per human patient per day. In some embodiments, the dosage of compounds of Formula I can be divided into 2-4 doses per day.

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active ingredient. In other embodiments, an active ingredient may comprise between about 2% to about 75% of the weight of the unit, or between about 25% to about 60%, for example, and any range derivable therein. Naturally, the amount of active ingredient(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158, 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.), and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating, preventing, or ameliorating a cancer. Thus, provided herein is a method for treating, preventing, or ameliorating a cancer in patients by administering to a patient in need thereof an effective amount of one or more inhibitors of eIF4A, LASP1, CXCR4, CXCL8, CXCL12, ROCK1, BIRC5, MDM2, CCND1, and c-MYC. In some embodiments, two or more inhibitors of eIF4A, LASP1, CXCR4, CXCL8, CXCL12, ROCK1, BIRC5, MDM2, CCND1, and c-MYC are administered. In some embodiments, the inhibitor(s) is/are administered in a pharmaceutical composition orally, parenterally, or topically. The compounds and compositions can also be used to various other advantageous purposes, such as to sensitive cancer cells to chemotherapeutic agents, to reduce the sternness of cancer cells such as breast cancer cells, to kill breast cancer stem cells, to reduce expression of oncogenic proteins in cells, to reduce tumor cell viability, or to overcome the drug resistance of drug resistant cancer cells.

Furthermore, the active ingredients and compositions herein can be used in combination therapies. That is, the active ingredients or compositions can be administered concurrently with, prior to, or subsequent to one or more other inhibitors of eIF4A, LASP1, CXCR4, CXCL8, CXCL12, ROCK1, BIRC5, MDM2, CCND1, and c-MYC, and/or one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active ingredient(s) in a way that the therapeutic effects of the first administered procedure or drug is not entirely disappeared when the subsequent procedure or drug is administered.

In some embodiments, a combination therapy of the present disclosure includes one or more inhibitors of eIF4A, LASP1, CXCR4, CXCL8, CXCL12, ROCK1, BIRC5, MDM2, CCND1, and c-MYC combined with one or more chemotherapeutic agents. Suitable chemotherapeutic agents include, but are not limited to: taxane compounds, such as paclitaxel; platinum coordination compounds; topoisomerase I inhibitors, such as camptothecin compounds; topoisomerase H inhibitors, such as anti-tumor podophyllotoxin derivatives; anti-tumor vinca alkaloids; anti-tumor nucleoside derivatives; alkylating agents; anti-tumor anthracycline derivatives; HER2 antibodies; estrogen receptor antagonists or selective estrogen receptor modulators; aromatase inhibitors; differentiating agents, such as retinoids, and retinoic acid metabolism blocking agents (RAMBA); DNA methyl transferase inhibitors; kinase inhibitors; farnesyltransferase inhibitors; HDAC inhibitors, or other inhibitors of the ubiquitin-proteasome pathway; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide, and trimethylomelamine; acetogenins; camptothecins, such as the synthetic analog topotecan; cryptophycins; nitrogen mustards, such as chlorambucil; nitrosoureas; bisphosphonates; mitomycins; epothilones; maytansinoids; trichothecenes; retinoids, such as retinoic acid; pharmaceutically acceptable salts, acids and derivatives of any of the above; and combinations thereof.

Non-limiting examples of specific chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology), temozolomide (4-methyl-5-oxo-2,3,4,6,8-pentazabicyclo [4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N, N-dimethyl-ethanamine, NOLVADEX®, ISTUBAL®, VALODEX®), doxorubicin (ADRIAMYCIN®), Akti-1/2, HPPD, rapamycin, lapatinib (TYKERB®, Glaxo SmithKline), oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), ABT-869 (multi-targeted inhibitor of VEGF and PDGF family receptor tyrosine kinases, Abbott Laboratories and Genentech), ABT-263 (Bcl-2/Bcl-xL inhibitor, Abbott Laboratories and Genentech), PTK787/ZK 222584 (Novartis), fulvestrant (FASLODEX®, AstraZeneca), leucovorin (folinic acid), lonafamib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifamib (ZARNESTRA™, Johnson & Johnson), capecitabine (XELODA®, Roche), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thioTepa and cyclosphosphamide (CYTOXAN®, NEOSAR®), bullatacin, bullatacinone, bryostatin, callystatin, CC-1065 (including its adozelesin, carzelesin and bizelesin synthetic analogs), cryptophycin 1, cryptophycin 8, dolastatin, duocarmycin (including the synthetic analogs, KW-2189 and CB1-TM1), leutherobin, pancratistatin, sarcodictyin, spongistatin, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimnustine, clodronate, esperamicin, neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin, methotrexate, 5-fluorouracil (5-FU), denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane, rhizoxin, sizofuran, spirogermanium, tenuazonic acid, triaziquone, 2,2',2"-trichlorotriethylamine, T-2 toxin, verracurin A, roridin A, anguidine, urethane, vindesine, dacarbazine, mannomustine, mitobronitol, mitolactol, pipobroman, gacytosine, arabinoside ("Ara-C"), cyclophosphamide, thioTepa, 6-thioguanine, mercaptopurine, vinblastine, etoposide (VP-16), ifosfamide, mitoxantrone, vincristine, vinorelbine (NAVELBINE®), novantrone, teniposide, edatrexate, daunomycin, aminopterin, ibandronate, CPT-11, topoisomerase inhibitor RFS 2000, and difluoromethylomithine (DMFO).

In some embodiments, a combination therapy of the present disclosure includes one or more inhibitors of eIF4A, LASP1, CXCR4, CXCL8, CXCL12, ROCK1, BIRC5, MDM2, CCND1, and c-MYC combined with a surgical procedural to remove tumor cells.

The compositions and methods described herein may also be made available via a kit containing one or more key components. A non-limiting example of such a kit comprises a first agent in one container, and a second agent in another container, where the first agent is an inhibitor of one or more of eIF4A, LASP1, CXCR4, CXCL8, CXCL12, ROCK1, BIRC5, MDM2, CCND1, and c-MYC, the second agent is a different inhibitor of one or more of eIF4A, LASP1, CXCR4, CXCL8, CXCL12, ROCK1, BIRC5, MDM2, CCND1, and c-MYC, and where the containers may or may not be present in a combined configuration. Many other kits are possible, such as kits further comprising a pharmaceutically acceptable diluent, adjuvant, or carrier. The kits typically further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example I—The CXCR4-LASP1-eIF4F Axis Promotes Translation of Oncogenic Proteins in Triple-Negative Breast Cancer Cells Triple-negative breast cancer (TNBC) remains clinically challenging as effective targeted therapies are lacking. In addition, patient mortality mainly results from the metastasized lesions. CXCR4 has been identified to be one of the major chemokine receptors involved in breast cancer metastasis. Previously, LIM and SH3 Protein 1 (LASP1) were identified to be a key mediator in CXCR4-driven invasion. To further investigate the role of LASP1 in this process, a proteomic screen was employed and identified a protein-protein interaction between LASP1 and components of eukaryotic initiation 4F complex (eIF4F). Activation of the CXCR4-LASP1-eIF4F axis contributes to the preferential translation of oncogenic mRNAs leading to breast cancer progression and metastasis. To demonstrate this, it was first confirmed that the gene expression of CXCR4, LASP1, and eIF4A are upregulated in invasive breast cancer. Moreover, it was demonstrated that LASP1 associated with eIF4A in a CXCL12-dependent manner via a proximity ligation assay. Then, this finding was confirmed, and the association of LASP1 with eIF4B via co-immunoprecipitation assays was evaluated. Furthermore, it is shown that that LASP1 can interact with eIF4A and eIF4B through a GST-pulldown approach. Activation of CXCR4 signaling increased the translation of oncoproteins downstream of eIF4A. Interestingly, genetic silencing of LASP1 interrupted the ability of eIF4A to translate oncogenic mRNAs into oncoproteins. This impaired ability of eIF4A was confirmed by a previously established 5'UTR luciferase reporter assay. Finally, lack of LASP1 sensitizes 231S cells to pharmacological inhibition of eIF4A by rocaglamide A as evident through BIRC5 expression. Overall, this example identifies the CXCR4-LASP1 axis to be a mediator in oncogenic protein translation. Thus, this axis is a target for TNBC therapies.

It is demonstrated in this example that LASP1 can interact with both eIF4A and eIF4B. Importantly, the LASP1-eIF4A and LASP1-eIF4B interaction is shown to be CXCL12-dependent. In addition, the ability of CXCR4 to impact the phosphorylation of eIF4F regulatory proteins is provided. Taken together, it is shown that activation of CXCR4 can promote eIF4F complex formation and activity through LASP1 and cell signaling. As a result, the translation of oncogenic proteins is promoted, thereby mediating an invasive and metastatic phenotype commonly associated with CXCR4.

Background

One possible approach to target TNBC cells has been through the inhibition of various chemokine receptors. Overall, this group of proteins plays an essential role in the tumor microenvironment to facilitate breast cancer progression and metastasis. More specifically, the CXCL12-CXCR4 signaling pathway has been associated with TNBC invasiveness and chemotactic homing. The C-terminal tail of CXCR4 directly binds to LIM and SH3 protein 1 (LASP1) and knock down of LASP1 ablated CXCR4-driven invasion. LASP1 is an adaptor protein that has been shown to mediate cell migration, proliferation, and survival in several breast cancer cell lines. Additionally, LASP1 dissociates from the CXCR4 C-terminal tail upon CXCL12 stimulation. Therefore, stimulation with CXCL12 may promote LASP1 to modulate the signaling network of CXCR4 via transient protein-protein interactions. Subsequently, a proteomic screen for LASP1 interacting proteins was performed. Eukaryotic initiation factors 4A and 4B (eIF4A and eIF4B) were identified to be interacting proteins. Both eIF4A and eIF4B are essential components of the eukaryotic initiation factor 4F complex (eIF4F).

The eIF4F complex consists of three core subunits: eIF4E, the cap binding subunit; eIF4A, an RNA helicase; and eIF4G1, a large scaffolding protein. Ultimately, selection of an mRNA by the eIF4F complex prepares it for successful recruitment of the 43S pre-initiation complex, and eventual ribosome assembly. More specifically, eIF4A catalyzes the ATP-dependent unwinding of RNA duplexes and requires the direct binding of its co-factor, eIF4B, along with eIF4G1, for its optimal activity. The eIF4F complex has been previously identified to be important for the initiation and maintenance of a malignant phenotype in human mammary epithelial cells. Suppression of eIF4F can also affect the maintenance, progression, and metastasis of breast cancer in in vivo models. Elevated protein expression levels of eIF4A and eIF4B have been observed in breast cancer patients. Moreover, eIF4A, eIF4B, and eIF4E are all independent predictors of poor outcome in ER-negative breast cancer.

Conventionally, it is believed that the eIF4F complex has been identified to be a critical node of cancer biology due to many oncogenic mRNAs containing secondary structures within their 5'untranslated regions (5'UTRs). Thus, cancer cells preferentially rely on eIF4A to unwind these structured 5'UTRs or stem-loop structures (SLS). Without eIF4F complex formation and activity, the secondary structure of the 5'UTR would stall ribosome scanning and detection of the methionine start codon (AUG). As a result, many oncogenic proteins would remain at steady-state levels and this would hinder malignancy. Several of these SLS-containing oncogenic mRNAs include: BIRC5 (Survivin), Cyclin D1 (CCND1), Ornithine Decarboxylase (ODC), Murine Double Minute 2 (Mdm2), Rho A kinase1 (ROCK1), Mucin-1C (MUC-1C), Sin1, and ADP Ribosylation Factor 6 (ARF6). BIRC5, CCND1, ROCK1, and Mdm2 were pursued in this example as eIF4A-dependent target genes.

Additionally, the influence of CXCR4 on the eIF4F complex through G-protein coupled receptor signaling is elucidated in this example. CXCR4 has been previously shown to activate both ribosomal S6 kinases: p90 ribosomal S6 kinase (p90rsk—via the ERK pathway) and p70-S6 kinase (p70rsk—via the mTORC1 pathway). These two major kinases have been established to feed into cap-dependent mRNA translation through modulation of regulatory proteins such as 4E-BP1. In its phosphorylated form, 4E-BP1 releases eIF4E to promote eIF4F complex formation. In addition, eIF4B is specifically phosphorylated on Ser422 by p90rsk and p70rsk kinases. This phosphorylated form of eIF4B increases the rate of translation. Finally, active p70rsk and p90rsk also induces the phosphorylation and degradation of the tumor suppressor, programmed cell death protein 4 (PDCD4), an endogenous inhibitor of eIF4A. Despite evidence on several signaling pathways feeding into the eIF4F complex, little is known about the phosphorylation status of these proteins following activation of CXCR4.

Materials and Methods

Bioinformatics Analysis

To determine the significance of the CXCR4-LASP1-eIF4A/B axis in patient tissues, gene expression data was obtained and analyzed using Oncomine™. Settings in the program were limited to a “cancer vs. normal analysis” and “breast cancer.” Data from two representative datasets are shown. Datasets include: Radvanyi Breast (PNAS, Aug. 2, 2005) and TCGA Breast (The Cancer Genome Atlas, Sep. 2, 2011). Box and whisker plots for each cancer subtype were generated in the ‘R’ statistical package and the generated graphics were modified in Inkscape.

Cell Culture

231S Cells

MDA-MB-231 human breast cancer cells (MDA-MB-231: ATCC HTB-26, Manassa, Va.) were previously sorted for high cell surface expression of CXCR4 (denoted as 231S cells).

293-HA-CXCR4 Cells

Human embryonic kidney 293 cells (HEK-293: ATCC CRL-1573, Manassas, Va.) stably expressing human CXCR4 are also known.

MCF7 Series

MCF7 breast cancer cells (MCF7: ATCC HTB-22, Manassas, Va.) expressing empty vector, wild-type CXCR4 (wild-type), or CXCR4 with a truncated C-terminal domain (ΔCTD) were characterized by others previously. Cells were maintained in Dulbecco's modified eagle medium (DMEM) supplemented with 4 mM L-glutamine, +4500 mg/L glucose, sodium pyruvate (GE Healthcare Life Sciences, Pittsburgh, Pa., Cat. No. SH30243.01), 10% heat-inactivated fetal bovine serum (FBS) (Denville Scientific, Swedesboro, N.J., Cat. No. FB5001-H), and penicillin (100 I.U.)/streptomycin (100 μg/ml) (Corning, Corning, N.Y., Cat. No. 30-002-CI).

Generation of LASP1 Knockdown and Knockout Cell Lines

LASP1 was stably knocked down (KD) in 231S cells using sh RNA constructs (V2LHS_64685 and V2LHS-64686, Open Biosystems, Huntsville, Ala.). A non-silicening (NS) sh RNA served as the wild type control (denoted as 231S LASP1 NS and KD). In order to obtain a genetic knockout (KO) of LASP1, LASp1 CRISPR/Cas9 knockout plasmids (a set of 3 plasmids) were purchased (Santa Cruz, Dallas, Tex., Cat. No. sc-404630). Cells were transfected using UltraCruz reagent (Santa Cruz, Dallas, Tex., Cat. No. sc-395739) according to the manufacturer's instructions. The supernatant was removed 24 h later and replaced with complete media. Cells were further cultured for 72 hours post-transfection. Subsequently, LASP1-KO cells were sorted for GFP and single KO cells were isolated by limiting dilution. KO of LASP1 was confirmed with Western blotting. Non-targeting CRISPR/Cas9 plasmids served as the control (Santa Cruz, Dallas, Tex., Cat. No. sc-418922). These plasmids encode the Cas9 nuclease and non-specific 20 nucleotide guide RNAs (denoted CRISPR control and LASP1 KO).

Co-Immunoprecipitation Assay

Subconfluent 231S cells were serum-starved for 1 hour and stimulated with 10-20 nM CXCL12 (PeptroTech, Rocky Hill, N.J., Cat. No. 300-28A) over different time points. Total cell lysates were prepared by lysing the cells in co-immunoprecipitation buffer (Co-IP buffer) (50 mM Tris pH 8.0, 100 mM NaCl, 0.1% IGEPAL CA-630, 0.1% deoxycholate, and 5 mM EDTA) supplemented with protease inhibitor cocktail (Sigma-Aldrich, St. Louis, Mo., Cat. No. P8340-5ML), phosphatase inhibitor cocktail 2 (Sigma-Aldrich, St. Louis, Mo., Cat. No. P5726), and phosphatase inhibitor cocktail 3 (Sigma-Aldrich, St. Louis, Mo., Cat. No. P0044) for 10 min at 4° C. Total protein in the clarified lysate was quantified using a Bradford protein assay (Bio-Rad, Hercules, Calif., Cat. No. 5000006). 1 mg of total protein lysate was employed in all immunoprecipitation reactions. eIF4B was immunoprecipitated by using 2 μg of eIF4B antibody (Cell Signaling Technology, Danvers, Mass., Cat. No. 13088). Mouse (G3A1) mAb IgG1 Isotype Control (Cell Signaling Technology, Danvers, Mass., Cat. No. 5415) served as the mock control. Next, eIF4A was immunoprecipitated using 2 μg of eIF4A1 antibody (Cohesion Biosciences, London, Purley, Cat. No. CQA1180). His-Tag (D3L10) XP® Rabbit mAb (Cell Signaling Technology, Danvers, Mass., Cat. No. 12698) was employed for the mock condition. Finally, in the reciprocal Co-IP, LASP1 was immunoprecipitated by using 2 μg LASP1 antibody (Biolegend, San Diego, Calif., Cat. No. 909301). As in the eIF4B Co-IP, mouse (G3A1) IgG1 isotype mAb was employed as the mock control. Prior to immunoprecipitation, lysates were pre-cleared with 20 μL of PureProteome™ Protein G Magnetic Beads (Millipore, Billerica, Mass., Cat. No. LSKMAGG10) for 2 H at 4° C. Immunoprecipitation reactions were then allowed to proceed with 20 μL of protein G magnetic beads and the appropriate amount of antibody for 2 h at 4° C. Beads were washed thrice with Co-IP buffer. To avoid heavy chain contamination (55 kDa) in the eIF4A Co-IP, antibodies were cross-linked using $BS^3$ (according to Millipore recommendations). Proteins of interest were analyzed by sodium dodecyl sulfate-polyacrylamide gel electrophoresis (SDS-PAGE) and Western blotting.

$m^7$-GTP Pull-Down Assay 231S cells were serum starved for 1 h and cells were stimulated (and prepared) as described in the co-immunoprecipitation section. 100 nM AMD3465 (CXCR4 antagonist, Sigma-Aldrich, St. Louis, Mo., Cat. No. SML1433-5MG) was incubated 30 min prior to stimulation. 1 mg of total protein lysate in 1 mL of Co-IP buffer was incubated with 25 μL of m7-GTP agarose beads overnight at 4° C. (Jena Biosciences, Jena, Germany, Cat. No. AC-155S). Following incubation, beads were washed with Co-IP buffer. Protein was eluted and analyzed by SDS-PAGE and Western blotting.

GST-LASP1 Pull-Down of eIF4A and eIF4B

The open reading frame of the human LASP1 gene (Open Biosystems, Huntsville, Ala.) was engineered with BamHI and XhoI cloning sites using the following gene specific primers: 5'-CTAGCTGGATCCATGAACC CCAACTGCGCC-3' (forward) (SEQ ID NO: 1), and 5'-CTAGCTCTCGAGTCAGATGGCCTCCA CGTA-3' (reverse) (SEQ ID NO: 2). Following amplification by polymerase chain reaction (PCR), LASP1 was inserted into the GST bacterial expression vector pGEX-6P-1 (GE Healthcare Life Sciences, Pittsburgh, Pa., Cat. No. 28954648). The verity of the DNA construct was confirmed by sequencing (Eurofins Genomics, Louisville, Ky.). Both the GST-LASP1 and empty pGEX-6P-1 vector (GST control) were transformed into *E. coli* BL21 strain for the production of GST and GST-LASP1 proteins using standard protocols described elsewhere. For the pull-down assays, 1.5 nmoles of the GST control protein (40.5 μg) and GSTLASP1 (85.1 μg) bound to glutathione agarose beads (Thermo Scientific, Rockford, Ill., Cat No. 16100) were equilibrated in Co-IP buffer and incubated with 1 mg of total protein lysates from 231S cells in 1 mL of Co-IP buffer for 2 h at 4° C. After washing the beads with Co-IP buffer, the bound proteins were eluted and analyzed by SDS-PAGE and Western blotting.

Direct Binding of LASP1 to eIF4A and eIF4B

Recombinant eIF4A and eIF4B were purified to homogeneity according to previously published protocols. In one set of direct binding experiments, 1.5 nmoles of GST-LASP1 and GST-control beads in 1 mL of Co-IP buffer were incubated with purified recombinant eIF4A and eIF4B overnight at 4° C. Beads were then washed with Co-IP buffer and bound protein was eluted by SDS-PAGE and Western blotting. To confirm that the binding is able to occur in a 1:1 molar ratio (and also in solution), GST-LASP1 and GST were eluted from the beads using glutathione elution buffer (10 mM L-glutathione, 50 mM Tris pH 8.0). Eluted protein was quantified using a Bradford protein assay. Equimolar amounts of proteins were incubated in a final volume of 1 mL of Co-IP buffer overnight at 4° C. Complexes were then re-captured with 10 μL glutathione agarose beads for 1 h at 4° C. Finally, beads were washed with Co-IP buffer and bound proteins were eluted and analyzed by SDS-PAGE and Western blotting. Purity of the recombinant proteins was confirmed by SDS-PAGE and staining with Imperial™ Protein Stain (Thermo Scientific, Rockford, Ill., Cat No. 24615) (5 ng detection limit).

Proximity Ligation Assay (PLA)

The Duolink In Situ Orange Fluorescent kit (Sigma/Aldrich, St. Louis, Mo., Cat. No. DUO92102-1KT) was employed to detect the endogenous interaction between LASP1 and eIF4A in situ in 231S cells. The PLA was performed according to the manufacturer's instructions using a rabbit eIF4A1 antibody (Cohesion Biosciences, London, Purley, Cat. No. CQA1180) and a mouse LASP1 antibody (Biolegend, San Diego, Calif., Cat. No. 909301). The single Ab control condition represents the PLA reaction with only the LASP1 antibody. In addition, cells were stained with phalloidin (Life Technologies, Carlsbad, Calif., Cat. No. A12379) and nuclei with DRAQ5 (Thermo Scientific, Rockford, Ill., Cat No. 62251). Cells were stimulated and inhibited as described. Moreover, cells were fixed, stained, and permeabilized with standard methods. The images were acquired by two-photon confocal microscopy and processed with Leica Application Suite X software (Leica, Wetzlar, Germany). Quantification of the interaction dots was performed using ImageJ.

Western Blotting

Cell lysates were prepared and quantified as described. Western blots were incubated with the following 1° Abs: Cyclin D1 (Cell Signaling Technology, Danvers, Mass., Cat. No. 2922), eIF4A C32B4 (Cell Signaling Technology, Danvers, Mass., Cat. No. 2013), eIF4B 1F5 (Cell Signaling Technology, Danvers, Mass., Cat. No. 13088), p-eIF4B S422 (Thermo Scientific, Rockford, Ill., Cat No. PA5-38362), eIF4E C46H6 (Cell Signaling Technology, Danvers, Mass., Cat. No. 2067), eIF4G C45A4 (Cell Signaling Technology, Danvers, Mass., Cat. No. 2469), GST 26H1 (Cell Signaling Technology, Danvers, Mass., Cat. No. 2624), LASP1 8C6 (Biolegend, San Diego, Calif., Cat. No. 909301), MDM2 SMP14 (Santa Cruz Biotechnology, Dallas, Tex., Cat. No. sc-965), PDCD4 D29C6 (Cell Signaling Technology, Danvers, Mass., Cat. No. 9535), p-PDCD4 S67 (Sigma-Aldrich, St. Louis, Mo., Cat. No. P0072), ROCK1 C8F7 (Cell Signaling Technology, Danvers, Mass., Cat. No. 4035), survivin 71G4B7 (Cell Signaling Technology, Danvers, Mass., Cat. No. 2808), 4E-BP1 53H11 (Cell Signaling Technology, Danvers, Mass., Cat. No. 9644), p-4E-BP1 Thr70 (Cell Signaling Technology, Danvers, Mass., Cat. No. 9455), and β-tubulin D66 (Sigma/Aldrich, St. Louis, Mo., Cat. No. T0198). Following primary incubation, Western blots were incubated with Goat anti-Mouse IgG (H+L) Superclonal™ Secondary Ab conjugated to HRP (Thermo Scientific, Rockford, Ill., Cat No. A28177) or Goat anti-Rabbit IgG (H+L) Superclonal™ Secondary Ab conjugated to HRP (Thermo Scientific, Rockford, Ill., Cat No. A27036). Finally, blots were developed with Amersham™ ECL™ Prime Western Blotting Detection Reagent (GE Healthcare Life Sciences, Pittsburgh, Pa., Cat. No. RPN2232) and HyBlot ES™ Autoradiography Film (Denville Scientific, Swedesboro, N.J., Cat. No. E3212). Densitometry of the Western blots was performed using ImageJ. Calculation of fold change is given in the figure legend for each experiment.

Real-Time PCR

Total RNA was extracted from 231S LASP1 NS and 231S LASP1 KD cells using an RNeasyR Mini Kit according to the manufacturer's instructions (Qiagen, Germantown, Md., Cat. No. 74104). Following RNA isolation, cDNA was synthesized using a SuperScript™ III First-Strand Synthesis Kit (Invitrogen, Carlsbad, Calif., Cat. No. 18080-400). 2000 ng of input RNA and random hexamer primers were used according to the manufacturer's instructions. Finally, real-time PCR was performed using 2× PowerUp™ SYBR™ Green Master Mix (Applied Biosystems, Foster City, Calif., Cat. No. A25741), 2 μL of cDNA, and 2 μL of the following forward and reverse primers (300 nM): ROCK1: 5'-AA-CATGCTGCTGGATAAATCTGG-3' (SEQ ID NO: 3) and 5'-TGTATCACATCGTACCATGCCT-3' (SEQ ID NO: 4); MDM2: 5'-CCT TCGTGAGAATTGGCTTC-3' (SEQ ID NO: 5) and 5'-CAACACATGACTCTCTGGAATCA-3' (SEQ ID NO: 6); CCND1: 5'-ATGTTCGTGGCCTCTAA-GATG A-3' (SEQ ID NO: 7) and 5'-CAGGTTCCACTT-GAGCTTGTTC-3' (SEQ ID NO: 8); BIRC5: 5'-A AGAACTGGCCCTTCTTGGA-3' (SEQ ID NO: 9) and 5'-CAACCGGACGAAT GCTTTT-3' (SEQ ID NO: 10); β-tubulin: 5'-TTGGCCAGATCTTTAGACCAGACAAC-3' (SEQ ID NO: 11) and 5'-CCGTACCA-CATCCAGGACAGAATC-3' (SEQ ID NO: 12). Real time data was analyzed using the 11Ct method with β-tubulin primers as the control. The values from 231S LASP1NS cells were then set to 1.

GQ 5'UTR Luciferase Assay

The GQ 5'UTR luciferase assay is a previously published method to assess the endogenous activity of eIF4A in cells. Four tandem repeats of the (CGG)4 12-mer motif (GQ 5'UTR) ("(CGG)4" is disclosed as SEQ ID NO: 13) or a random sequence matched for length and GC content (Random GQ 5'UTR) were cloned into the 5'UTR of firefly pGL4.10 luc2 (Promega, Madison, Wis., Cat. No. E6651) containing the CMV promoter. To create these constructs, CMV was first cloned into pGL4.10 luc2 by employing KpnI and XhoI restriction sites. The CMV promoter was amplified from pcDNA3.0 (Invitrogen, Carlsbad, Calif., Cat. No. V79020) using the following primers: 5'-TTTGTAGGTACCGATGTACGGGCCAGATATAC-3' (SEQ ID NO: 14) and 5'-TTTGTACTCGAGGTATTAAT-TTCGATAAGC-3' (SEQ ID NO: 15). After successful insertion and verification of the CMV promoter, both 5'UTR sequences (GQ and Random GQ) were cloned before the luciferase open reading frame via added BglII and HindIII sites. This was accomplished with the following annealed oligonucleotides obtained commercially (Eurofins Genomics, Louisville, Ky.): GQ 5'UTR: 5'-GATCTCTAGGTT-GAAAGTACTTTGACGGCGGCGGCGGTCAATCT-TACGGCGGCGGCGGA CATAGATACGGCGGCGGC-GGTAGAAACTACGGCGGCGGCGGATTAGAATAG-TAAAA-3' (SEQ ID NO: 16) and 5'-AGCTTTTTACTAT-TCTAATCCGCCGCCGCCGTAGTTTCTACCGCCGC-CGCCGTATCTATG TCCGCCGCCGCCGTAAGAT-TGACCGCCGCCGCCGTCAAAGTACTTTCAAC-CTAGA-3' (SEQ ID NO: 17). Random GQ 5 UTR: 5'-GATCTCTAGGGCGCACGTACTTCGACAACGTCA-GCGTTCAGCGTTCCAACGTCAGCGTA CCAGC-GATCCAACGTCAGCGTTCTGCGCTACAACGTCAG CGTATCCGCGTAGCACAA-3' (SEQ ID NO: 18) and 5'-AGCTTTGTGCTACGCGGATACGCTGACGTTGT-AGCGCAGAACGCTGACGTTGGATCGCT GTACGC-TGACGTTGGAACGCTGAACGCTGACGTTGTCGAA-GTACGTGCGCCCTAGA-3' (SEQ ID NO: 19). 40 ng of each firefly luciferase construct was transfected along with 40 ng of pGL4.74 hRluc (Promega, Madison, Wis., Cat. No. E6921). Following transfection, cells were incubated in serum free media overnight. Cells were lysed, protein lysates were then collected the next day. Firefly and renilla luciferase activity were assessed by employing the Dual-Luciferase R Reporter Assay System (Promega, Madison, Wis., Cat. No. E1910). Data reflects firefly luciferase activity normalized to renilla readings with the CMV-pGL4.10 luc2 set to 1 for each cell type.

Pharmacological Inhibition of eIF4A in 231S LASP1 NS and KD Cells

231S LASP1 NS/KD cells were plated into 96-well dishes (3,000 cells/well) and incubated with various amounts of rocaglamide A (RocA) (Sigma/Aldrich, St. Louis, Mo., Cat. No. SML0656) in low serum media (LSM-DMEM/0.5% FBS). Images were acquired via an IncuCyte R S3 Live-Cell Analysis System (Essen BioScience, Ann Arbor, Mich.). Two images per well were acquired every 2 h. Data was processed on the IncuCyte S3 software (Essen BioScience, Ann Arbor, Mich.). Only cells with an area >150 $\mu m^2$ were analyzed to avoid cellular debris. Data is reflective of the percent confluence of each image at 36 h RocA incubation. Percent inhibition was calculated in reference to the DMSO control. The readings from 231S LASP1 NS cells were set to 1. In the cell viability experiments, 231S LASP1 NS/KD cells were seeded at 6,000 cells/well and allowed to attach and spread overnight. The following day, complete media was replaced with LSM and RocA. Cell viability was then determined 36 h later using a cell counting kit-8 (Sigma/Aldrich, St. Louis, Mo., Cat. No 96992) according to the manufacturer's instructions. Data is reflective of the absorbance at 450 nm (A450). The DMSO controls were set to 100%.

Statistical Analysis and Graph Preparation

Data analysis was performed using the R statistical program (version 3.5.1). Statistical significance between groups was determined by unpaired Student's t-tests with a "p"-value set to <0.05. Graphs were first generated in R and then modified in Inkscape (version 0.92.3).

Results

Breast Cancer Patient Samples Contain Elevated Levels of CXCR4, LASP1, eIF4A, eIF4B, and the Downstream Targets of eIF4A In order to evaluate the gene expression profile of CXCR4, LASP1, eIF4A, and eIF4B in breast cancer patients, breast cancer data sets were analyzed using "Oncomine." This online resource is a cancer microarray database and an integrated data-mining platform. Differential expression analyses were performed on "The Cancer Genome Atlas" (TCGA) and Radvanyi data sets. In each analysis, the gene expression profile of normal breast tissue was compared with invasive lobular carcinoma (ILC) and invasive ductal carcinoma (IDC) samples. A significant elevation of gene expression was observed for CXCR4, LASP1, eIF4A, and eIF4B. In addition, the genes downstream of eIF4A (BIRC5, CCND1, ROCK1, and MDM2) were also observed to have elevated expression levels (p<0.05) (FIGS. 1A-1D). Overall, this indicates the clinical significance of the axis. Elevated mRNA levels of these genes established the premise that these proteins may play a vital role in oncoprotein translation to promote metastatic breast cancer.

LASP1 Associates with eIF4A Endogenously in a CXCL12-Dependent Manner In Situ

Figure 2:
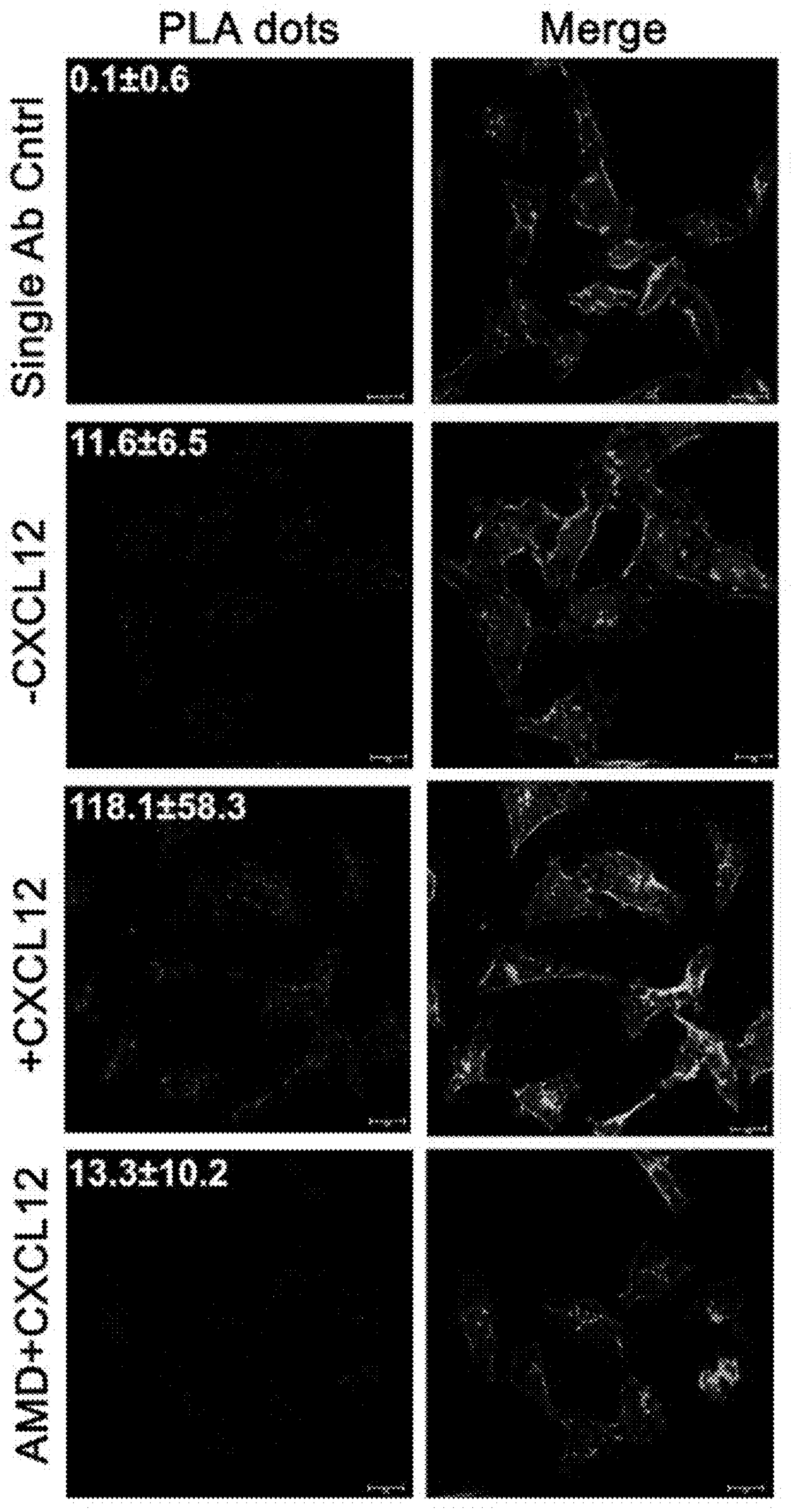
FIG. 2: The LASP1-eIF4A interaction increases with CXCL12 stimulation in situ. The Proximity Ligation Assay (PLA) was used to visual the in situ interaction between LASP1 and eIF4A in 231S cells. Cells were stimulated with 20 nM CXCL12 for 5 min. 100 nM AMD3465 was added 30 min prior to stimulation. The single antibody control employs the PLA reaction using only the LASP1 antibody. Representative images of the PLA experiment are provided. Quantification indicates the average number of interactions/cell across multiple independent fields. (Single Ab Control: n=39, −CXCL12: n=46, +CXCL12: n=29, +CXCL12/AMD3465: n=15); Red-LASP1-eIF4A interaction, Green-phalloidin (actin), and Blue-DRAQ5 (nucleus); Scale bar—10 μm.

To initially confirm the LASP1-eIF4A interaction, whether LASP1 would associate with eIF4A endogenously in 231S cells in situ was examined. Following stimulation or inhibition of CXCR4, the endogenous interaction between LASP1 and eIF4A was probed by a proximity ligation assay (PLA). The single antibody control displayed almost no interaction dots (0.09±0.6 dots—from 39 cells). In the unstimulated state (−CXCL12), a basal interaction was detected between LASP1 and eIF4A (11.6±6.5 dots—from 46 cells). With CXCL12 incubation for 5 min, there was a 3-fold stimulation of the interaction between LASP1 and eIF4A (118±58.3 dots—from 29 cells). The CXCL12-stimulated interaction between LASP1 and eIF4A can be abrogated to the basal level by the CXCR4 antagonist AMD3465 (13.3±10.2 dots—from 15 cells) (FIG. 2).

Figure 3A:
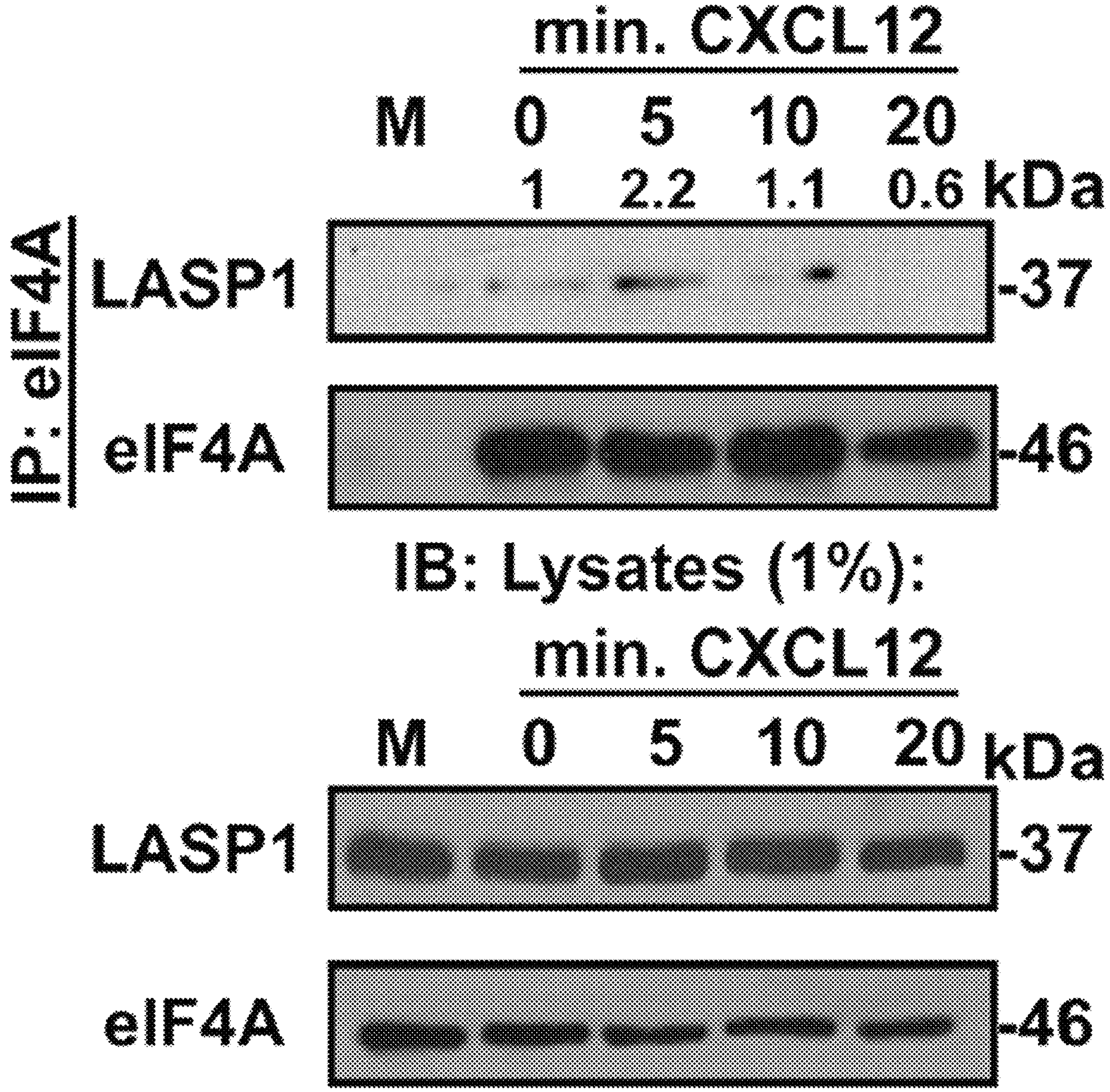
FIGS. 3A-3E: LASP1 interacts with the eIF4F complex in a CXCL12-dependent manner
Figure 3B:
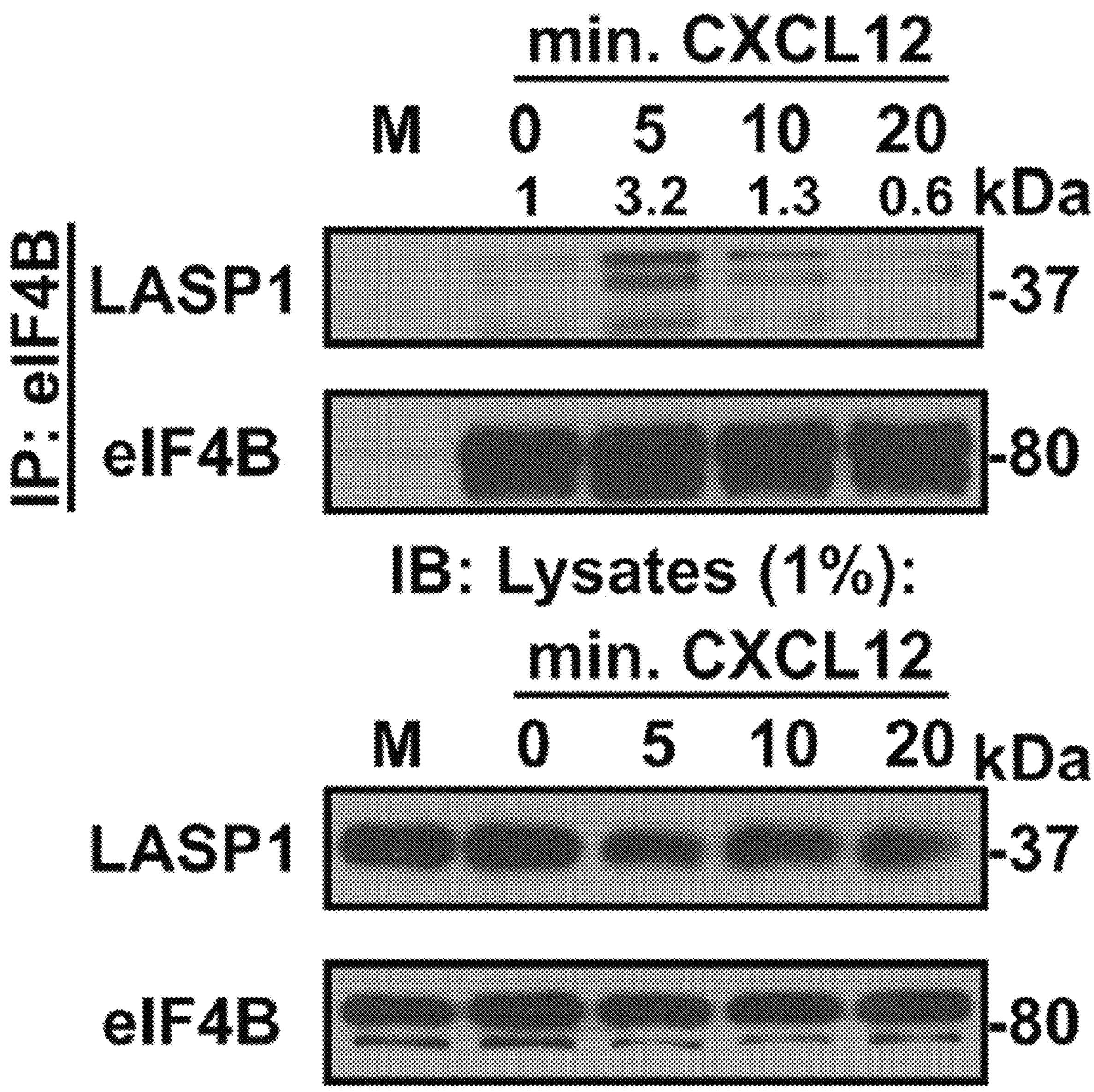
Figure 3C:
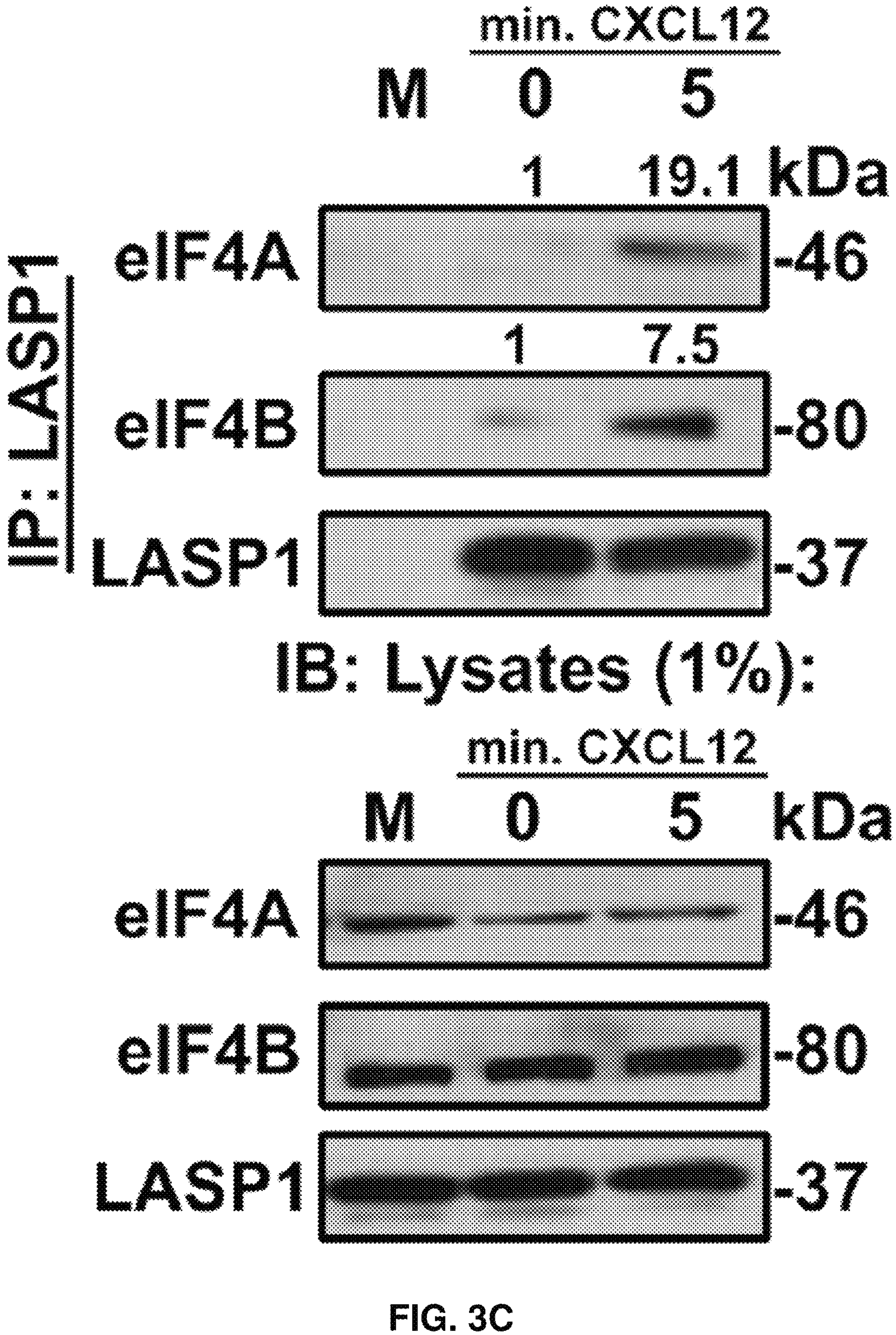

LASP1 Co-Immunoprecipitates with eIF4A and eIF4B Endogenously in a CXCL12-Dependent Manner In order to further evaluate the association between LASP1, eIF4A1, and eIF4B, co-immunoprecipitation assays were performed with and without CXCL12 stimulation in 231S cells. In each of these co-immunoprecipitation experiments, both eIF4A and eIF4B associated with LASP1 endogenously in a CXCL12-dependent manner with peak interaction at 5 min (FIGS. 3A-3B). To further validate the interaction, LASP1 was also immunoprecipitated and the presence of eIF4A and eIF4B was probed for in the reciprocal Co-IP. There was a slight basal association of endogenous LASP1 and eIF4A1 which increased to 19.1-fold upon stimulation of CXCR4 for 5 min. Similarly, there was a 7.5-fold increase in association of LASP1 with eIF4B upon activation of CXCR4 (FIG. 3C).

Endogenous LASP1 Associates with the eIF4F Complex in a CXCL12-Dependent Manner

Figure 3D:
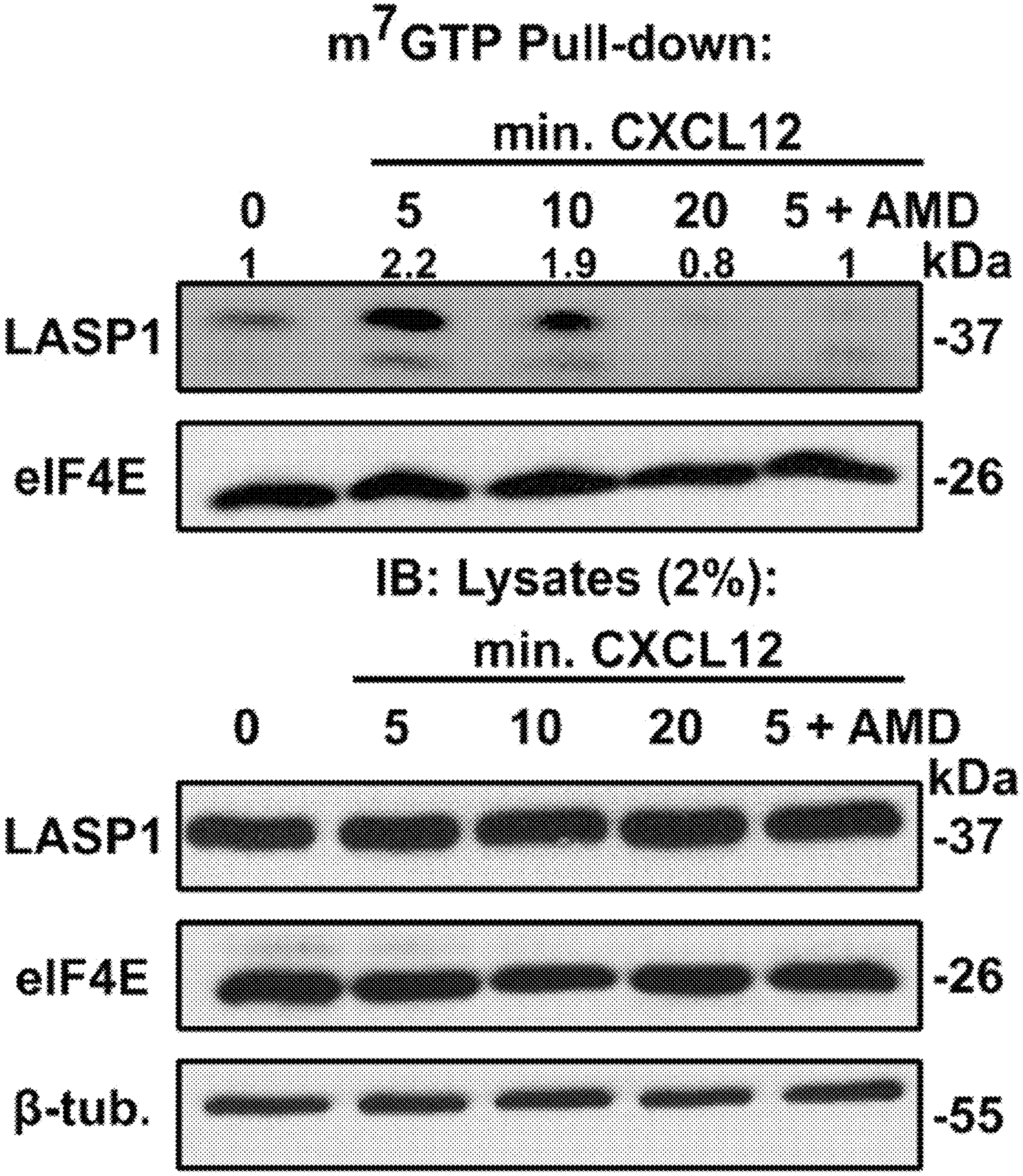
Figure 3E:
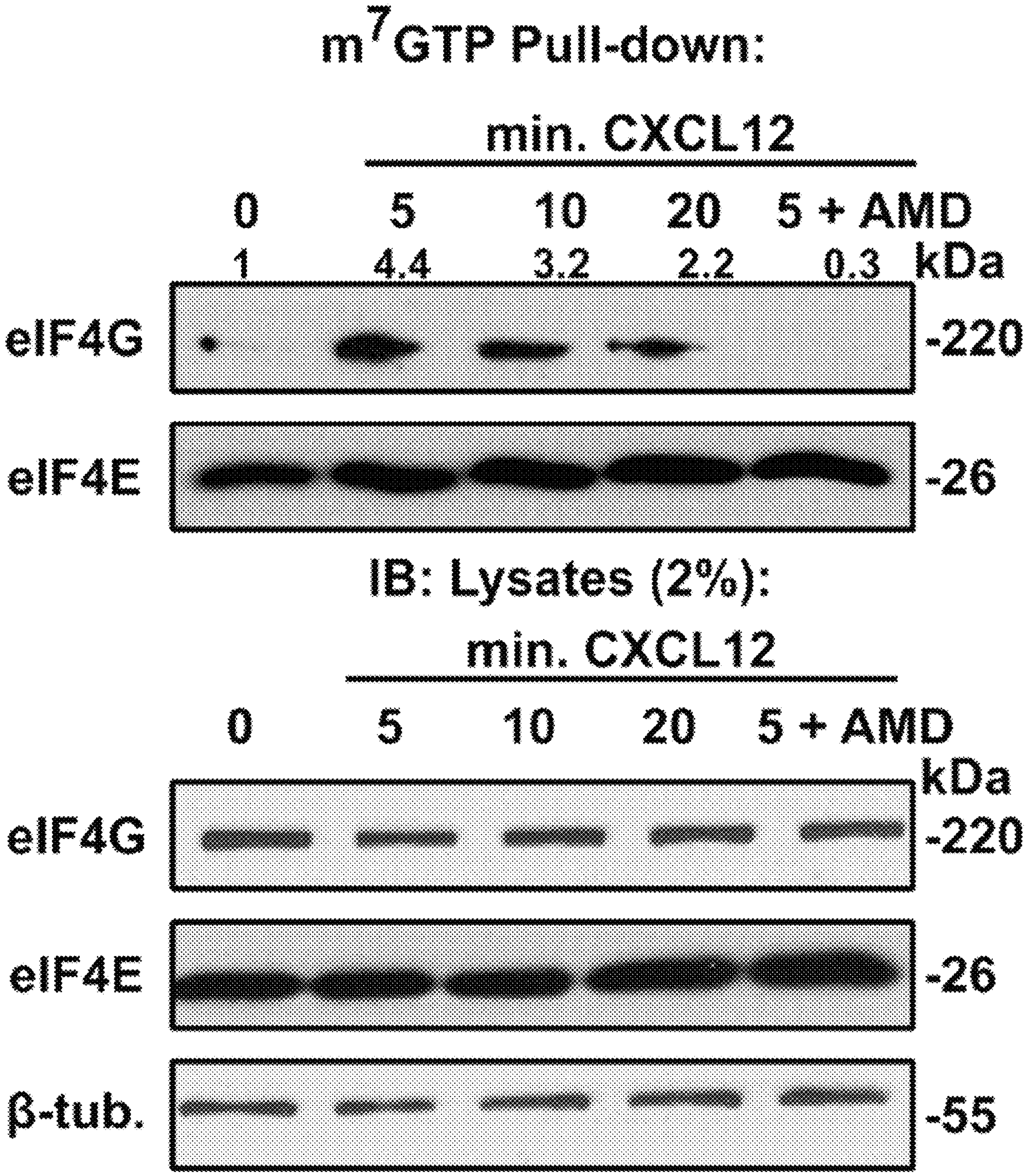

Whether LASP1 could be incorporated into the eIF4F complex upon stimulation of CXCR4 was evaluated. To address this question, the previously established m7GTP-pulldown assay was employed. Activation of CXCR4 in 231S cells resulted in an increased association of endogenous LASP1 with eIF4E. This association peaked at 5 (2.2-fold) min before returning to basal level at 20 min. Importantly, the CXCL12-dependent recruitment of LASP1 at 5 min can be abrogated by pre-treatment of the cells with AMD3465 (FIG. 3D). Furthermore, the eIF4G-eIF4E interaction has been commonly accepted to give an indication of eIF4F complex formation. As such, the influence of CXCR4 on the eIF4G-eIF4E interaction was explored. eIF4G was incorporated in a CXCL12-dependent manner with a peak recruitment at 5 min (4.4-fold) and slowly declined to 2.2-fold at 20 min, well above the baseline level. This peak recruitment at 5 min of CXCL12 treatment can also be reduced by AMD3465 (FIG. 3E).

LASP1 Directly Binds to Both eIF4A and eIF4B

Figure 4A:
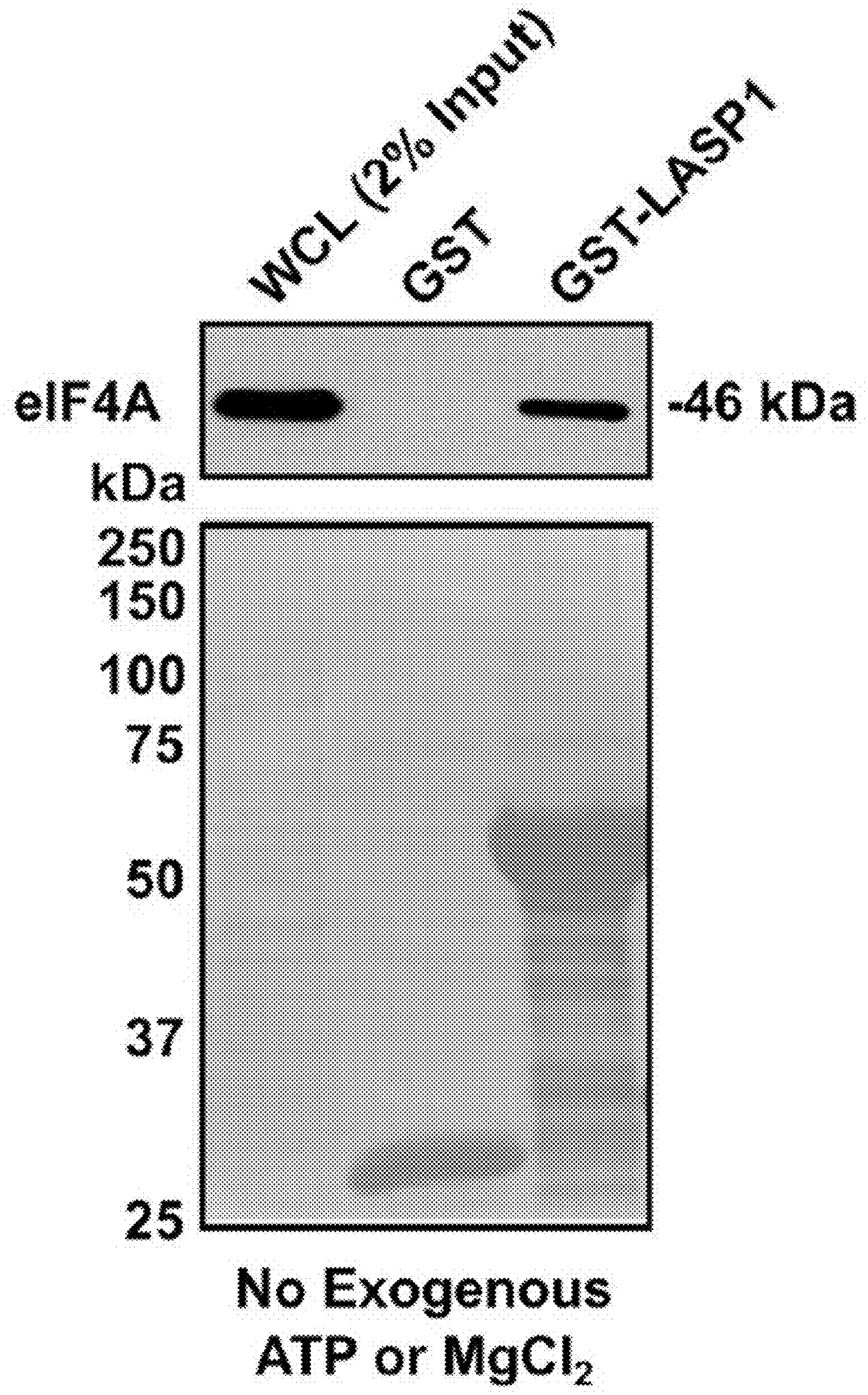
FIGS. 4A-4F: LASP1 directly interacts with both eIF4A and eIF4B.
Figure 4B:
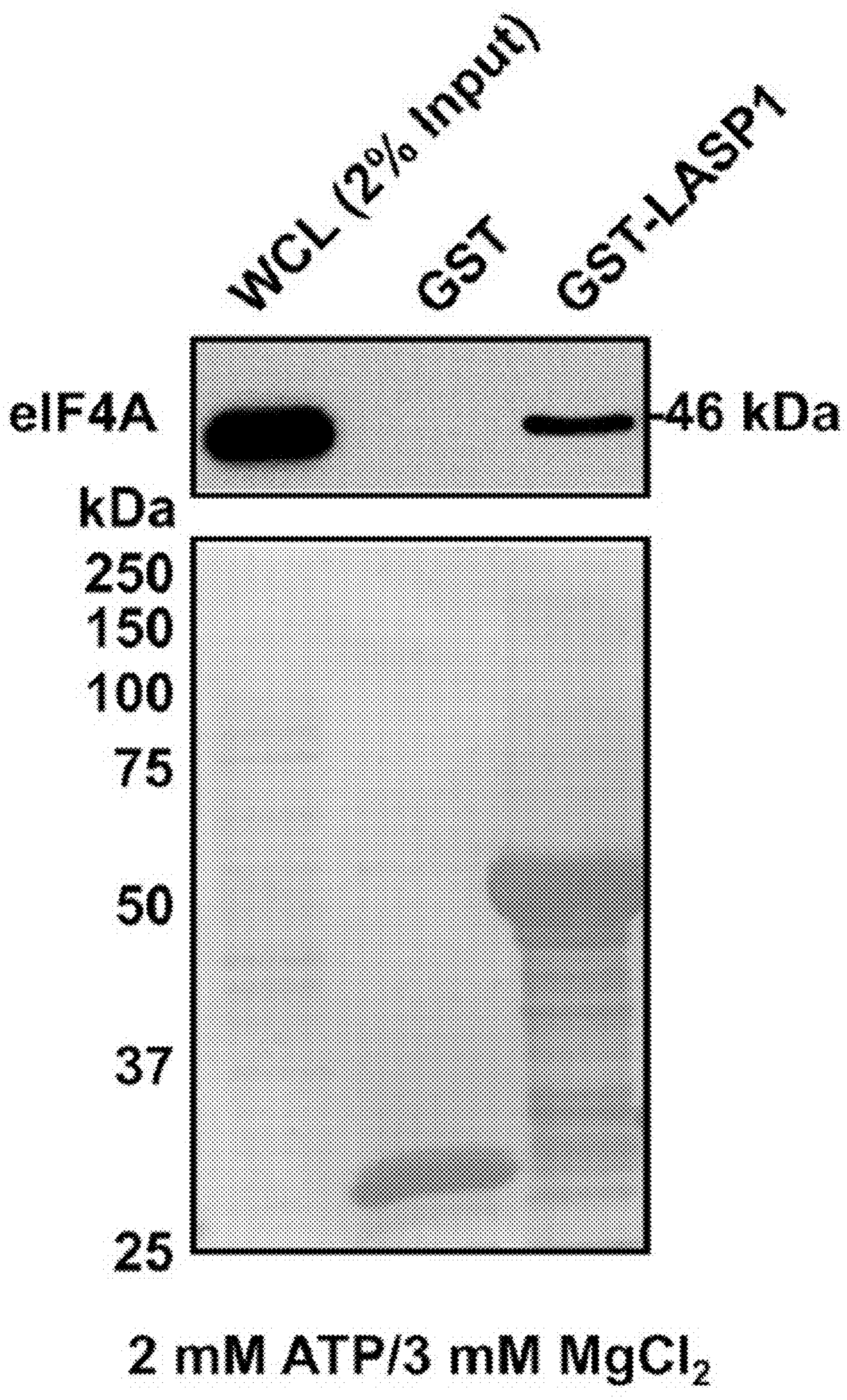
Figure 4C:
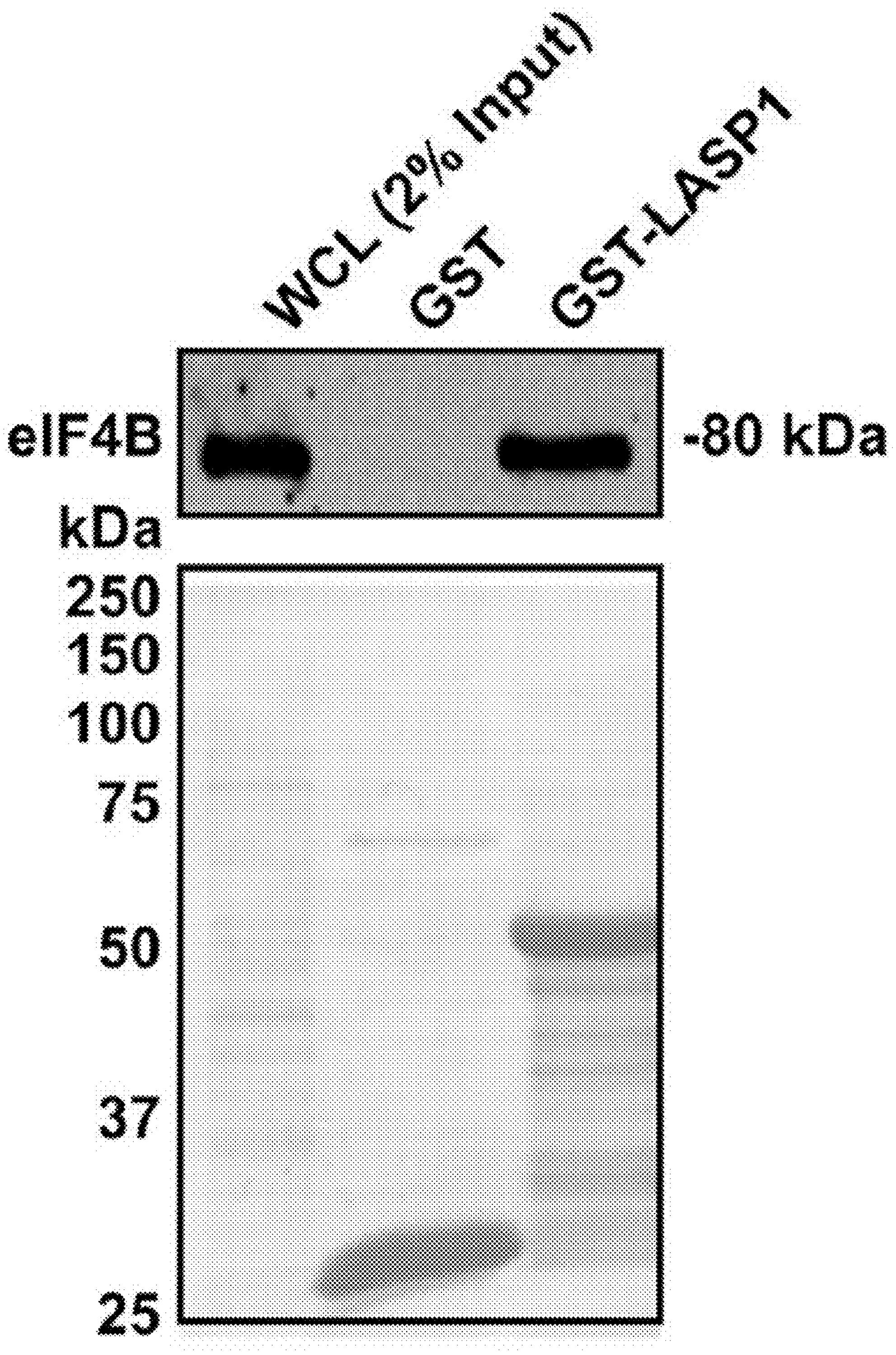
Figure 4D:
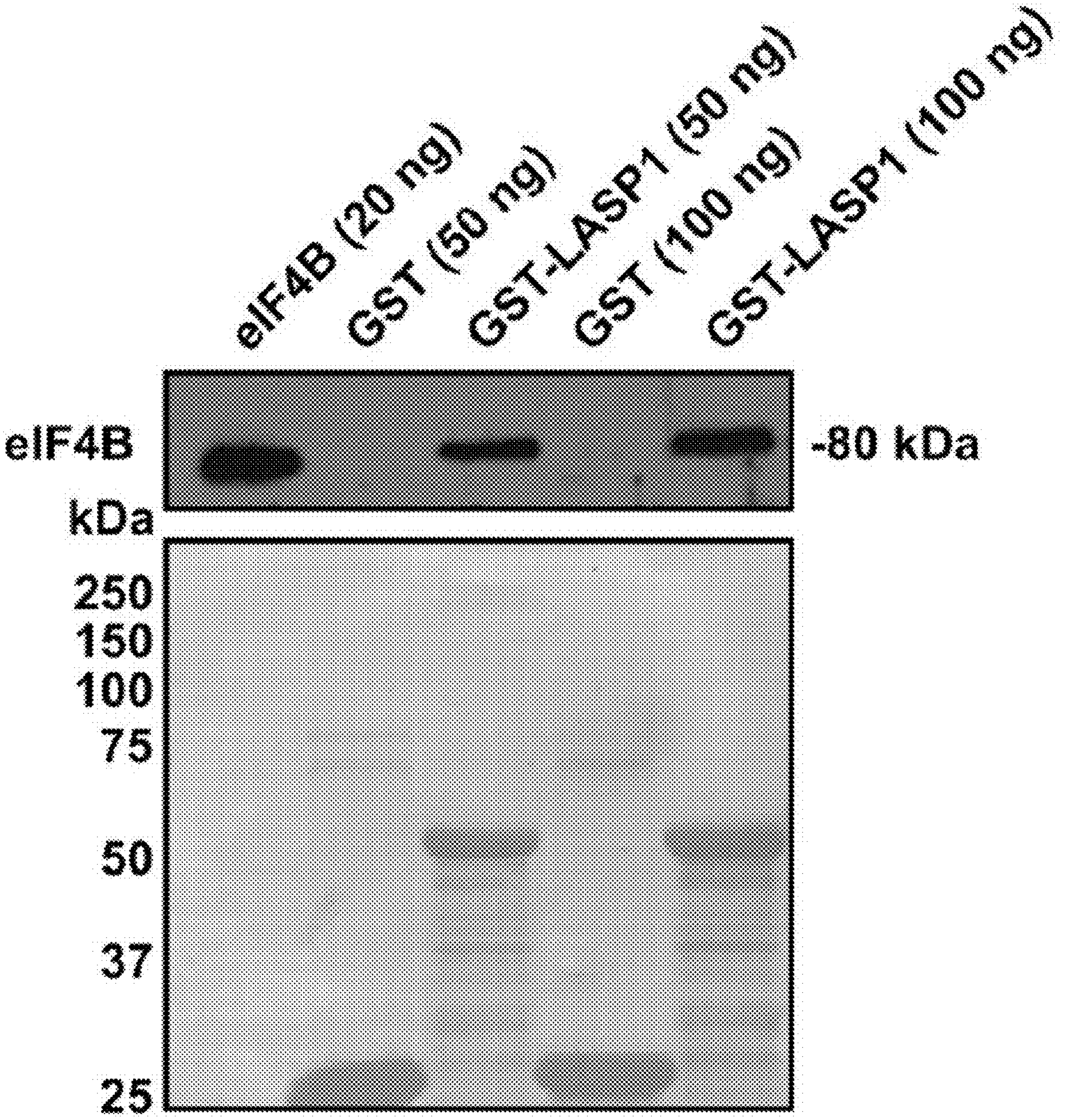
Figure 4E:
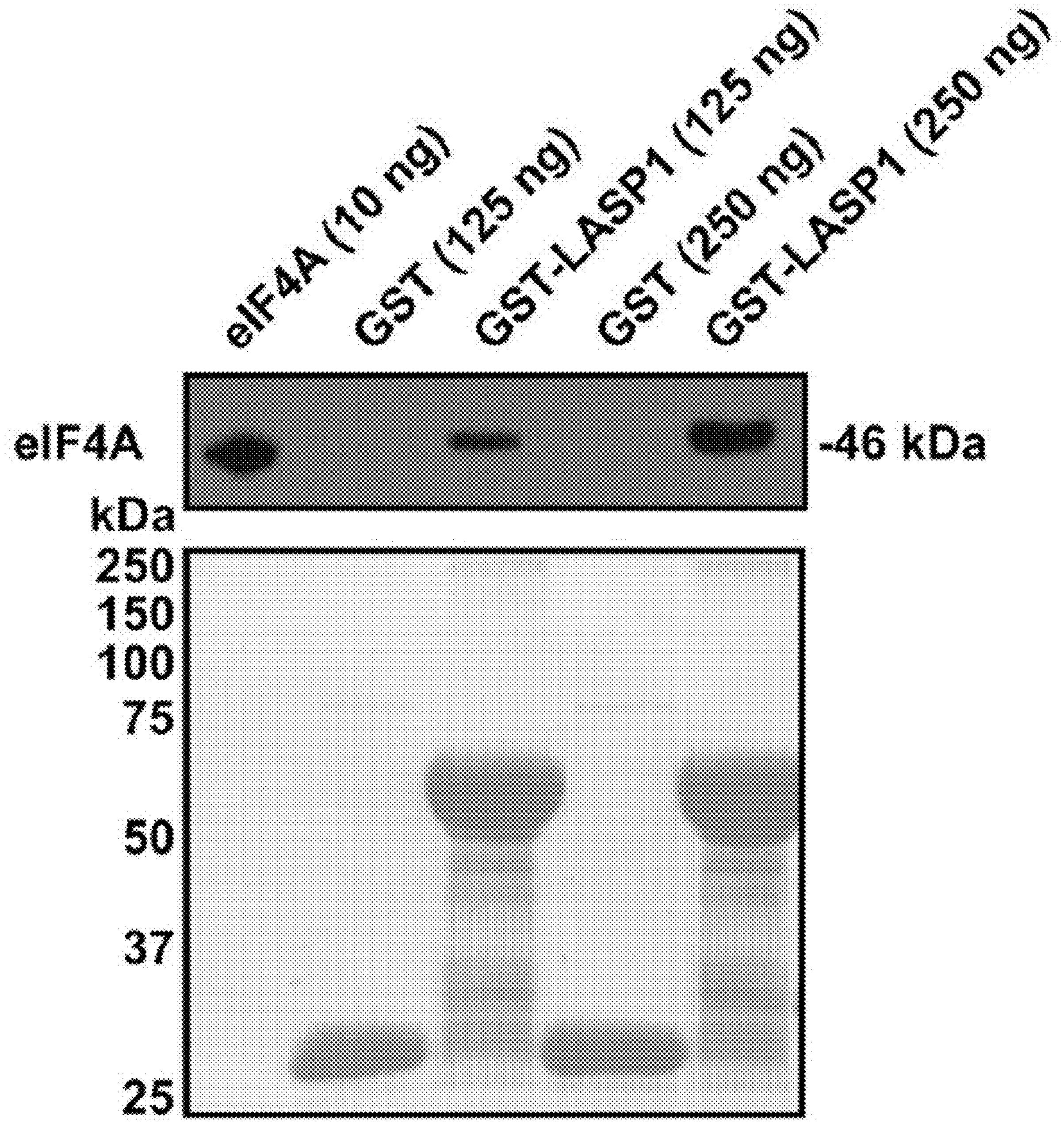
Figure 4F:
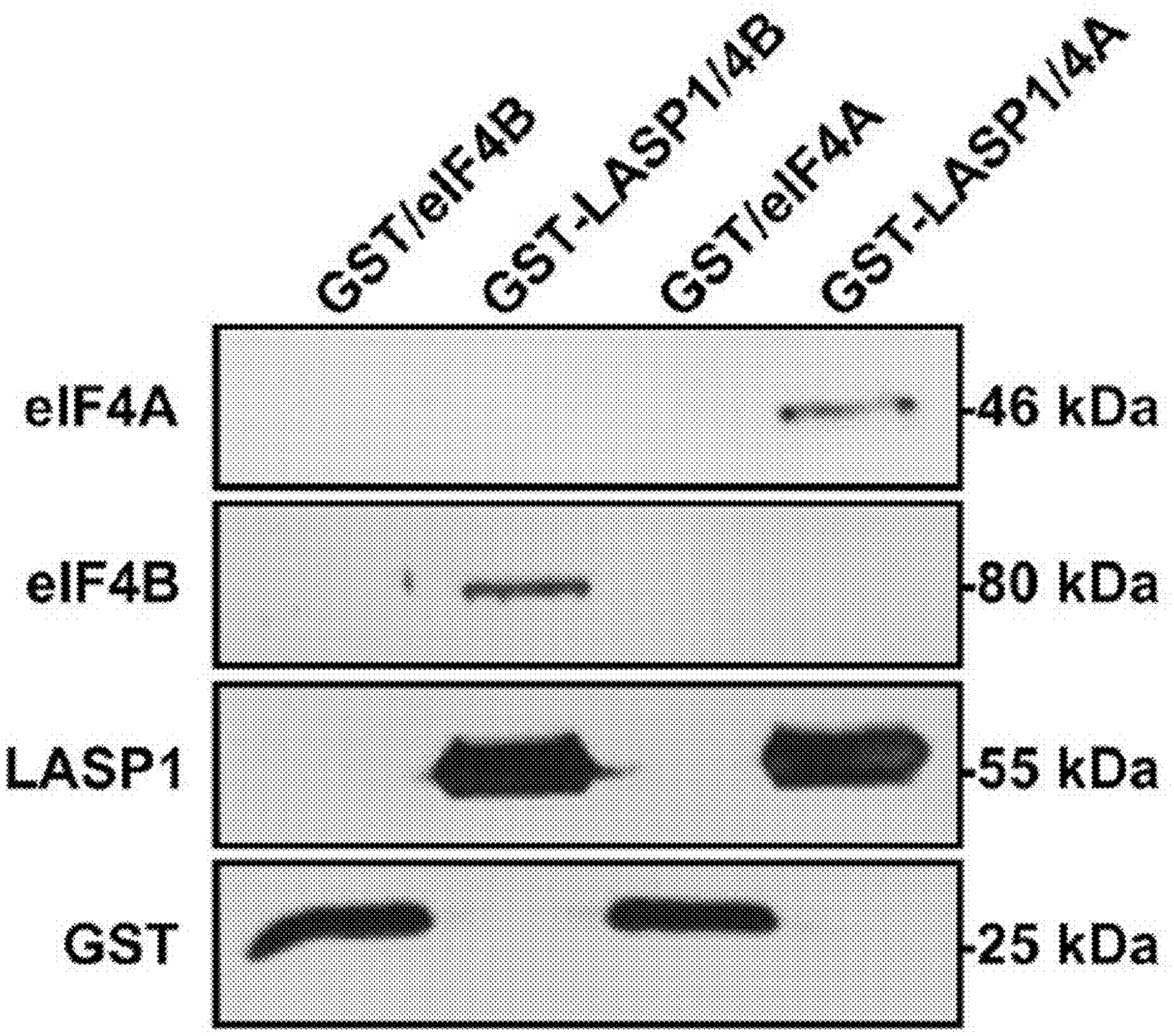
Figure 4G:
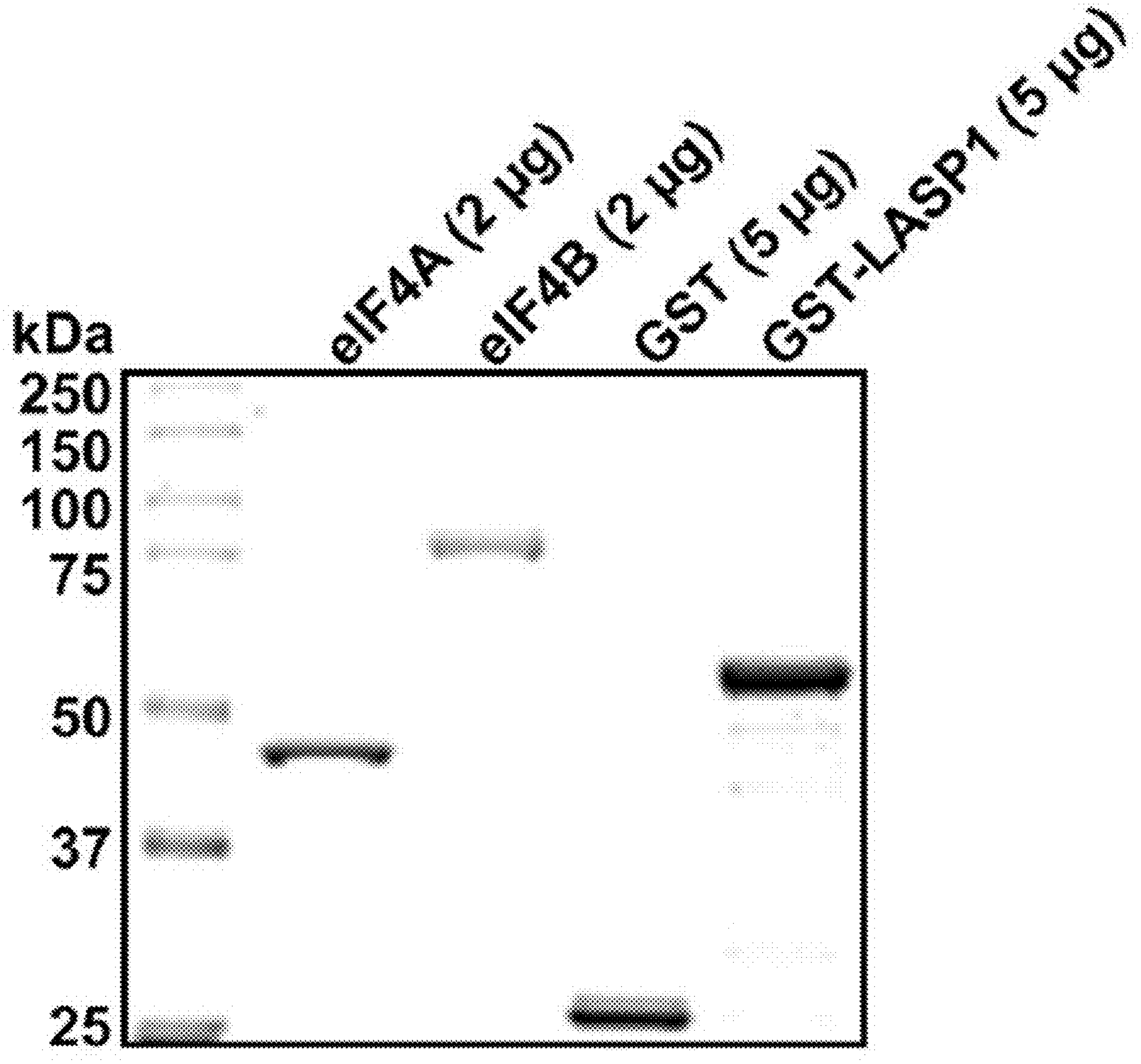
FIG. 4G shows imperial protein stain of purified eIF4A, eIF4B, GST, and GST-LASP1 (n=1).

To further prove the interaction of LASP1 with eIF4A and eIF4B, a GST-pulldown assay was employed. In the eIF4A pulldown, exogenous ATP (2 mM) and $MgCl_2$ (3 mM) were also added since eIF4A is an ATP-dependent enzyme. LASP1 associated robustly with eIF4A regardless of any exogenous addition of ATP and $MgCl_2$ (FIGS. 4A-4B). In addition, LASP1 robustly associated with eIF4B as well (FIG. 4C). This experimental system was also used to test if LASP1 could directly bind to both eIF4A and eIF4B. Previous interaction experiments were unable to distinguish a direct interaction between these proteins. LASP1 directly bound to both purified, recombinant eIF4B and eIF4A in a dose-dependent manner (FIGS. 4D-4E). Finally, to further confirm the validity of the direct binding experiments, equimolar amounts of purified GST-LASP1 were mixed with eIF4A or eIF4B in a solution and captured the complex with glutathione beads. LASP1 directly bound to both eIF4A and eIF4B (FIG. 4F). The purity of the proteins employed in these experiments is shown FIG. 4G.

Activation of CXCR4 Promotes Phosphorylation of PDCD4, eIF4B, and 4E-BP1

Figure 5A:
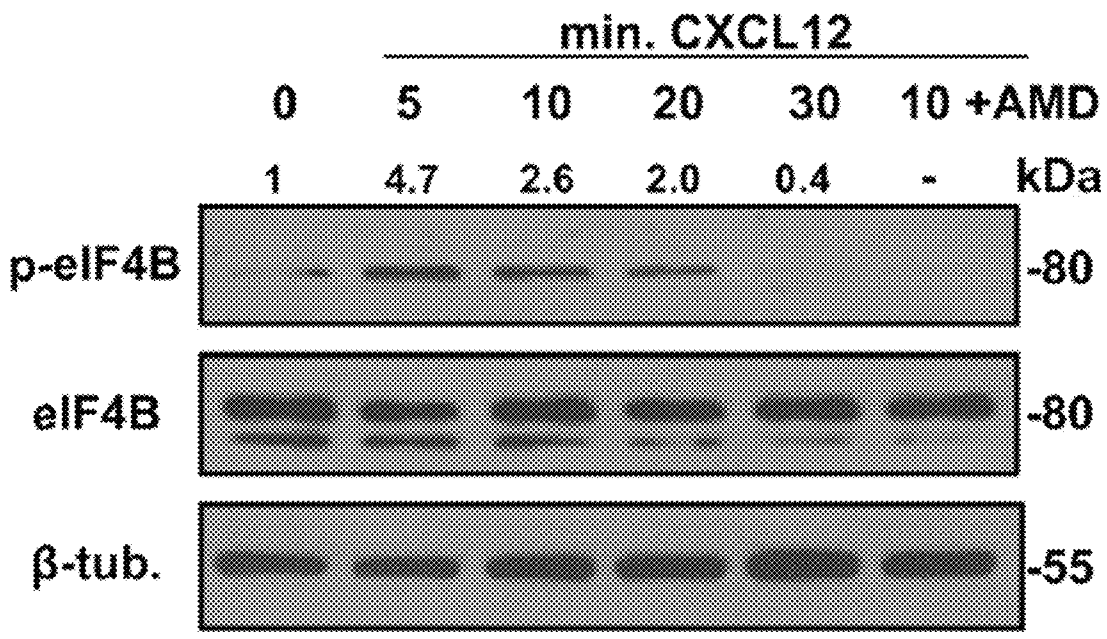
FIGS. 5A-5E: Activation of CXCR4 promotes phosphorylation of eIF4B, 4E-BP1, and PDCD4. 231S cells were stimulated with 10-20 nM CXCL12 for the indicated period. Phosphorylation status of p-eIF4B S422 (FIG. 5A), p-PDCD4 S67 (FIG. 5B), and p-4E-BP1 Thr70 (FIG. 5C) was determined by Western blotting (n=3). Fold change indicates the densitometry ratio of (phospho-protein/total protein)/b-tubulin signal with 0 min. set to 1.
Figure 5B:
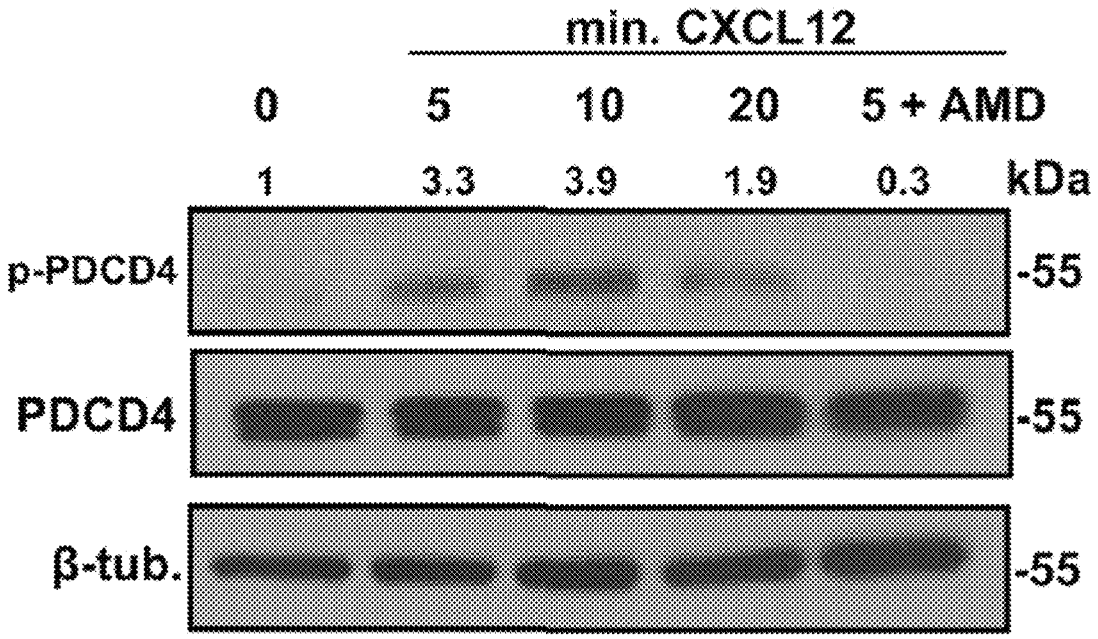
Figure 5C:
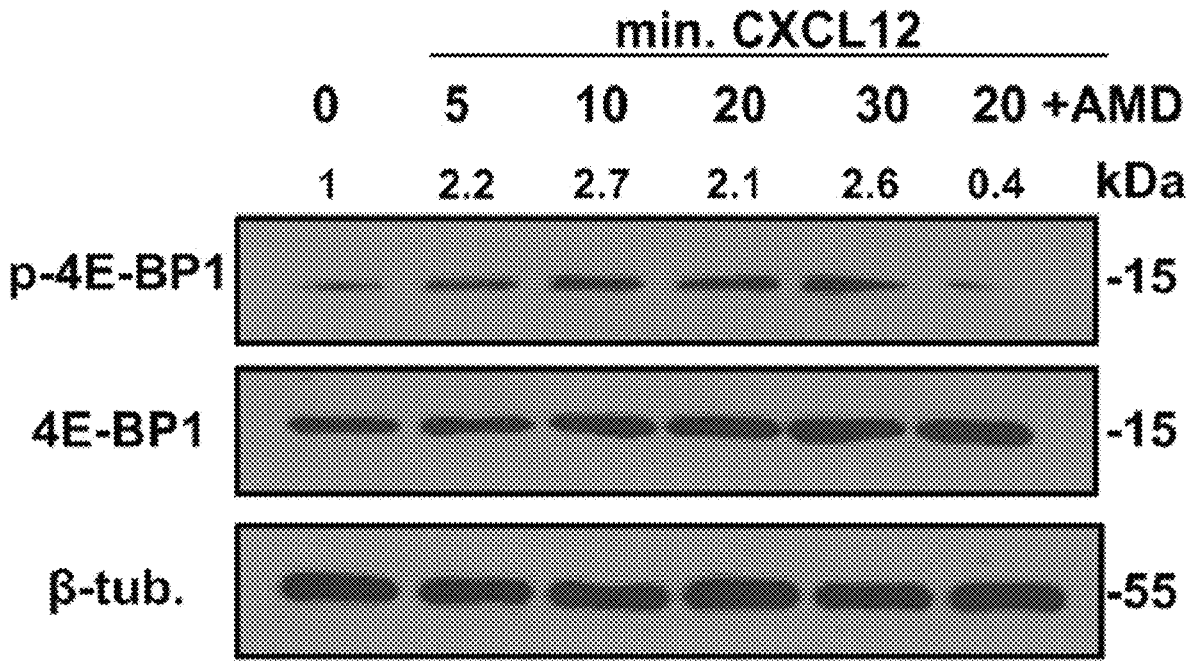
Figure 5D:
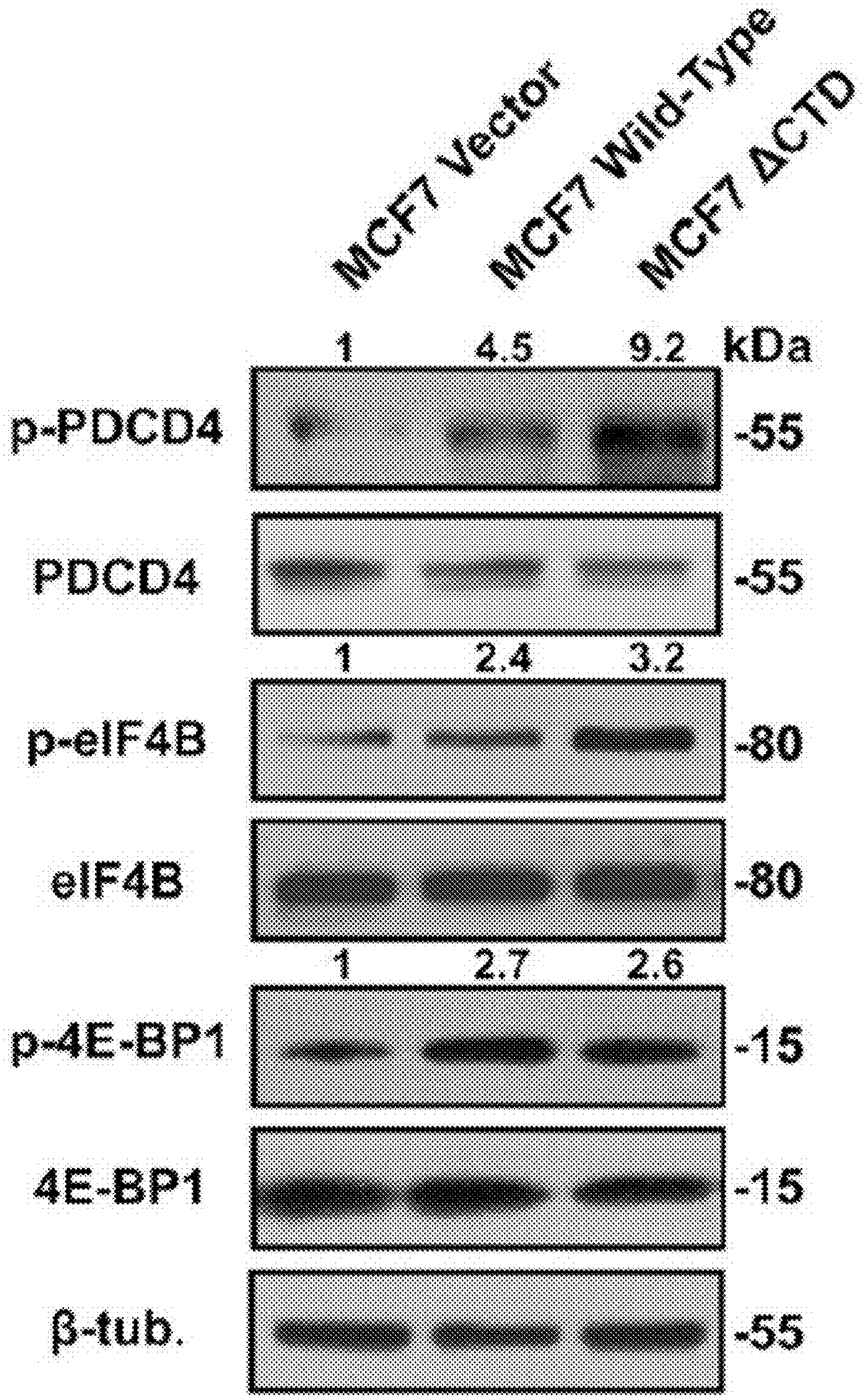
Figure 5E:
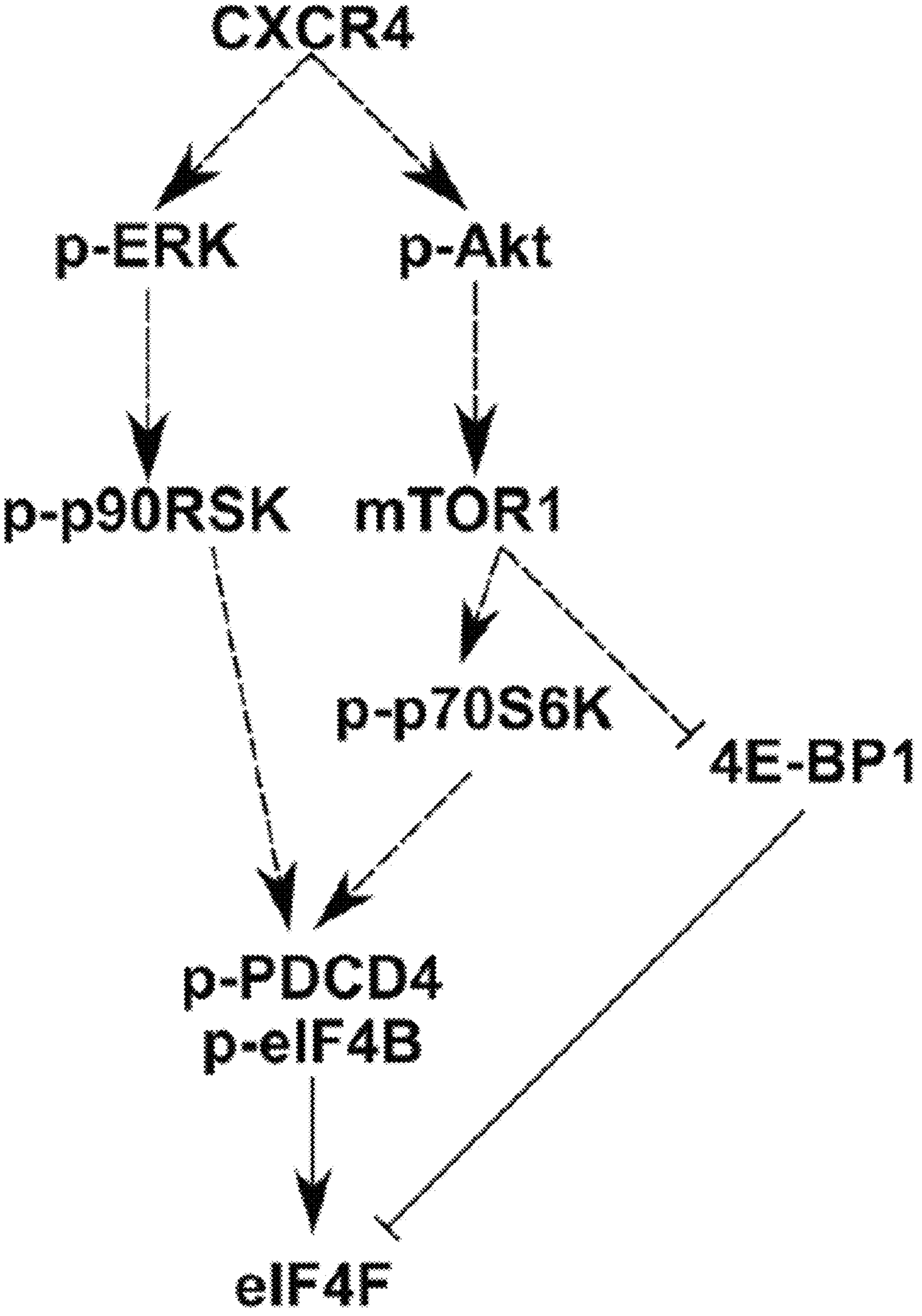

Aside from the influence of LASP1 on eIF4A and eIF4B, whether activation of CXCR4 would feed into the activation of eIF4F complex through cell signaling was evaluated. Interestingly, activation of CXCR4 led to phosphorylation of eIF4B on 5422 by 5 min before declining (FIG. 5A). The increase at 10 min in p-eIF4B levels can be abrogated with AMD3465. Next, whether CXCR4 could promote the phosphorylation of PDCD4 was evaluated. With CXCR4 activation, the phosphorylation increased to 3.3-fold at 5 min and peaked at 10 min (3.9-fold). The increase at 5 min in pS67-PDCD4 level can be abrogated by pretreatment of cells with AMD3465 (FIG. 5B). Then, the phosphorylation of 4E-BP1, which releases eIF4E and allows its incorporation into the eIF4F complex, was examined. Upon activation of CXCR4, pT70-4E-BP1 levels increased by 5 min and this effect could be abrogated with AMD3465 (FIG. 5C). Finally, to further prove these findings, a MCF7-CXCR4 cell series which contains increased basal activity of CXCR4 was utilized. MCF7-CXCR4 wild-type and 1CTD cells had increases in levels of p-4E-BP1, p-PDCD4, and p-eIF4B over that of the vector control (FIG. 5D). Based on these findings, FIG. 5E provides a model of CXCR4 signaling and its effects on the eIF4F complex.

Figure 6A:
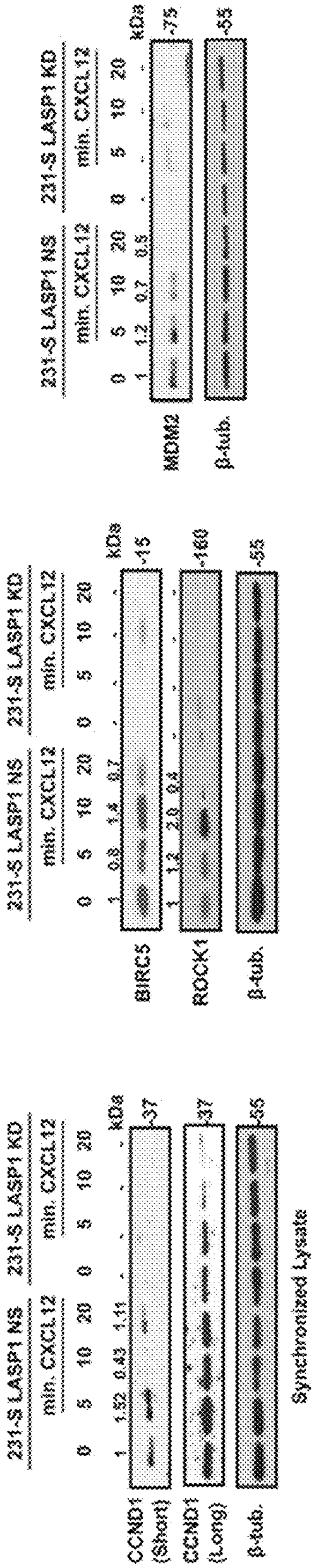
FIGS. 6A-6G: Activation of the CXCR4-LASP1 axis enhances selective expression of eIF4A-dependent genes.

Activation of the CXCR4-LASP1 Axis Enhances Selective Expression of Genes Downstream of eIF4A To determine the functional consequence of CXCR4 and LASP1on the eIF4F complex, eIF4A-dependent oncogenes commonly associated with cancer were examined. Activation of CXCR4 and the selective expression of cyclin D1 (CCND1), Mdm2, BIRC5, and Rho kinase 1 (ROCK1) in 231S LASP1 NS and KD cells were tested. Stimulation of CXCR4 in control-silenced (LASP1 NS) 231S cells resulted in considerable increases in the protein levels of CCND1, BIRC5, Mdm2, and ROCK1 (FIG. 6A). On the contrary, when LASP1 is silenced, CXCR4 signaling could not sustain the expression of these proteins downstream of eIF4A1 at comparable control levels.

Figure 6B:
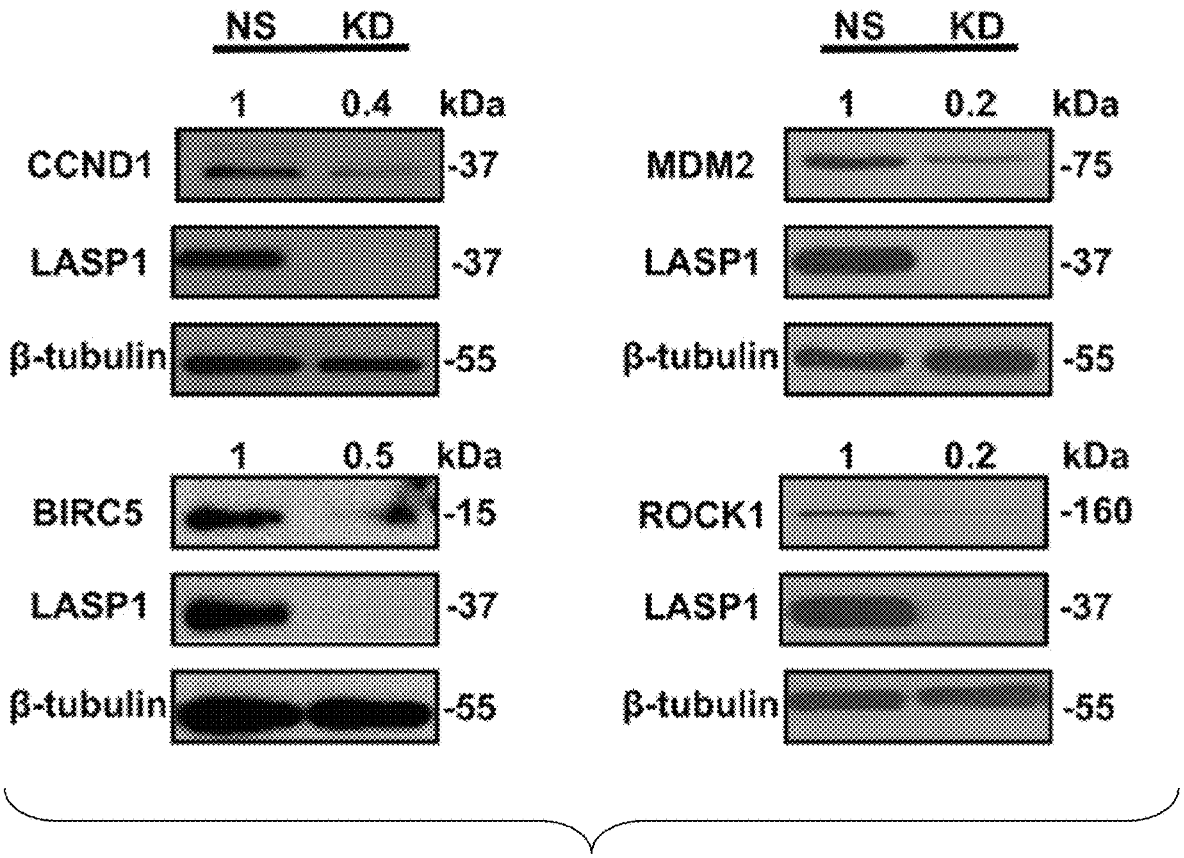
Figure 6C:
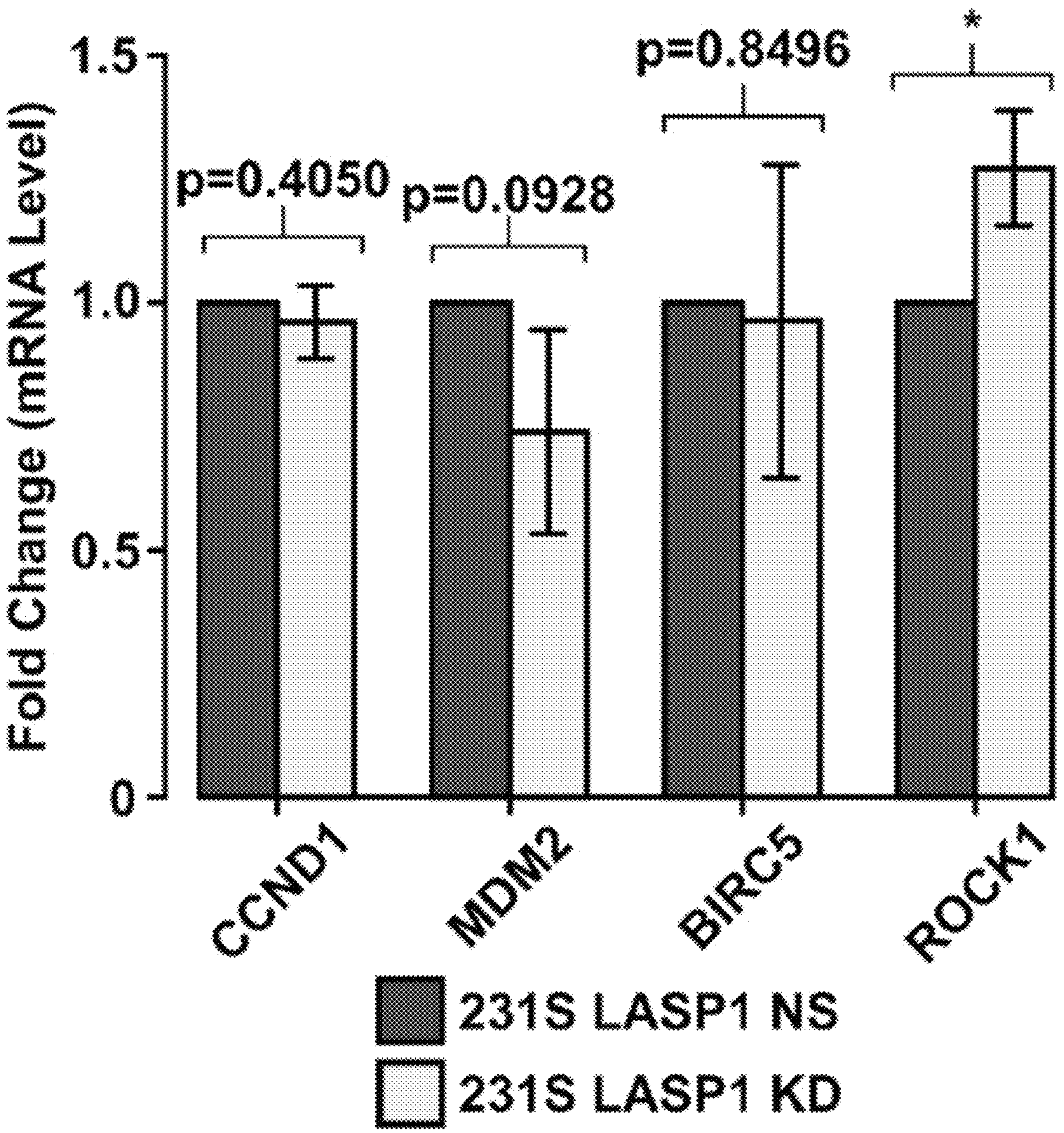
Figure 6D:
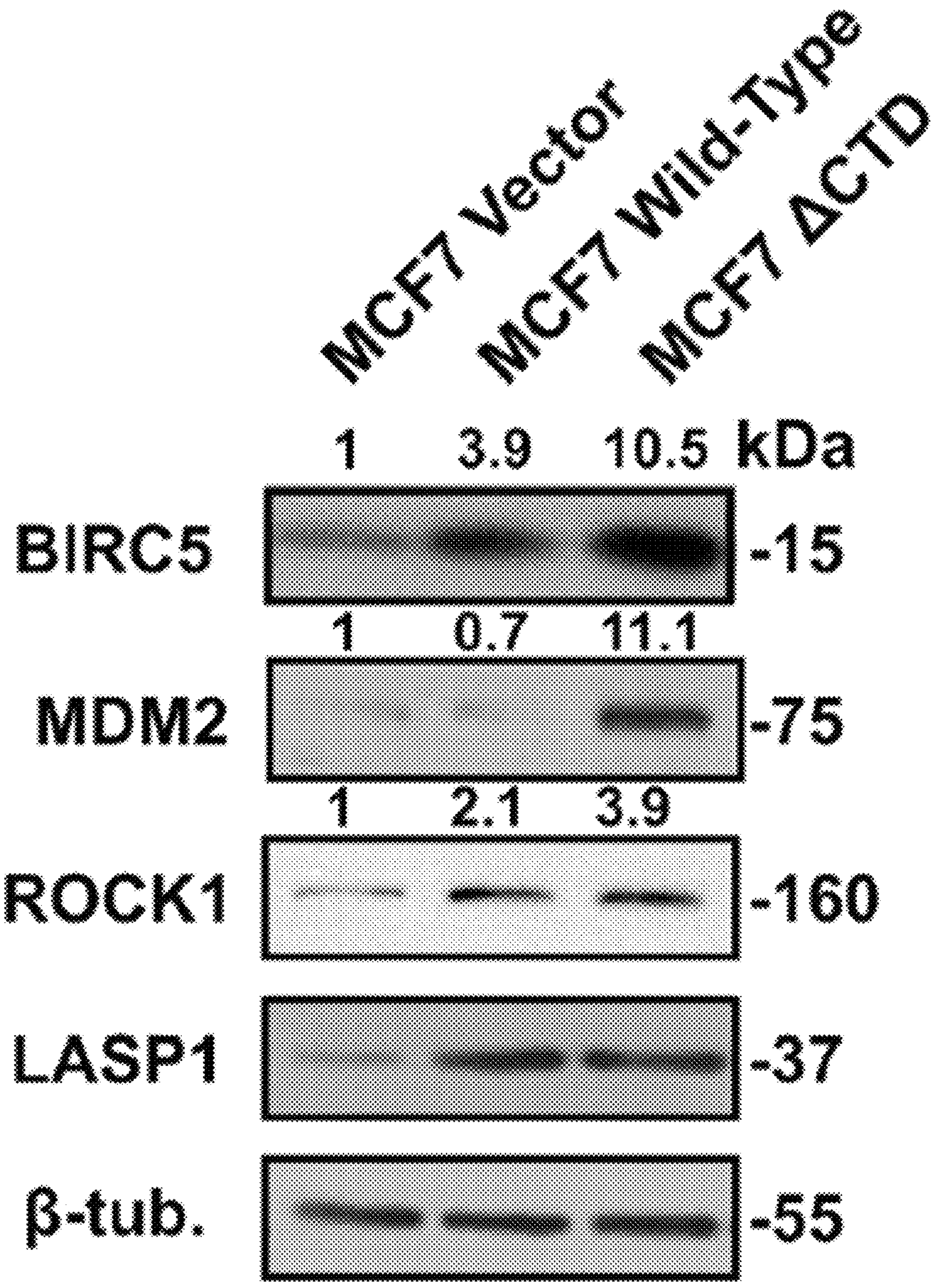

The steady state levels of oncogenic proteins that are dependent on the activity of eIF4A in the 231S LASP1 KD cells and serum-starved were then examined. There was a marked reduction of protein levels of CCND1 (60% reduced), BIRC5 (50% reduced), Mdm2 (80% reduced), and ROCK1 (80% reduced) compared to LASP1 NS cells (FIG. 6B). There was no significant reduction in the mRNA levels of these genes as assessed by qPCR to indicate that this difference is occurring at the translational level (FIG. 6C). Next, the MCF7 series was utilized to further validate the translational findings of the 231S LASP1 NS/KD cells. The levels of BIRC5, ROCK1, Mdm2, and including LASP1 itself were increased when CXCR4 was constitutively active (FIG. 6D).

Figure 6E:
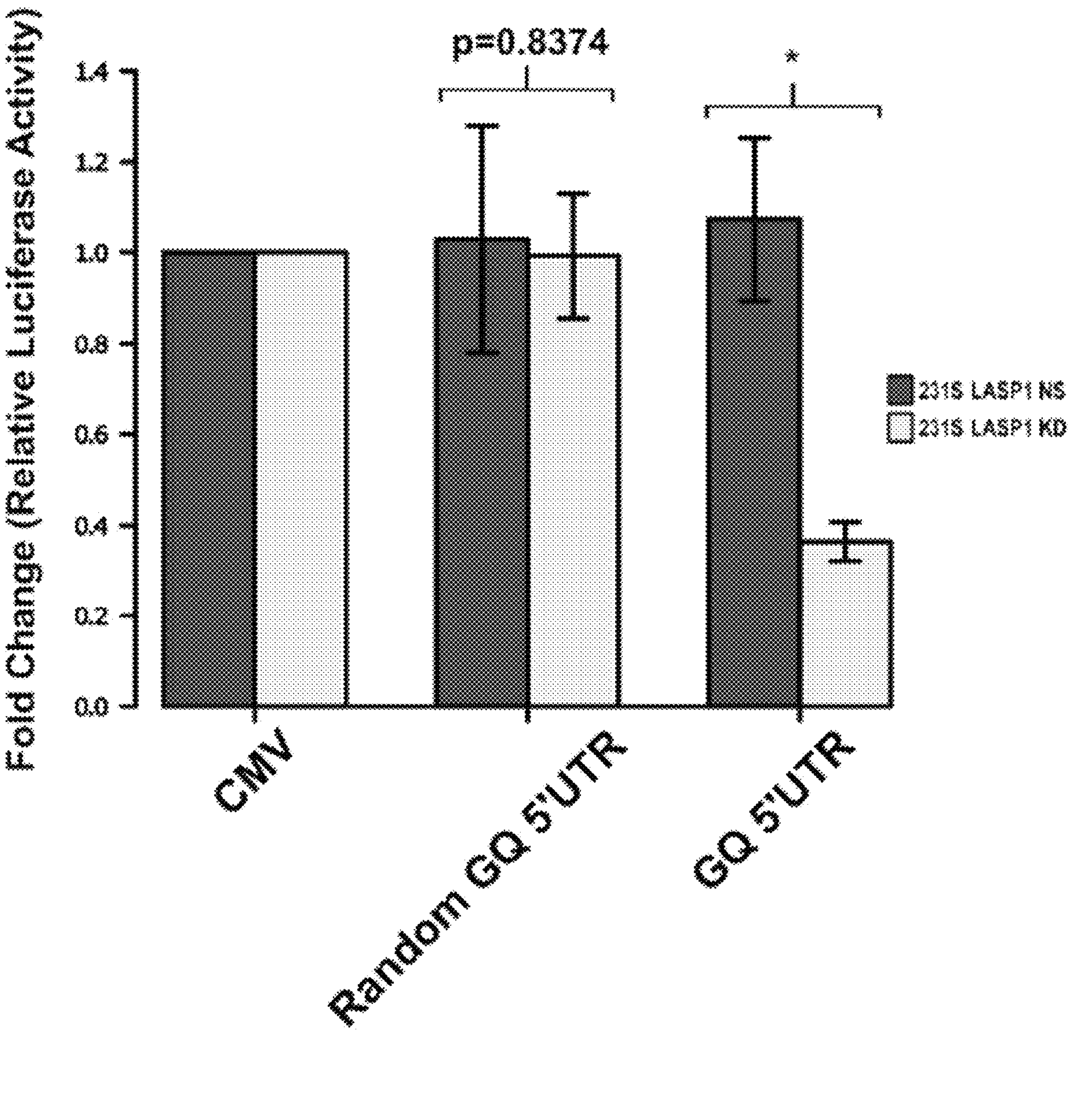
Figure 6F:
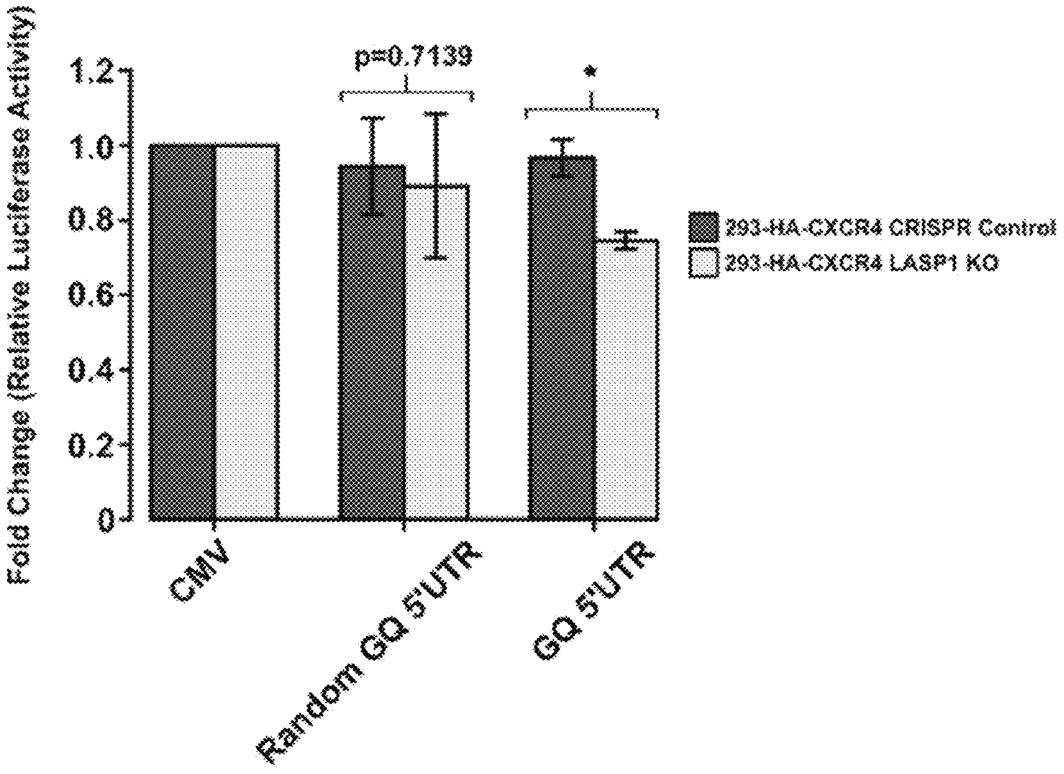
Figure 6G:
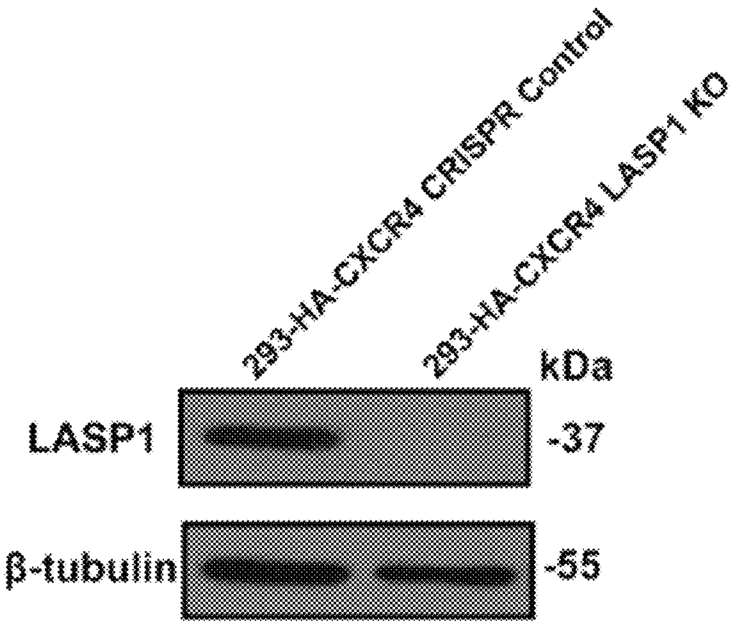

To investigate the role of LASP1 in modulating the activity of eIF4A, a synthetic GQ 5'UTR luciferase reporter assay from a documented and validated method was employed. This assay allowed for the evaluation of the functional activity of eIF4A. Corresponding to the activity of eIF4A, the luciferase activity will either increase or decrease. When LASP1 was stably knocked down, there was a 60% reduction in reporter luciferase activity (less unwinding of GQ 5'UTR) in 231S cells (FIG. 6E). This highlights an important role of LASP1 in modulating the activity of eIF4A/4B in the eIF4F complex in TNBC cells. To test the effects of LASP1 in other cell types, a KO cell line was generated in 293-HA-CXCR4 cells (FIG. 6G). In the 293-HA-CXCR4 LASP1 KO cells, there was a 20% decrease in eIF4A activity (FIG. 6F). Taken together, data obtained from the 231S and 293-HA-CXCR4 cells indicates that LASP1 does play a role in modulating the activity of eIF4A. However, the cancer cells are highly reliant on the functional consequence of this interaction.

Stable Knock Down of LASP1 Sensitizes TNBC Cells to eIF4A Inhibition

Figure 7A:
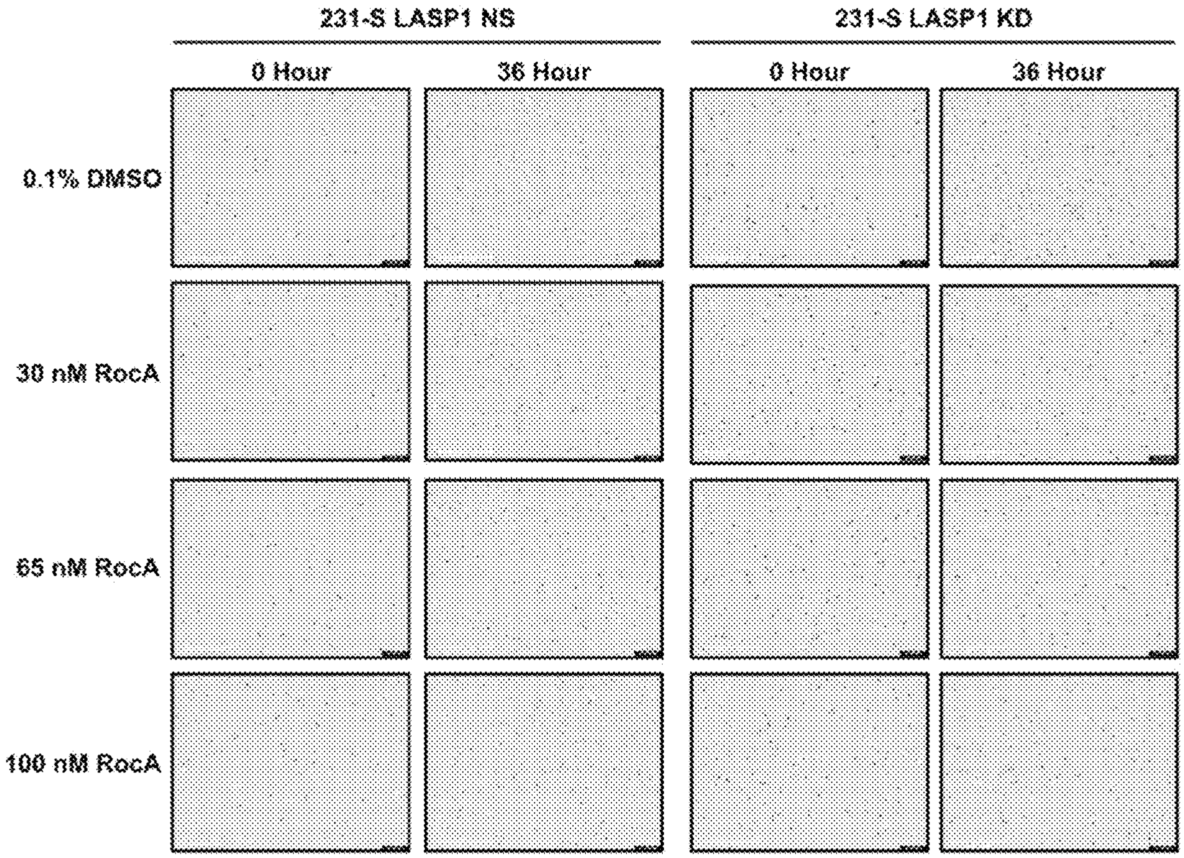
FIGS. 7A-7D: Stable knockdown of LASP1 sensitizes TNBC cells to inhibition by rocaglamide A.
Figure 7B:
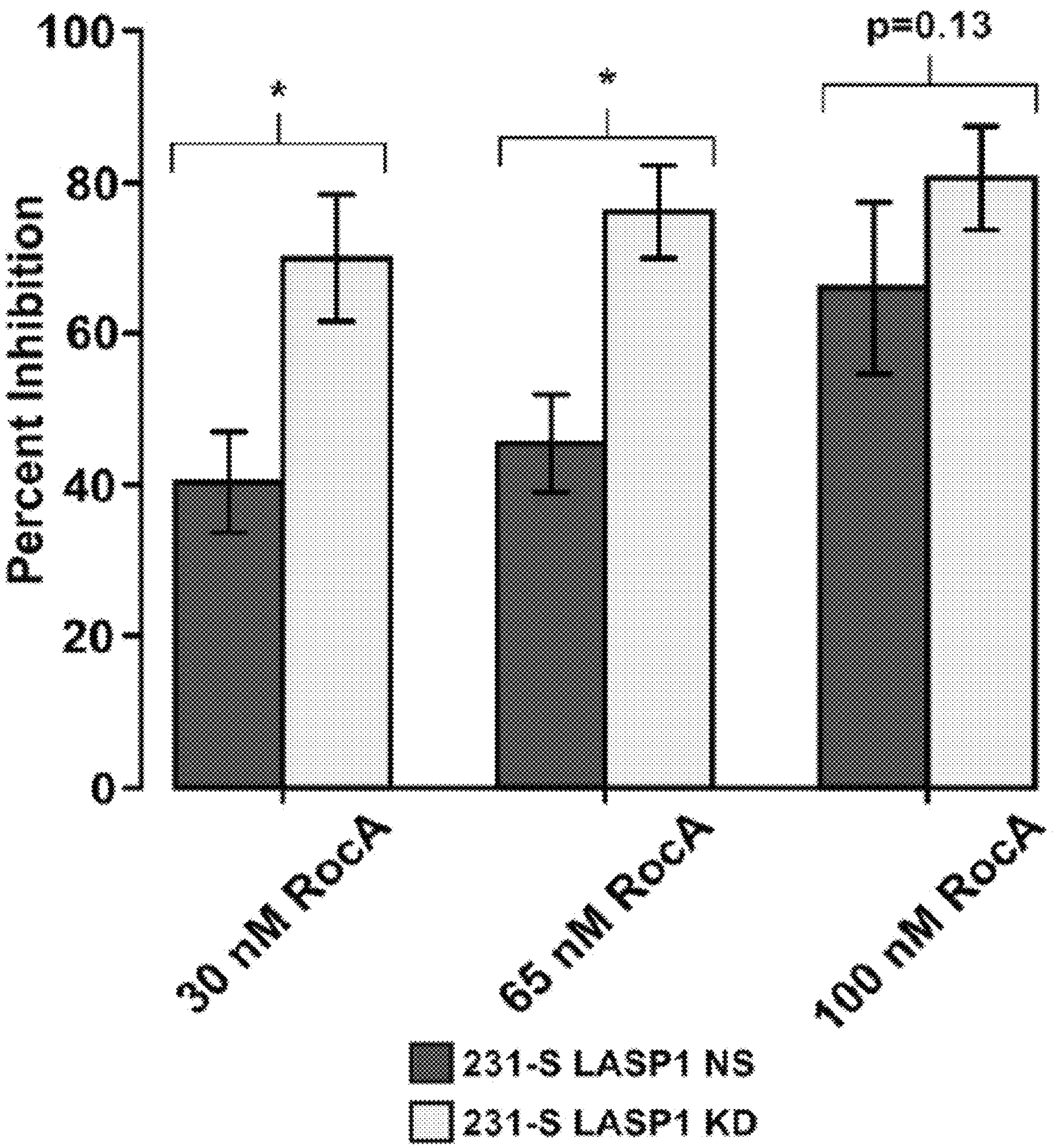
Figure 7C:
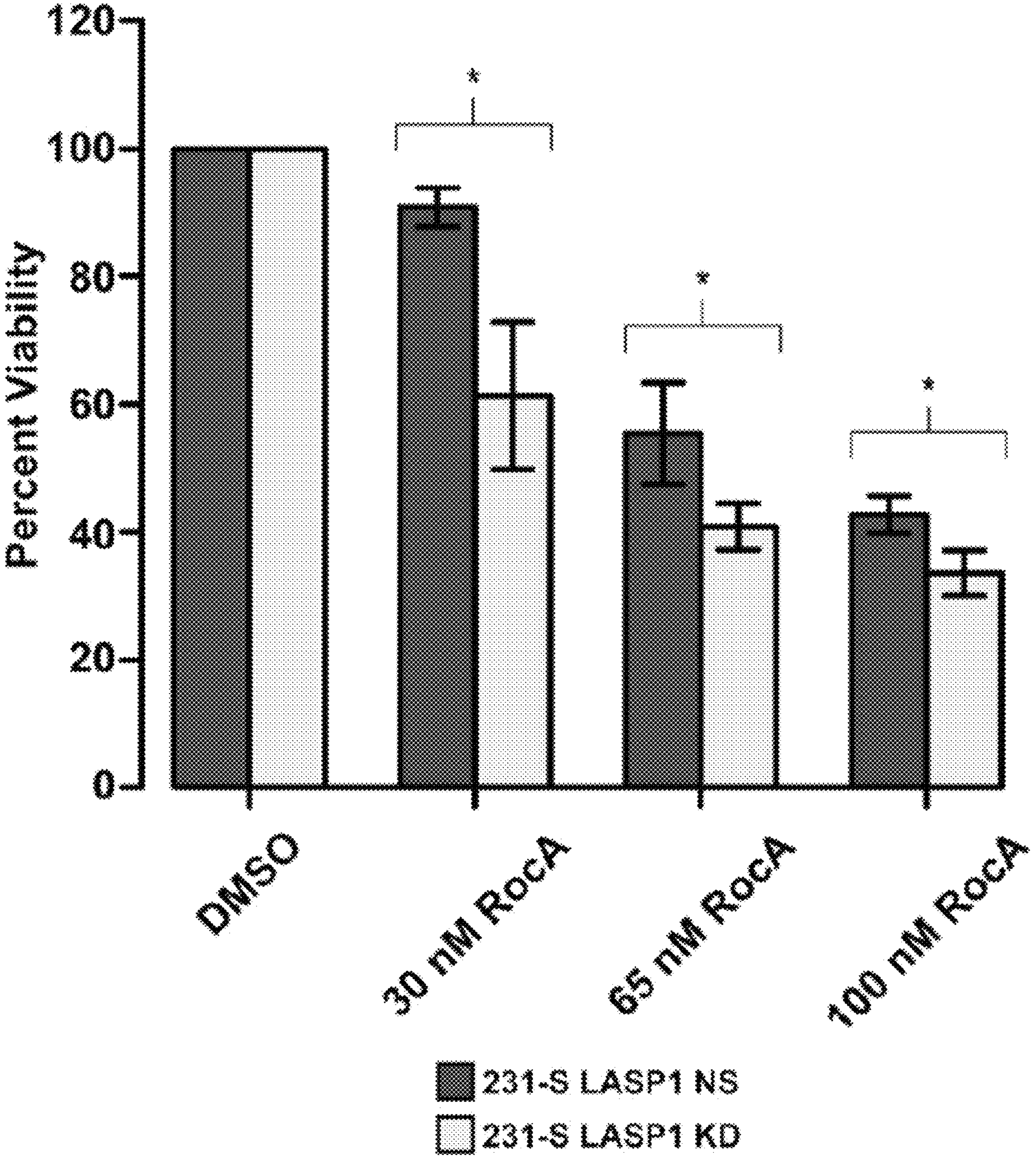
Figure 7D:
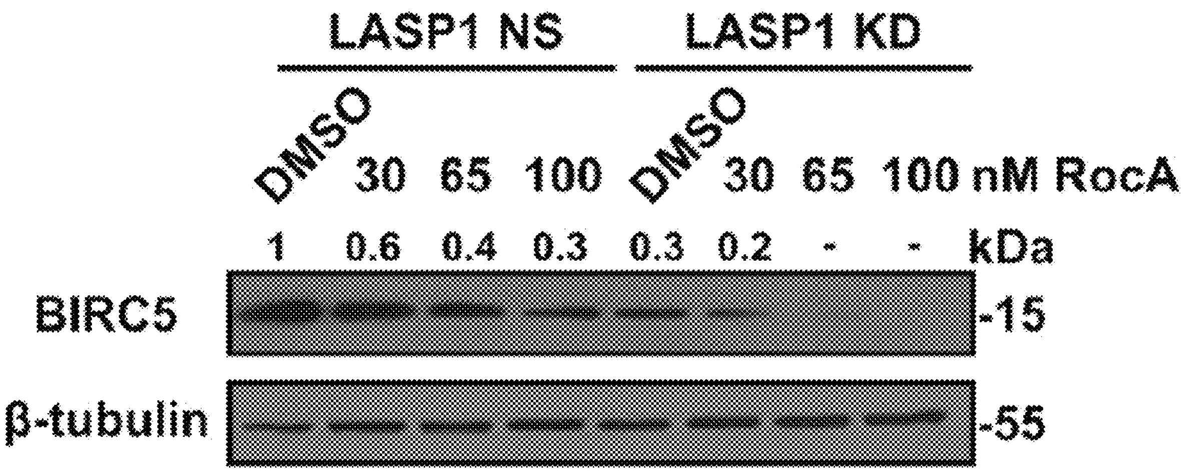

Inhibition of eIF4A has been investigated as a chemotherapeutic target. As such, whether the LASP1 deficiency would sensitize 231S TNBC cells to pharmacological inhibition of eIF4A by rocaglamide A (RocA) was examined. Silvestrol, a flavagline family member of rocaglamide A, was found to have an $IC_{50}$ value of 60 nM in MDA-MB-231 cells. Therefore, the 231S LASP1 NS and KD cells were subjected to RocA treatment ranging from 30 to 100 nM (FIG. 7A). Stable knock down of LASP1 sensitized the 231S cells to RocA treatment especially at the lowest treatment dose of 30 nM (FIG. 7B). Cellular viability also significantly decreased in the LASP1 KD cells with RocA drug treatment (FIG. 7C). Whether RocA inhibited eIF4A was verified by blotting for levels of BIRC5 protein in LASP1 NS and KD cells. LASP1 NS cells had a dose-dependent decrease in BIRC5 levels. In the LASP1 KD cells, a 70% loss of BIRC5 occurred with LASP1 knock down alone and further decreased with RocA treatment (FIG. 7D).

Discussion

Figure 8:
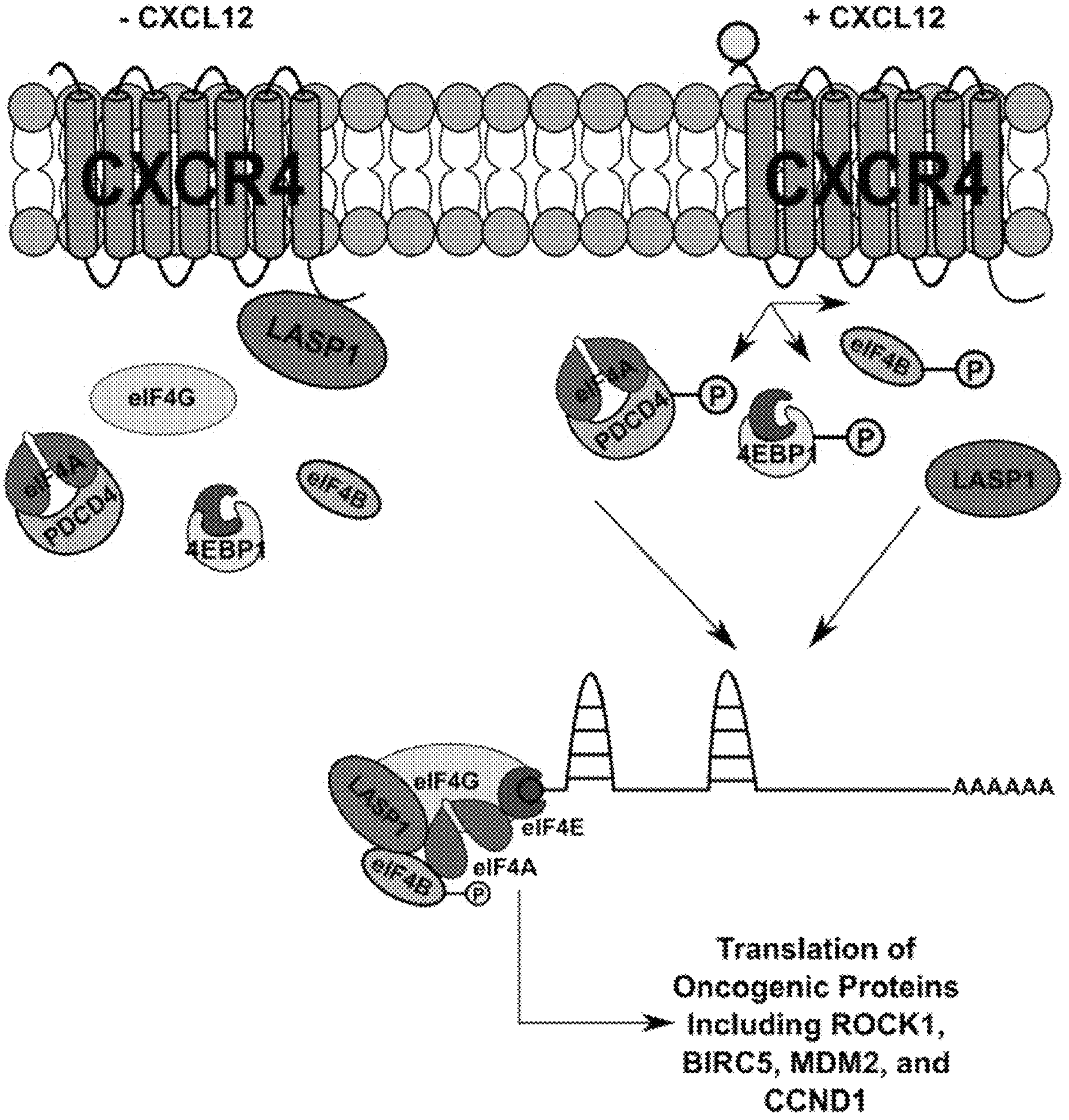
FIG. 8: Model of the CXCR4-LASP1-eIF4F axis. An illustration of CXCR4 and its relation to the eIF4F complex upon stimulation with CXCL12 is shown. This relationship is occurring through two distinctive mechanisms. First, LASP1 dissociates from CXCR4 and directly interacts with eIF4A and eIF4B. Second, phosphorylation of PDCD4, 4E-BP1, and eIF4B is promoted through G protein-coupled receptor signaling. As a result, both complex formation increases along with the function of eIF4A. Consequently, the translation of oncogenic proteins is promoted. The CXCR4-LASP1 pathway feeds into eIF4A and eIF4B, leading to translation of oncoproteins such as survivin (BIRC5), Mdm2, and cyclin D1.

It is shown in this example that the CXCR4-LASP1 pathway regulates eIF4A1-mediated translation of oncogenic proteins with long and structured 5'UTRs. A model based on these findings is provided in FIG. 8. The findings in this example are important as a dysregulation in translational control can rewire the proteome through selective translation of oncogenic mRNAs. The resultant oncoproteins are critical for breast cancer cell survival, tumor progression, local invasion, and metastasis. Protein synthesis is a tightly regulated process. To date, translational initiation has been identified as the rate limiting step. This step of translational regulation is primarily controlled by the eukaryotic initiation 4F complex (eIF4F). In this example, it is shown that CXCR4 can feed into this complex thereby having a significant impact on synthesis of oncogenic proteins needed for breast cancer survival and invasion. CXCR4 may also influence the protein translational machinery, occurring through an interaction with eIF2B.

In the initial proteomic screen, eIF4A and eIF4B were identified to interact with LASP1. To confirm this finding, several pieces of experimental evidence further characterizing this interaction are provided in this example. In the co-immunoprecipitation where eIF4B was immunoprecipitated and blotted for LASP1, three distinctive bands were produced. The one below the LASP1 band (37 kDa) is LASP2 as clone 8C6 anti-LASP1 antibody is known to react with LASP2. However, the band above 37 kDa is a doubly-phosphorylated form of LASP1 (pY171 and pS146). The human LASP1 that is singly phosphorylated has not been reported to shift above 37 kDa. The phosphorylation status of LASP1 and the functional consequences interacting with eIF4A and eIF4B are not currently known. Furthermore, LASP1 associated with eIF4A robustly regardless of the presence or absence of exogenous ATP and $Mg^{2+}$ in the GST-pulldown assay. This may mean that the binding site for LASP1 on the surface of eIF4A is always accessible in spite of conformational changes induced by ATP and $Mg^{2+}$.

Aside from the LASP1 interaction, activation of the CXCR4 pathway led to the formation of the eIF4F complex as evident through several phosphorylation events. First, 4E-BP1 was phosphorylated in a CXCL12-dependent manner similar to the time frame reported in renal cell carcinoma. Second, phosphorylation of eIF4B at 5422 was similarly observed to increase with CXCL12 stimulation and would affect the rate of translation. Third, an increase in the phosphorylation of PDCD4 following CXCL12 treatment would release eIF4A to incorporate into the eIF4F complex. In all, these three phosphorylation events, in addition to phosphorylation of eIF4E, may contribute to active and selective synthesis of oncogenic proteins.

To establish the possibility that LASP1 gets actively recruited into the eIF4F complex upon stimulation with CXCL12, the m7-GTP pulldown assay was employed. However, the m7-GTP pulldown assay only tells that components are bound to a complex that "contains" eIF4F. Based on the findings of the m7-GTP experiment and direct binding studies, LASP1 gets actively recruited into the eIF4F complex in a CXCL12-dependent manner. This indicates that LASP1 may assist eIF4A and eIF4B in the unwinding of SLS at the 5'UTR of oncogenic mRNAs. Another key finding of this experiment is the interaction between eIF4G and eIF4E increased in a CXCL12-dependent manner. eIF4G has two binding sites for eIF4A, one of which is necessary for translation and the other plays a modulatory role. This brings out the key role played by CXCR4 in enabling the recruitment of eIF4G and LASP1 to enable the synthesis of oncogenic proteins involved in tumor progression and metastasis. Interestingly, LASP1 directly binds to the C-termini of other chemokine receptors including CXCR1, CXCR2, and CXCR3. LASP1 can augment CXCR2-mediated cell migration. Therefore, it is possible that additional chemokine receptors may feed into the eIF4F complex via interactions with LASP1.

If CXCR4 activation led to recruitment of LASP1 and eIF4G into the eIF4F complex and influenced the activity of eIF4A, it would promote the translation of oncogenic mRNAs downstream of eIF4A. Consequently, many oncogenic mRNAs with SLS situated at their 5'UTRs including survivin or BIRC5, cyclin D1, Mdm2, and ROCK1 were translated in response to CXCL12 stimulation. These proteins have appreciable roles in breast cancer biology. BIRC5 is involved in cell survival through inhibition of caspase-mediated apoptosis. Cyclin D1 is a pivotal protein in the cell cycle. Although nuclear cyclin D1 is known for its role in cell proliferation, the cytoplasmic cyclin D1 has a non-canonical role in cell migration. Cyclin D1 activates CDK4/6, which is a clinical target for chemoresistant cases of breast cancer. Next, ROCK1 promotes cell polarization, and persistent directional migration (chemotaxis). Additionally, perturbation of the CXCL12-CXCR4 axis promotes breast cancer cell migration by regulating tumor cell adhesion events through provision of an optimal level of ROCK activity for effective cell migration. Finally, Mdm2 has been shown to promote invasive ductal breast carcinoma (IDC) and metastasis and is thought to have additional roles beyond p53. Taking these proteins into account, CXCR4 therefore has significant (and multifaceted) effects on breast cancer cells through modulation of this translational mechanism.

In summary, this example has explored a mechanistic relationship between the CXCR4-LASP1 axis and the regulation of oncoprotein synthesis through specific components of the eIF4F complex. As a result of characterizing this protein axis, small molecule or cell-permeant biopeptide inhibitors may be utilized for therapeutic purposes. More specifically, inhibiting the interaction between LASP1 and eIF4A is a useful approach to sensitize triple-negative breast cancer cells to other inhibitors. Targeting the eIF4F complex may overcome plasticity and heterogeneity issues associated residual disease and chemoresistance. This example facilitates different modalities of therapy against TNBC breast cancer progression and metastasis.

Figure 9:
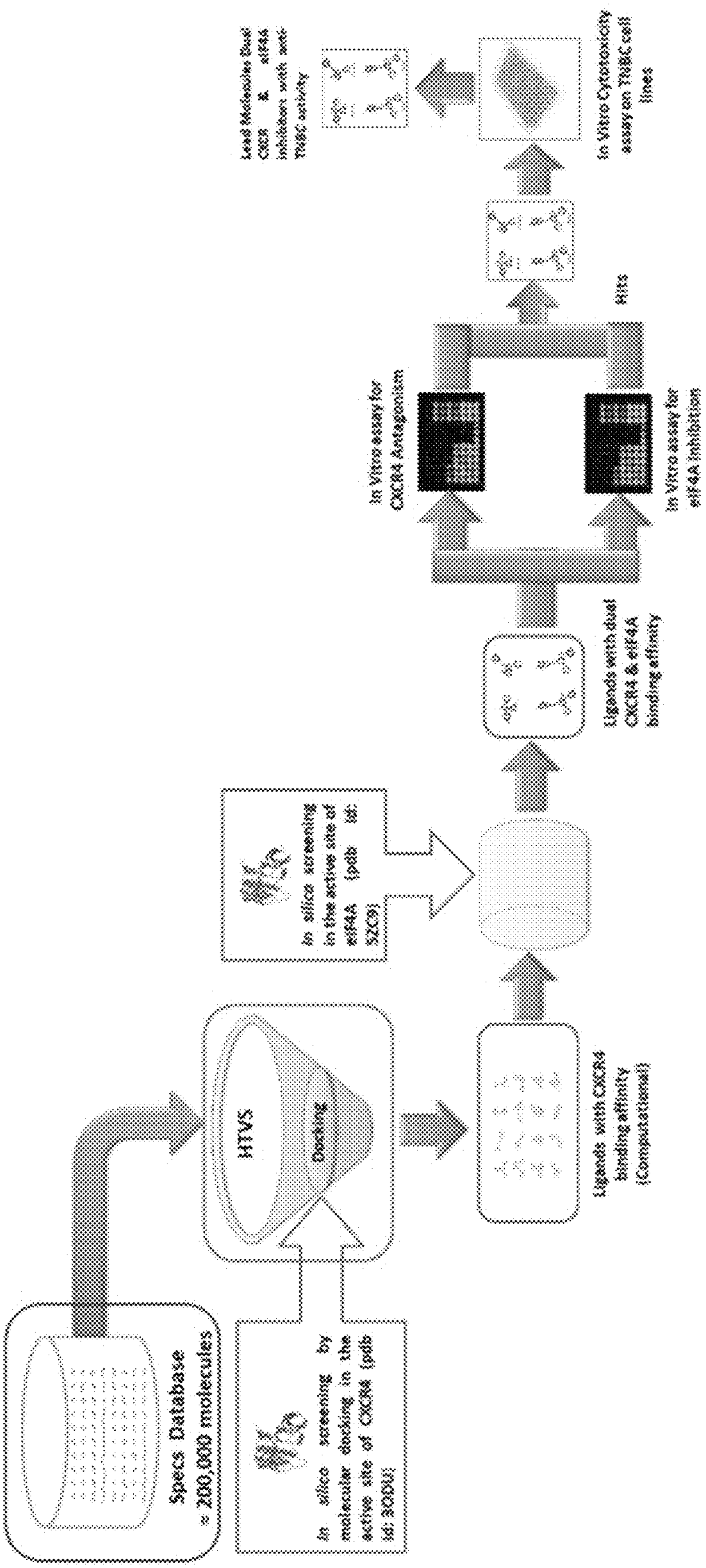
FIG. 9: Illustration of a computational, high-throughput virtual screening (HTVS) strategy for finding molecules with dual inhibitory activity against CXCR4 & eIF4A activity.

Example II—High Throughput Virtual Screening (HTVS) of Chemical Libraries Against CXCR4 & eIF4A to Discover Lead Molecules with Dual Inhibitory Activity With an objective to identify molecules with dual inhibitory activity against CXCR4 & eIF4A. activity, a computational, high-throughput virtual screening (HTVS) protocol as shown in FIG. 9 was employed. X-ray crystal structure of CXCR4 (pdb id: 3ODU) & eIF4A (pdb id: 5ZC9) with co-complexed ligands were retrieved from a protein data bank and used as a target for HTVS studies.

Prior to docking studies, the molecules in the specs database (approx. 200,000 molecules) were screened using a Lipinski filter and PAINS filter to remove 'non-drug-like' and promiscuous ligands from the dataset. The resultant drug-like compound library was docked into the ligand binding site of the CXCR4 using a "glide docking" algorithm and the docked poses were ranked on the basis of "G-score". The top 10% of the highest scoring, ligands were visually analyzed for interactions with residues deemed important for CXCR4 inhibitor binding, unfavorable conformation, ease of synthesis, ease of structural derivatization, and structural diversity. Those compounds which showed favorable interactions with amino acid side chains in the active site of CXCR4 were then selected for docking studies against eIF4A, and those ligands with computational binding affinity with both CXCR4 eIF4A were considered as hits. The structures of the obtained hits are given in FIG. 10A.

Figure 11A:
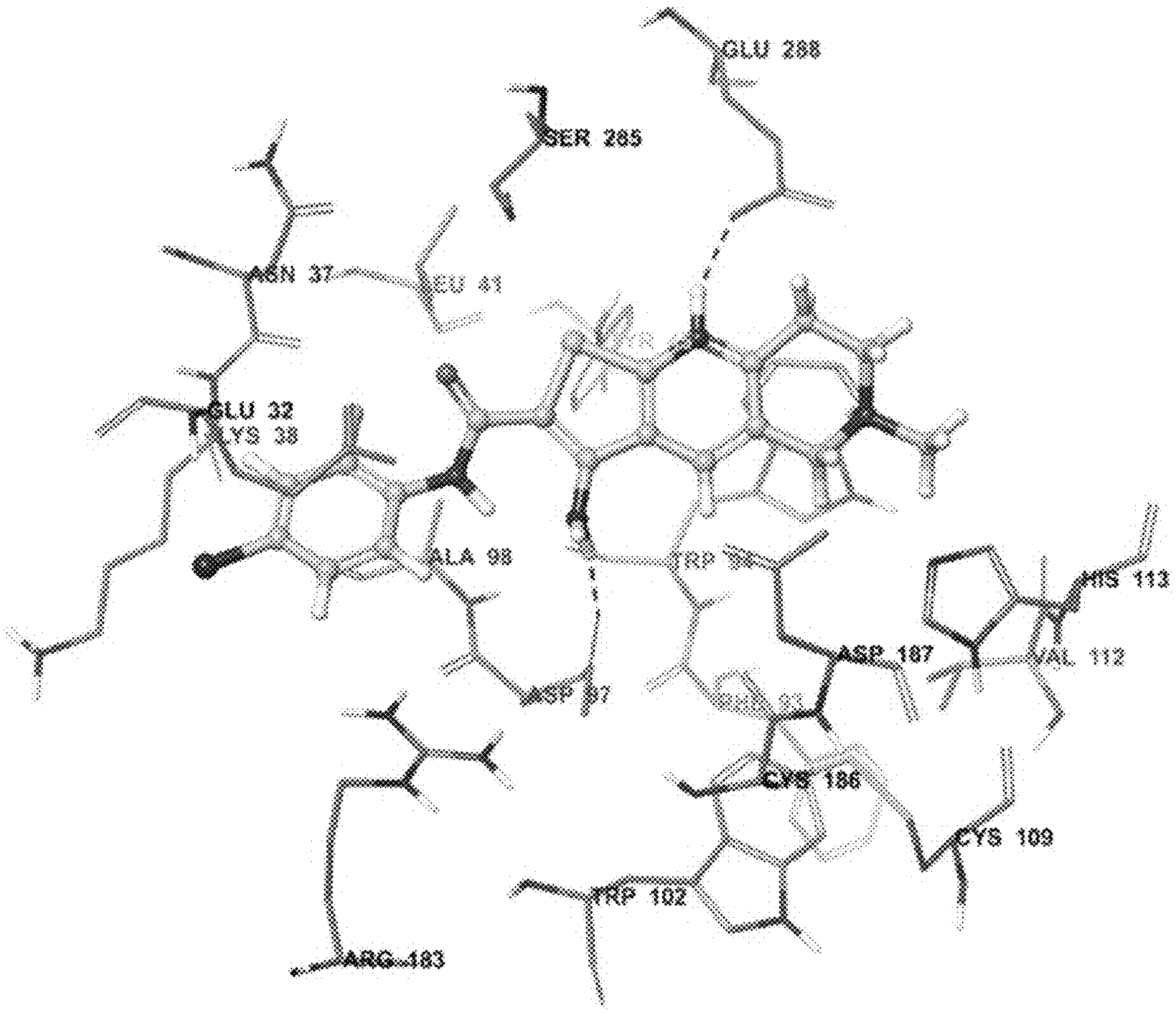
FIGS. 11A-11B: XP-Glide predicted binding mode of AM-807/42860436 in the active site of CXCR4 (Pdb id: 3ODU, 2.5 Å) (FIG. 11A), and a schematic diagram of the protein-ligand interaction is shown for the ligand (FIG. 11B).
Figure 11B:
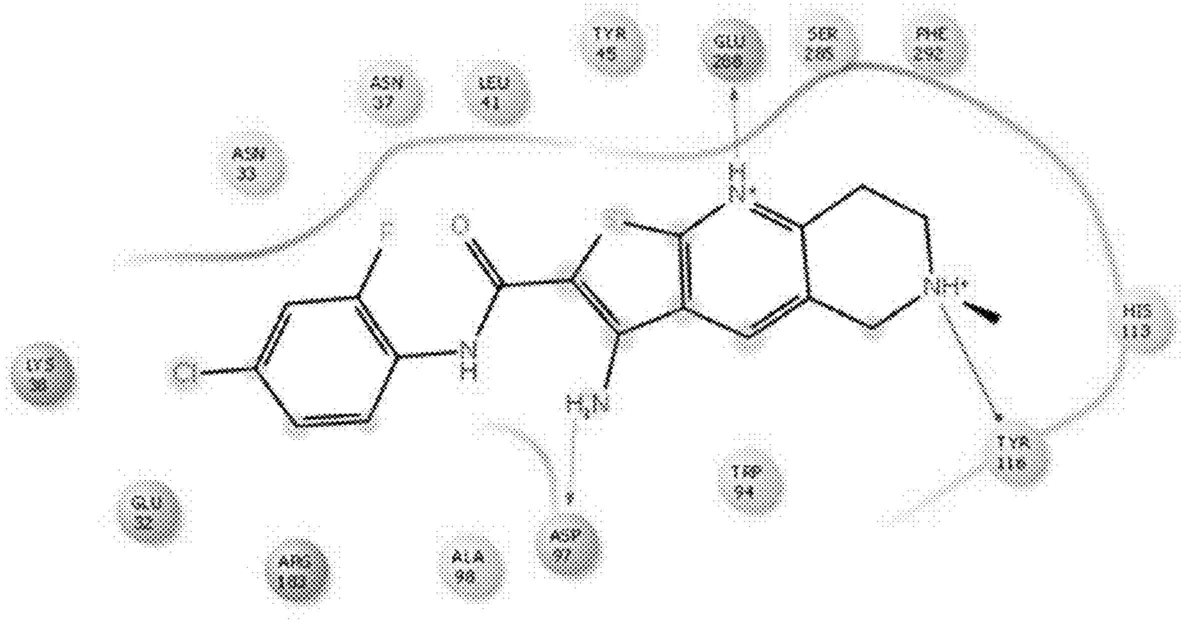

FIG. 11A shows the XP-Glide predicted binding mode of AM-807/42860436 in the active site of CXCR4 (Pdb id: 3ODU, 2.5 Å). Important amino acids are depicted as sticks with the atoms colored as carbon—green, hydrogen—white, nitrogen—blue, oxygen—red, sulfur—yellow, whereas the ligand is shown with the same color scheme as above except for carbon atoms which are represented in yellow. The red dotted lines represent hydrogen bond. FIG. 11B shows a schematic diagram of the protein-ligand interaction is shown for ligand. Blue circles code polar amino acids, hydrophobic amino acids are coded by green circles, the purple arrows depict side chain donor/acceptor interactions, the green lines depict pi-pi stacking interactions, and the blue-red lines represent salt bridge.

Figure 12A:
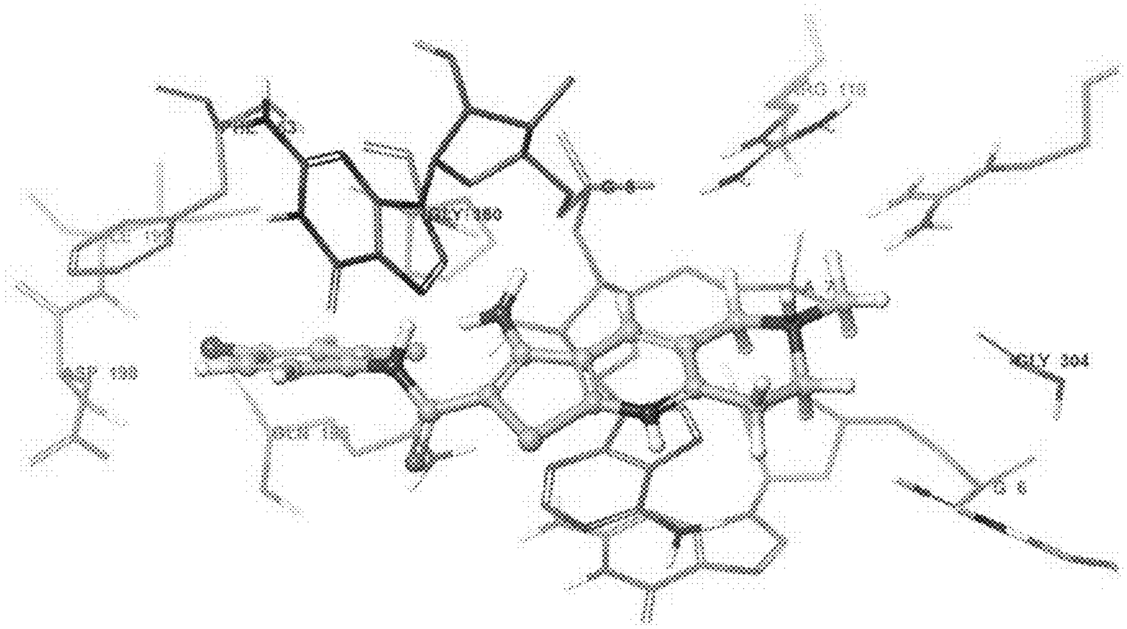
FIGS. 12A-12B: XP-Glide predicted binding mode of AM-807/42860436 in the active site of Eukaryotic initiation factor 4A-I (Pdb id: 5ZC9, 2 Å) (FIG. 12A), and a schematic diagram of the protein-ligand interaction for ligand (FIG. 12B).
Figure 12B:
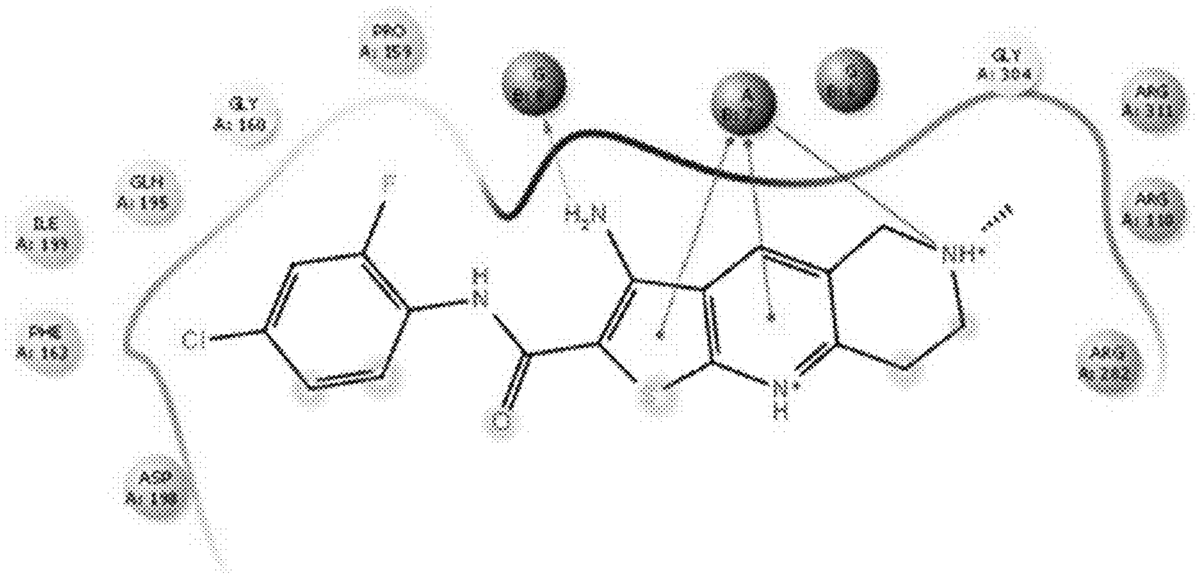

FIG. 12A shows the XP-Glide predicted binding mode of AM-807/42860436 in the active site of Eukaryotic initiation factor 4A-I (Pdb id: 5ZC9, 2 Å). Important amino acids are depicted as sticks with the atoms colored as carbon—green, hydrogen—white, nitrogen—blue, oxygen—red, sulfur—yellow, whereas the ligand is shown with the same color scheme as above except for carbon atoms which are represented in yellow. The red dotted lines represent hydrogen bond. FIG. 12B shows a schematic diagram of the protein-ligand interaction for ligand. Blue circles code polar amino acids, hydrophobic amino acids are coded by green circles, dark blue circles codes for nucleotides of RNA, the purple arrows depict side chain donor/acceptor interactions, the green lines depict pi-pi stacking interactions, and the blue-red lines represent salt bridge.

Figure 13A:
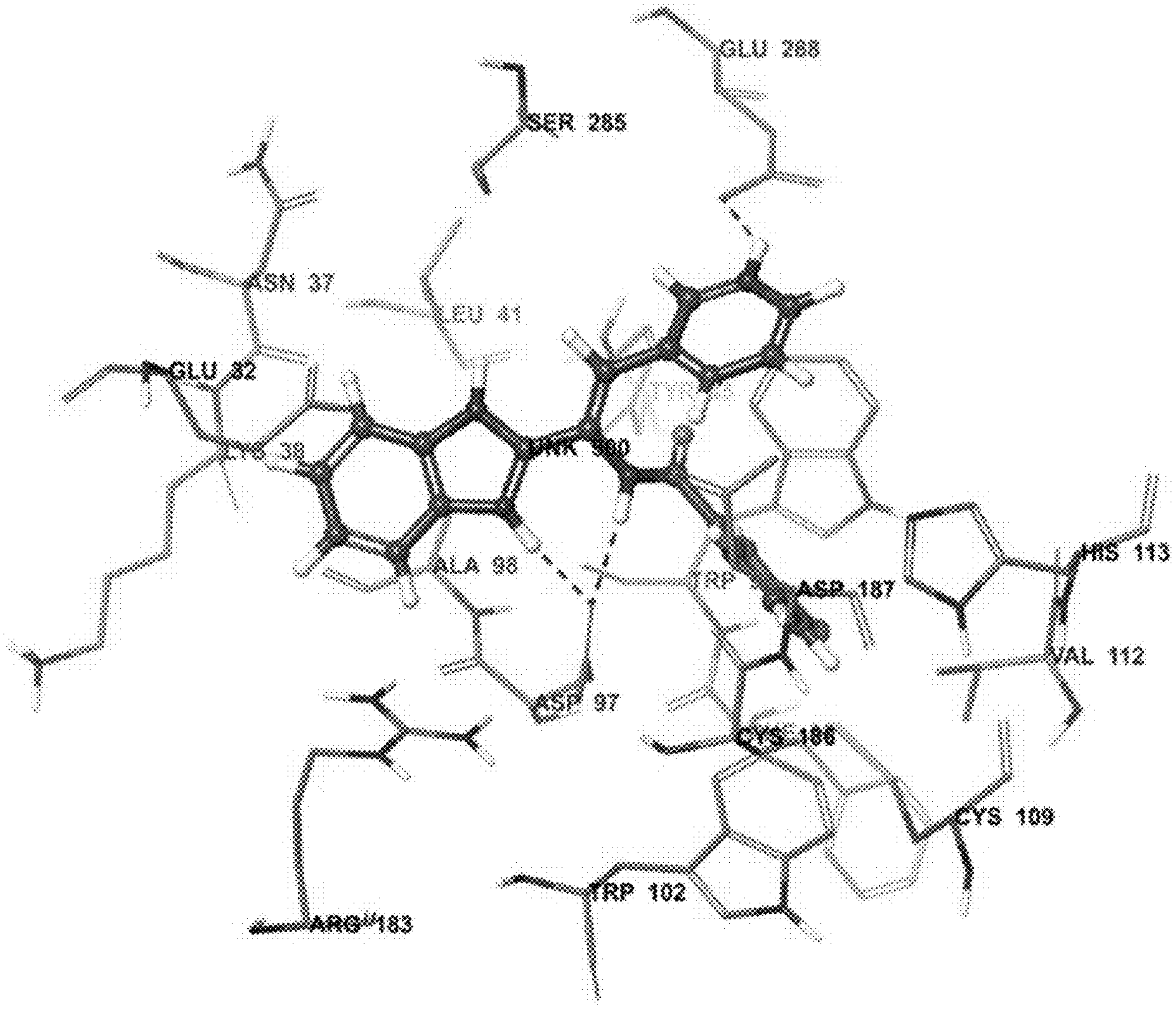
FIGS. 13A-13B: XP-Glide predicted binding mode of AE-848/14270010 in the active site of CXCR4 (Pdb id: 3ODU, 2.5 Å) (FIG. 13A), and a schematic diagram of the protein-ligand interaction is shown for ligand (FIG. 13B).
Figure 13B:
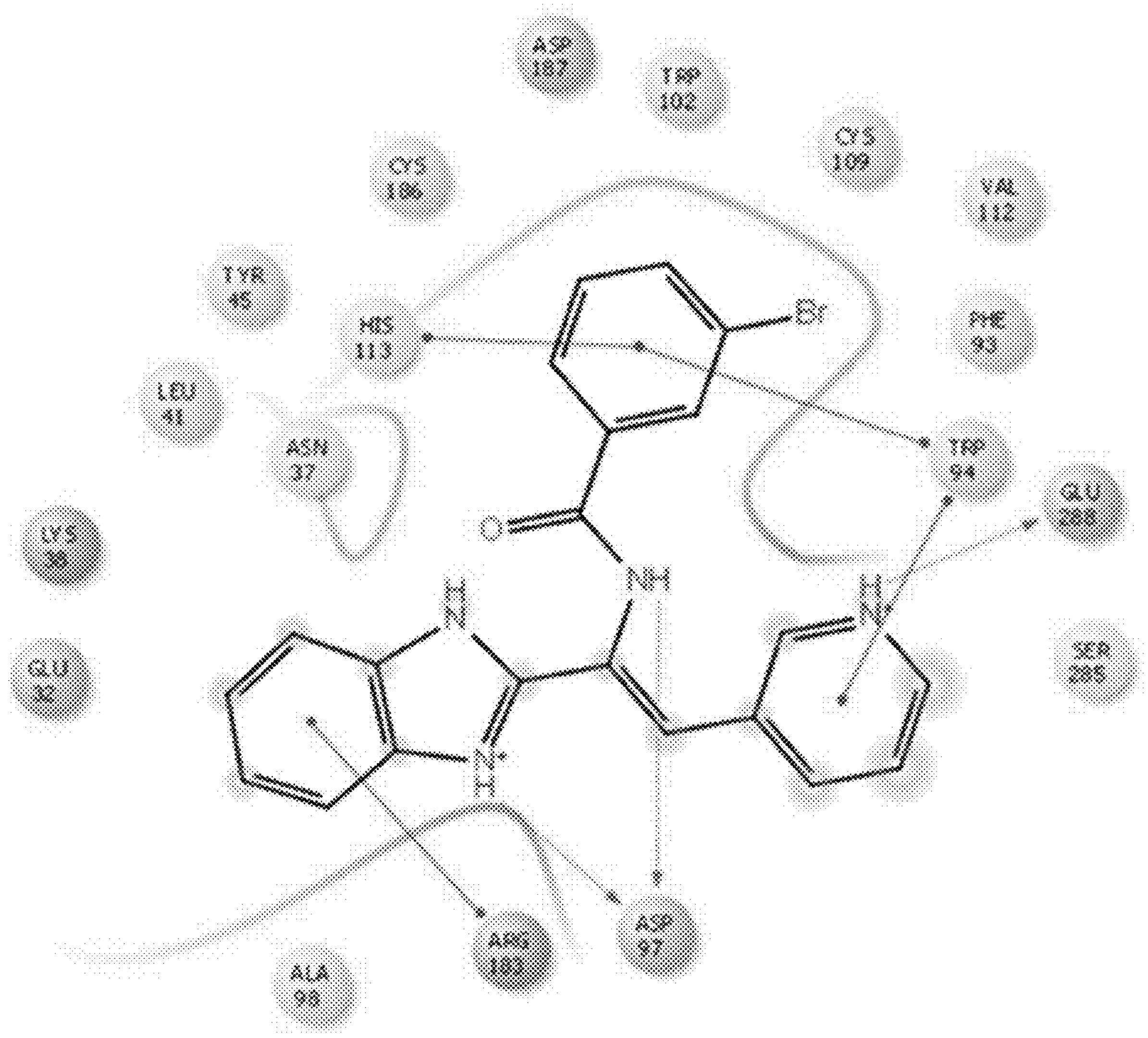

FIG. 13A shows the XP-Glide predicted binding mode of AE-848/14270010 in the active site of CXCR4 (Pdb id: 3ODU, 2.5 Å). Important amino acids are depicted as sticks with the atoms colored as carbon—green, hydrogen—white, nitrogen—blue, oxygen—red, sulfur—yellow, whereas the ligand is shown with the same color scheme as above except for carbon atoms which are represented in red. The red dotted lines represent hydrogen bond. FIG. 13B shows a schematic diagram of the protein-ligand interaction is shown for ligand. Blue circles code polar amino acids, hydrophobic amino acids are coded by green circles, the purple arrows depict side chain donor/acceptor interactions, the green lines depict pi-pi stacking interactions, and the blue-red lines represent salt bridge.

Figure 14A:
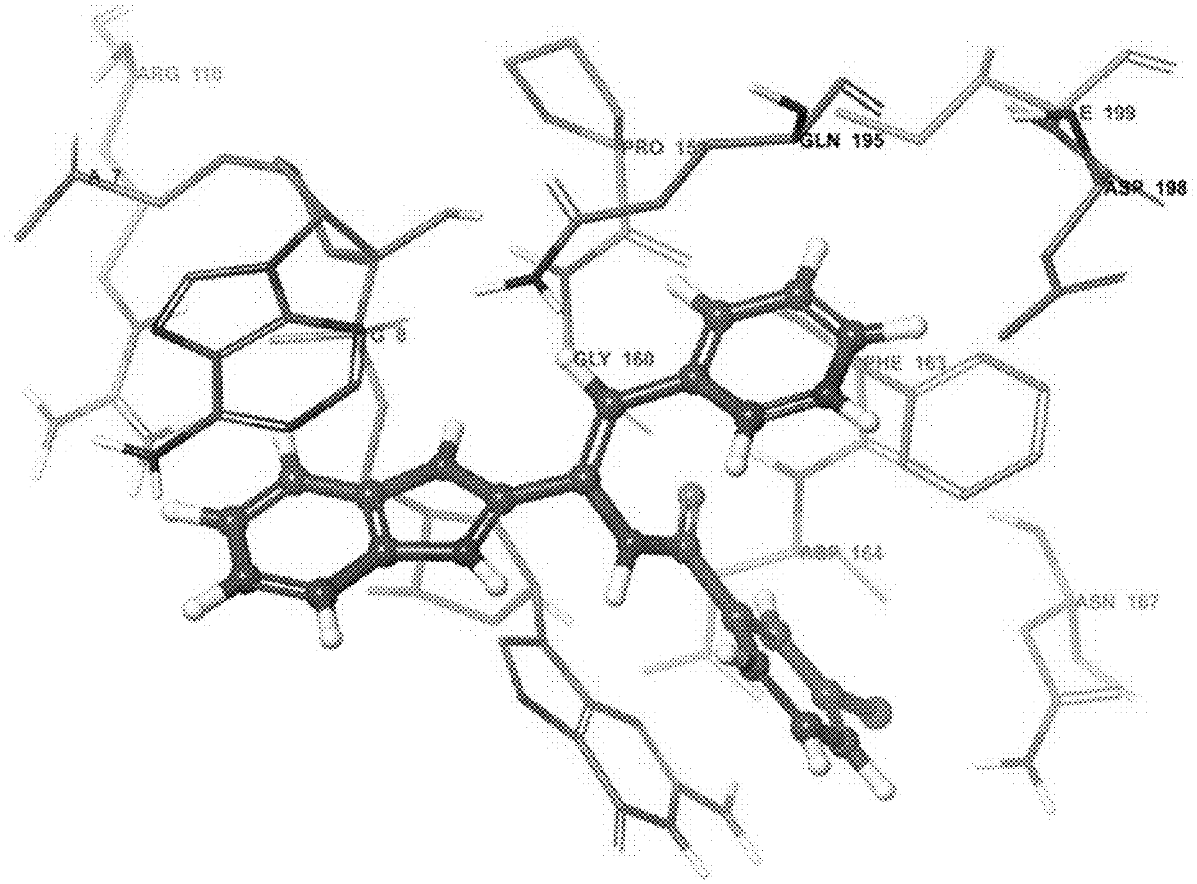
FIGS. 14A-14B: P-Glide predicted binding mode of AE-848/14270010 in the active site of Eukaryotic initiation factor 4A-I (Pdb id: 5ZC9, 2 Å) (FIG. 14A), and a schematic diagram of the protein-ligand interaction is shown for ligand (FIG. 14B).
Figure 14B:
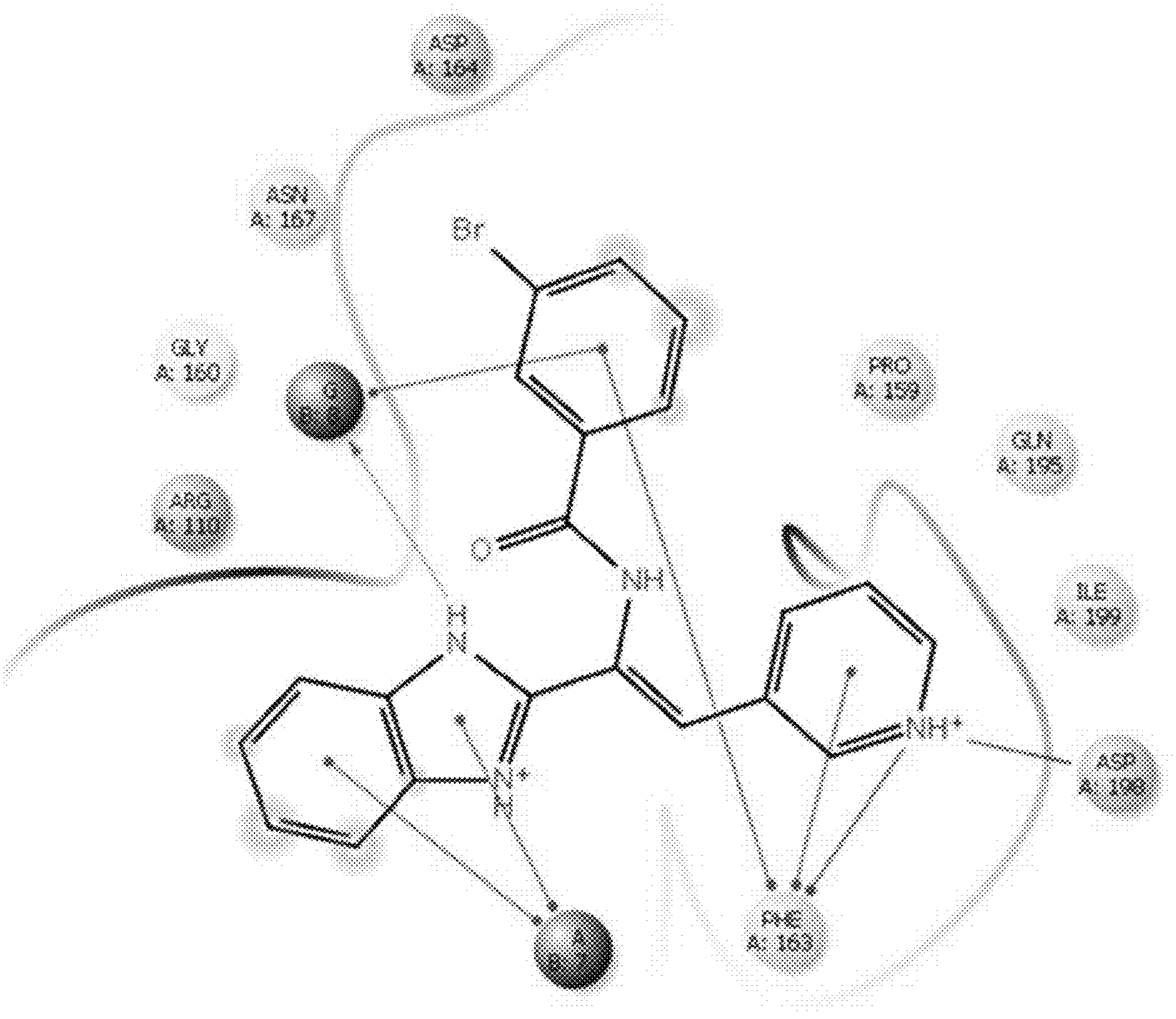

FIG. 14A shows a P-Glide predicted binding mode of AE-848/14270010 in the active site of Eukaryotic initiation factor 4A-I (Pdb id: 5ZC9, 2 Å). Important amino acids are depicted as sticks with the atoms colored as carbon—green, hydrogen—white, nitrogen—blue, oxygen—red, sulfur—yellow, whereas the ligand is shown with the same color scheme as above except for carbon atoms which are represented in red. The red dotted lines represent hydrogen bond. FIG. 14B shows a schematic diagram of the protein-ligand interaction is shown for ligand. Blue circles code polar amino acids, hydrophobic amino acids are coded by green circles, dark blue circles codes for nucleotides of RNA, the purple arrows depict side chain donor/acceptor interactions, the green lines depict pi-pi stacking interactions, and the blue-red lines represent salt bridge.

FIG. 15A shows a dual inhibitor molecule referred to as AE-848/14270010, and the structural derivation of AE-848/14270010. FIGS. 15B-15C show further dual inhibitor molecules.

Cell Viability Studies with CAST Compounds

In FIGS. 13-14, in silico binding of a dual inhibitor molecule referred to as AE-848/14270010, designed to inhibit both CXCR4 and eIF4A1, is demonstrated. A good glide score of −8.1 was obtained for eIF4A1 and −6.714 was obtained for CXCR4. This finding was further confirmed with in vitro tests where the molecule AE-848/14270010 performed well in triple-negative breast cancer (TNBC) cell viability assays performed in 3 biological replicates (FIG. 15D, middle panel). In CRISPR/control cells, the viability of TNBC cells were lost by about 35% at the lowest concentration of 50 μM. Upon combining with LASP1-knockout, the cell viability dropped further to 50% with synergy due to the combinatorial genetic loss of LASP1 and pharmacological inhibition of eIF4A1 and CXCR4. When eIF4A1 was knocked out there was a gain in viability of cells, indicating the specificity of AE-848/14270010 towards eIF4A1 (FIG. 15D, middle panel). Furthermore, tweaking the structure of AE-848/14270010, the derivative or an analogue called AT-2 (the structure of which is seen in FIG. 15D) was obtained. When AT-2 was applied to TNBC cells, the inhibitory activity in terms of cell viability was lost with only minimal inhibition at the lowest concentration of 50 μM when LASP1− was knocked out, pointing to the specificity of the molecule AE-848/14270010 to inhibition of eIF4A1 and CXCR4 (FIG. 15D, bottom panel). Finally, the compound AN-465/41673523 was also similarly efficacious, but at a slightly higher concentration of 75 μM, and the viability remained inhibited at higher concentrations up to 300 μM.

Figure 15E:
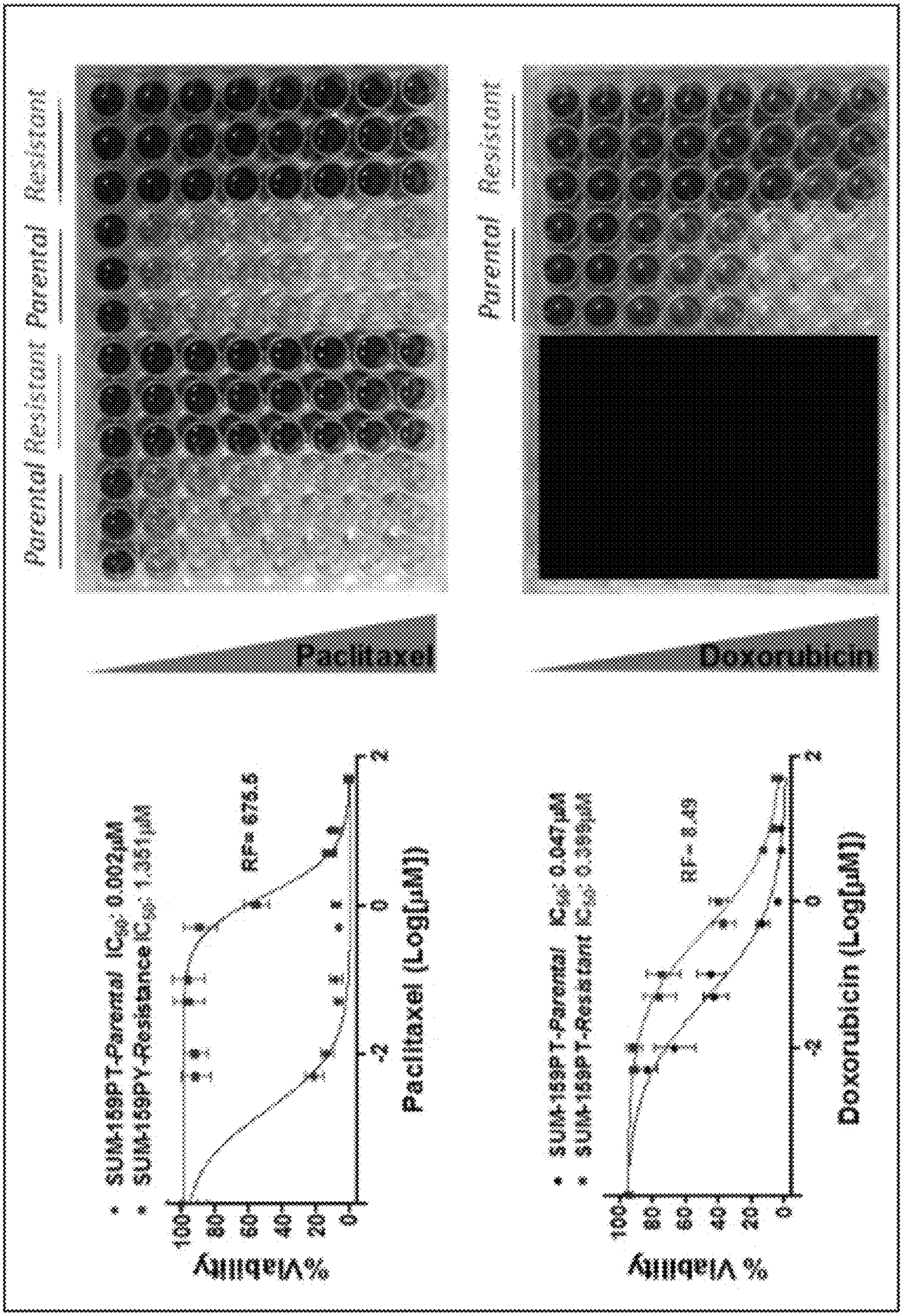

The utility of these compounds and CAST analogues is more valuable when combined with the conventional chemotherapies currently employed in TNBC therapy, such as taxanes and anthracyclines. They can be employed to overcome acquired multidrug resistance (MDR) and thus aggressiveness of TNBC cancer. Towards that effort, paclitaxel-resistance has been developed and evaluated in SUM-159-PT TNBC cells. (FIG. 15E).

Parental SUM-159-PT cells had an $IC_{50}$ of 0.002 μM, whereas the paclitaxel-resistant cells had an $IC_{50}$ of 1.351 μM with a resistance factor of 675.5-fold. Interestingly, these paclitaxel-resistant cells were also cross-resistant to doxorubicin (FIG. 15E, bottom panel). Based on this data and the data in the other examples herein, a combination of inhibitors of LASP1, CXCR4, and/or eIF4A, with or without conventional chemotherapy, can overcome multi-drug resistance in aggressive TNBC cancers.

Example III—Targeting of the Eukaryotic Translation Initiation Factor 4A Against Breast Cancer Stemness Breast cancer stem cells (BCSCs) are intrinsically chemoresistant and capable of self-renewal. Following chemotherapy, patients can develop minimal residual disease due to BCSCs which can repopulate into a relapsed tumor. Therefore, it is imperative to co-target BCSCs along with the bulk tumor cells to achieve therapeutic success and prevent recurrence. It is vital to identify actionable molecular targets against both BCSCs and bulk tumor cells. Inhibition of eIF4A with rocaglamide A (RocA) is efficacious against triple-negative breast cancer cells (TNBC). RocA specifically targets the pool of eIF4A bound to the oncogenic mRNAs that requires its helicase activity for their translation. This property enables specific targeting of tumor cells. However, the efficacy of RocA against BCSCs is currently unknown. In this example, it is shown that eIF4A can be a vulnerable node in BCSCs. In order to test this, a paclitaxel-resistant TNBC cell line which demonstrated an elevated level of eIF4A along with increased levels of cancer stemness markers (ALDH activity and CD44), pluripotency transcription factors (SOX2, OCT4, and NANOG) and drug transporters (ABCB1, ABCG2, and ABCC1) was generated. Furthermore, genetic ablation of eIF4A resulted in reduced expression of ALDH1A1, pluripotency transcription factors, and drug transporters. This indicates that eIF4A is associated with selected set of proteins that are critical to BCSCs, and hence targeting eIF4A may eliminate BCSCs. Therefore, BCSCs were isolated from two TNBC cell lines: MDA-Bone-Un and SUM-159PT. Following RocA treatment, the self-renewal ability of the BCSCs was significantly reduced as determined by the efficiency of the formation of primary and secondary mammospheres. This was accompanied by a reduction in the levels of NANOG, OCT4, and drug transporters. Exposure to RocA also induced cell death of the BCSCs as evaluated by DRAQ7 and cell viability assays. RocA treatment induced apoptosis with increased levels of cleaved caspase-3. Overall, it is demonstrated in this example that RocA is effective in targeting BCSCs, and eIF4A is an actionable molecular target in both BCSCs and bulk tumor cells. Therefore, anti-eIF4A inhibitors may be combined synergistically with existing chemo-, radio- and/or immunotherapies.

Introduction

As noted above, among the cancer fatalities in women, breast cancer (BC) ranks as a second leading cause of death. The metastasis of BC to the lungs, bone, and brain is the main precipitating cause of lethality. The inter- and intra-tumor clonal heterogeneity and plasticity of tumor cells observed in triple-negative BC (TNBC) form the leading cause of chemoresistance, tumor relapse, and poor prognosis. A small subset of tumor cells residing in the tumor called BC stem cells (BCSCs) or tumor initiating cells are attributed to such clinically resistant cases of BC.

Cancer stem cells (CSCs) were identified as a "side population" (SP) by flow cytometric analyses based on the effux of Hoechst dye by the family of adenosine triphosphate (ATP)-binding cassette (ABC) drug transporters such as ABCB1 and ABCG2 present at the plasma membrane. This is one of the mechanisms by which CSCs bypass chemotherapy through effux of xenobiotics (including anti-cancer drugs) to the exterior of the cell leading to their survival in patients. Interestingly, SP cells were found to be significantly enriched in ER- and TNBC patient biopsies. BCSCs are generally characterized by increased intracellular aldehyde dehydrogenase (ALDH) activity and/or the transmembrane glycoprotein referred to as cluster of differentiation 44 (CD44). ALDHs are a set of detoxification isoenzymes implicated in retinoid metabolism. Retinoid-mediated signaling plays an important role in embryonic stem cells and detoxification of drugs in a cancer setting. CD44 is generally involved in cell-cell and cell-matrix adhesions as well as cell migration. A subset of BCSCs co-expresses both CD44 and ALDH markers and these BCSCs are considered highly aggressive and metastatic. BCSCs usually express a combination of pluripotency transcription factors such as SOX2, OCT4, and NANOG. In TNBC, SOX2 promotes proliferation and metastasis. An increased expression of NANOG serves as a prognostic indicator and indicated to be co-expressed with the CD133 marker (prominin1) In surgical TNBC patients, OCT4 has been shown to predict poor patient outcome. Expression of SOX2, NANOG, and OCT4 transcription factors correlated with poor differentiation, advanced BC stage, and worst survival in BC patients.

The expression of cell surface and subcellular markers of BCSCs adapt in response to the alterations in the tumor microenvironment (TME). Mesenchymal and epithelial phenotypes of BCSCs have been reported to display differential gene expression profiles which may contribute to heterogeneity and differential chemoresistance. Interconversion between the two BCSC phenotypes occurs at a slow rate. BCSCs can also bi-directionally interconvert between bulk tumor cell and stemness states based on temporal and spatial cues in the microenvironment of the BCSCs. This creates a remarkable genetic and/or epigenetic heterogeneity and cellular plasticity in BCSCs and bulk tumor cell pools which presents a clinical challenge. The ability of BCSCs to self-renew, differentiate into bulk tumor cells and resist radio- and chemotherapy allows them to remain viable following therapy constituting the minimal residual disease (MRD). Subsequently, the BCSCs can differentiate and repopulate the whole tumor leading to relapse. Therapy failure after multiple rounds of exposure to the chemotherapeutic agents will lead to aggressive tumor behavior resulting in distant metastases or metastasis of the metastases that culminates in mortality.

TNBC patients often exhibit the paradox of an initial response followed by refractoriness to neoadjuvant chemotherapy. This is especially true in taxane therapy with docetaxel wherein there is a therapy response initially followed by development of resistance. Therefore, there is an unmet need for specific therapies to overcome the chemoresistance arising from BCSCs, i.e., for BCSC-directed therapies. Also, considering the interconversions between the bulk tumor cells and BCSCs, it is important to co-target BCSCs along with bulk tumor cells in order to achieve clinical success and, most importantly, improve the longevity in patients with metastatic BC.

In a drug screen for developing BCSC-directed therapy, it was found that rocaglamide A (RocA), a flavagline compound that targets the eukaryotic translation initiation factor 4A1 (eIF4A1), is effcacious against BCSCs. eIF4A1 (also referred to as eIF4A) is a vital component of the eukaryotic translation initiation eIF4F complex that facilitates translation of many oncogenic proteins. eIF4A, being an mRNA helicase, unwinds key stem-loop-structured (SLS), oncogenic mRNAs such as baculoviral IAP repeat containing 5 (BIRC5) or survivin (survival), MDM2 (antagonizes p53), MCL1 and BCL2 (anti-apoptotic factors), Rho kinase1 (ROCK1, cell migration), SIN1 (part of mTORC2 complex, cell migration), Mucin1-C (MUC1-C), Cyclin D1 and D3 (proliferation), among others, for efficient ribosome scanning and their translation. Overall, these proteins are implicated in survival and metastasis of BCSCs and bulk tumor cells. Example I above and this example together indicate that RocA is a useful compound to target both BCSCs and bulk tumor cells.

Methods

Cell Culture

The human triple-negative breast cancer cell lines MDA-MB-231, lung trophic MDA-MB-231-LM2-4175 (represented as MDA-MB-4175), bone-trophic MDA-MB-231-BoM-1833 [represented as MDA-MB-1833 (35)], MDA-Bone-Un (MDA-MB-231 cells re-isolated from mouse bone metastatic lesions), and SUM-159PT were routinely maintained in Dulbecco's modified eagle medium (DMEM) (GE Healthcare Life Sciences, Pittsburgh, Pa., Cat. #—SH30243.01) supplemented with 4 mM L-glutamine, 4.5 g/L glucose, sodium pyruvate, 10% heat-inactivated fetal bovine serum (FBS) (Denville Scientific, Swedesboro, N.J., Cat. #—FB5001-H), and 1% penicillin (100 I.U.)/streptomycin (100 μg/ml) (Corning, Corning, N.Y., Cat. #—30-002-CI) at 37° C. in a humidified incubator containing 5% $CO_2$.

Isolation of BCSCs Based on Aldehyde Dehydrogenase (ALDH) Activity

MDA-Bone-Un and SUM-159PT tumor cells, MDA-Bone-Un eIF4A CRISPR control (CC), and knockout cells (KO) cultured in a monolayer were trypsinized and BCSCs with high ALDH activity were isolated by employing the ALDEFLUOR™ Kit (Stem Cell Technologies, Vancouver, BC, Canada, Cat. #—01700) following the manufacturer's protocol. Briefly, 0.5×106 (MDA-Bone-Un), $1\times10^6$ cells (SUM-159PT), and $0.3\times10^6$ cells (MDA-Bone-Un CC and KO) were employed for each of the unstained gating control, DEAB (N,N-diethylaminobenzaldehyde) negative control and the test sample. Following the addition of the reagents, the cells were incubated at 37° C. for 45 min. Subsequently, the cells were centrifuged, resuspended in ice-cold assay buffer, and isolated based on the ALDH activity (conversion and retention of fluorescent BAA end product inside the cells) through fluorescence activated cell sorting (FACS).

Isolation of BCSCs Based on Cell Surface Expression of $CD44^+/CD24^-$

A single cell suspension of cells cultured under low attachment conditions on poly-HEMA plates was produced by trituration and/or trypsinization. These cells were incubated at 37° C. for 2 h to allow for the recovery of cell surface receptors. Cell surface CD44 and CD24 antigens were stained by incubating with FITC-CD44 (BD Biosciences, Cat. #—555478) PE-Cy7-CD24 (BD Biosciences, Cat. #—561646) antibodies for 1 h on ice. Unstained cells, along with corresponding isotype antibodies (Cat. #—552868 and Cat. #—555742—BD Biosciences) served as the appropriate controls.

Maintenance of BCSCs

The FACS-sorted ALDH+ BCSCs were maintained under ultra-low attachment conditions in poly-HEMA coated 96-well plates (Corning™ Ultra-Low Attachment Microplates, Cat. #—07200603) or 6-well plates (Corning™ Ultra-Low Attachment Microplates, Cat. #—07200601). DMEM/F-12 (Dulbecco's Modified Eagle's Medium/Hams F-12 50/50 Mix) (Corning, Cat. #—10-090-CM) supplemented with 500 ng/μL basic fibroblast growth factor (bFGF) (Invitrogen GIBCO, Cat. #—PHG0263), 500 ng/μL human epidermal growth factor (hEGF) (Invitrogen GIBCO, Cat. #—PHG0311L), 2% B27 (Gibco™, Cat. #—17504044), and 1% penicillin/streptomycin was employed to maintain the FACS-sorted BCSCs routinely.

Mammosphere Formation Efficiency (MFE) Assay

The evaluation of MFE was performed as described previously. Briefly, $1\times10^3$ ALDH+ BCSCs of MDA-Bone-Un or SUM-159PT origins were seeded onto 96-well ultra-low attachment plates. They were maintained in DMEM/F12 media supplemented with 500 ng/μL bFGF, 500 ng/μL hEGF, 2% B27 mixture, and 1% penicillin/streptomycin for 7 days. The mammosphere images were obtained longitudinally by employing IncuCyte® S3 Live-Cell Analysis System (Essen BioScience, Ann Arbor, Mich.). On day 7, MFE was calculated by employing the formula: (number of mammospheres formed/total number of cells seeded)×100. A diameter of 100 μm was used as a cut-off in the determination of the mammosphere forming ability. For the assessment of secondary MFE, the BCSCs from primary MFE were collected, centrifuged, and re-seeded onto 96-well plates coated with poly 2-hydroxyethyl methacrylate (poly-HEMA). The cells were monitored, and the mammospheres were counted using IncuCyte.

Cell Viability Assays

The induction of cell death by the small molecule inhibitor rocaglamide A (RocA) (Sigma/Aldrich, St. Louis, Mo., Cat. #—SML0656) was followed by employing Deep Red Anthraquinone 7 (DRAQ7) dye (Abcam, Cat. #—ab109202). DRAQ7 is a cell impermeable, far-red fluorescent DNA dye that stains the nuclei of dead and plasma membrane-compromised cells. Importantly, it does not enter the live and intact cells. For the cell death analysis, ALDH+ BCSCs were treated with the indicated drug dosage for 7 days. On day 7, DRAQ7 was added to the cells (1:2,000 dilution) and incubated overnight. Dead BCSCs were tracked by DRAQ7 fluorescence by employing the EVOS cell imaging system (ThermoFisher Scientific, Rockford, Ill.).

The cell viability was alternatively determined on day 7 following treatment with RocA by employing the CellTiter-Glo® luminescent cell viability kit (Promega, Cat. #—G7570) as per the manufacturer's instructions. This quantitative assay is a homogeneous method of determining the number of viable cells in culture based on the amount of adenosine triphosphate (ATP) present inside the cells.

Briefly, to assess the cell viability, $3\times10^3$ cells/well (SUM-159PT, SUM Pac 200 nM, MDA-Bone-Un eIF4A CC and KO) were seeded and the cells were allowed to attach and spread overnight under adherent or non-adherent low attachment conditions. Following treatment with RocA or paclitaxel, the viability of the cells was measured after 48h using CellTiter-Glo® luminescent cell viability kit.

Development of Paclitaxel-Resistant TNBC Cell Lines

Paclitaxel-resistant cell lines were generated by a step-wise escalation of paclitaxel dosage with a recovery period in drug-free media between successive dosages over a total period of 6 months.

Immunoblotting

BCSCs were harvested, washed with 1× phosphate-buffered saline, pH 7.5 (PBS), and lysed with lysis buffer (50 mM Tris, pH 7.5, 100 mM NaCl, 0.1% NP-40, 0.1% deoxycholate, 5 mM EDTA), supplemented with protease inhibitor cocktail (Sigma-Aldrich, St. Louis, Mo., Cat. #—P8340-5ML), phosphatase inhibitor cocktail 2 (Sigma-Aldrich, St. Louis, Mo., Cat. #—P5726), and phosphatase inhibitor cocktail 3 (Sigma-Aldrich, St. Louis, Mo., Cat. #—P0044). The samples were separated by 10% sodium-dodecyl-sulfate polyacrylamide electrophoresis (SDS-PAGE), transferred onto nitrocellulose membrane overnight, and incubated with primary antibodies. The appropriate secondary antibodies conjugated to horse-radish peroxidase (HRP) were then added. The proteins with bound HRP were detected by employing an enhanced chemiluminescence-based kit (Amersham™ ECL™ Prime, GE Healthcare Life Sciences, Pittsburgh, Pa., Cat. #—RPN2232).

Primary antibodies that were used were from Cell Signaling and Technology (unless otherwise indicated) are as follows: SOX2 (Cat. #—3579), OCT4 (Cat. #—2750), NANOG (Cat. #—4903) CD44 (Cat. #—5640), ALDH1A1 (Cat. #—54135), β-actin (Cat. #—49705) ROCK1 (Cat. #—4035), Survivin (Cat. #—2808), Cyclin D1 (Cat. #—2922), Cyclin D3 (Cat. #—2936), eIF4A (Cat. #—2013), ABCG2 (Cat. #4477), ABCB1 (Cat. #13342), Cleaved caspase-3 (Cat. #—9664), Snail (Cat. #—C15D3), β-tubulin D66 (Sigma/Aldrich, St. Louis, Mo., Cat. #—T0198), ABCC1 (Novus Biologicals, Cat. # IU2H10), ABCG2 (Novus Biologicals, Cat. #—3G8), and E-cadherin (BD Biosciences, Cat. #—610181). The ABC transporter antibodies from Novus Biologicals and Cell Signaling and Technology were used interchangeably.

The secondary antibodies were as follows: Goat anti-Mouse IgG (H+L) Superclonal™ Secondary Ab conjugated to HRP (Thermo Scientific, Rockford, Ill., Cat. #—A28177) or Goat anti-Rabbit IgG (H+L) Superclonal™ Secondary Ab conjugated to HRP (Thermo Scientific, Rockford, Ill., Cat. #—A27036).

Genetic Ablation of eIF4A1

For generation of CRISPR/Cas9-mediated eIF4A1 knockout (KO), a set of CRISPR/Cas9 plasmids (Santa Cruz, Dallas, Tex., Cat. #—sc-402623) were transfected into therapy-naïve and paclitaxel-resistant tumor cells using UltraCruz reagent (Santa Cruz, Dallas, Tex., Cat. #—sc-395739) following the manufacturer's instructions. After 24 h, the supernatant was removed and replaced with regular media and cells were further cultured for a total of 72 h. eIF4A1 KO cells were sorted out based on the expression of green fluorescent protein (GFP). Single KO cells were isolated by limiting dilution in 96-well plates. The KO was verified by immunoblotting for eIF4A. Non-targeting CRISPR/Cas9 plasmids were employed to obtain the CRISPR-control cells (Santa Cruz, Dallas, Tex., Cat. #—sc-418922).

Statistical Analysis

All statistical analyses were performed using GraphPad Prism software, ver. 7.0 (San Diego, Calif., USA). In order to determine the statistical significance in our experiments, Students t-tests were performed as indicated with the "p" value set to <0.05. The results were expressed as the mean±standard error of mean (S.E.M.).

Results

In this example, whether eIF4A is involved in mediating or modulating the chemoresistance in breast cancer cells and whether it can be employed as an actionable molecular target in BCSC-directed therapy was evaluated.

Figure 16A:
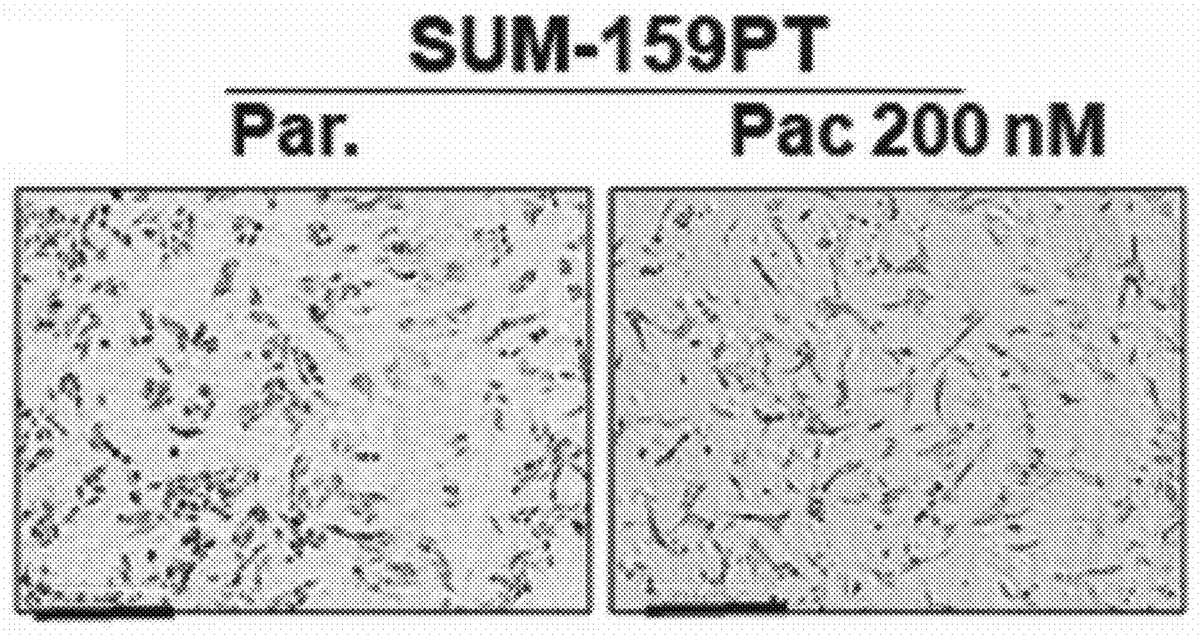
FIGS. 16A-16I: Upregulation in the levels of eIF4A, pluripotency transcription factors, and ABC transporter proteins following chronic paclitaxel treatment in SUM-159PT cells.
Figure 16B:
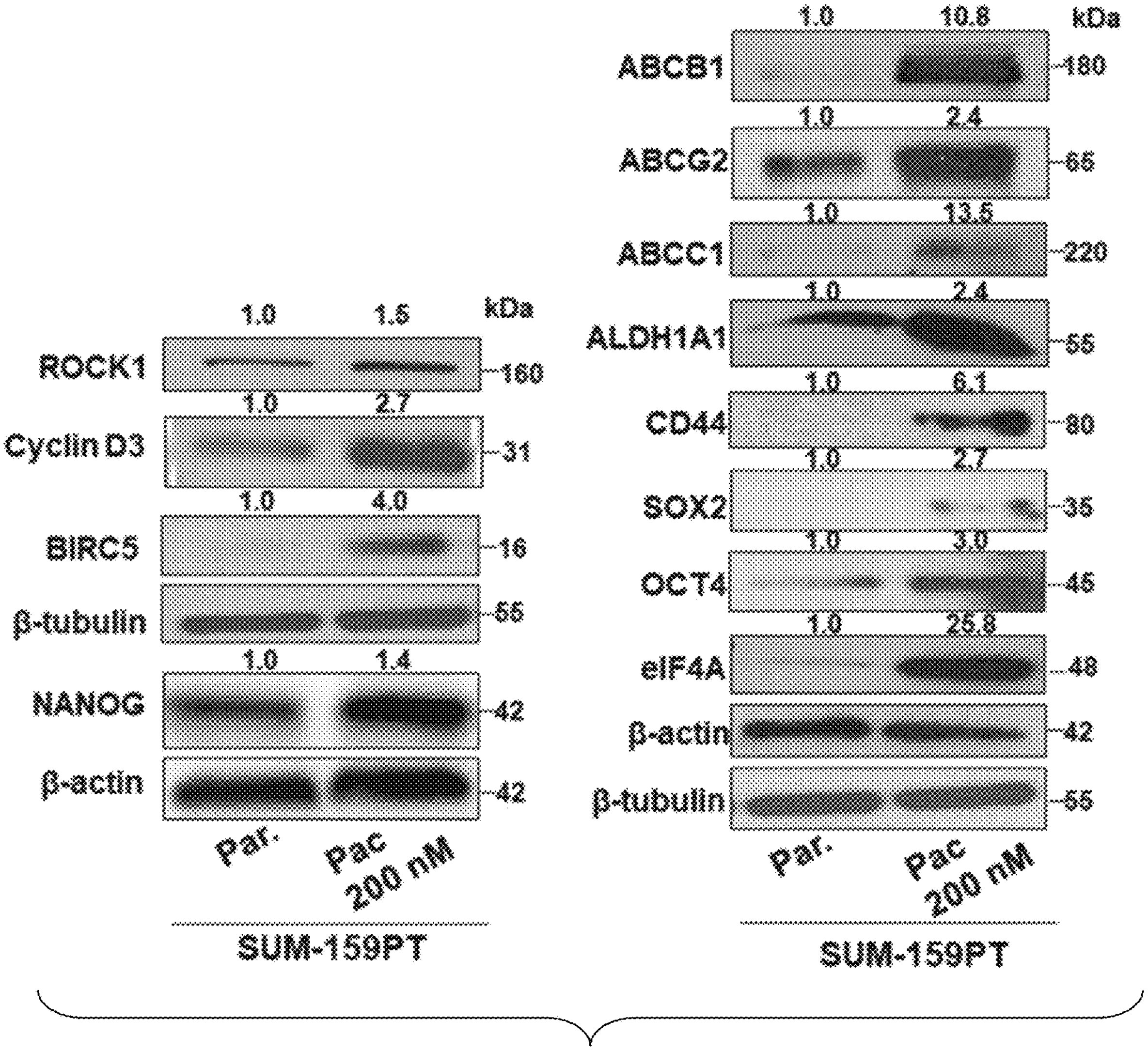
Figure 16C:
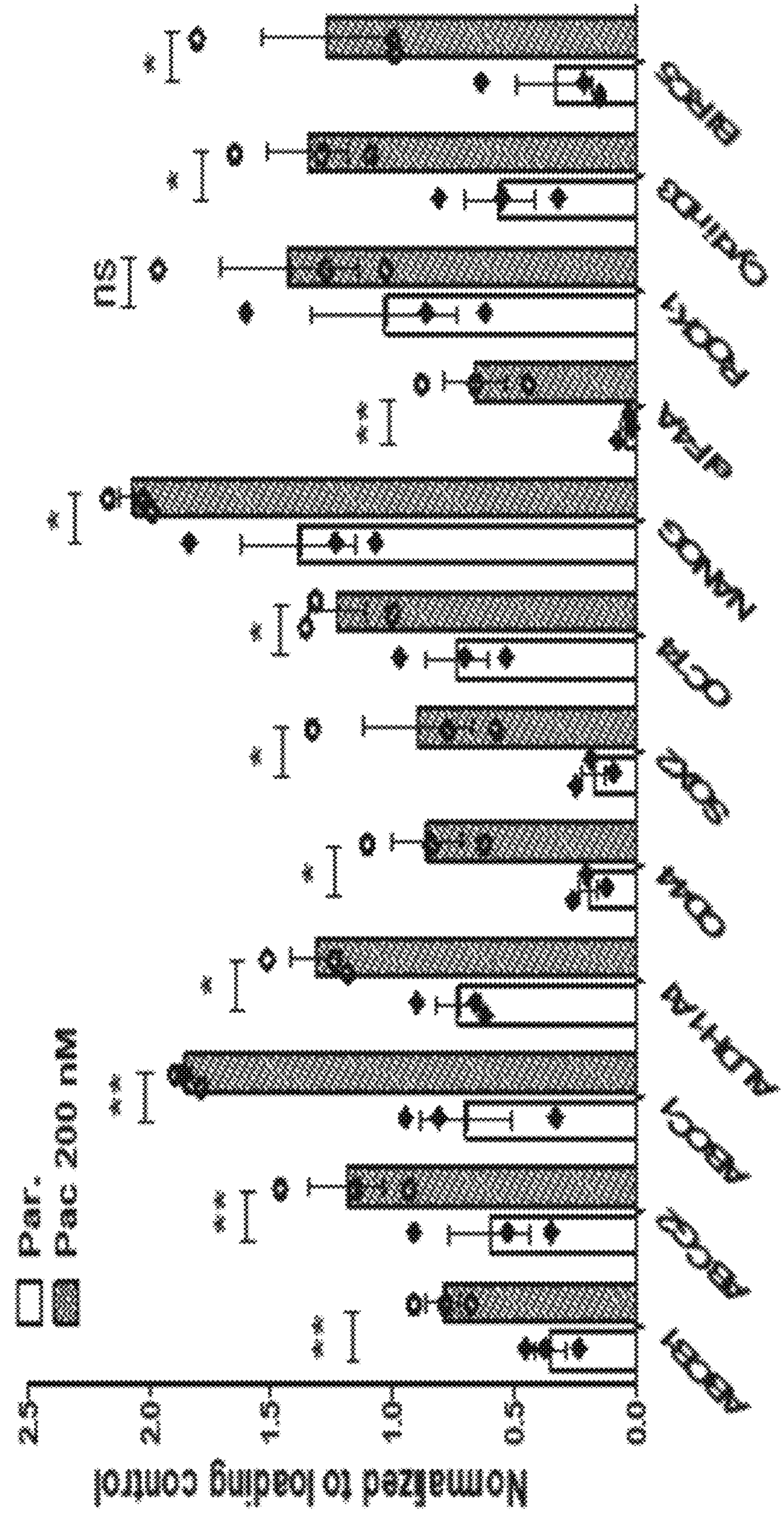
Figure 16D:
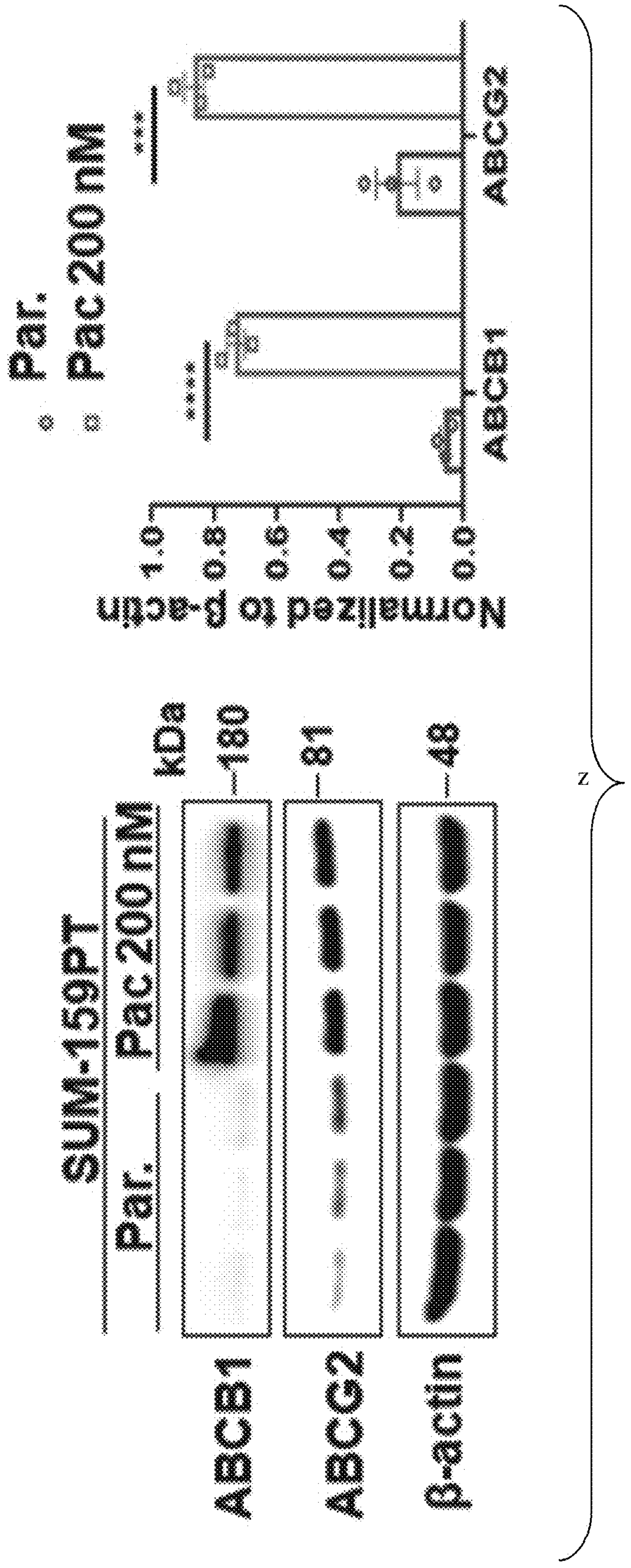

Protein Levels of eIF4A, Pluripotency Transcription Factors, and ABC Drug Transporters are Up Regulated Upon Longitudinal Paclitaxel Treatment Therapy resistance to the first-line chemotherapeutics is a problem in the clinic with frequent relapse in TNBC. To investigate this clinical scenario, a paclitaxel-resistant SUM-159PT cell line model was established with escalating doses of paclitaxel (Pac) over a period of 6 months. Paclitaxel or docetaxel is an antineoplastic drug commonly employed for a wide range of cancer types. The final drug-resistant cells were routinely cultured at 200 nM paclitaxel (Pac 200). As breast cancer stem cells are known to play a vital role in chemoresistance and minimal residual disease, whether the breast cancer sternness would be modulated by the paclitaxel treatment was evaluated. There were phenotypic and molecular changes that occurred after chronic exposure to paclitaxel. First, there was an alteration in the morphology in the "Pac 200" group which displayed a more elongated shape and a less tendency to group together than the control cells (FIG. 16A). Second, an increase in the level of sternness markers such as ALDH1A1 (2.4-fold) and CD44 (6.1-fold) was observed. Third, there was an enhanced expression of the pluripotency transcription factors such as SOX2 (2.7-fold), OCT4 (3-fold), and NANOG (1.4-fold) (FIGS. 16B-16C). Fourth, the protein level of the ABC drug transporters namely ABCG2 or breast cancer resistance protein (BCRP), ABCB1 (P-glycoprotein) or multi-drug resistance protein (MDR1) and ABCC1, were also increased 2.4-, 10.8-, and 13.5-fold, respectively. Finally, and most importantly, there was a significant increase in the expression of eIF4A (25.8-fold) (FIG. 16B). This increase in the total level of eIF4A directly correlated with an enhanced expression of its downstream targets such as survivin or BIRC5 (4-fold), Cyclin D3 (2.7-fold), and ROCK1 (1.5-fold), indicative of an enzymatically active eIF4A, in the paclitaxel-resistant model (FIG. 16C). The quantification of the bands from Western analysis from FIGS. 16B-16C is graphically represented at the bottom. Most of the proteins examined in FIGS. 16B-16C, except ROCK1, had statistically significant increase upon longitudinal exposure to 200 nM paclitaxel. ROCK1 expression showed an increasing trend, albeit not statistically significant. The enhanced expression of the drug transporters was independently verified in three biological replicates (FIG. 16D). The protein levels of ABCB1 and ABCG2 were significantly increased by 14-fold ($p<0.0001$) and 4-fold ($p<0.001$), respectively, similar to the initial findings (FIG. 16B).

Figure 16E:
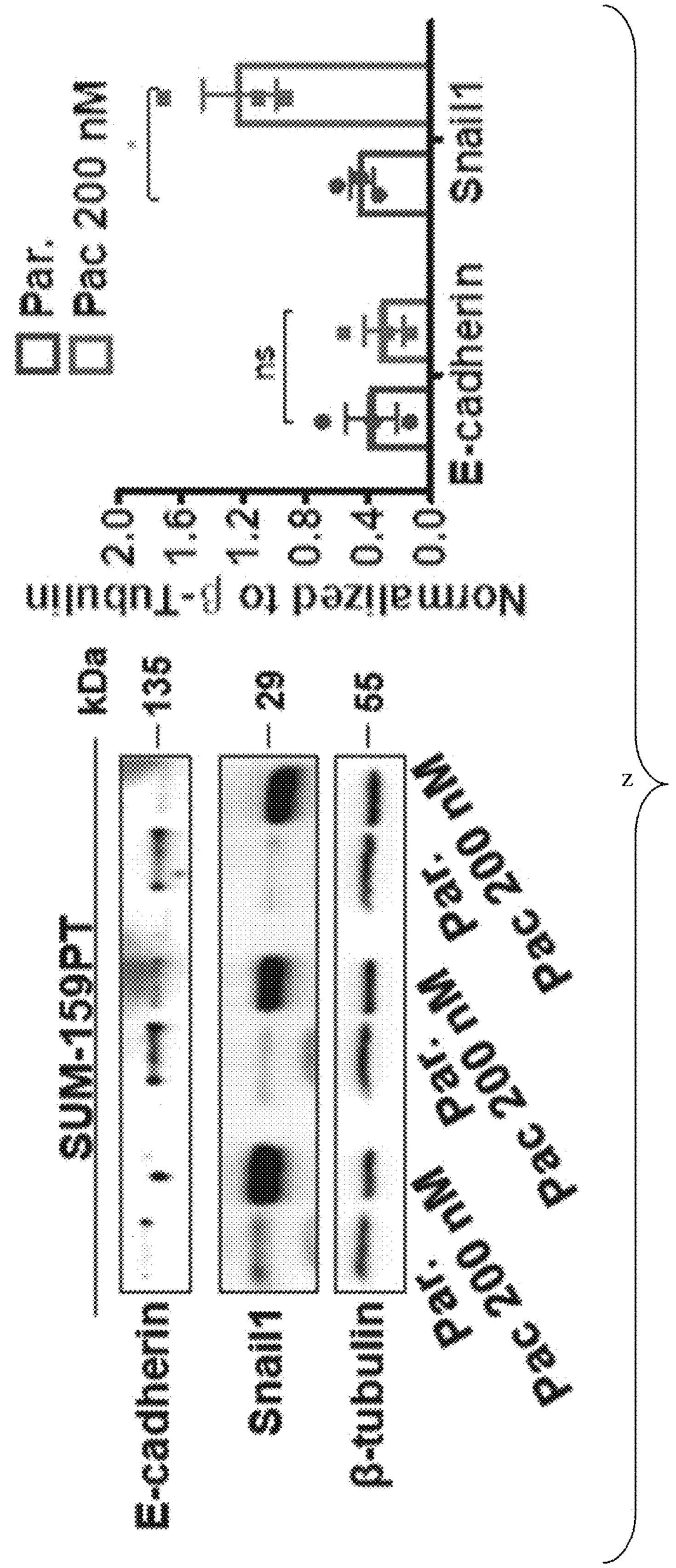
Figure 16F:
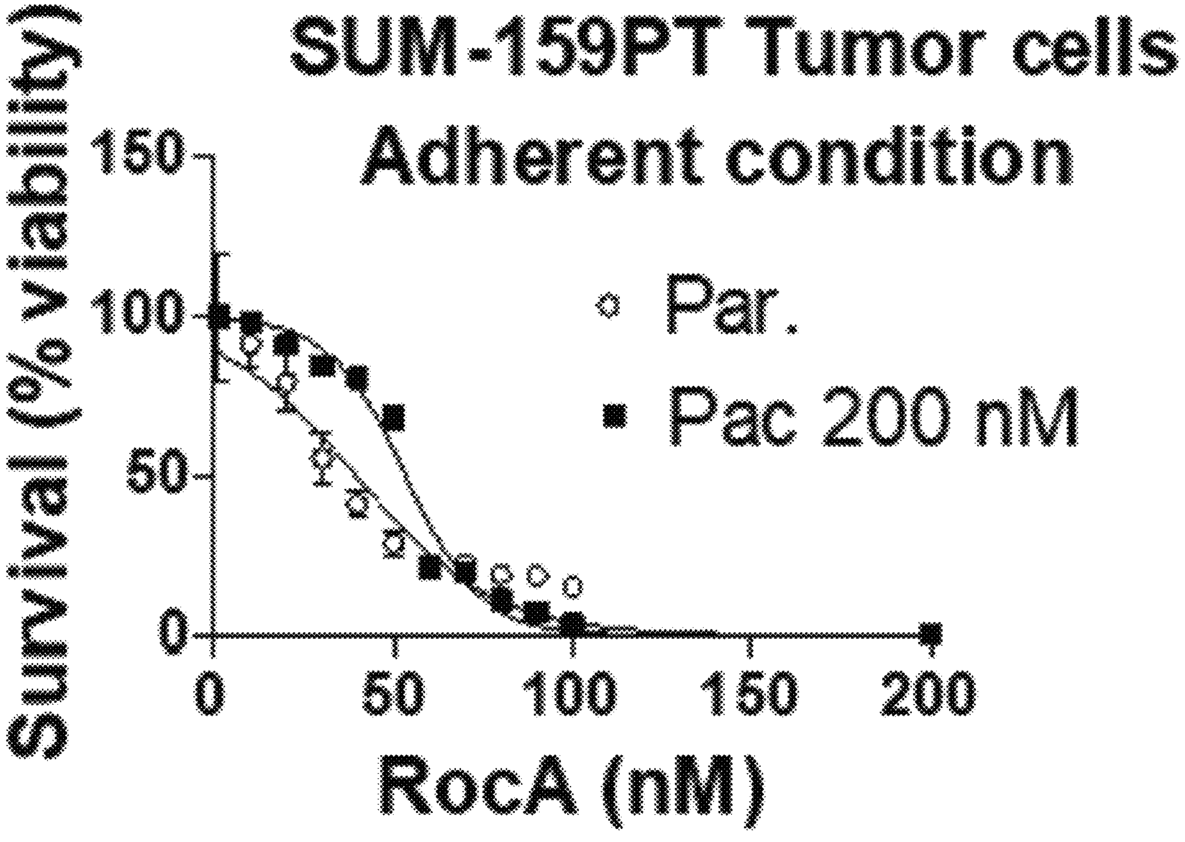
Figure 16G:
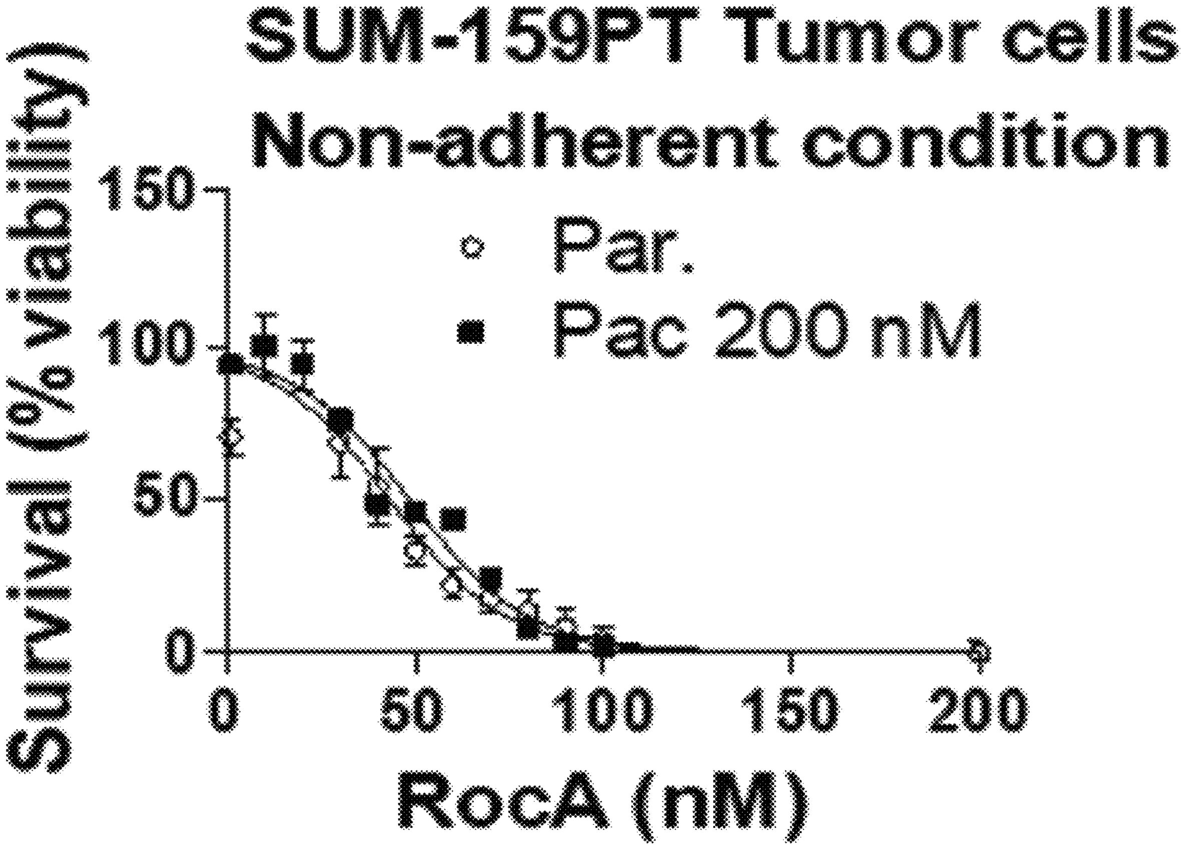
Figure 16H:
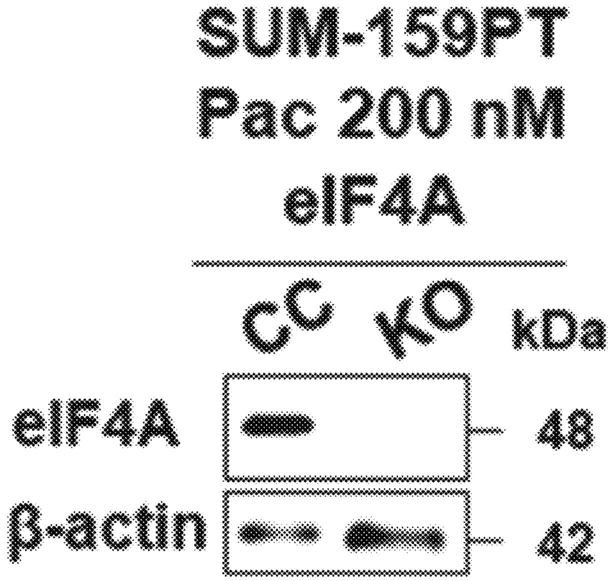
Figure 16I:
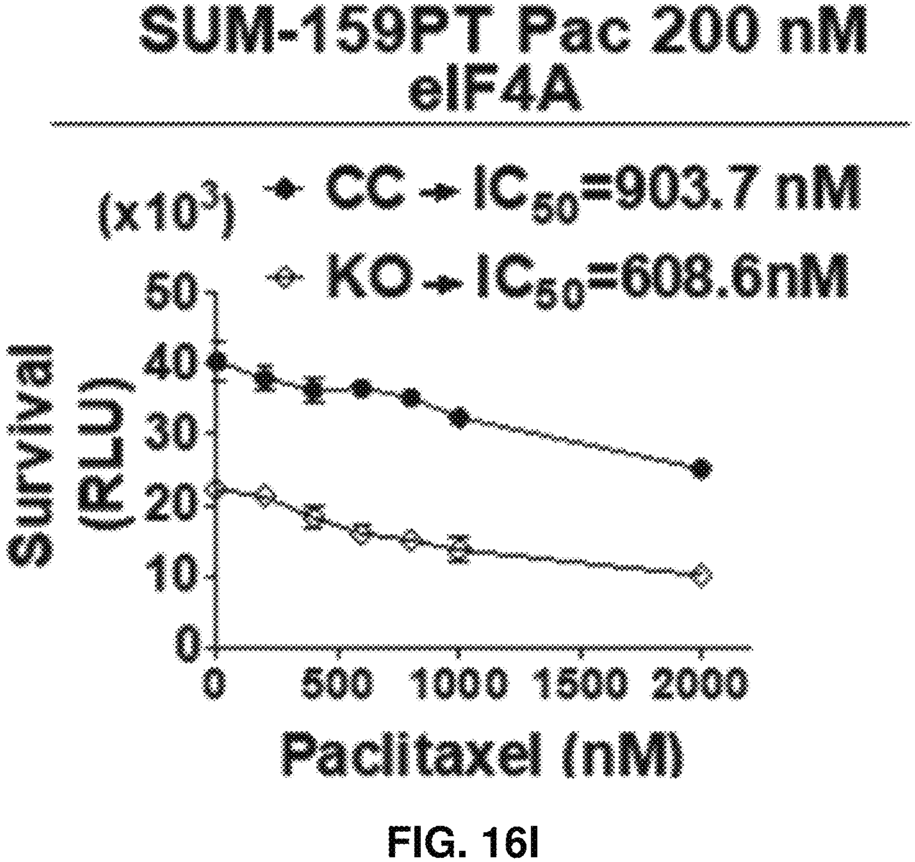

Several epithelial-mesenchymal transition (EMT) markers including Snail1 have been shown to play a key role in chemoresistance. To further validate the model, the expression levels of E-cadherin (a hallmark epithelial marker) and Snail1 (a mesenchymal marker) were examined in therapy-naïve and Pac 200 SUM-159-PT cells. In paclitaxel-resistant cells, the protein level of Snail1 was significantly increased (2-fold) with a concurrent decreasing trend in the expression of E-cadherin (FIG. 16E). As eIF4A showed a dramatic increase following longitudinal paclitaxel exposure, eIF4A was pharmacologically targeted with RocA in therapy-naïve and Pac 200 SUM-159PT tumor cells under both adherent and non-adherent (low attachment poly-HEMA coated) conditions. It was found that RocA is effective in targeting not only in the therapy naïve but also the paclitaxel-resistant cells (FIG. 16F-16G). To demonstrate if eIF4A plays a role in chemoresistance, eIF4A was knocked out in Pac 200 SUM-159PT tumor cells, using the CRISPR-Cas9 approach (FIG. 16H). The guide RNAs target eIF4A1 isoform specifically. Following the validation of the gene ablation of eIF4A1 by immunoblotting, the viability assay was performed to examine if genetic loss of eIF4A confers any chemosensitivity to paclitaxel in these drug-resistant cells. In particular, any gain in sensitivity following eIF4A1-KO that was derived from Pac 200 nM resistant cells was looked for by treating with escalating doses of paclitaxel up to 2 μM for 48 h (cell viability assay using CellTiterGlo kit). Importantly, the viability of the eIF4A1-KO cells decreased by 2-fold (at 0 nM paclitaxel). The CRISPR-control SUM-159PT cells had an $IC_{50}$ of 903.7 nM and in the eIF4A1-KO cells, the $IC_{50}$ decreased to 608.6 nM for paclitaxel (−1.5-fold change) (FIG. 16I).

Figure 17:
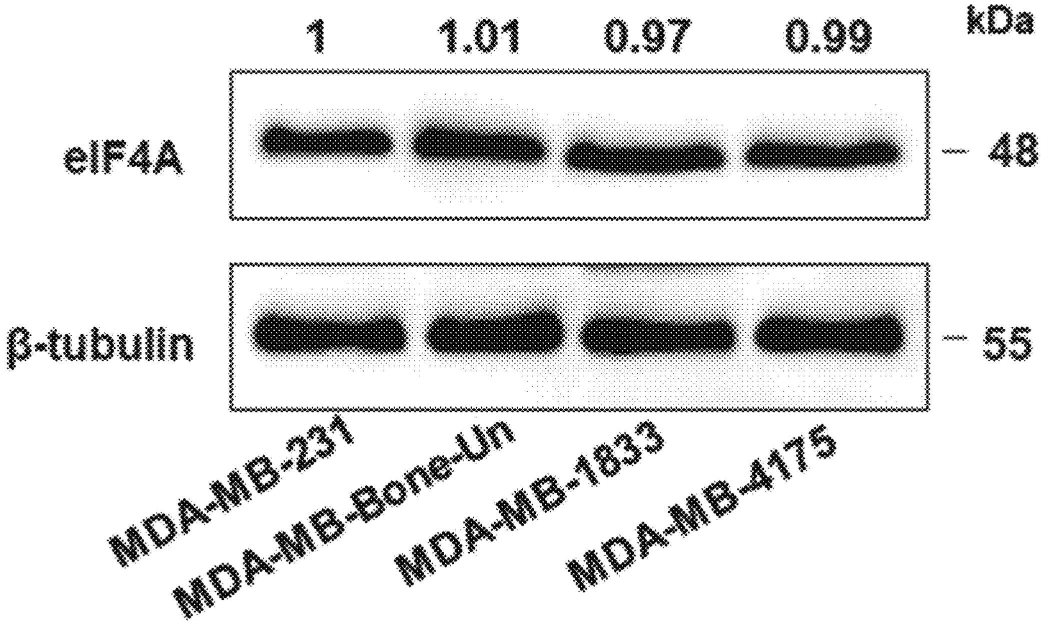
FIG. 17: eIF4A expression was assessed across the different metastatic variants of MDA-MB-231 cells. MDA-Bone-Un and MDA-MB1833 metastasize to the bone whereas MDA-MB-4175 metastasizes to the lungs. (n=4)
Figure 18A:
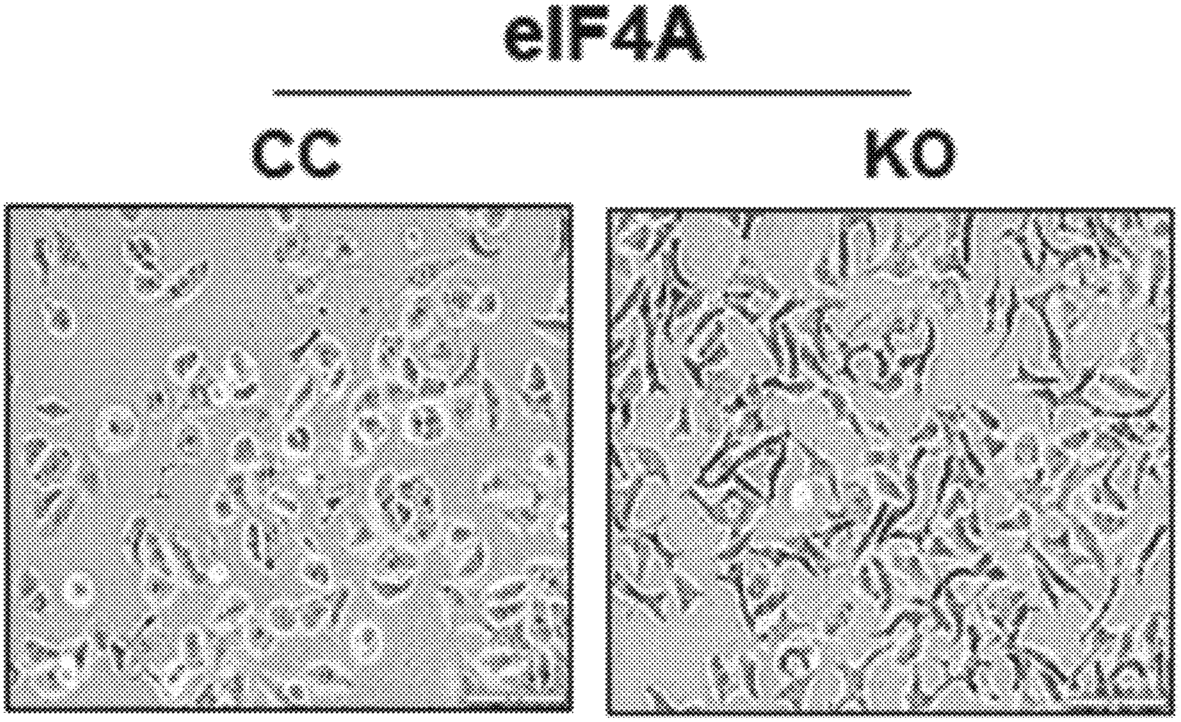
FIGS. 18A-18E: Genetic ablation of eIF4A reduces the expression of sternness transcription factors, drug transporter proteins, and downstream mediators of eIF4A signaling.
Figure 18B:
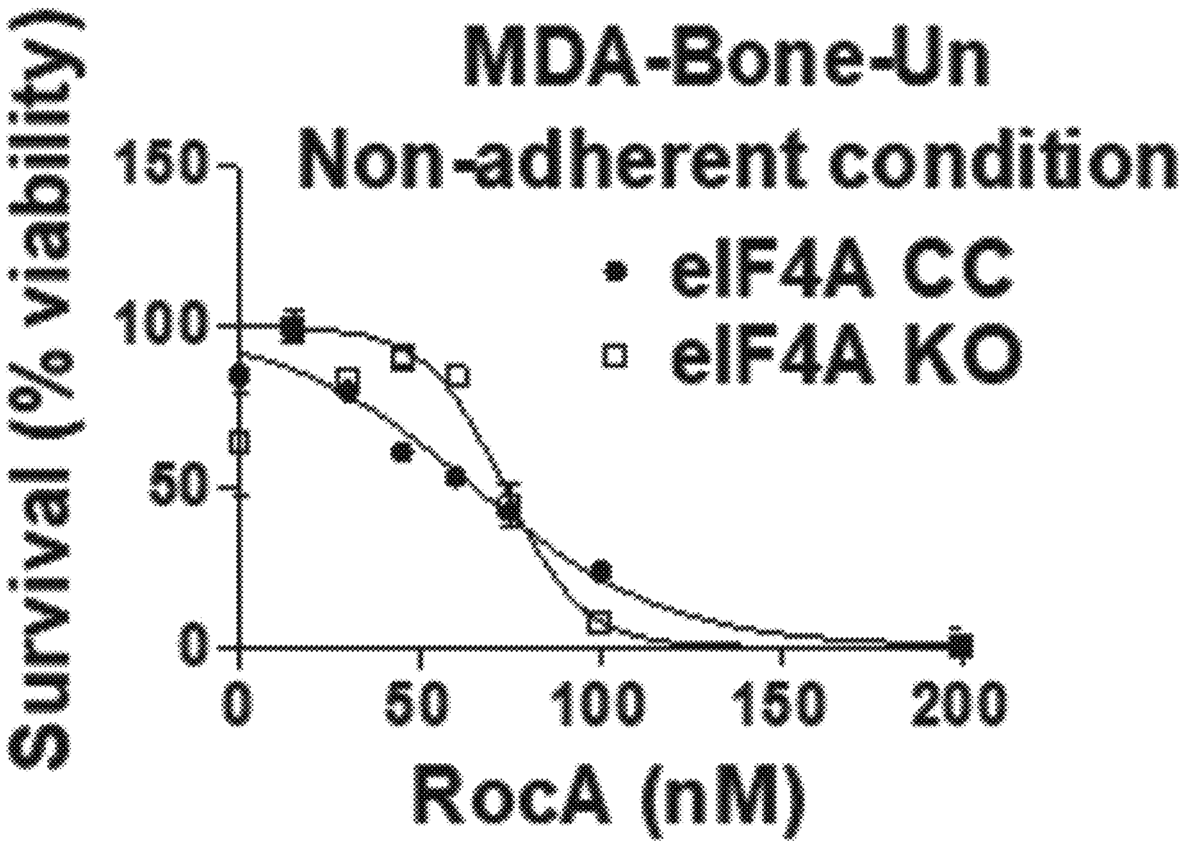

Genetic Ablation of eIF4A Reduced the Expression of Sternness Transcription Factors, Drug Transporters, and Downstream Effectors of eIF4A Activity The expression level of eIF4A was assessed in parental, lung, and bone-trophic variants of MDA-MB-231 cell line. It was found that eIF4A expression remained consistently similar across the cell lines (FIG. 17). Further experiments with MDA-Bone-Un cells that have a higher bone-metastasizing propensity were conducted. In order to ascertain whether the dramatic increase in the expression of eIF4A in the drug-resistant 'Pac 200' model has any causal relationship to the protein level of the drug transporters, eIF4A was knocked out (KO) by employing the CRISPR-Cas9 approach in therapy-naïve MDA-Bone-Un cells. The genetic loss of eIF4A induced a phenotypic change (more elongated morphology and multiple pseudopodia) (FIG. 18A). To check for the specificity of RocA in targeting eIF4A, MDA-Bone-Un eIF4A CC and KO cells were treated with RocA for 48 h and measured the cellular viability. It was observed that the MDA-Bone-Un eIF4A KO cells were relatively insensitive up to 60 nM RocA, whereas in MDA-Bone-Un eIF4A CC cells, there was a steep decrease in viability following the RocA challenge. Following further dose escalation, the drop in the viability was consistent across both cell populations (FIG. 18B). This shows the specificity of RocA in targeting eIF4A in the system.

Figure 18C:
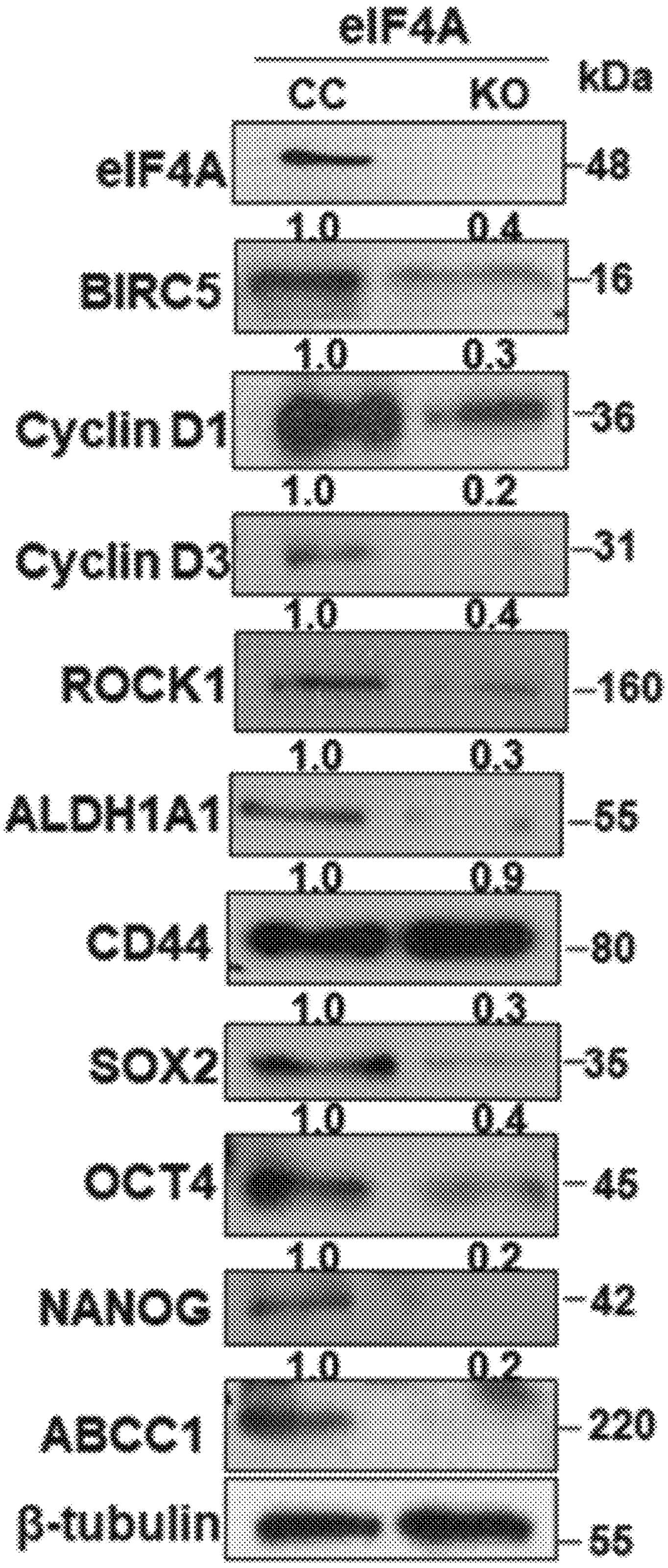
Figure 18D:
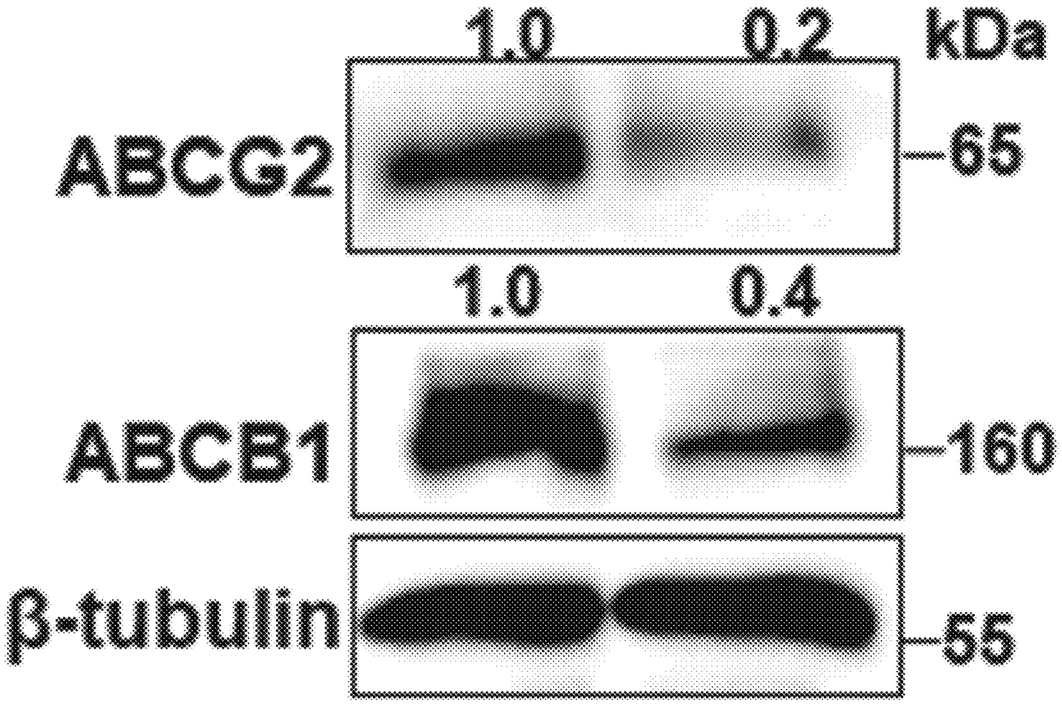
Figure 18E:
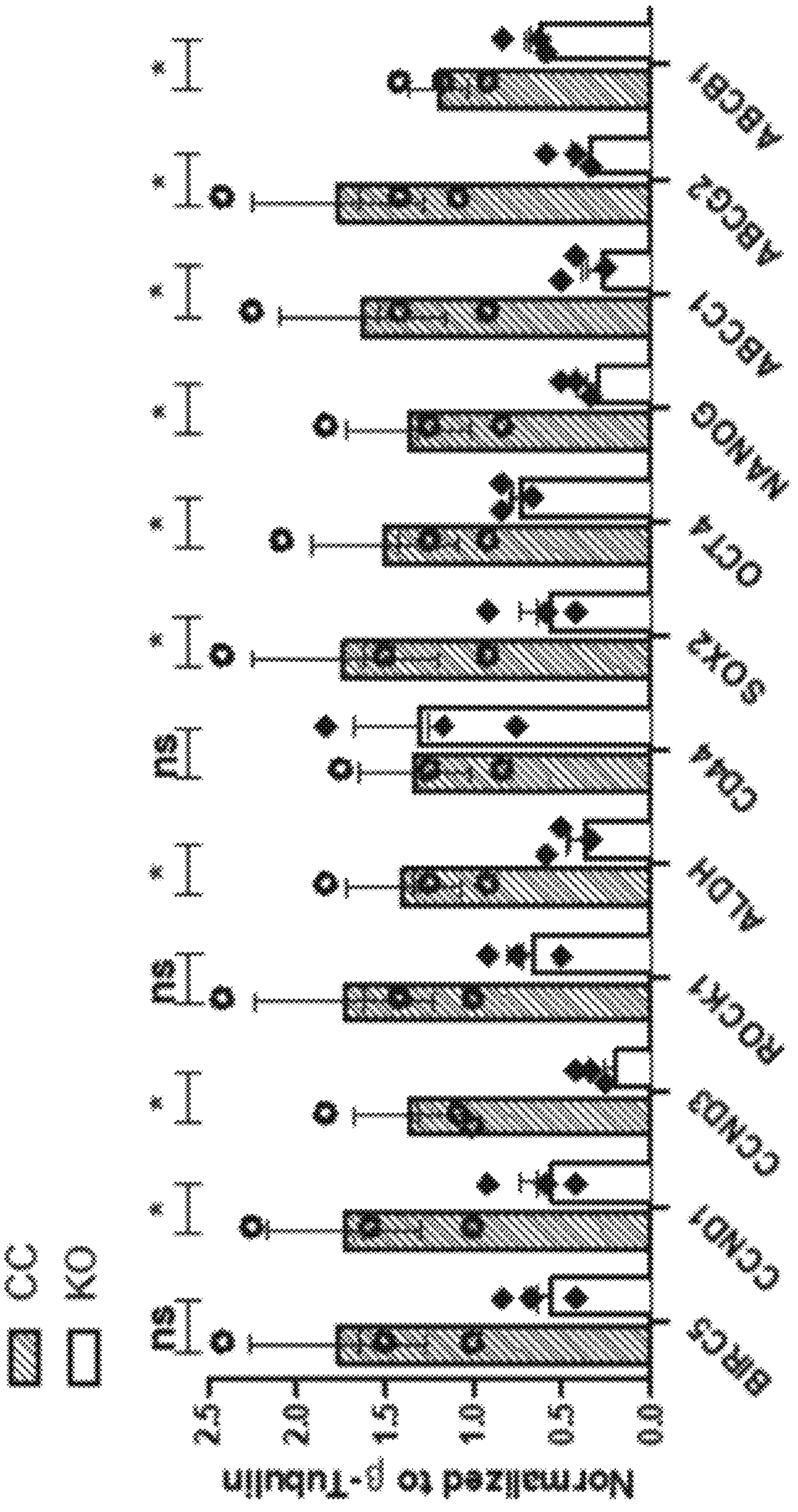

When eIF4A was genetically ablated, there was a marked decrease in the expression of the downstream targets of eIF4A such as BIRC5 (−2.5 fold), Cyclin D1 (−3.3 fold), Cyclin D3 (−5 fold), and ROCK1 (−2.5 fold) in the eIF4A-KO cells (FIG. 18C). Importantly, among the two BCSC markers employed here, only the level and activity of ALDH1A1 selectively plummeted (−3.3 fold) while the expression of CD44 remained unaffected (−1.1 fold) (FIG. 18C and Table 2). Interestingly, this was accompanied by a drastic reduction in the expression of the stemness transcription factors such as SOX2 (−3.3 fold), OCT4 (−2.5 fold), and NANOG (−5 fold). Finally, there was a precipitous decrease in the level of drug transporter ABCC1 (−5 fold) and marked decreases in ABCB1 (−2.5 fold) and ABCG2 (−5 fold) (FIGS. 18B & 18D).

TABLE 2

Differential yield of ALDH-positive cells following the genetic ablation of eIF4A1 in therapy-naïve MDA-Bone-Un TNBC cells; eIF4A knockout in MDA-Bone-Un cells drastically reduces ALDH activity

| MDA-Bone-Un | Biological replicate(% yield of ALDH$^+$ cells) | | | |
|---|---|---|---|---|
| eIF4A | n = 1 | n = 2 | n = 3 | Mean |
| CC | 27.5 | 30.8 | 32.4 | 30.23 |
| KO | 2.8 | 4.5 | 1.8 | 3.03 |

Table 2 depicts the drastic reduction in ALDH activity following eIF4A knockout in MDA-Bone-Un cells assessed by FACS analysis. CC stands for CRISPR control and KO stands for knockout. (n=3)

Figure 19A:
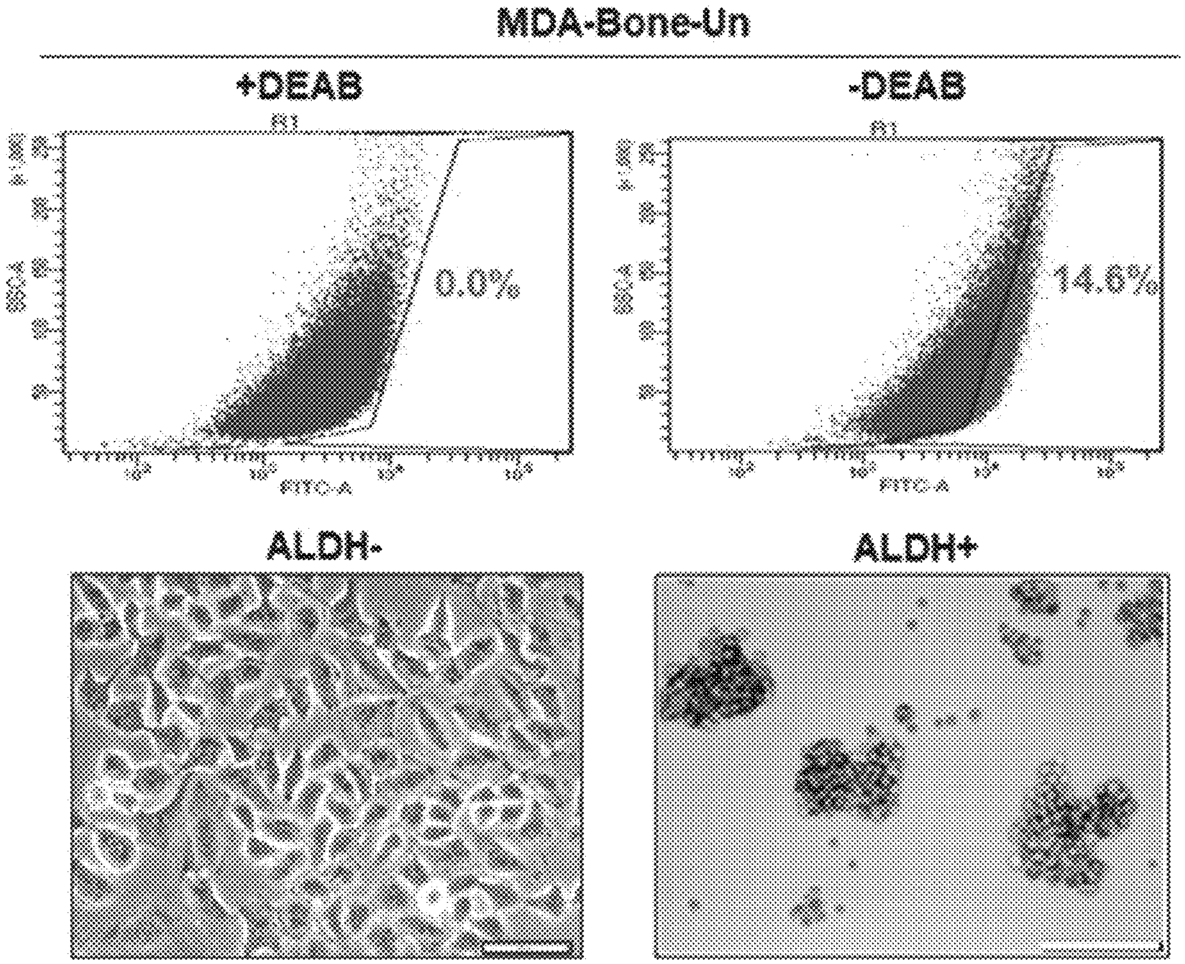
FIGS. 19A-19B: ALDEFLUOR assay depicting the isolation of $ALDH^+$ cell population obtained after gating with the negative control DEAB and analysis by flow cytometry in MDA-Bone-Un cells (FIG. 19A) and SUM-159PT (FIG. 19B) along with the corresponding representative micrographs of $ALDH^-$ cells cultured in monolayer and $ALDH^+$ population grown under low attachment poly-HEMA coated plates in the bottom panel. Scale bar—50 μm for the $ALDH^-$ and $ALDH^+$ populations from MDA-Bone-Un and SUM-159PT cells.
Figure 19B:
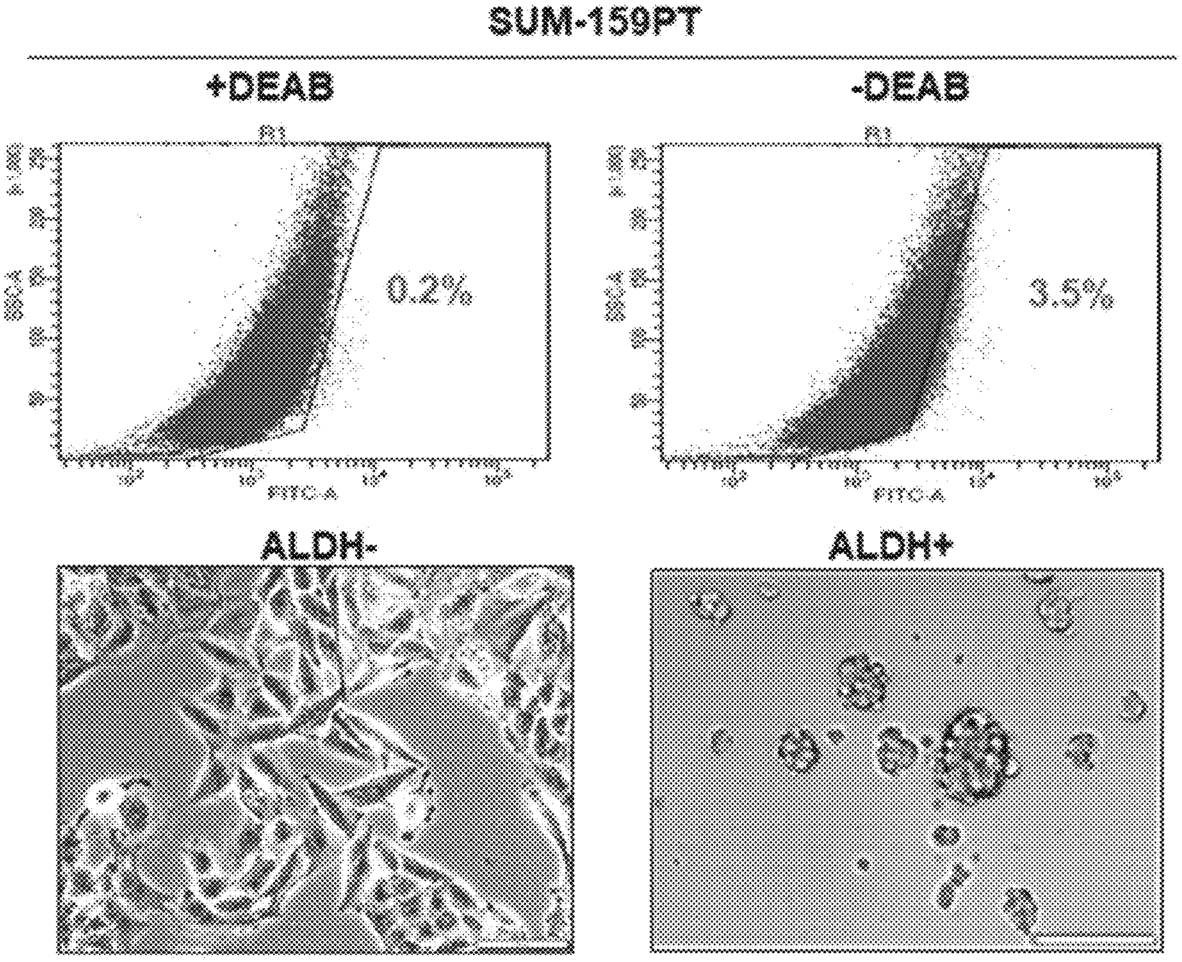

Isolated ALDH Cells are Enriched in the Expression Levels of Pluripotency Transcription Factors and Display a Higher Self-Renewal Capability As observed in FIGS. 16, 18, the pharmacological treatment with paclitaxel induced an increased level of eIF4A and the breast cancer stemness. Furthermore, genetic ablation of eIF4A in TNBC cells resulted in a decrease in breast cancer stemness (reduced expression of SOX2, OCT4, and NANOG levels) mirroring the level of eIF4A. Based on these findings, whether breast cancer stemness is causally related to eIF4A by pharmacologically targeting eIF4A was examined. RocA was employed in the study to inhibit eIF4A. In order to do so, breast cancer stem cells (BCSCs) were isolated from MDA-Bone-Un and SUM-159-PT TNBC cell lines based on the enrichment of aldehyde dehydrogenase (ALDH) activity. This was accomplished by FACS based isolation using the 'ALDEFLOUR' kit. With the DEAB inhibitor serving as the negative control, 14.6% of MDA-Bone-Un (FIG. 19A) and 3.5% of SUM-159PT (FIG. 19B) tumor cells were enriched for ALDH activity. Following isolation, the ALDH cells were maintained under low attachment conditions in poly-HEMA coated plates where the cells formed distinct mammospheres (FIGS. 19A-19B).

Figure 20A:
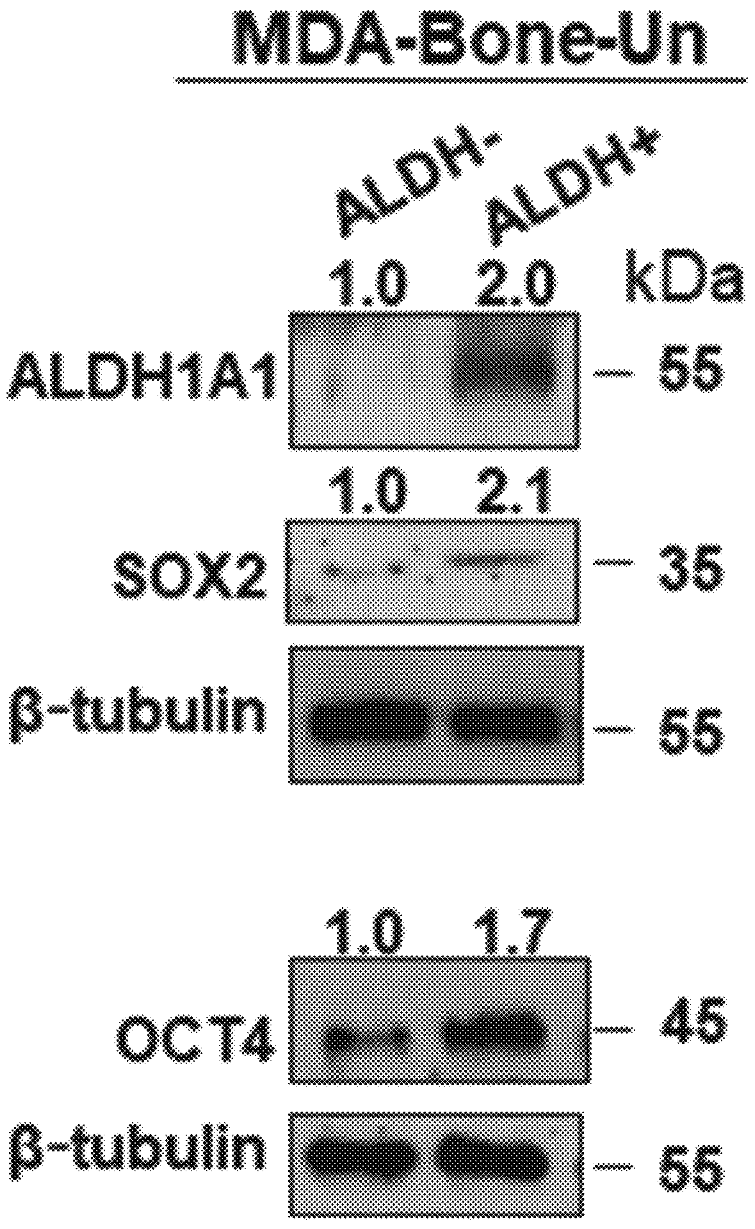
FIGS. 20A-20F: Isolated $ALDH^+$ cells are enriched in the expression of pluripotency transcription factors and display a higher ability for self-renewal.
Figure 20B:
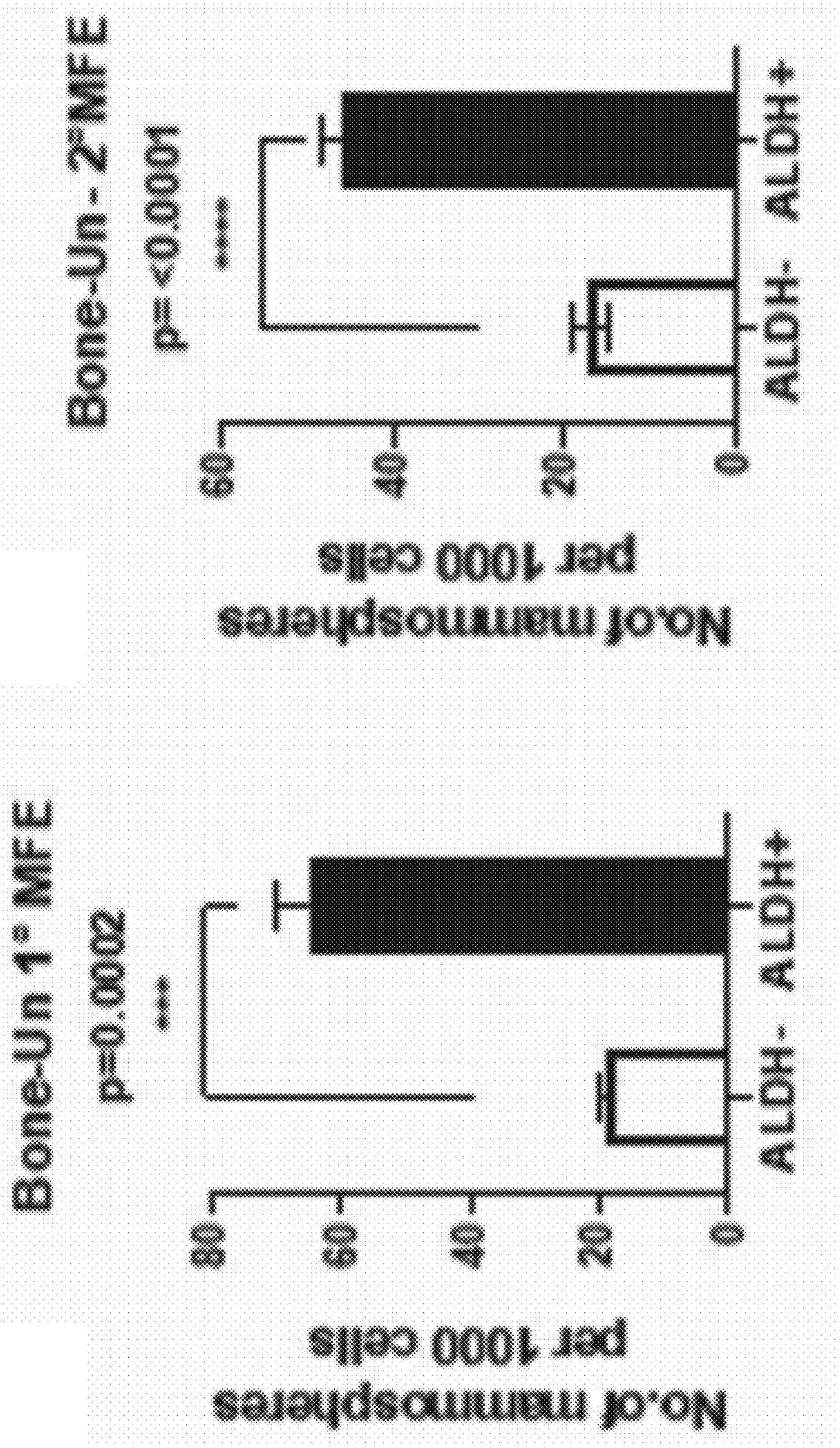
Figure 20C:
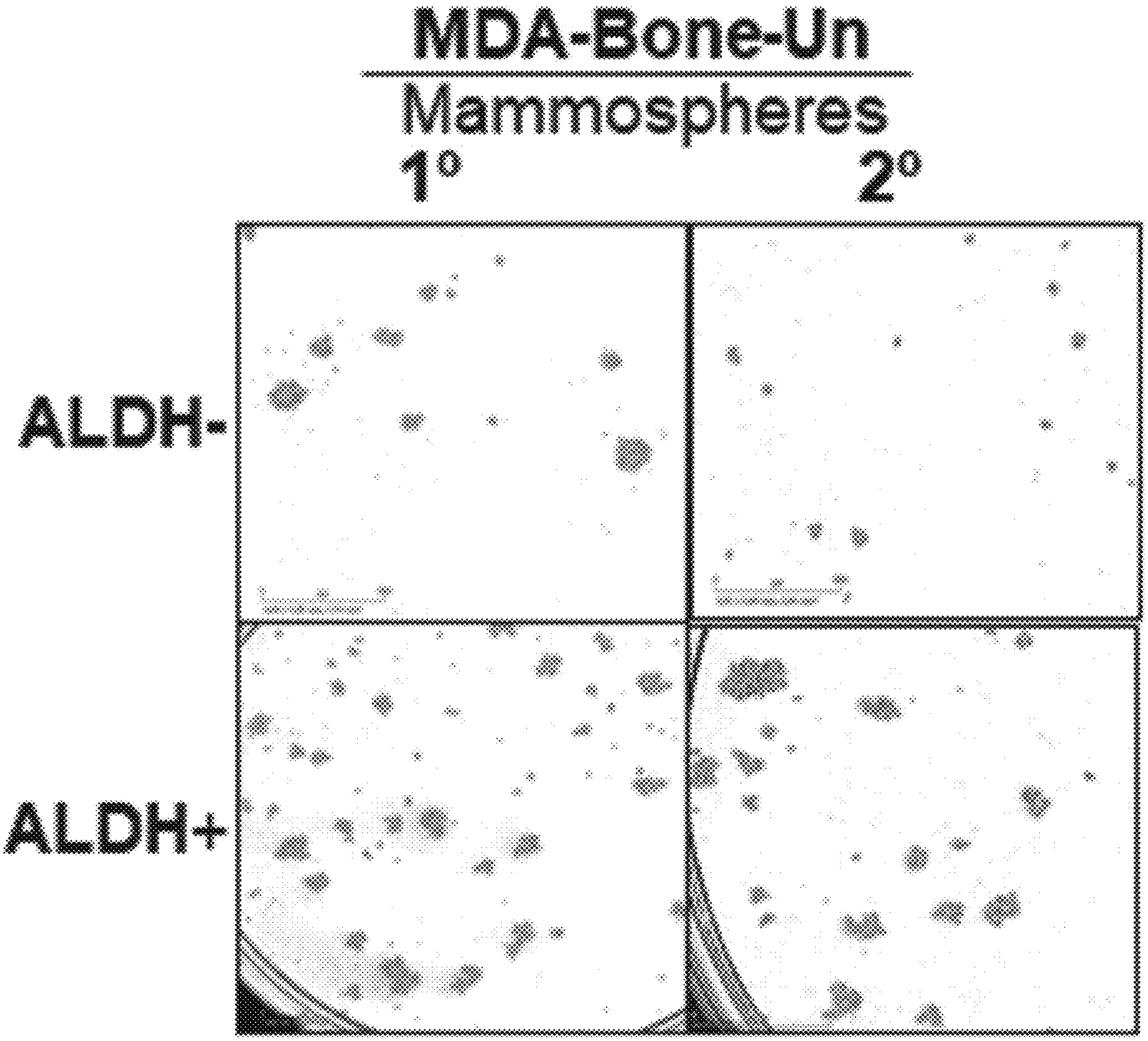
Figure 20D:
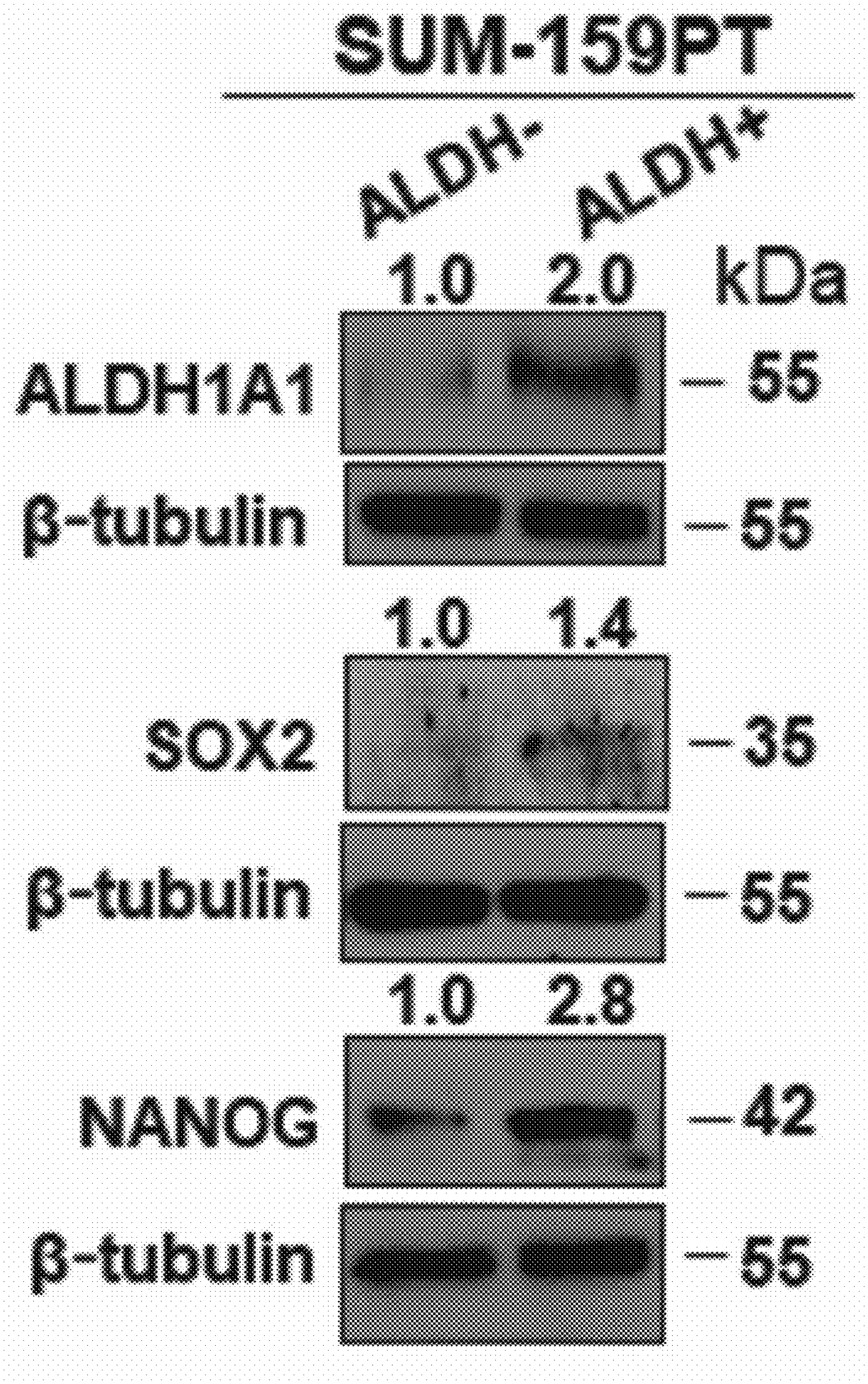
Figure 20E:
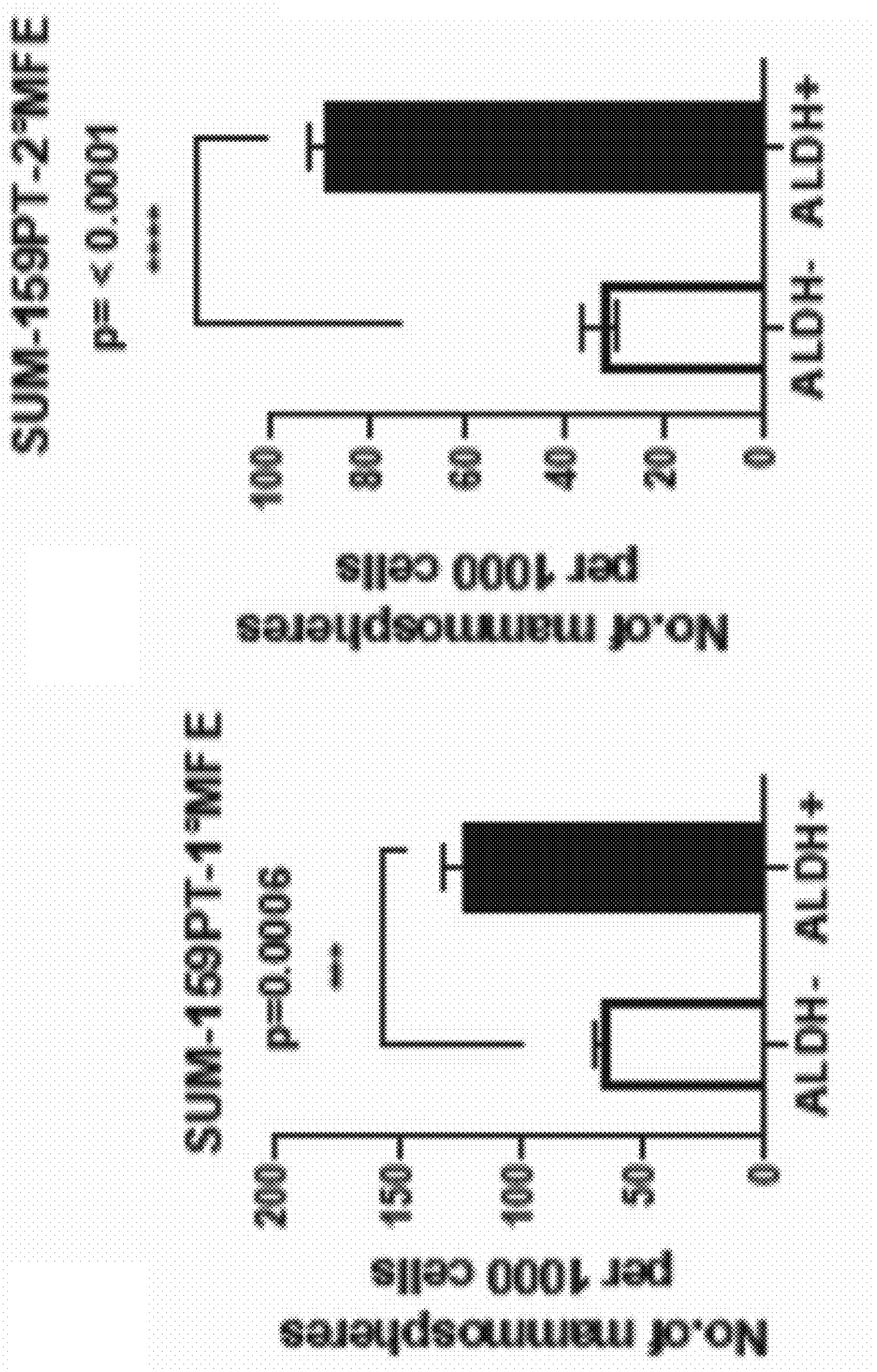
Figure 20F:
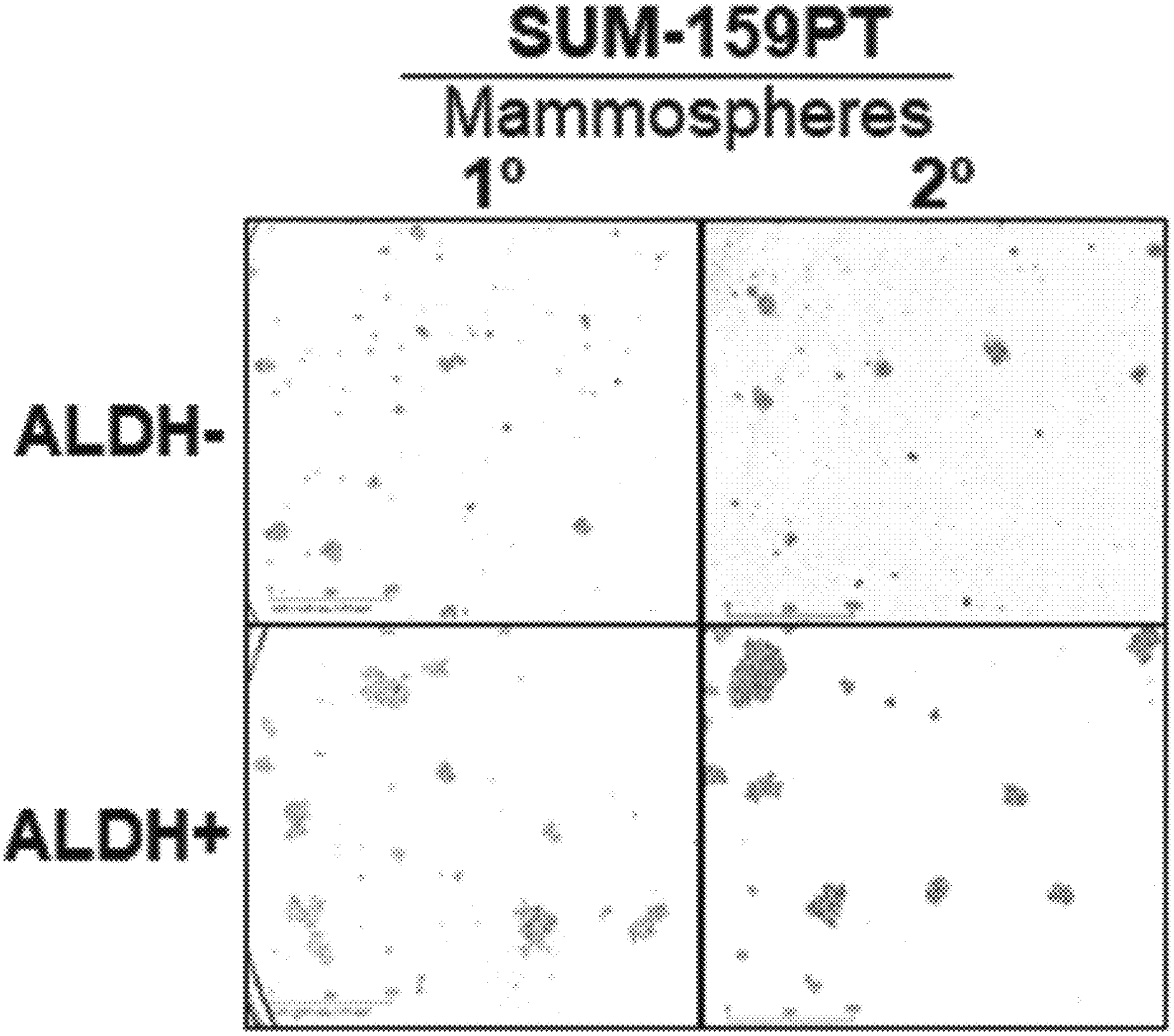

In order to evaluate whether the isolated ALDH$^+$ populations were enriched for cancer stemness, the expression level of the pluripotency transcription factors such as SOX2, OCT4, and NANOG, along with ALDH1A1 (one of the key isoforms in the ALDH family of enzymes regulating the cancer stem cell phenotype), were examined by immunoblotting of total lysates from ALDH$^+$-BCSCs. The levels of proteins implicated in pluripotency were enhanced in BCSCs with high ALDH activity. In particular, a 2-fold increase in the expression of ALDH1A1 and SOX2 and 1.7-fold increase in OCT4 levels was observed in ALDH$^+$ cells compared to ALDH$^-$ cells (FIG. 20A). The NANOG levels were comparably similar between the ALDH and ALDH$^-$ populations. Next, the ability to self-renew by the ALDH$^-$ and the ALDH$^+$ populations was compared through the determination of the efficiency of formation of the primary and secondary mammospheres (MFE). The primary (3-fold, $p<0.0002$) (FIGS. 20B-20C (left) and the secondary (3-fold, $p<0.0001$) (FIGS. 20B-20C (right) MFE were significantly higher for MDA-Bone-Un ALDH$^+$-BCSCs compared to their ALDH$^-$ counterparts. Next, the cancer stemness characteristics for the ALDH cells isolated from a second TNBC cell line, SUM-159PT cells, were similarly examined. There was a 2-fold increase in the level of ALDH1A1 protein in the BCSCs from SUM-159PT cells. The BCSCs were also enriched for SOX2 and NANOG (2.8-fold) than the ALDH$^-$ cells (FIG. 20D). The primary and the secondary MFE were also significantly higher for ALDH (2-fold, $p<0.0006$ for primary and 3-fold, $p<0.0001$ for secondary mammospheres) than the ALDH$^-$ cells (FIG. 20E(i),(ii) and FIG. 20F).

ALDH$^+$ Cells Co-Express CD44 Marker

Figure 21A:
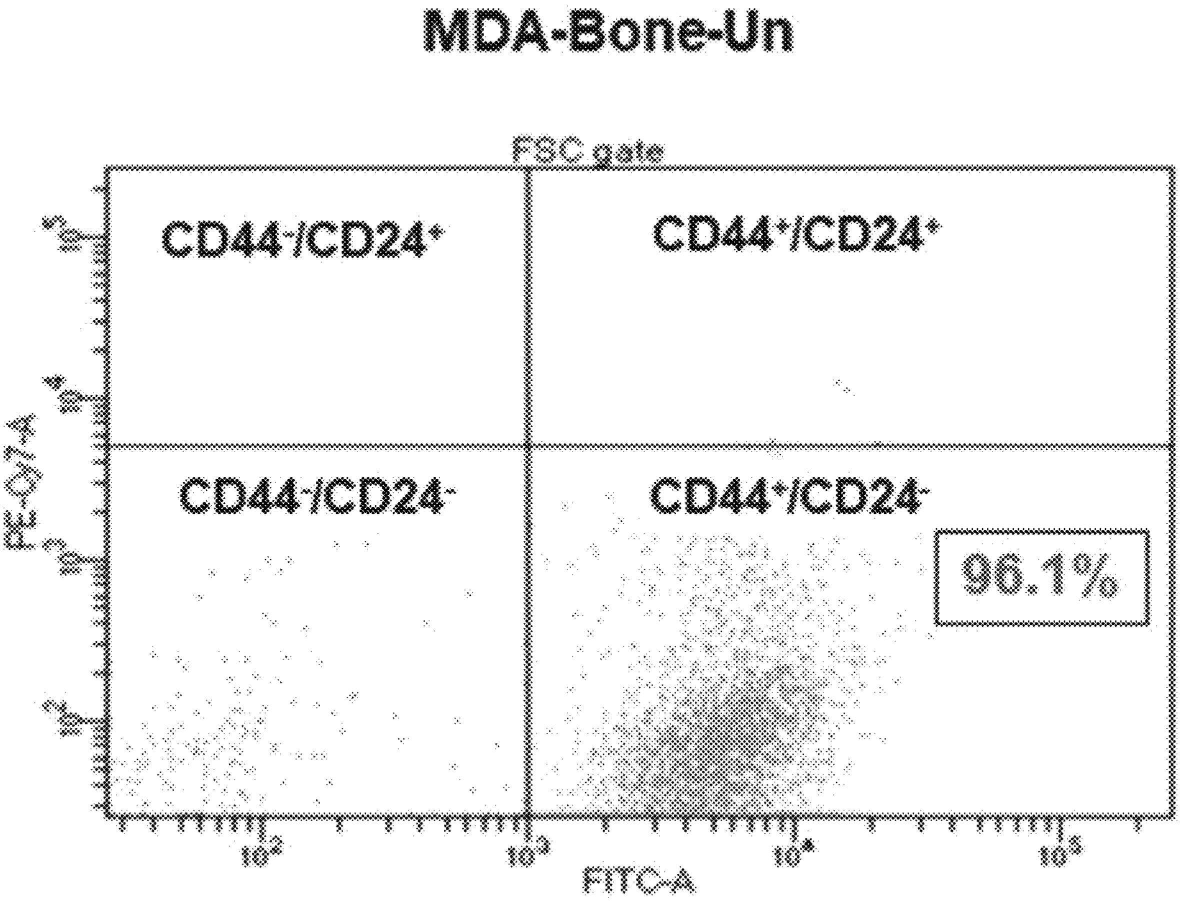
FIGS. 21-21D: $ALDH^+$ cells co-express CD44. The $ALDH^+$ BCSCs co-express CD44, the cell surface BCSC marker as assessed by flow cytometric analysis in FIG. 21A and FIG. 21C and confirmed by immunoblotting for CD44 in FIG. 21B and FIG. 21D in MDA-Bone-Un and SUM-159PT cells, respectively; (n=3).
Figure 21B:
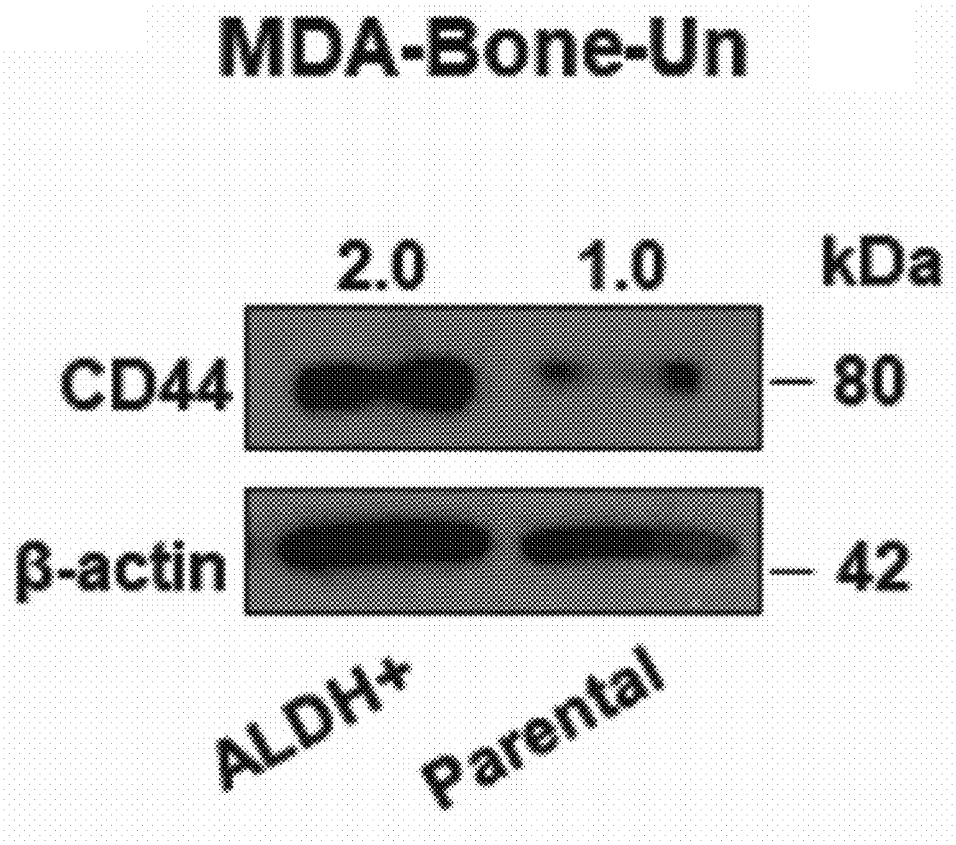
Figure 21C:
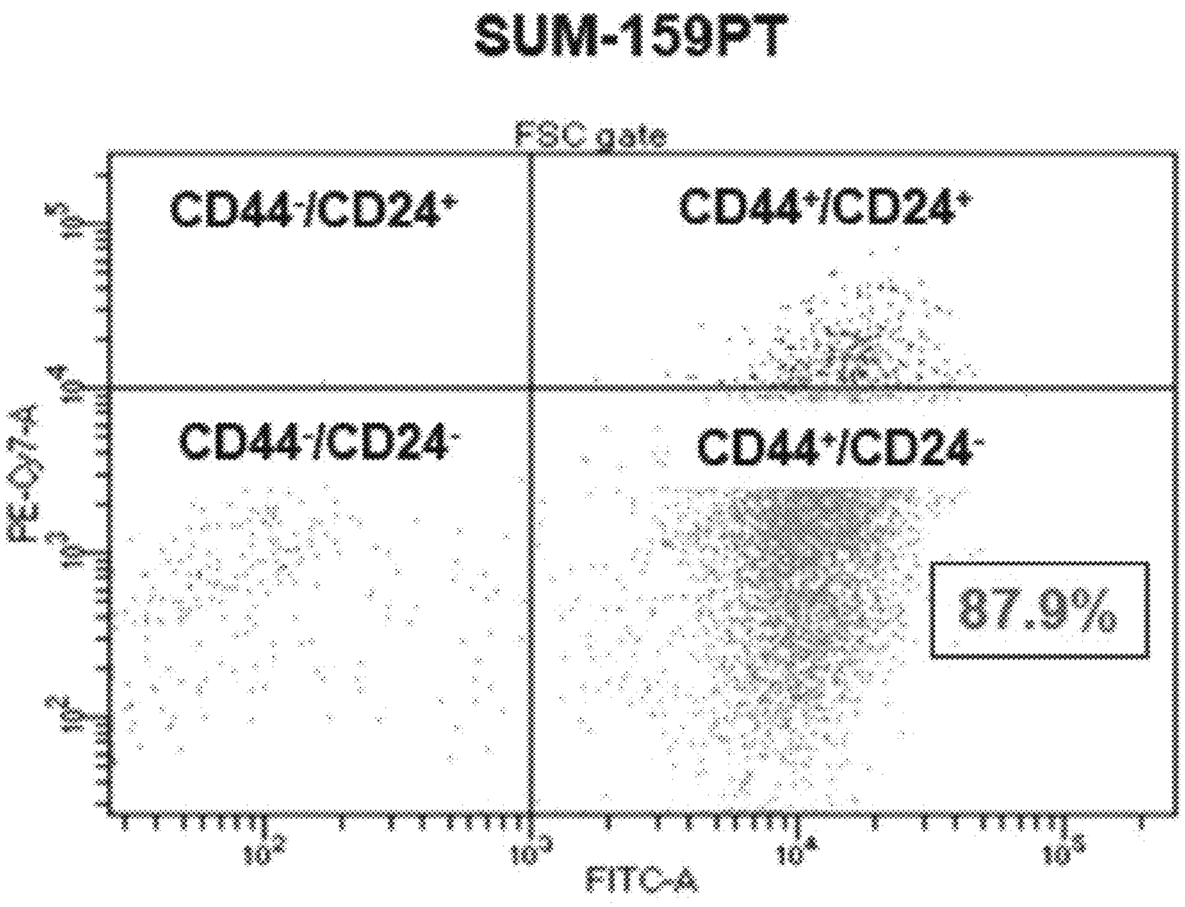
Figure 21D:
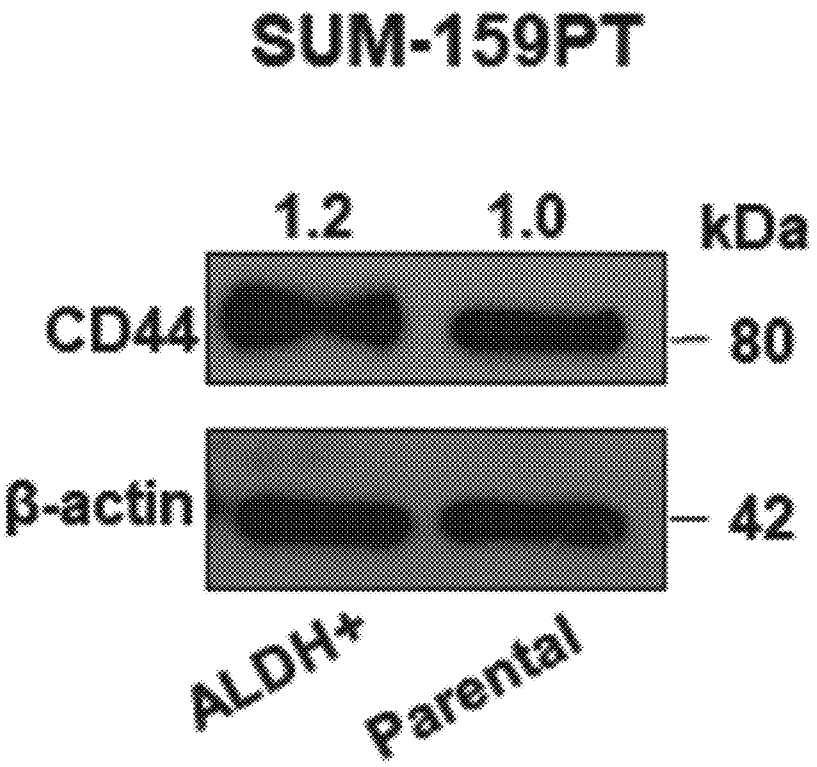

Increased ALDH activity and CD44 ($CD44^{hi}/CD24^{low}$) expression have been identified as some of the key markers for breast cancer stemness. To evaluate if the isolated ALDH cells also express CD44, its expression was examined by FACS analysis as well as immunoblotting. FACS analysis revealed that more than 90% of the isolated ALDH$^+$-BCSCs co-expressed CD44 ($CD44^{hi}/CD24^{low}$), both from MDA-Bone-Un (FIG. 21A) and SUM-159PT (FIG. 21C) cells. Further validation by immunoblotting also revealed a high co-expression of CD44 along with ALDH1A1 marker (FIG. 21B and FIG. 21D). Thus, it was confirmed that more than 90% of were ALDH and $CD44^{hi}$ and $CD24^{low}$ double positives.

Figure 22A:
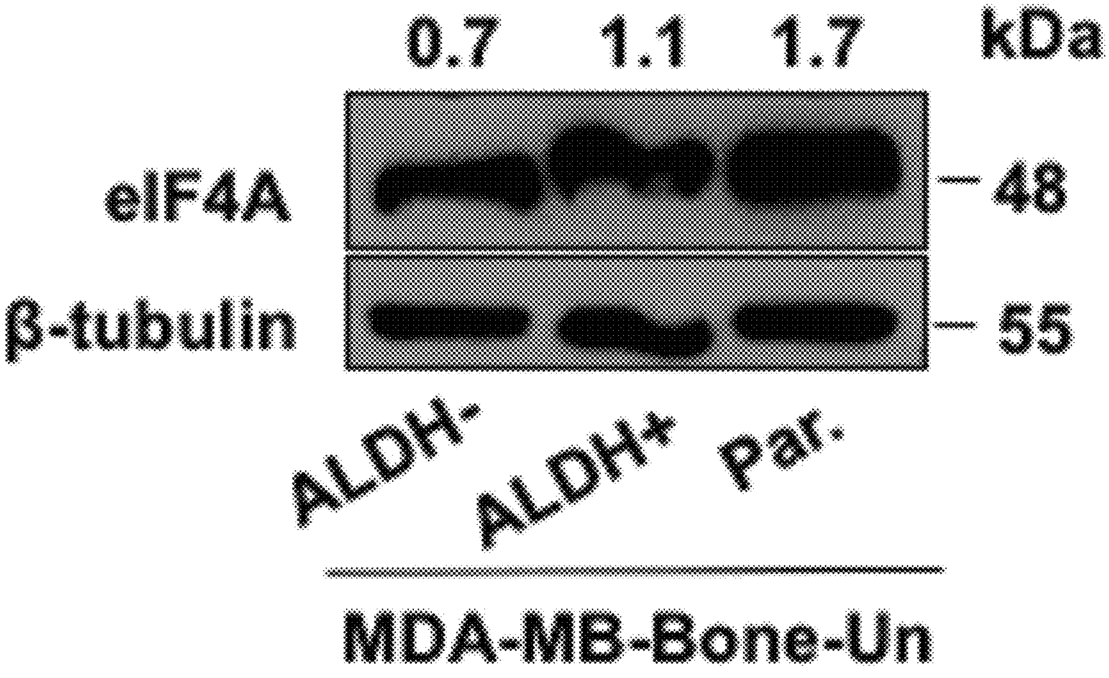
FIGS. 22A-22E: Targeting eIF4A induces cell death and reduces the self-renewal ability of BCSCs derived from MDA-Bone-Un cells.
Figure 22B:
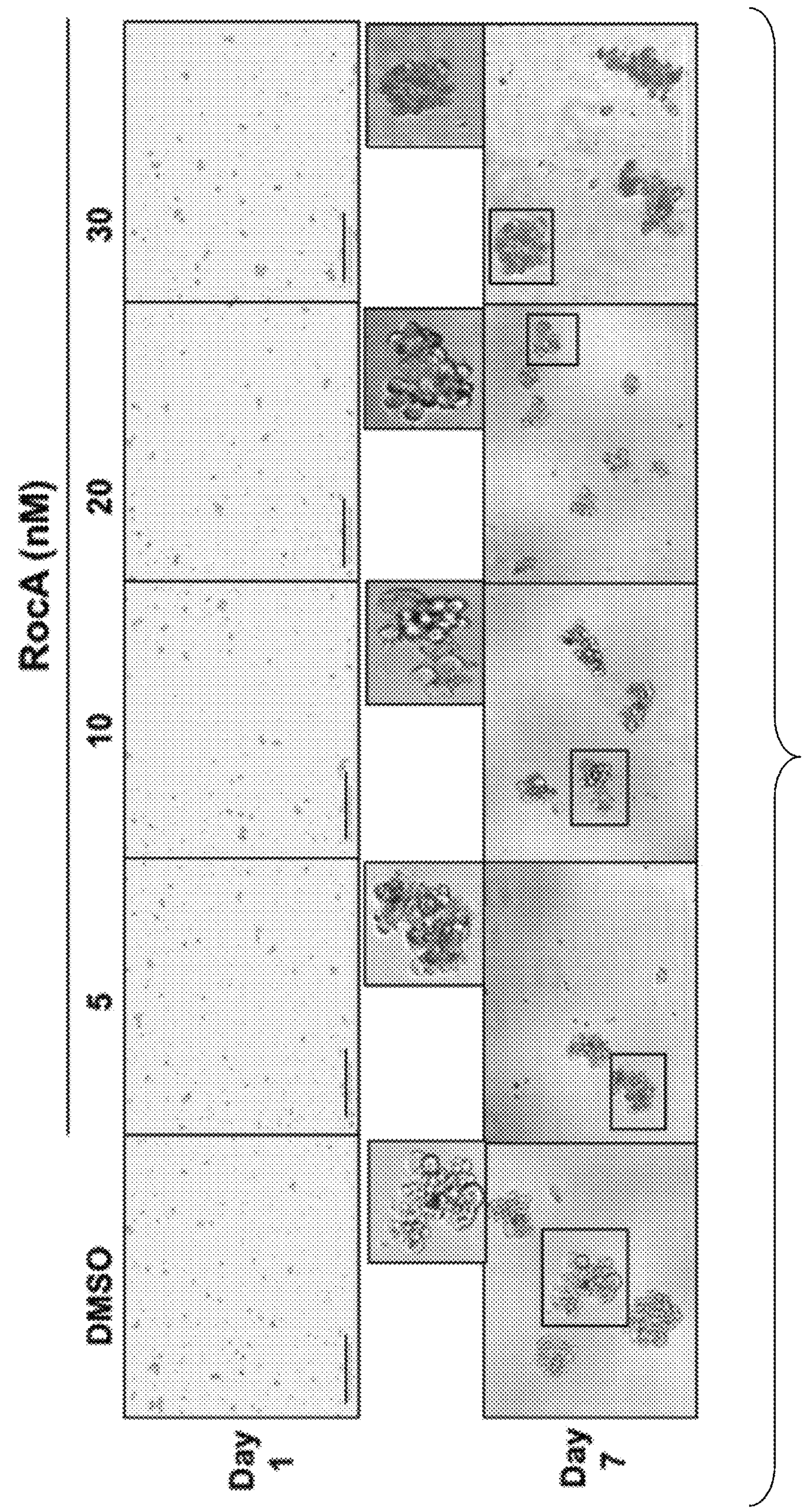
Figure 22C:
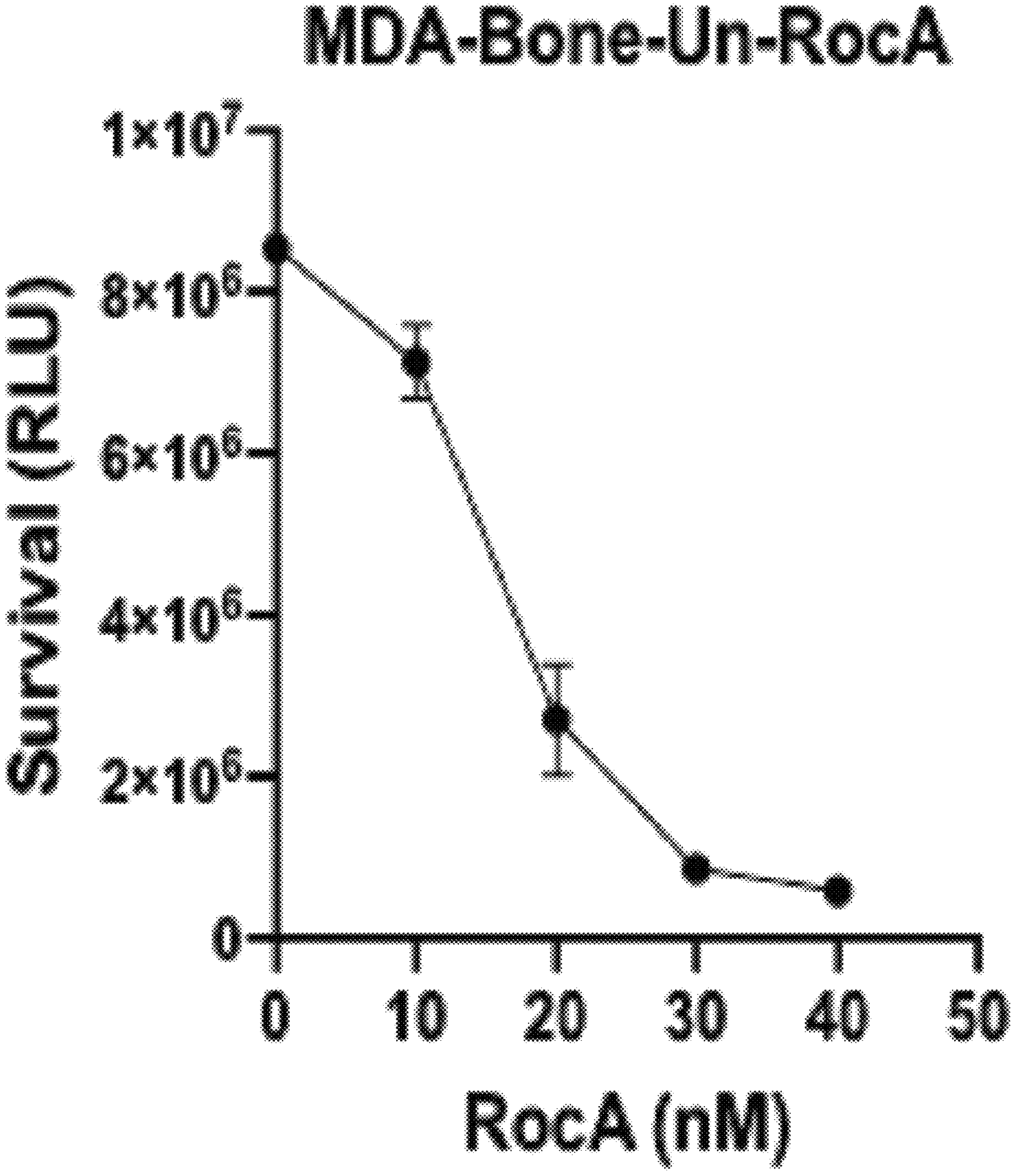
Figure 22D:
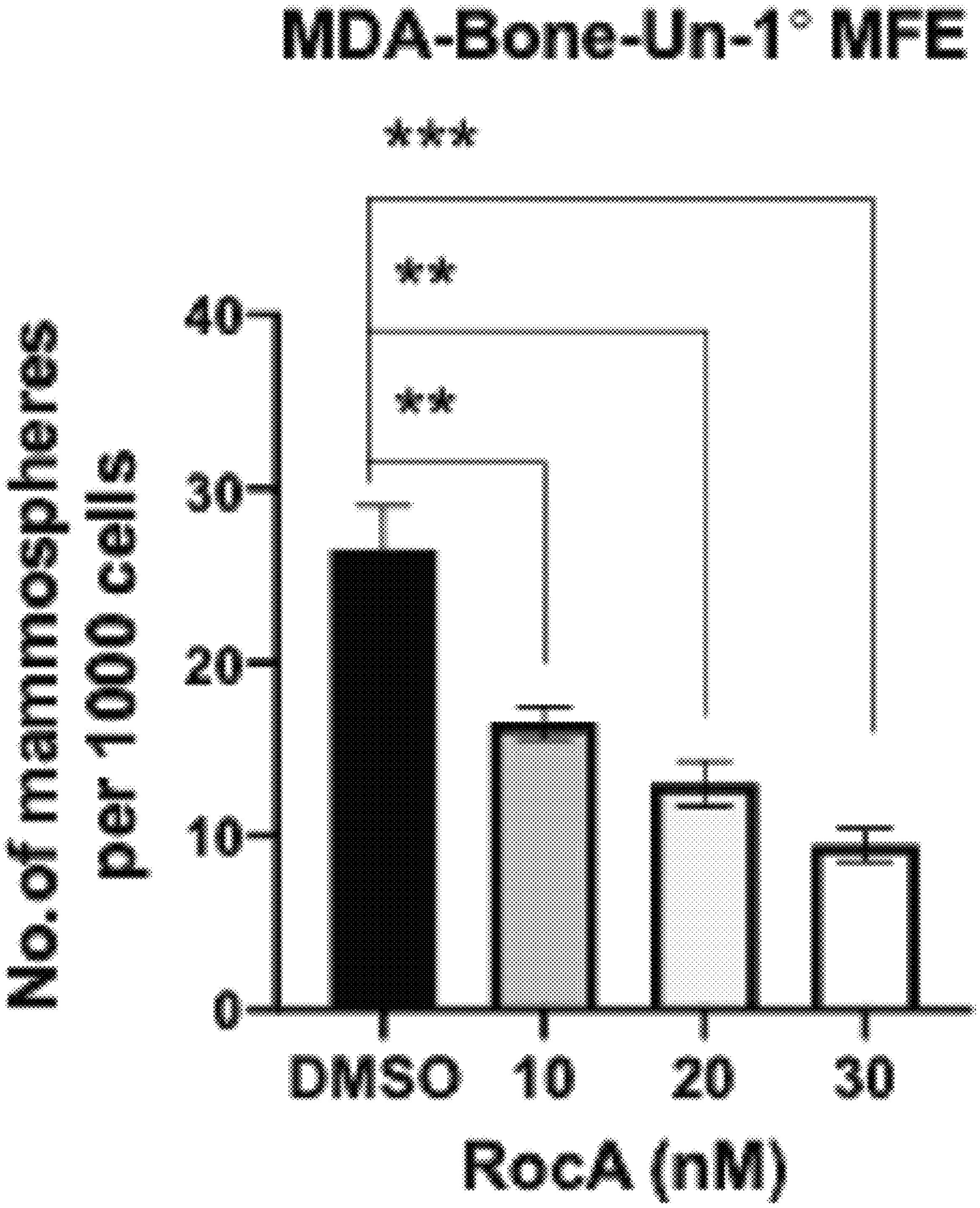
Figure 22E:
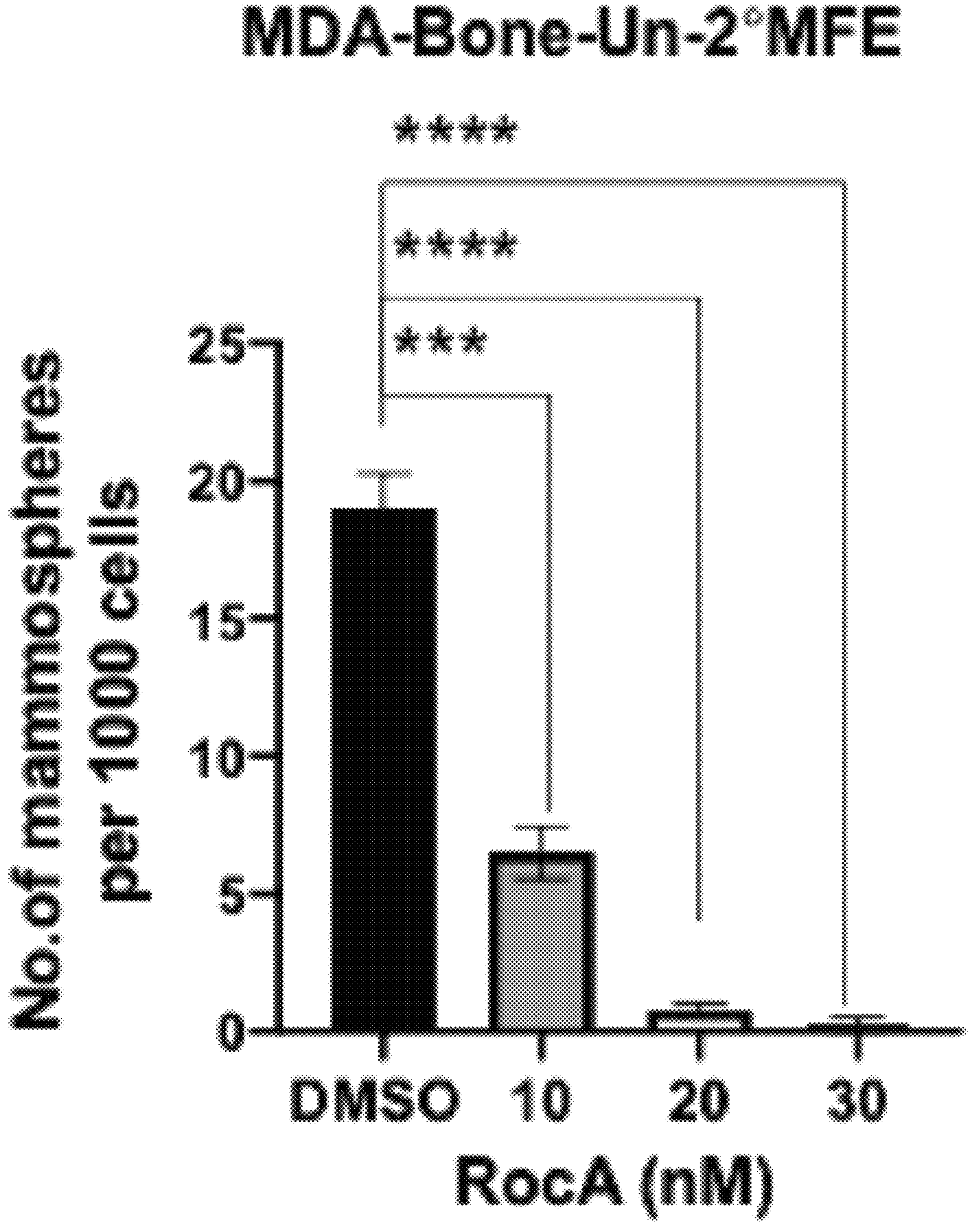

Targeting of eIF4A Induced BCSC Death and Reduction in the Self-Renewal Ability of the BCSCs As eIF4A expression dramatically increased in drug-resistant tumor cells, whether eIF4A may be a drug target in BCSCs was evaluated. Initially, whether eIF4A is expressed in the double positive BCSCs (ALDH$^+$ and CD44$^+$), ALDH$^-$ cells and the non-sorted, parental tumor population from MDA-Bone-Un cells was examined. It was found that eIF4A was consistently and uniformly expressed in parental and bulk tumor cells (ALDH$^-$ cells) and BCSCs from the MDA-Bone-Un tumor cell line (FIG. 22A). As the target eIF4A was expressed in the isolated BCSCs, RocA was employed to inhibit eIF4A. The mammospheres that were routinely cultured in 6-well dishes were uniformly seeded onto a 96-well plate under low attachment conditions and termed as "Day 1" for DMSO control and RocA treatment (5-30 nM) (FIG. 22B, top panel). To assess the impact of RocA on BCSCs, the BCSCs were continually incubated with various concentrations of RocA for 7 days. The effects of RocA on the survival and the self-renewal abilities of the BCSCs were evaluated at the end of the 7$^{th}$ day. The cell death was assessed by DRAQ7 assay. It is clearly evident that DRAQ7 failed to stain the control BCSCs while RocA treated groups demonstrated intense DRAQ7 staining depicting dead BSCSs (pseudo-colored purple) even at 30 nM of RocA (FIG. 22B, bottom panel). At higher concentrations of RocA (60-100 nM), the size of the mammospheres were reduced and more fragmented purple cellular debris was evident. Next, the cell survival (or death) was quantified by employing an alternate approach that examined the level of cellular ATP as a measure of viability using the 'CellTiter-Glo' assay. The half maximal inhibitory concentration ($IC_{50}$) of RocA was found to be 15 nM and at 30 nM nearly all BCSCs were wiped out based on the ATP level reflecting the mitochondrial activity (FIG. 22C). This correlated well with the DRAQ7 assay where almost BCSCs appear to be stained by DRAQ7 (FIG. 22B, bottom panel). Finally, the ability of the BCSCs to self-renew was assessed by the efficiency of the primary and secondary mammosphere formation (MFE). The control group formed the mammospheres efficiently under low attachment conditions (30 primary mammospheres/1000 cells). However, in the RocA-treated group, the self-renewal capability of BCSCs was significantly impaired with nearly a 50% reduction of the primary mammospheres even at 10 nM RocA concentration ($p<0.0001$) (FIG. 22D). The secondary MFE was severely impacted at 10 nM RocA with a significant reduction in the mammospheres ($p<0.0001$) (FIG. 22E).

Figure 23A:
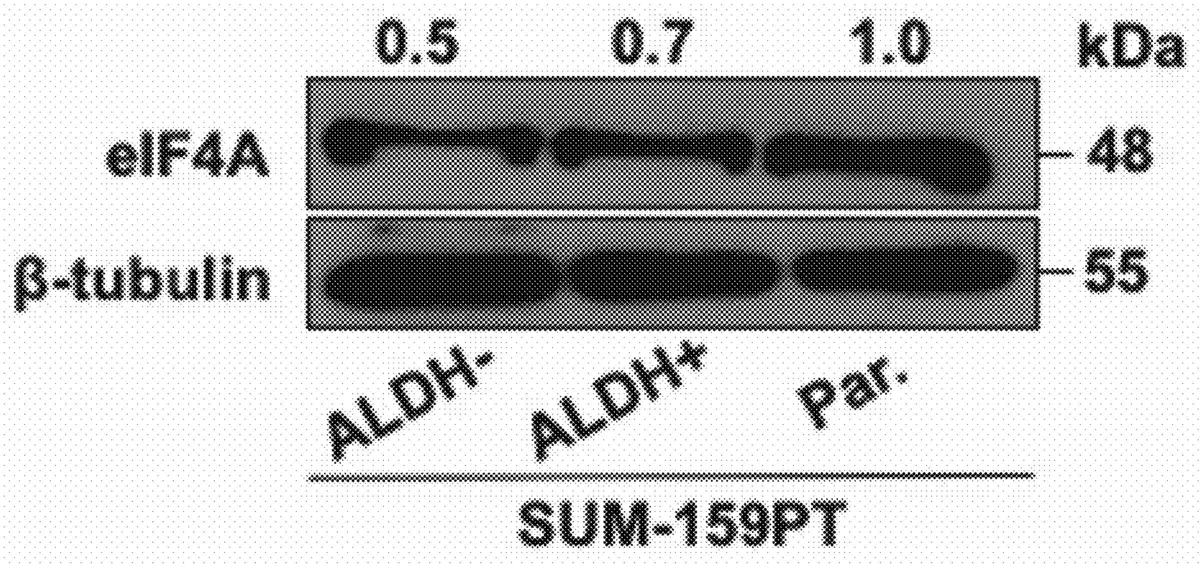
FIGS. 23A-23E: Targeting eIF4A induces cell-death and reduces the self-renewal ability of BCSCs derived from SUM-159PT cells.
Figure 23B:
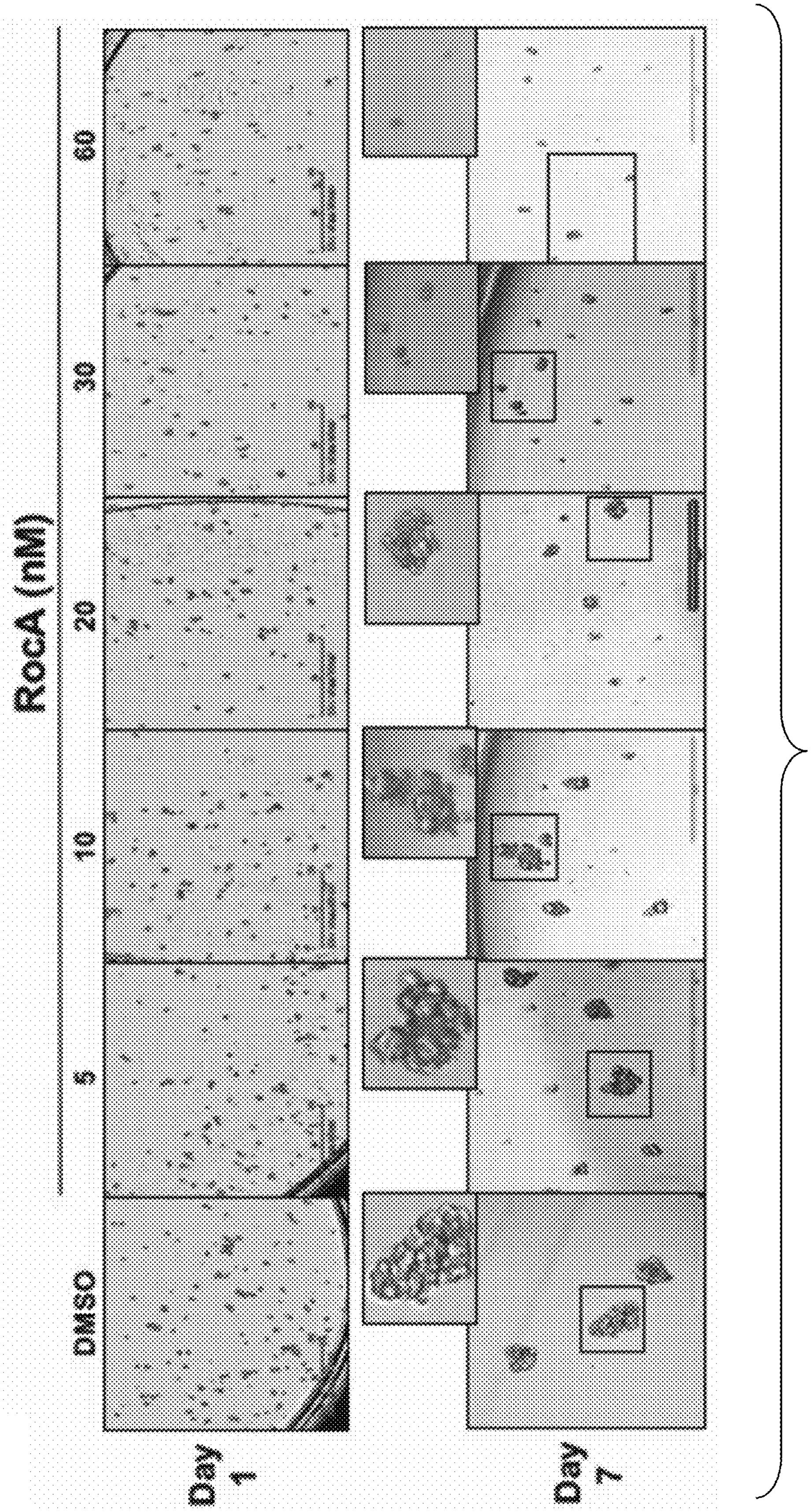
Figure 23C:
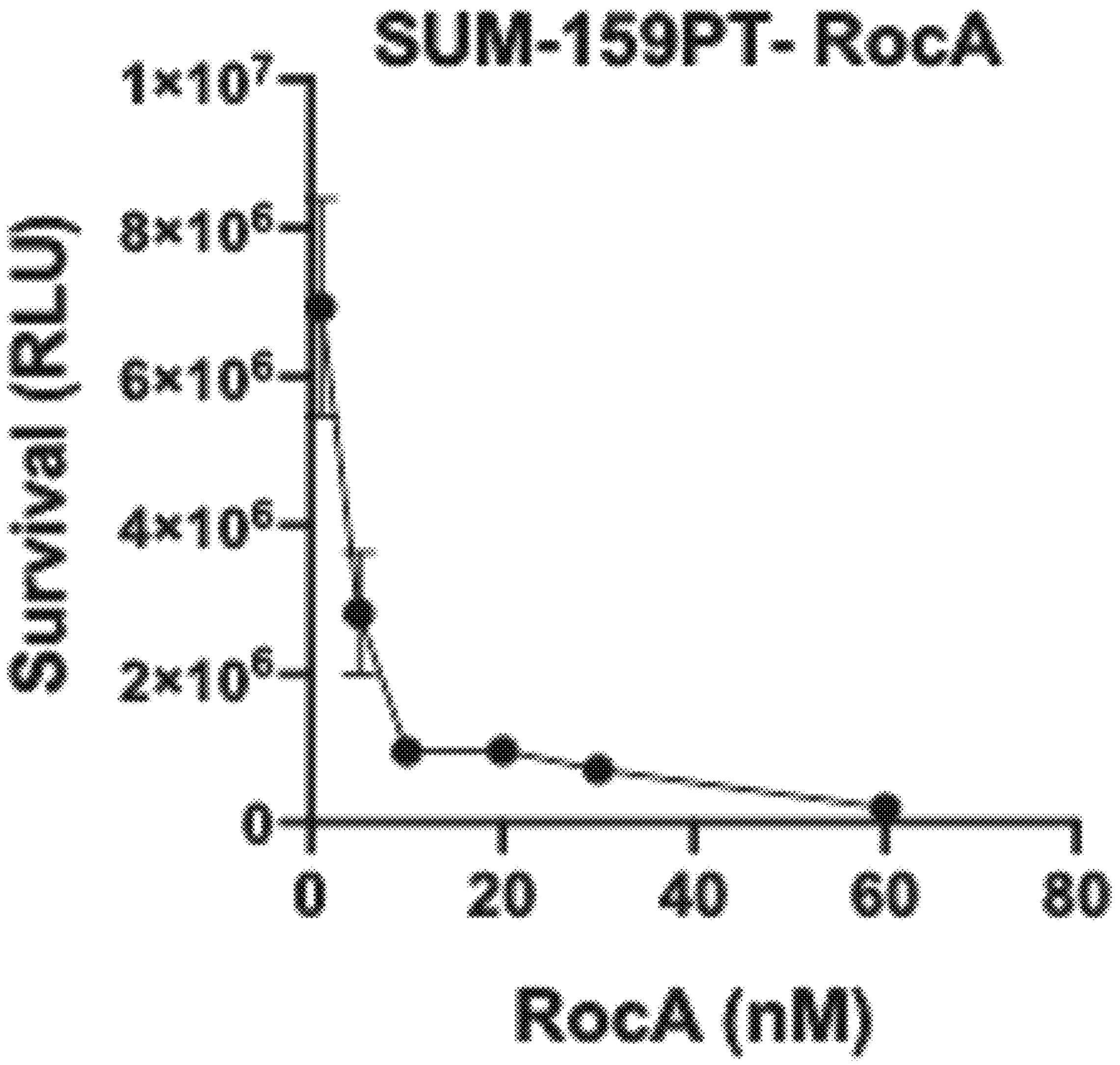
Figure 23D:
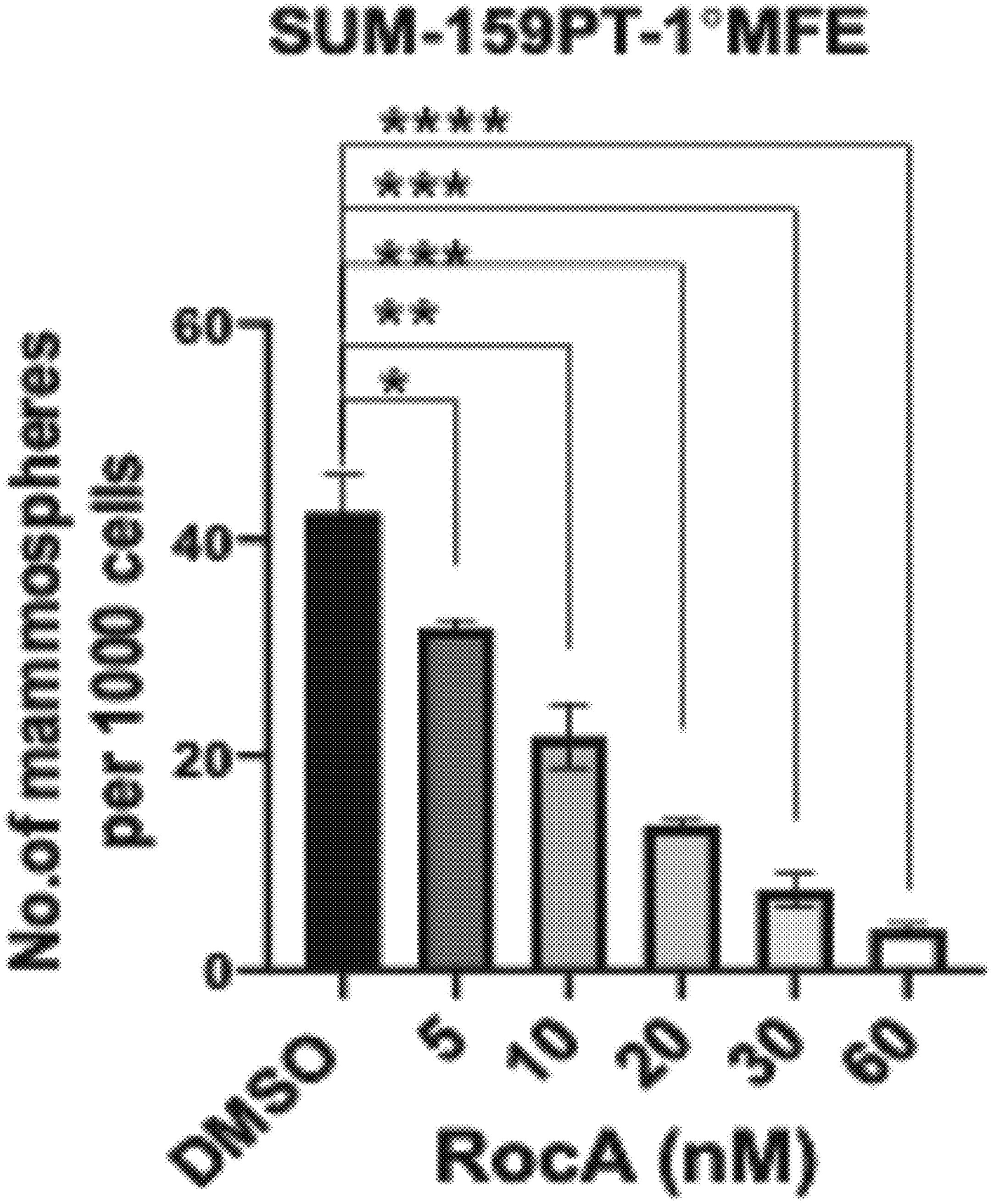
Figure 23E:
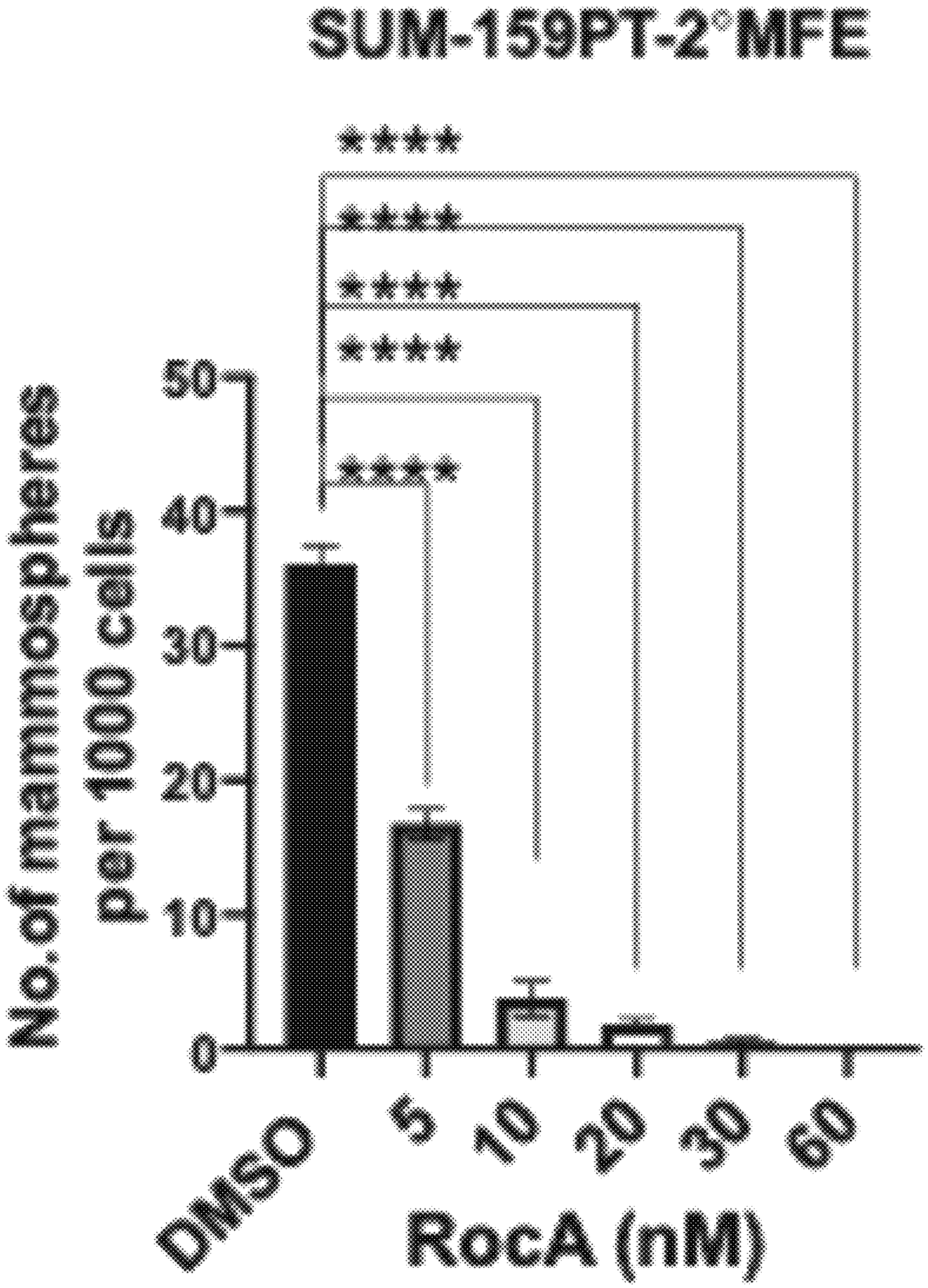

Next, eIF4A was targeted pharmacologically in the BCSCs derived from a second cell line SUM-159-PT. eIF4A was uniformly expressed in the parental, bulk tumor cells (ALDH⁻ cells) and BCSCs (FIG. 23A). As the BCSCs from SUM-159-PT cells were found to be more sensitive to RocA, the efficacy of RocA in inducing cell death was examined from 5-60 nM (FIG. 23B). More than 50% of the BCSCs were intensely stained with DRAQ7 at 5 nM of RocA. At higher concentrations of RocA, a similar trend was observed, i.e., intense staining of 50% of the cells but also additional milder staining of more cells was noted. Next, the viability was evaluated by the CellTiter-Glo' assay (FIG. 23C). When BCSCs were incubated with 5 nM RocA, more than 50% of cells were dead as opposed to 15 nM of RocA for BCSCs derived from MDA-Bone-Un for a similar outcome. With regard to the formation of the primary mammospheres, there was a 50% reduction at 10 nM RocA which further plummeted at higher concentrations of RocA (FIG. 23D). The decrease in secondary MFE was more drastic (FIG. 23E).

Figure 24A:
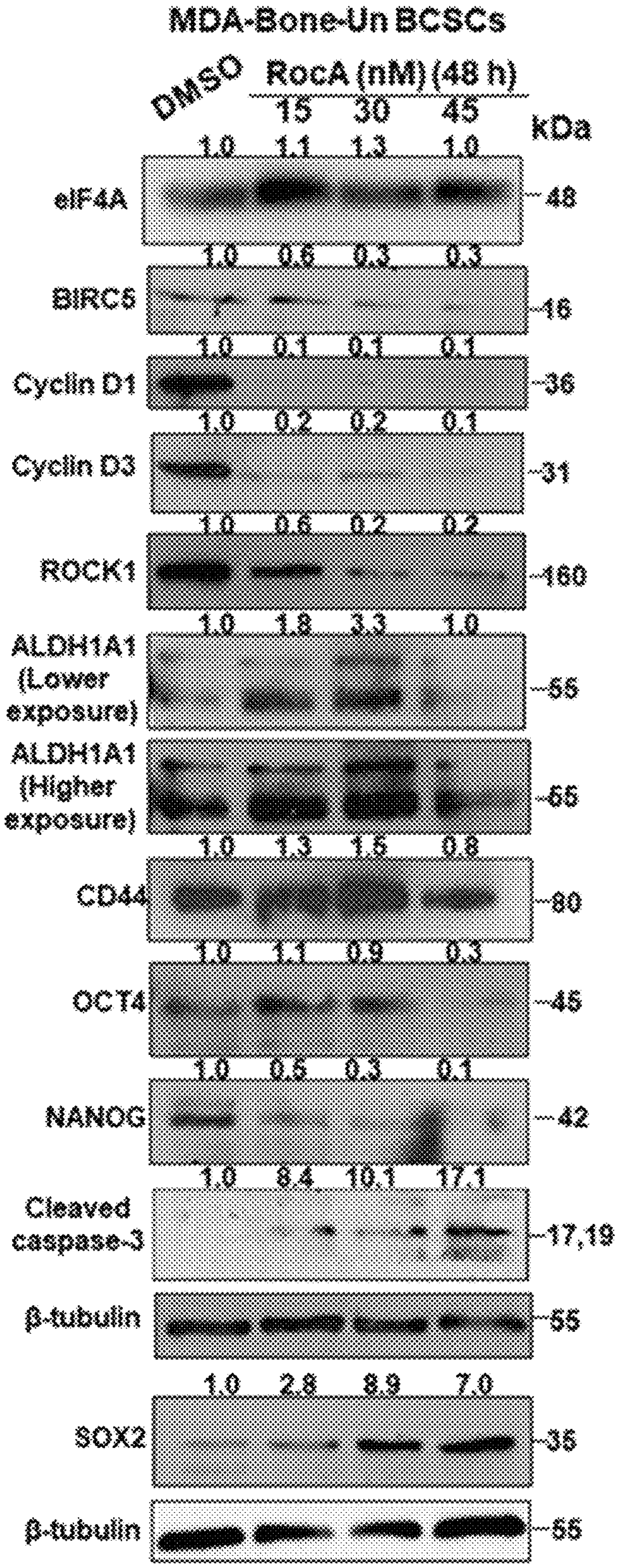
FIGS. 24A-24C: Targeting of eIF4A in BCSCs derived from MDA-Bone-Un cells affects the pluripotency transcription factors, ALDH1A1, drug transporter ABCB1, and induced apoptotic cell death.
Figure 24B:
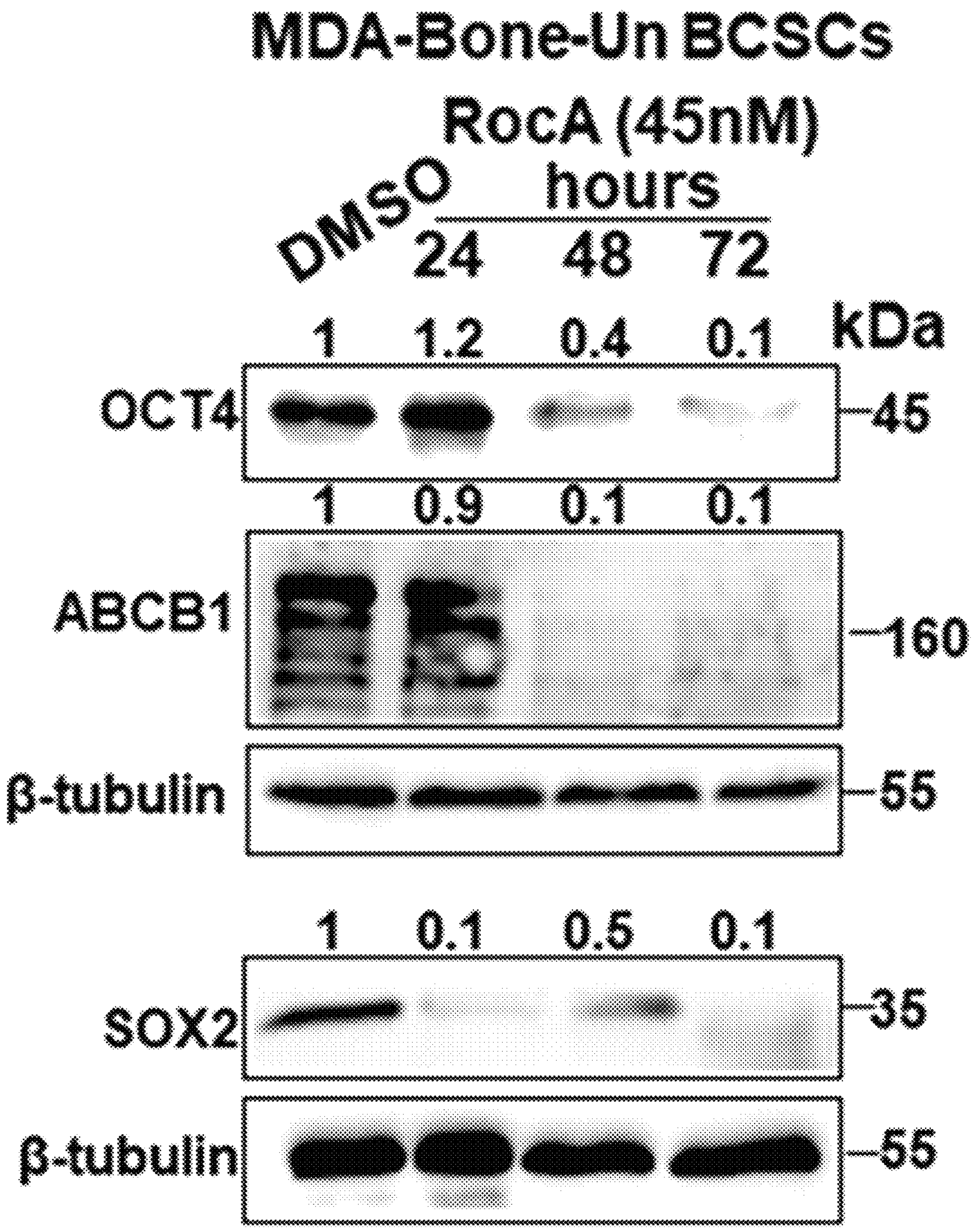
Figure 24C:
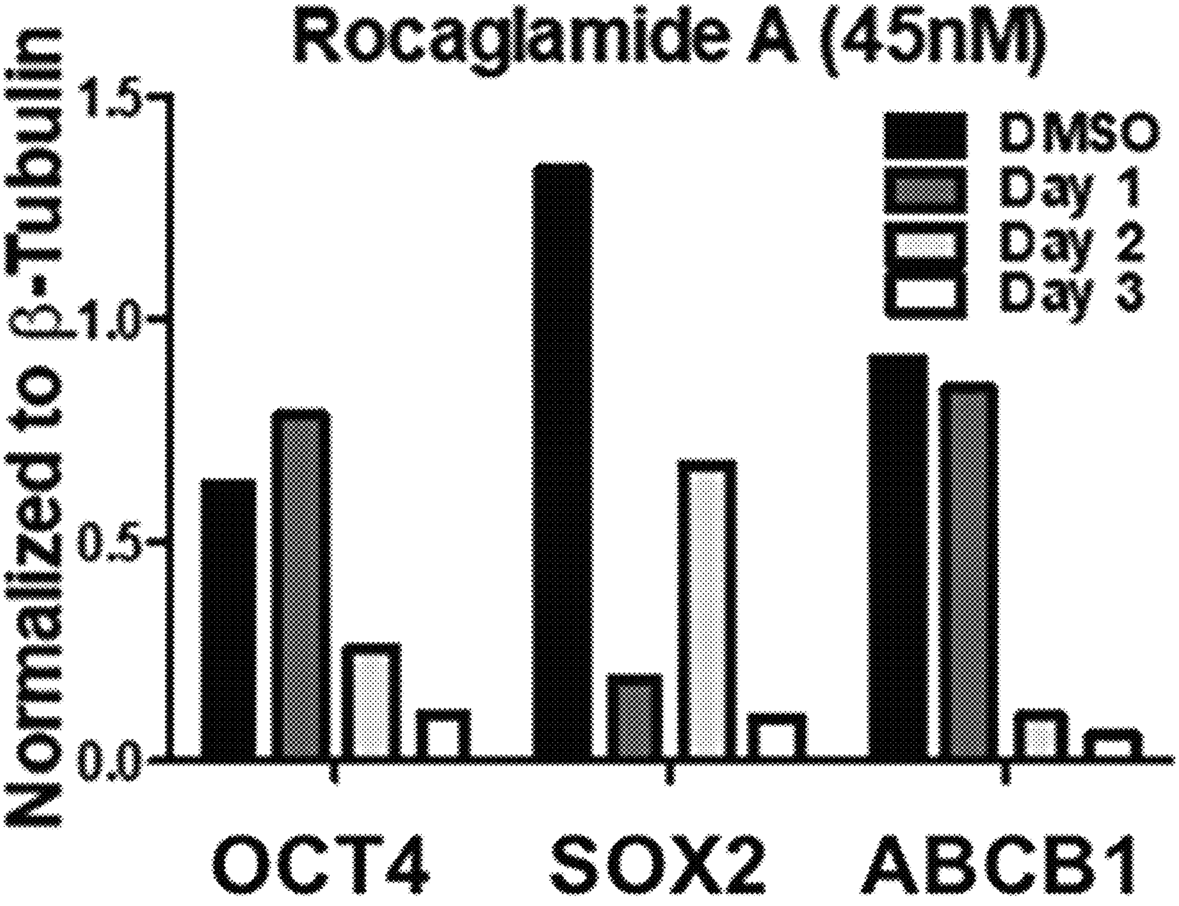
Figure 25A:
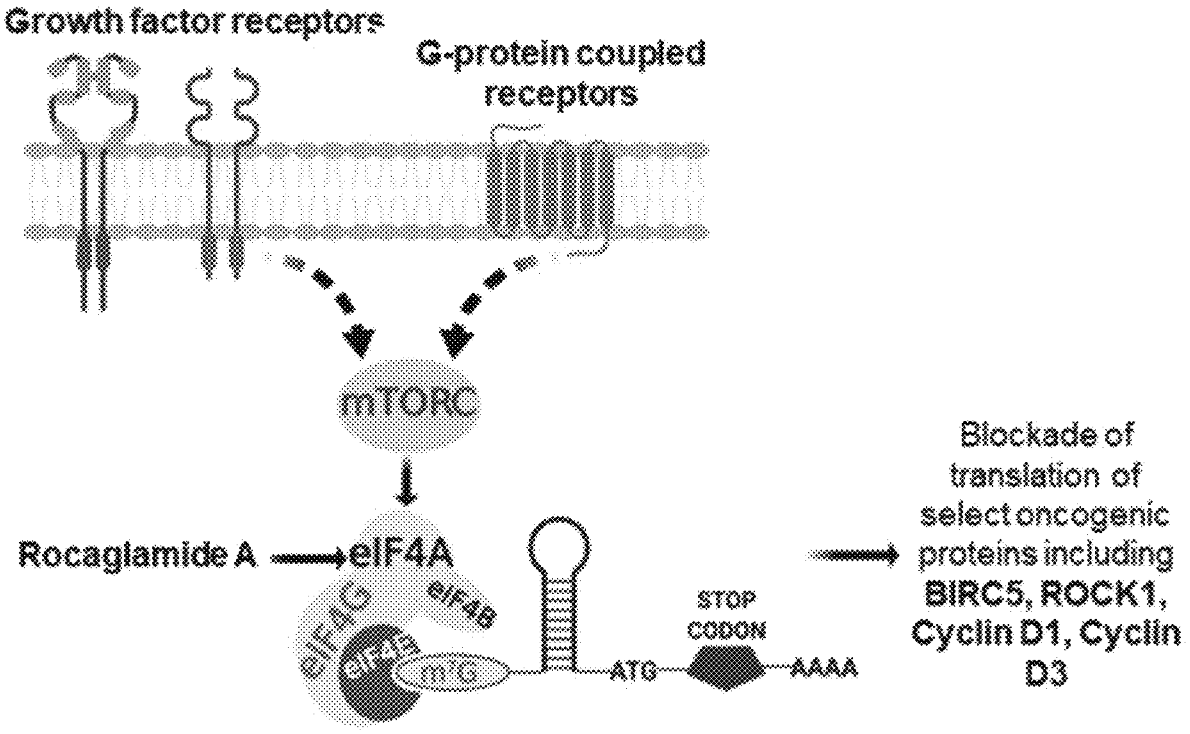
FIGS. 25A-25B: Diagrammatic illustration of the effects of targeting eIF4A.
Figure 25B:
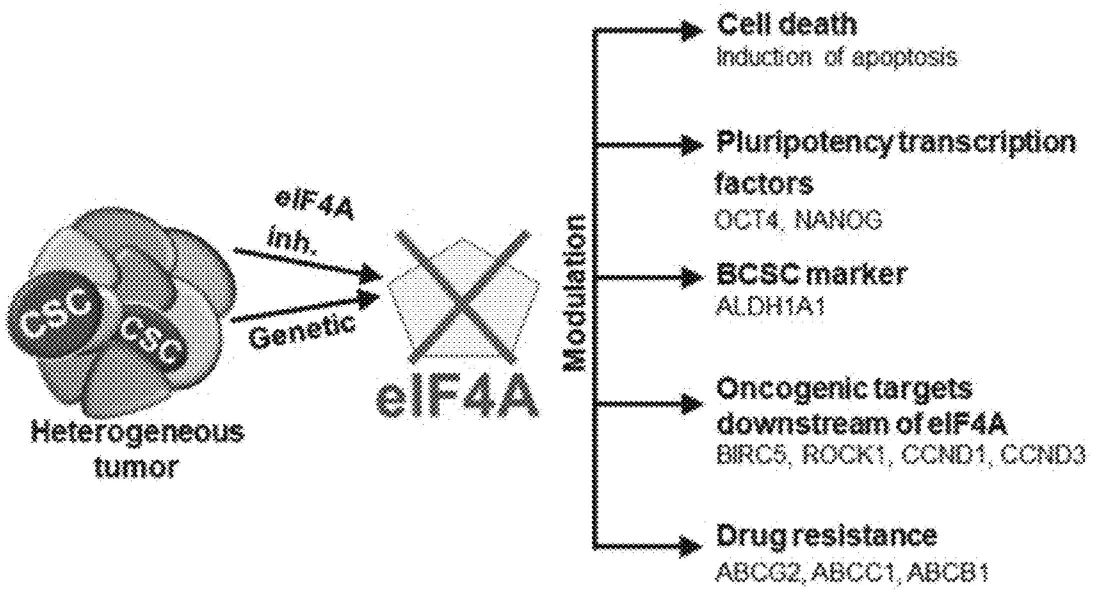

Pharmacological Targeting of eIF4A in MDA-Bone-Un BCSCs Affects the Expression of Pluripotency Transcription Factors, ALDH1A1, and Induces Apoptotic Cell Death To assess the mechanism of cell death in RocA-treated BCSCs from MDA-Bone-Un, BCSCs were treated with 15, 30, and 45 nM of RocA for 48 h (short-term exposure as opposed to the chronic paclitaxel treatment). Initially, whether RocA had hit the target eIF4A was assessed by immunoblotting for the expression of the downstream effectors (BIRC5, Cyclin D1, Cyclin D3, and ROCK1) of eIF4A activity. Following treatment, a dramatic reduction in the expression of BIRC5, Cyclin D1, Cyclin D3, and ROCK1 was observed (FIG. 24A). RocA treatment did not affect the total protein level of eIF4A. Having confirmed that the activity of eIF4A was compromised following RocA treatment, whether the level of the pluripotency transcription factors would be modulated was tested. Of the three transcription factors examined, the expression of NANOG was significantly reduced (a 2- and 10-fold reduction in NANOG level at 15 and 45 nM RocA respectively). OCT4 was reduced by 3.3-fold at 45 nM RocA level while the SOX2 level remained elevated above the basal level at all concentrations of RocA for 48 h. The levels of the BCSC markers ALDH1A1 and CD44 were not affected at 48 h. Importantly, there was an induction of cleaved caspase-3 (up to 17.1-fold increase) when treated with RocA. This clearly indicates that cell death in BCSCs occur through apoptosis following the RocA treatment (FIG. 24). Next, the concentration of RocA was fixed at 45 nM and the levels of OCT4, SOX2, and ABCB1 were examined over 72 h. The 3 biological replicates were pooled and analyzed. OCT4 decreased by 2.5-fold at 48 h and 10-fold at 72 h. SOX2 level decreased by 10-fold in 24 h and increased back by 2-fold in 48 h. At 72 h, degradation of SOX2 was observed though the loading control β-tubulin band was intact. Importantly, the ABC transporter ABCB1 was dramatically reduced by 10-fold at 48 and 72 h. The normalized ratiometric quantitation is shown in the graph in FIG. 24C. A general schema of various molecular signaling pathways impinging on eIF4A and the impact of RocA on oncogenic targets in BCSCs and the resultant outcome are presented pictorially in FIGS. 25A-25B.

Discussion

Oncogenic protein synthesis is a tightly regulated process, with translation initiation being the rate limiting step governed by the eIF4F complex. The eIF4F complex consists of three core subunits: eIF4E, the cap binding subunit; eIF4A, an RNA helicase; and eIF4G1, a large scaffolding protein. The auxiliary protein eIF4B enhances the activity of eIF4A. The core component eIF4A has been documented to promote the translation of oncogenic mRNAs with stem-loop structure (SLS) in their 5'-untranslated region (5'-UTR) in cancer. The resultant oncoproteins constitute the rewired pro-tumor proteome that is vital for breast cancer cell survival, tumor progression, local invasion, and metastasis.

The role of the eIF4F complex is increasingly evident in all types of solid tumors and hematological malignancies. Chemoresistance and therapy failure is a frequent clinical issue in cancer patients. Interestingly, the eIF4F complex is reported to form a *nexus* of drug resistance to antineoplastic therapies in melanoma. Disrupting the eIF4F complex formation by targeting eIF4A and other core subunits has been shown to synergize with BRAF inhibitors. Thus, targeting of the eIF4F complex can alleviate the drug resistance or sensitize cancer cells to other forms of chemotherapy. The role of eIF4A in breast cancer has not been extensively studied. Suppression of eIF4A activity is believed to affect maintenance and progression of breast cancer, and the expression of eIF4A and eIF4B can predict the clinical outcome in estrogen receptor-negative (ER−)breast cancer independently from other known prognostic factors. eIF4A is a clinically relevant target in combating chemoresistance and therapy failure in metastatic breast cancer.

As discussed in Example I above, the CXCR4-LASP1-eIF4A axis promotes translation of oncogenic proteins such as survivin, cyclin D1, MDM2, and ROCK1 in TNBC. In this example, it is demonstrated that there is an upregulation in the level of eIF4A following chronic paclitaxel treatment in SUM-159-PT cells. This change in eIF4A level positively correlated with the protein level of its downstream targets such as survivin and cyclin D1, reflecting an increase in enzymatically active eIF4A in the paclitaxel-resistant TNBC cells. This was accompanied by an increase in breast cancer sternness (SOX2, OCT4, and NANOG levels) and significant increase in the levels of key drug transporters (ABCG2, ABCB1, and ABCC1). The associated morphological changes appeared to be pro-migratory in nature. This is similar to a clinical situation where the patients have been subjected to multiple clinical trials or receiving multiple drugs over a period of time. On the contrary, the CRISPR-Cas9-mediated genetic ablation of eIF4A in MDA-Bone-Un cells (MDA-MB-231 cell line that had undergone mesenchymal-epithelial transition at the metastatic site as this was re-isolated from mouse bone metastatic lesions) resulted in altered morphology. The eIF4A-KO led to a severe reduction in the expression of its target genes validating the genetic loss of eIF4A. The expression of the pluripotency transcription factors SOX2, OCT4, and NANOG was impaired, which will reduce the sternness and render them more susceptible to therapy. Interestingly, the ALDH1A1 level decreased dramatically and rendered these cells susceptible to chemotherapeutic drugs as a result of impairment of the ability to detoxify drugs. The selective decrease in the level of ALDH1A1 was interesting as the level of the other major BCSC marker CD44 was unaltered. This explains their susceptibility to RocA and also sensitization to other therapeutic agents, as the upregulation of the ALDH activity is correlated with high tumorigenic potential, self-renewal capability, and the generated tumors from the minimal residual disease recapitulate the heterogeneity of the parental tumor. Importantly, the ALDH1 detected by immunohistochemical staining has been correlated with poor prognosis. Furthermore, the key drug transporter levels (ABCG2 and ABCC1) were greatly reduced. This is a noteworthy finding as targeting of eIF4A sensitizes the tumor cells to tumor necrosis factor-related apoptosis-inducing ligand (TRAIL)-induced apoptosis or break TRAIL resistance in tumor cells.

The uniform presence of eIF4A in parental, BCSCs, and $ALDH^-$ cells (bulk tumor cells) indicates that targeting of eIF4A eliminates both bulk tumor cells and BCSCs simultaneously. Blocking the activity of eIF4A in BCSCs through RocA treatment curtailed the self-renewal capability, as indicated by the significant decrease in primary and secondary MFE. NANOG level was severely reduced while OCT4 level plummeted at 45 nM RocA. The variability in levels of SOX2 was observed in the first 48h of RocA treatment, but by 72 h even SOX2 was observed as degraded products. The regulatory pathways downstream of NANOG through its direct or indirect activity regulates several aspects of tumorigenesis, self-renewal, epithelial-mesenchymal transition (EMT), cell motility, immune evasion, and drug resistance. So, the decrease in level of NANOG would have a significant bearing on the clinical outcome. On the contrary, ectopic expression of OCT4 and NANOG in lung adenocarcinoma induced cancer sternness and EMT. The eukaryotic translation initiation factor eIF4G is known to function as a scaffold protein and activate eIF4A. When 4EGI-1, an inhibitor of the interaction between eIF4E and eIF4G and hence inhibition of eIF4A activation, was applied to BCSCs, it effectively inhibited their proliferation. The resultant protein profile of the 4EGI-1 treated BCSCs was very similar to the findings in that NANOG, OCT4 levels were downregulated. On the contrary, some variability in SOX2 response was observed as SOX2 may compensate for the loss of NANOG and OCT4. Interestingly, the expression of OCT4 but not SOX2 has been correlated with poor prognosis in surgical TNBC patients. SOX2 has been shown to transactivate the Cyclin D1 promoter, which would facilitate proliferation and clonogenicity working in conjunction with cyclin-dependent kinases 4/6. However, in this example, there was a paradoxical increase in SOX2 expression but with drastic reduction in the level of cyclin D1, indicating that this is due to the blockade of eIF4A by RocA. DRAQ7 and viability assays indicated cell death in BCSCs following RocA treatment. Induction of cleaved caspase-3 indicated that the BCSCs are primarily undergoing cell death through an apoptotic process upon exposure to RocA. Importantly, treatment of BCSCs with 45 nM RocA showed a dramatic decrease in ABCB1 by 48 and 72 h, indicating a reversal of chemoresistance in BCSCs. Later time points demonstrated that the BCSCs were dying as per the viability assay. Furthermore, a decrease in proteins products of housekeeping genes like β-tubulin was observed.

Overall, targeting of eIF4A is a useful strategy against breast cancer sternness. It also has the advantage of clearing out both bulk tumor cells and BCSCs simultaneously with a single drug. Alternatively, the small molecule inhibitors against eIF4A may be synergistically combined with the first-line of therapy or other targeted inhibition modalities including immunotherapy.

Example IV—Digoxin-Rocaglamide A Combinations

As described above, targeting LASP1, eIF4A1, eIF4B, and CXCR4 with modulators and combinations involving these target proteins is a useful therapeutic strategy in cancer.

The Prestwick chemical library was screened to reposition FDA-approved compounds (i.e., compounds having known bioavailability and toxicity profiles) as inhibitors of eIF4A-mediated oncoprotein synthesis. The Prestwick chemical library is a collection of 1280 small molecules, 99% of which are drugs approved by the FDA, EMA, and other agencies. The small molecules in the library are chemically and pharmacologically diverse (WHO ATC classification 5), and have a mean molecular weight of 383.

Figure 26A:
FIGS. 26A-26D: Screening of Prestwick chemical library. Cardiac glycosides were major hits. Digoxin was further validated in 3 cell lines with a known inhibitor of eIF4A1, rocaglamide A (Roc A).
Figure 26B:
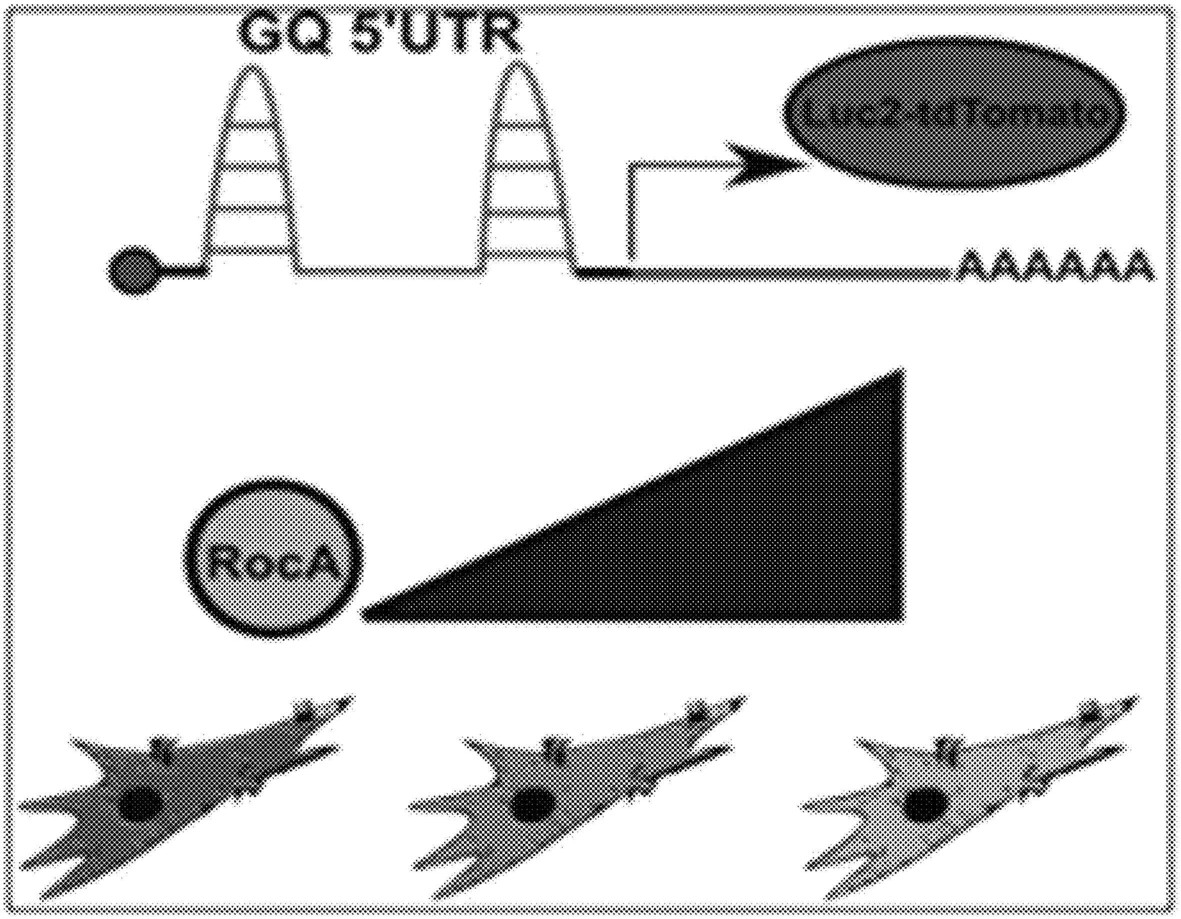
Figure 26C:
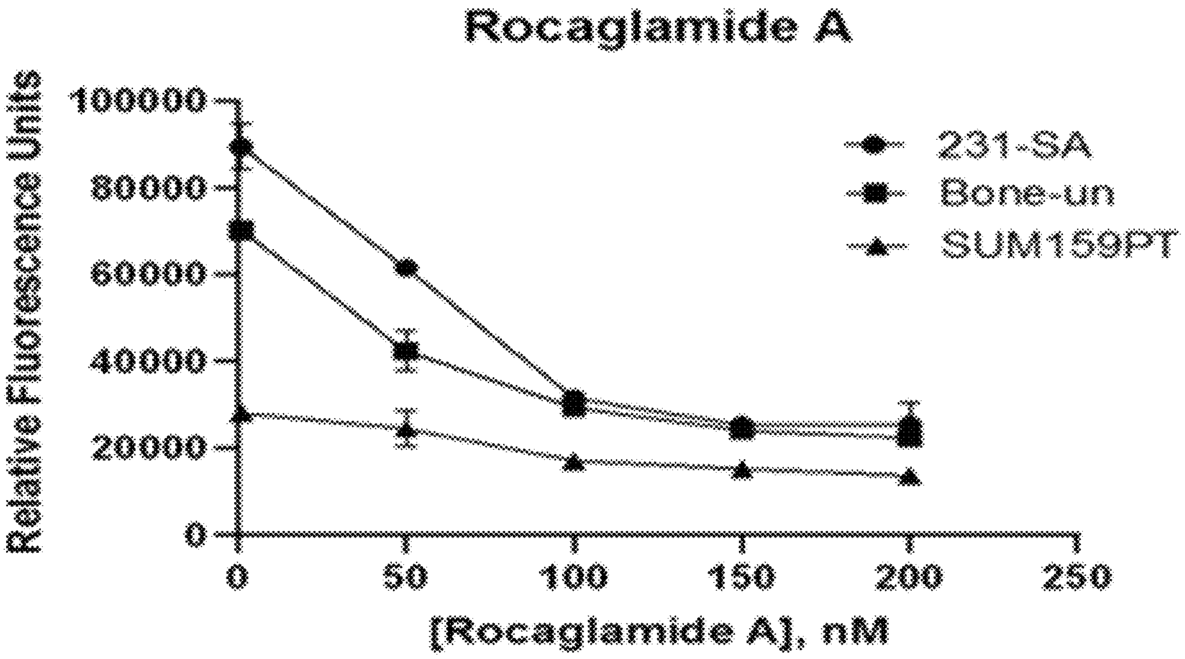
Figure 26D:
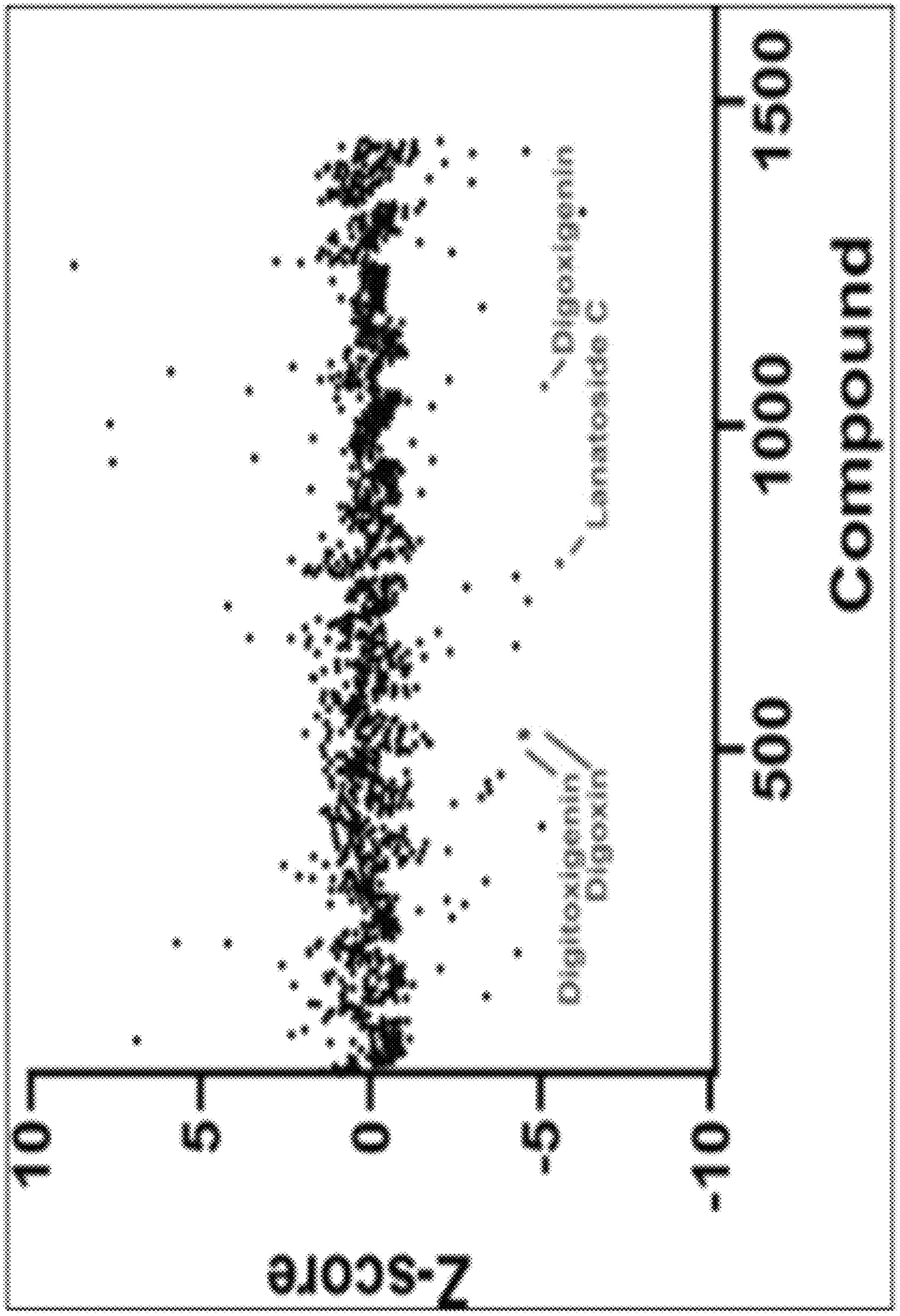
Figure 27:
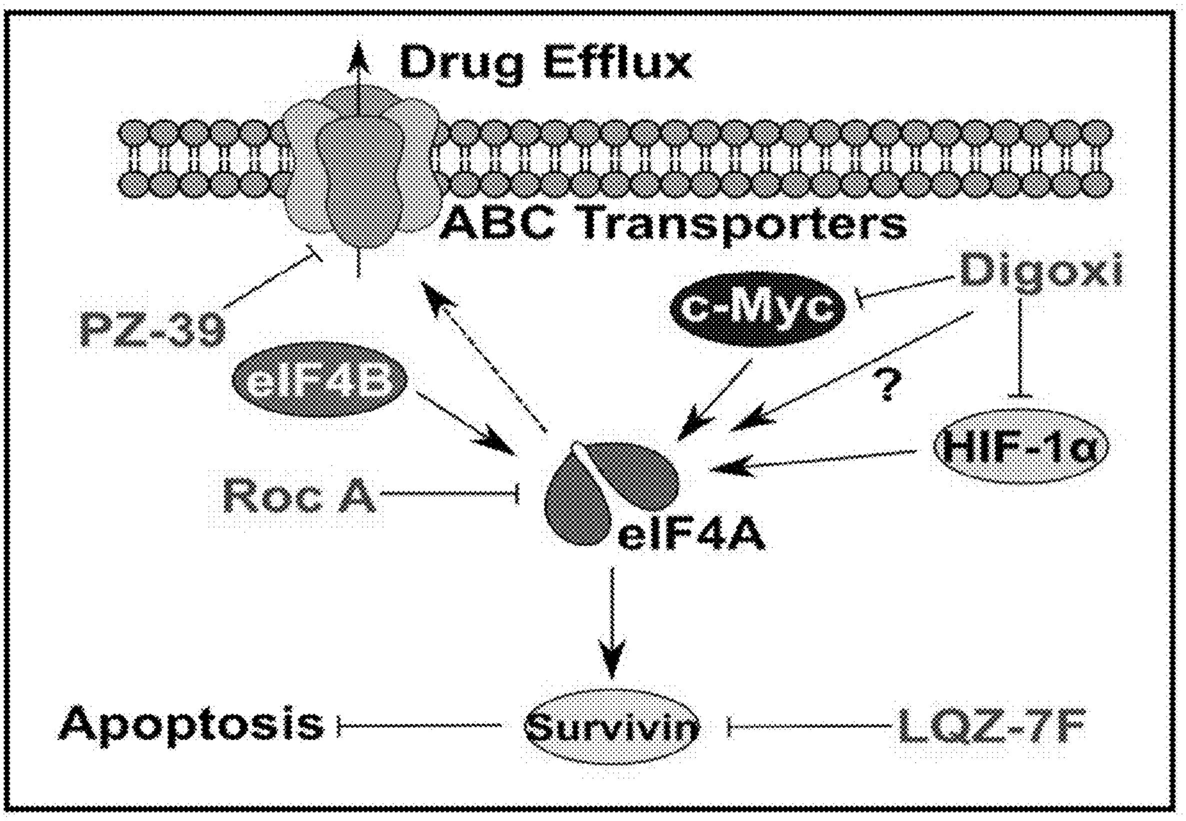
FIG. 27: Schematic of non-limiting example combination treatments in accordance with the present disclosure.

A GQ-5'-UTR dual reporter was created in breast cancer cell lines which would report either a reduction in td-Tomato fluorescence or luciferase activity if eIF4A1 is inhibited by any of the compounds in the Prestwick library (FIGS. 26A-26B). The GQ-5'-UTR dual reporter construct was tested and validated in 3 different triple-negative breast cancer cell lines with a known inhibitor of eIF4A1, rocaglamide A (RocA) (FIG. 26C). The Prestwick Chemical Library was then screen, and it was found that several of the cardiac glycoside family of drugs such as digoxin, digoxigenin, digitoxigenin, and lanotoside C, potently inhibited the activity of eIF4A1 in 3 different TNBC cell lines (FIG. 26D). Among the cardiac glycosides, digoxin was selected and validated further in CellTiter-Glo cell viability assay and by immunoblotting for proteins downstream of eIF4A1, implicating its enzymatic activity. Furthermore, with in silico data mining, it was found that c-MYC transcription factor is a target for digoxin. c-MYC transcription factor is upstream of eIF4A1 and thus can control the transcription of eIF4A1. Interestingly, enzymatically active eIF4A1 help translate c-MYC. This creates a vicious activating feed-forward loop and this is targeted by digoxin (FIG.

Figure 28:
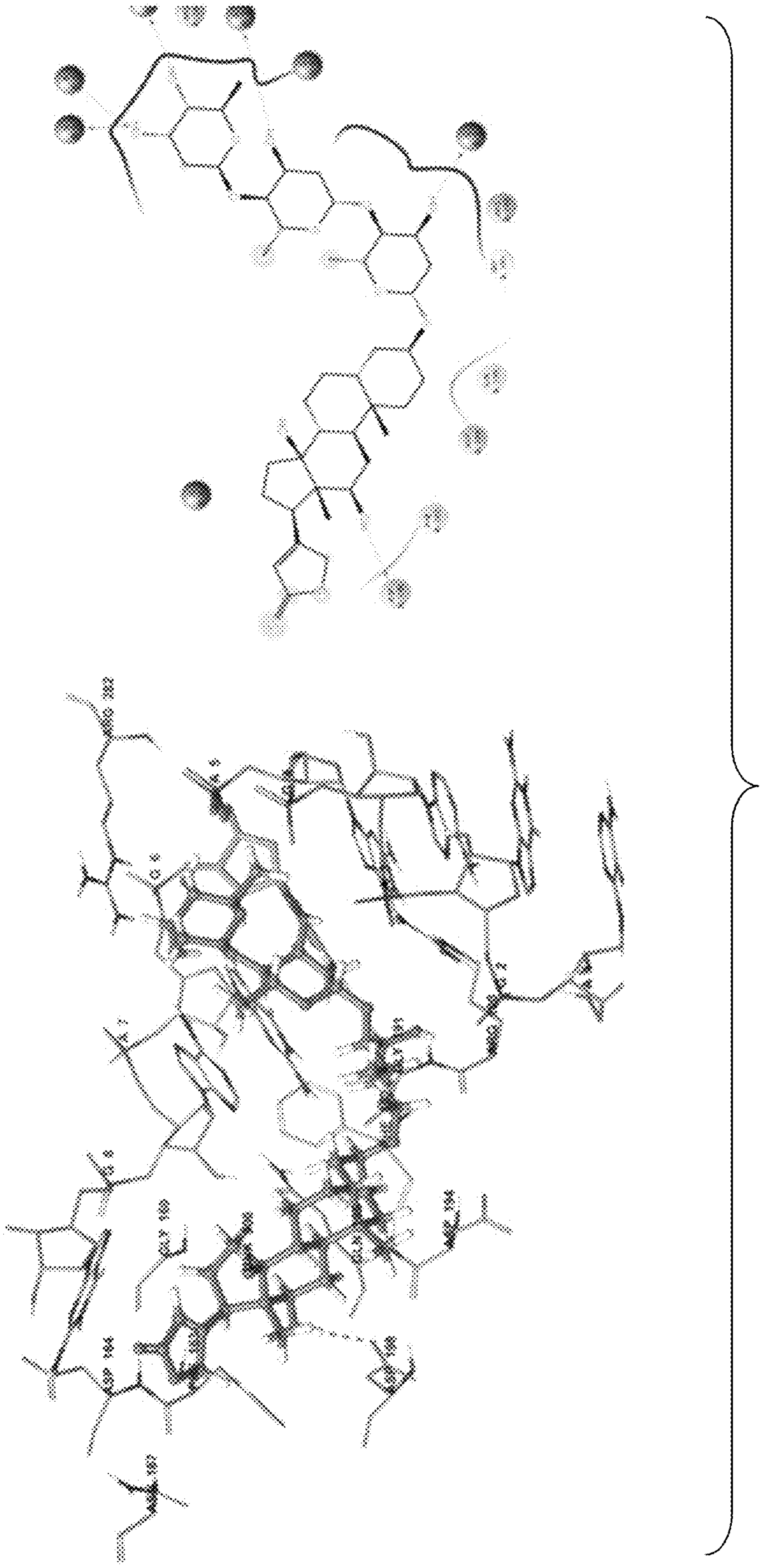
FIG. 28: Docking of digoxin to the N-terminal domain of eIF4A. In the docking model, the steroidal moiety of digoxin occupies the cavity formed between the eIF4A1 NTD and polypurine RNA, similar to rocaglamide A interacting with the residues ASN167, PHE163, ASP194, GLN195, and ASP198. The hydroxyl group at C12 of the steroidal moiety of digoxin interacts with the carboxyl group of ASP198 through a hydrogen bond. Furthermore, the oxygen atom of the lactone ring is favorably aligned towards amido $NH_2$ group of ASN167, indicating a hydrogen bonding interaction with the protein. In addition, the glyosidic part of digoxin extensively interacts with RNA complexed with the eIF4A1.

Additionally, an in-silico docking evaluation of digoxin with the eIF4A crystal structure was performed at 2A resolution. A good Glide XP score of −5.890 was obtained, indicating direct binding of digoxin to eIF4A (FIG. 28.) This corroborates the GQ-5'-UTR dual reporter assay, which is a read out of activity of eIF4A, in that digoxin can indeed directly bind to eIF4A and inhibit its activity. Additionally, digoxin can act upstream of eIF4A4 by inhibiting c-MYC.

Given that the in-silico analysis demonstrated direct binding, whether digoxin can affect the activity of eIF4A1 was tested. Indeed, a reduction in downstream effectors of eIF4A1 activity such as c-Myc, BIRC5 (survivin), and Rho Kinase 1 (ROCK1) was observed (FIGS. 29A-29B). As C-Myc (a transcription factor for eIF4A1) is also upstream of eIF4A1, a 60% reduction of C-Myc resulted in a 50% downregulation of the levels of eIF4A1 (FIG. 29A). Interestingly, digoxin treatment of MCF7 breast cancer cells has induced a decrease in C-Myc mRNA level based on RNA-Seq data with a 'p' value of $4.3E^{-10}$ and an adjusted 'p' value of $8.5E^{-7}$, which is highly significant.

Figure 29E:
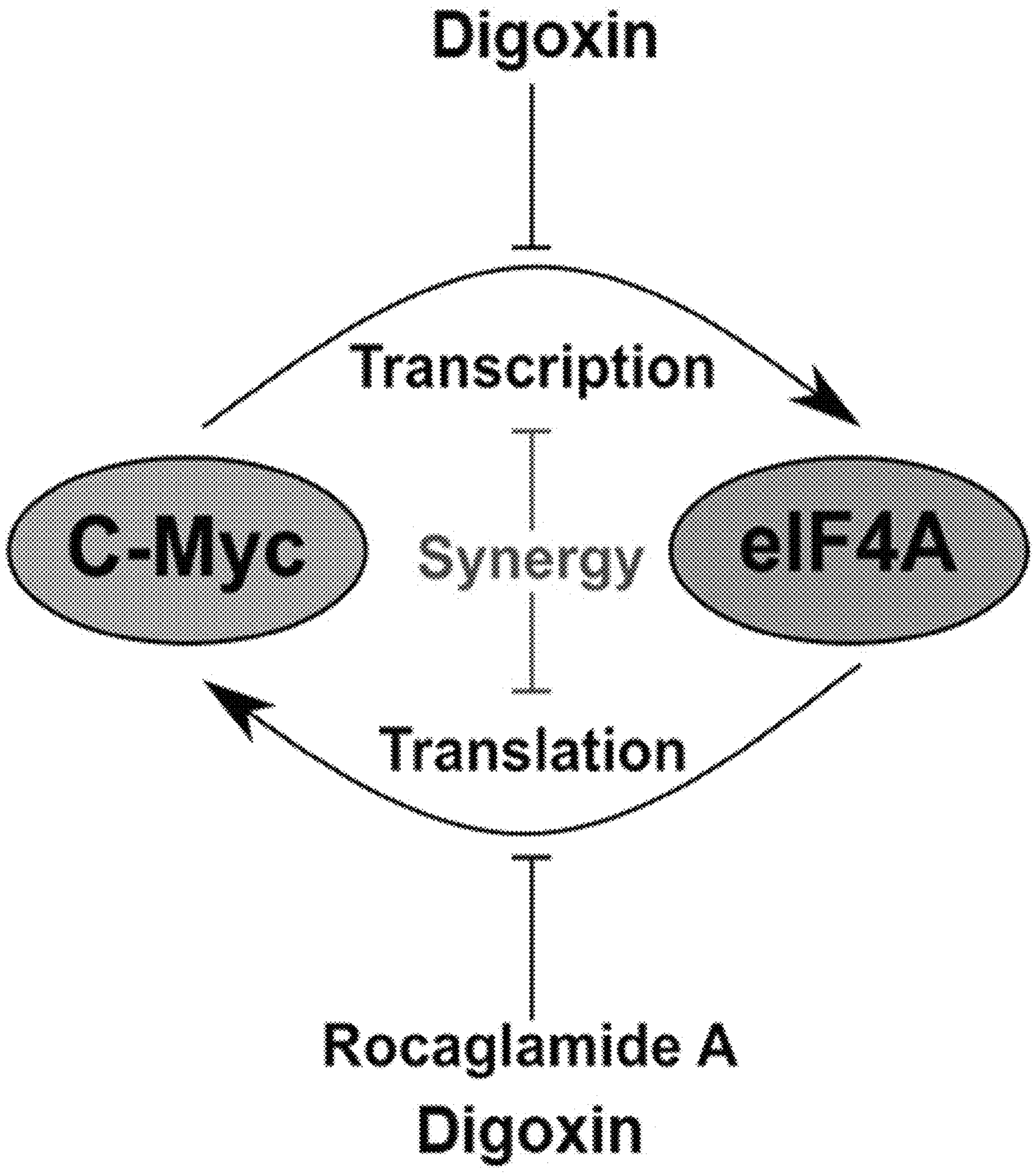

Then, whether the combination of rocaglamide A and digoxin would be efficacious in the subset of breast tumor cells called breast cancer stem cells (BCSCs) was tested. BCSCs are inherently resistant to standard cytotoxic therapy as well as to targeted therapy. Isolated BCSCs from triple-negative breast cancer cells were subjected to a viability test to the treatment combinations of rocaglamide A and digoxin. The combinatorial treatment with rocaglamide A and digoxin was synergistic at lower dose and had a synergistic-additive effect at higher dose combinations (FIGS. 29C-29D). In sum, by performing a Prestwick chemical library screening, it was identified that digoxin is an inhibitor of eIF4A1 activity in triple-negative breast cancer cells. By employing in silico analysis, digoxin was docked to the catalytic pocket of eIF4A1 helicase domain in complexation with mRNA. Then it was proven that indeed the activity of eIF4A1 is inhibited as indicated by a drastic reduction in downstream effectors of eIF4A1 activity such as c-Myc, BIRC5 or survivin, and Rho kinase 1 (ROCK1). Furthermore, it was demonstrated that the treatment combinations involving rocaglamide A and digoxin are highly efficacious in curtailing the viability of chemotherapy-resistant subset of tumor cells, which is a serious and recurring problem in the clinic. This overall scheme is depicted in the illustration in FIG. 29E.

Figure 30A:
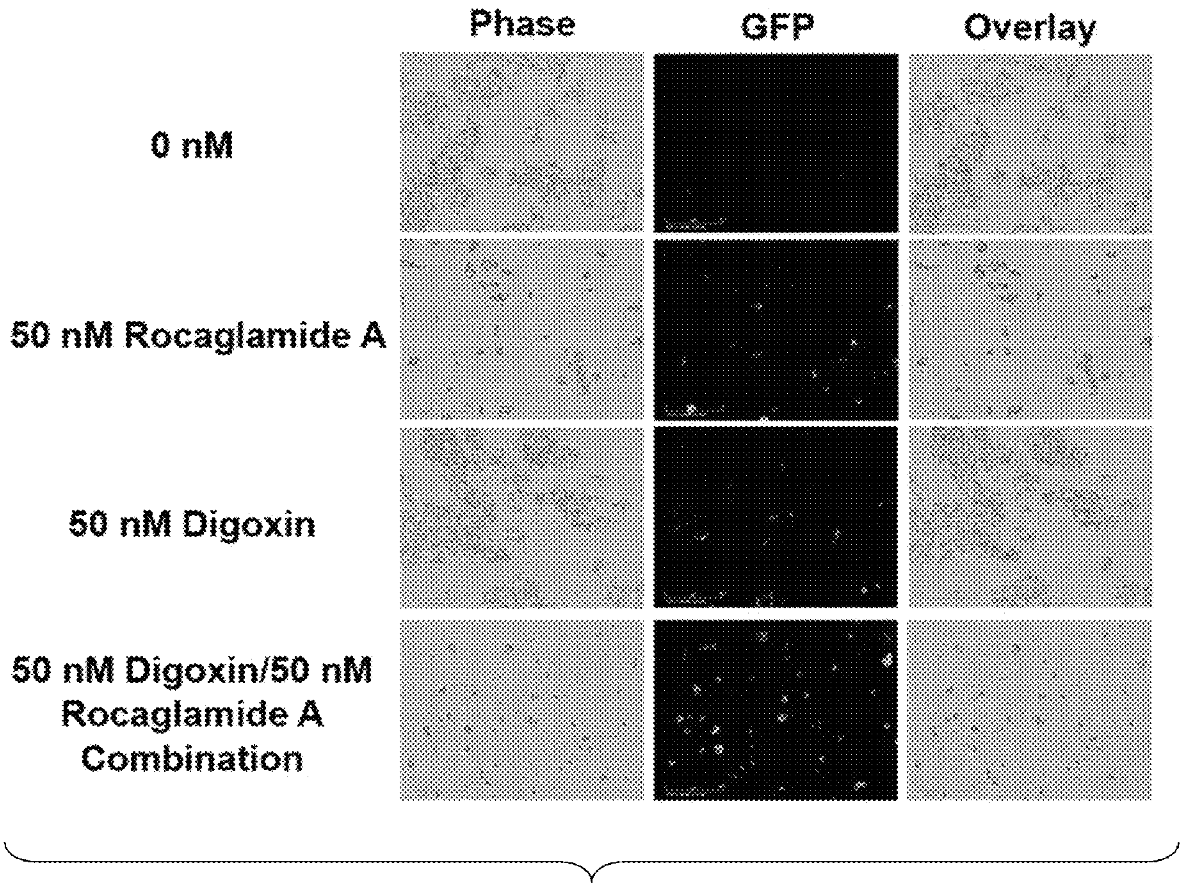
FIGS. 30A-30B: The combination of RocA and digoxin also results in increased cleaved caspase 3.
Figure 30B:
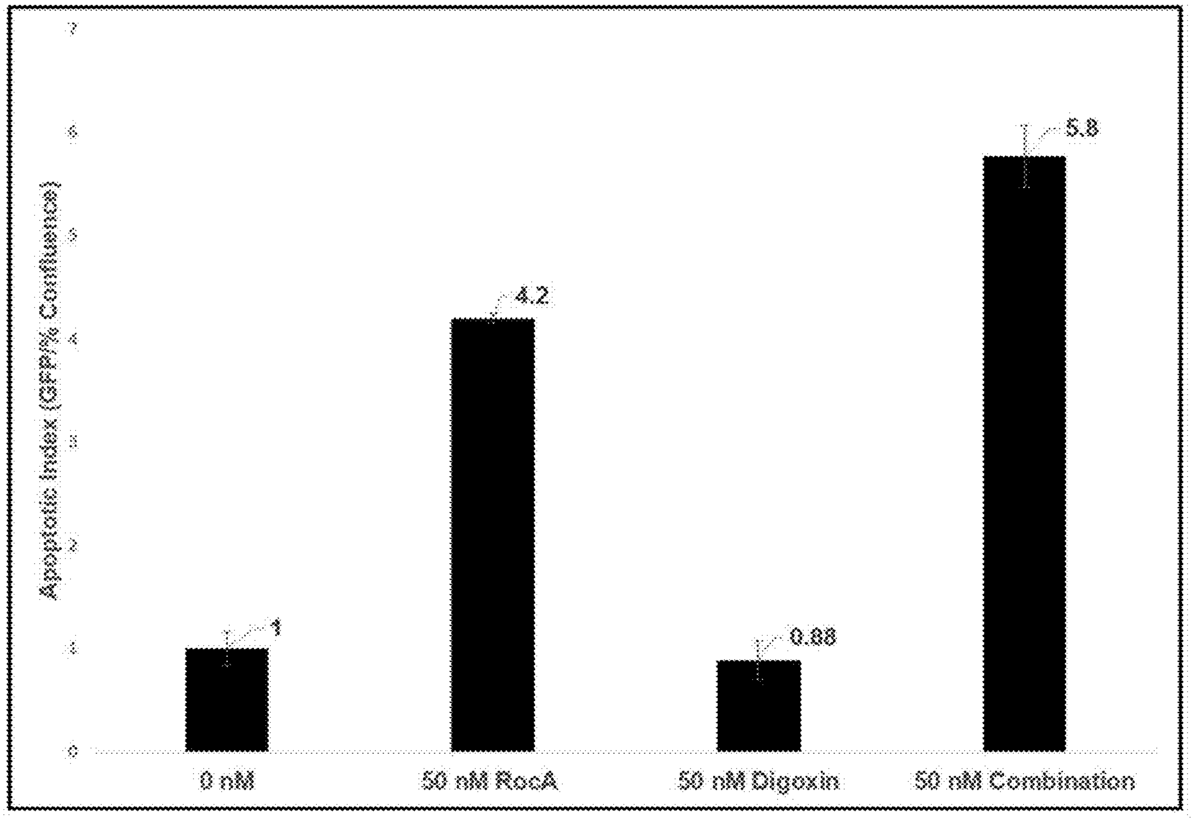
Figure 31:
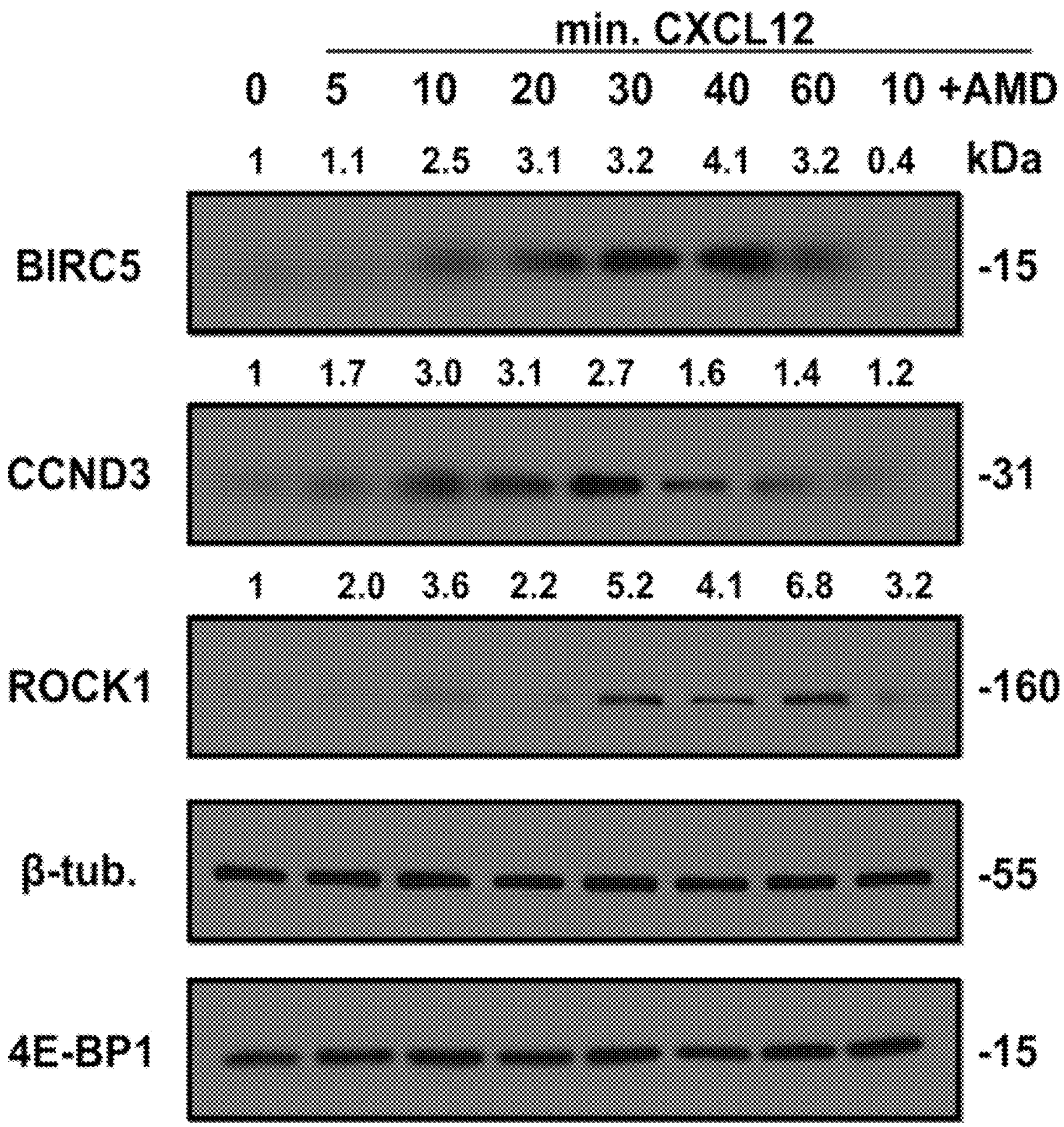
FIG. 31: Strong induction of synthesis of SLS proteins downstream of eIF4A by transient activation of CXCR4 in 231S cells pretreated with MG132. 231S cells were pretreated with the proteosomal inhibitor MG132 for 1 h following which the cells were stimulated with 20 nM CXCL12 for the indicated time points.

The combination of RocA and digoxin also results in increased cleaved caspase 3 (FIGS. 30A-30B).

Example V—Rocaglamide A-LQZ-7F Combinations

As shown by the examples above, the present disclosure demonstrates that the CXCR4-LASP1-eIF4A/eIF4B axis plays a role in TNBC. CXCR4 is a chemokine receptor with elevated expression and activity in TNBC and is highly involved in metastasis. It is noteworthy that balixafortide (CXCR4 antagonist) in combination with eribulin (non-taxane microtubule inhibitor) was recently fast-track approved by FDA for late stage HER2-negative metastatic BC patients. The activation of the CXCR4 signaling pathway [by its ligand CXCL12 secreted by carcinoma associated fibroblasts in the tumor microenvironment (TME)] is a well-established driver of tumor progression and metastasis in TNBC. Previously, it was demonstrated that the chemokine receptor CXCR4 directly binds to an adaptor protein LIM and SH3 protein 1 (LASP1). LASP1 mediates cell adhesion, migration, proliferation, and survival in several breast cancer cell lines. The LIM domain of LASP1 mediates its direct binding to the C-termini of CXCR4 and CXCR2. These chemokine receptors play a vital role in the TME facilitating BC progression and metastasis. In particular, CXCR2-mediated cell migration is augmented by LASP1, while its knock down ablated CXCR4-mediated invasion. By employing proteomics and further validation studies, a protein-protein interaction (PPI) between LASP1 and the eukaryotic translation initiation factors eIF4A/eIF4B (FIG. 8) was discovered. Both eIF4A and eIF4B have an established vital role in the translation of oncogenic mRNAs with stem-loop structures (SLS) by unwinding the SLS and allowing ribosome scanning to initiate protein synthesis. The disruption of the LASP1-eIF4A/eIF4B interaction is useful for finding targets against BC progression and metastasis. Interestingly, analysis of the BC patient data sets using 'Oncomine' revealed an elevated gene expression for CXCR4, LASP1, eIF4A, and downstream targets of eIF4A. This indicates a vital role for these regulatory proteins involved in oncoprotein translation that may promote metastatic BC. The mechanistic connection between the CXCR4-LASP1 axis and the regulation of oncoprotein synthesis by eIF4A/4B is useful for the development of small molecule or cell-permeant biopeptide inhibitors. Targeting the eIF4F complex may overcome plasticity and heterogeneity in cancer. Furthermore, the dependence on eIF4F complex in cancer cells outweighs normal cells and correspondingly minimal toxicity on normal cells. Thus, targeting eIF4F complex may reduce primary and metastatic tumor burden and increase the TNBC patient longevity.

CXCL12-CXCR4 signaling pathway is a pro-migratory and pro-metastatic module implicated in metastatic breast cancer (MBC). This example shows a paradigm shift as a role for this pathway in facilitating the protein translation of oncogenic mRNAs with long, structured 5'-untranslated regions (5'-UTRs) or stem-loop structures (SLS) is seen through activation of eIF4A and eIF4B. The secondary structure affords stability of SLS-UTR mRNAs but precludes ribosome scanning, leading to heavy dependence on the mRNA helicase, eIF4A, and its cofactor eIF4B. Specifically, the impact of CXCR4-LASP1 axis in modulating the activity of the eIF4A/eIF4B complex through translation of SLS oncogenic mRNAs such as survivin, cyclin D1, and D3, Rho kinase 1 (ROCK1), Murine double minute 2 (Mdm2), Myeloid cell leukemia 1 (Mcl1), Mucin-1C (MUC-1C), and other similar SLS mRNAs was evaluated. These oncoproteins play a pivotal role in BC progression and metastasis. Identifying the direct interaction between LASP1 and eIF4A and eIF4B may provide new therapeutic avenues to combat TNBC.

Figure 33:
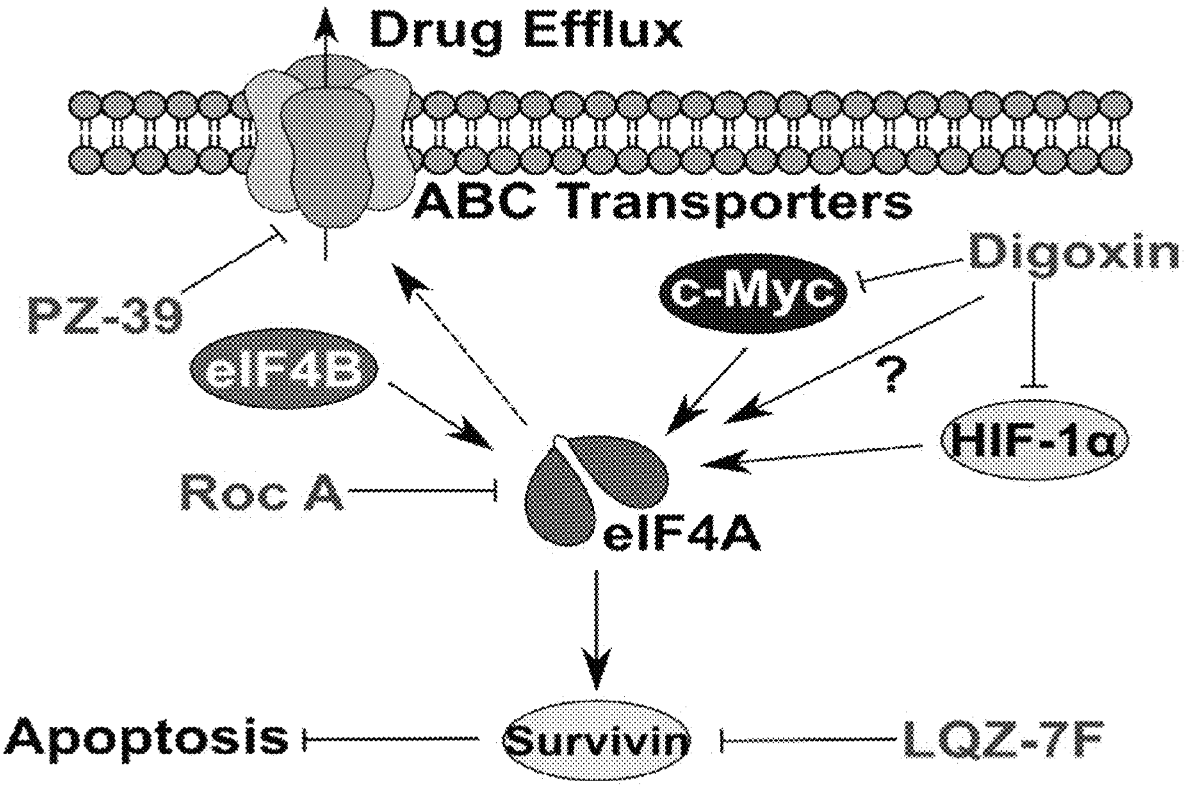
FIG. 33: Schematic of non-limiting example combination treatments in accordance with the present disclosure.

BIRC5, or survivin, belongs to a family of inhibitor of apoptosis proteins (IAPs). It is highly expressed in cancer and imparts chemoresistance. The enhanced expression of survivin is linked to poor patient outcome. Survivin is also a marker for BCSCs. It plays a pivotal role as a functional checkpoint for both mitosis and apoptosis in cancer cells. It also plays a role in stress response, cell migration, tumor progression, and metastasis. The dimerization of survivin is essential for its function. In this example, it is shown that the survivin dimerization inhibitor LQZ-7F inhibits dimerization of survivin by binding to its dimerization interface. This exposes the interface that is energetically unstable, subjecting it to proteasome-mediated degradation. As survivin is a downstream effector of 4A1, eIF4A1 and survivin are co-targeted with RocA and LQZ-7F to achieve an efficacious treatment response as indicated in FIG. 33.

Figure 32A:
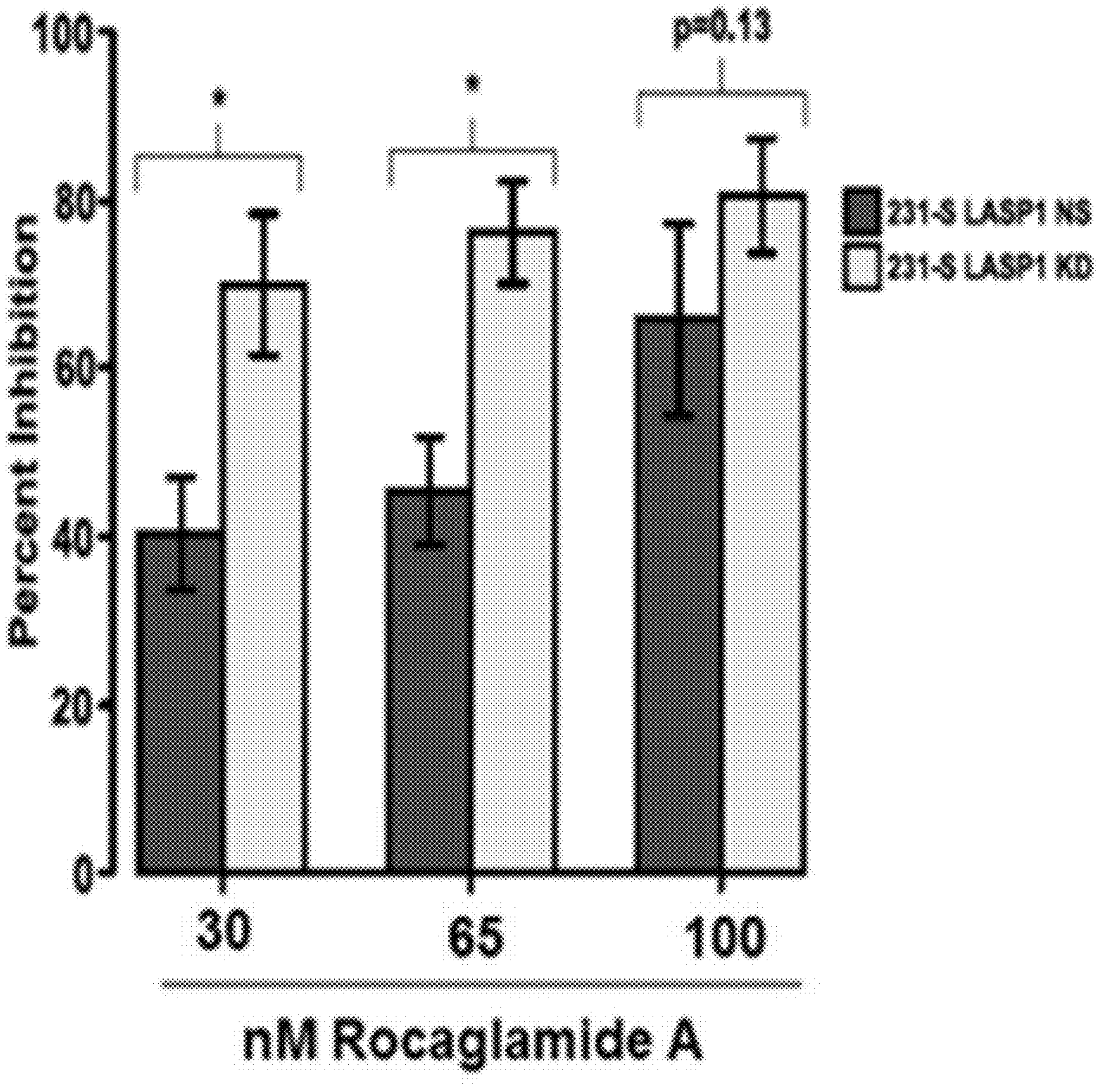
FIGS. 32A-32C: Stable knockdown of LASP1 synergized with rocaglamide A treatment.
Figure 32B:
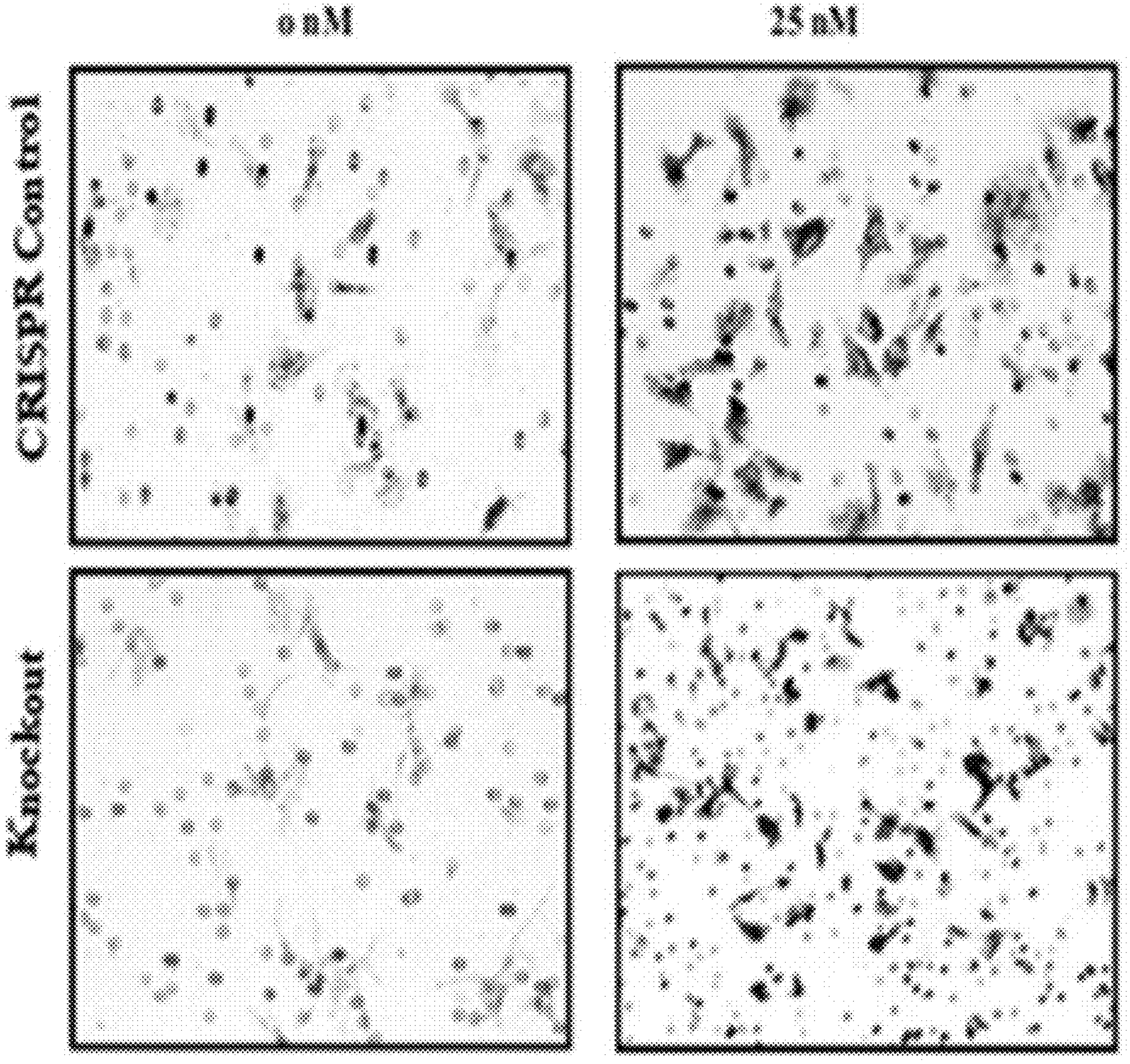
Figure 32C:
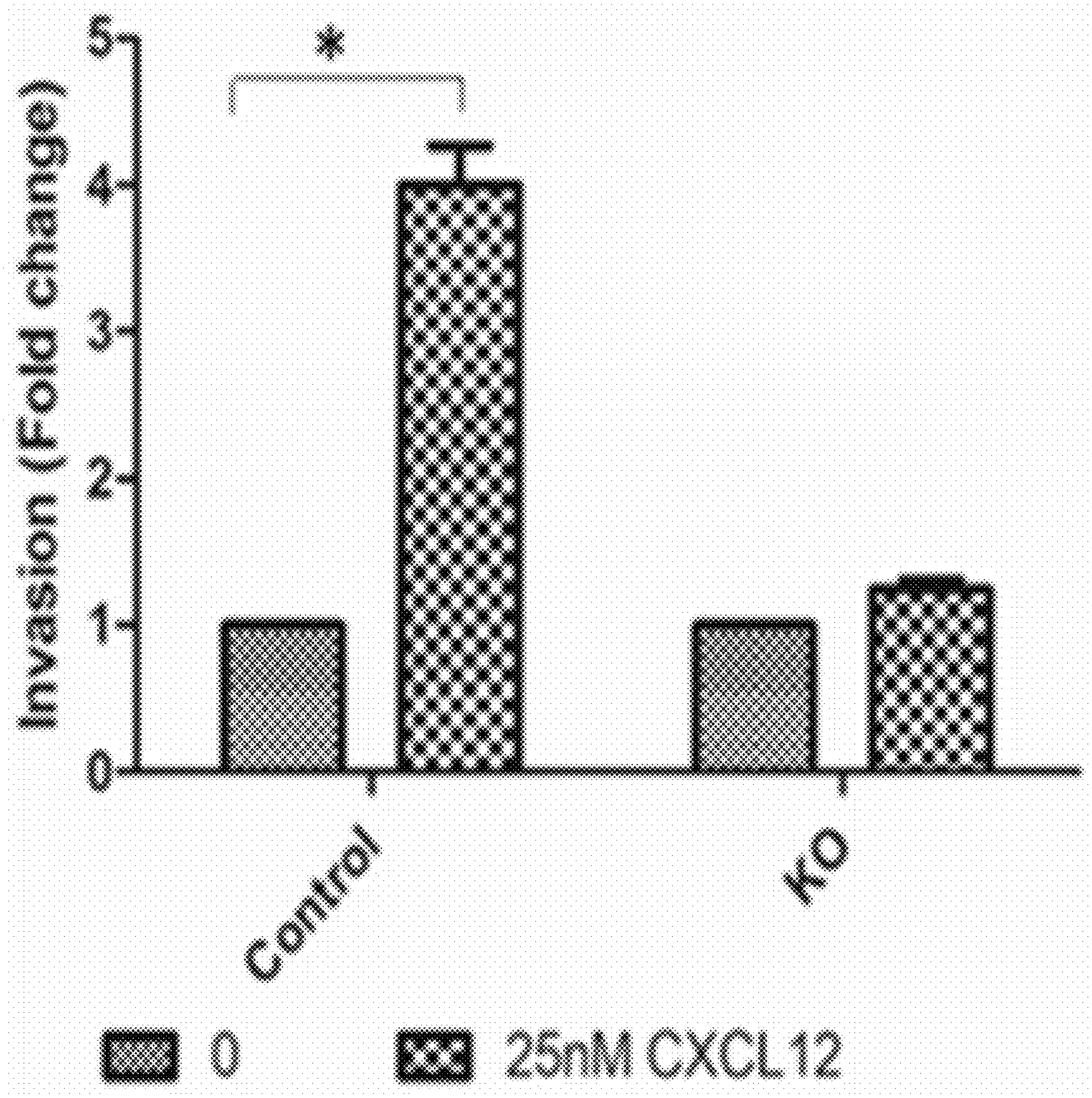
Figure 34:
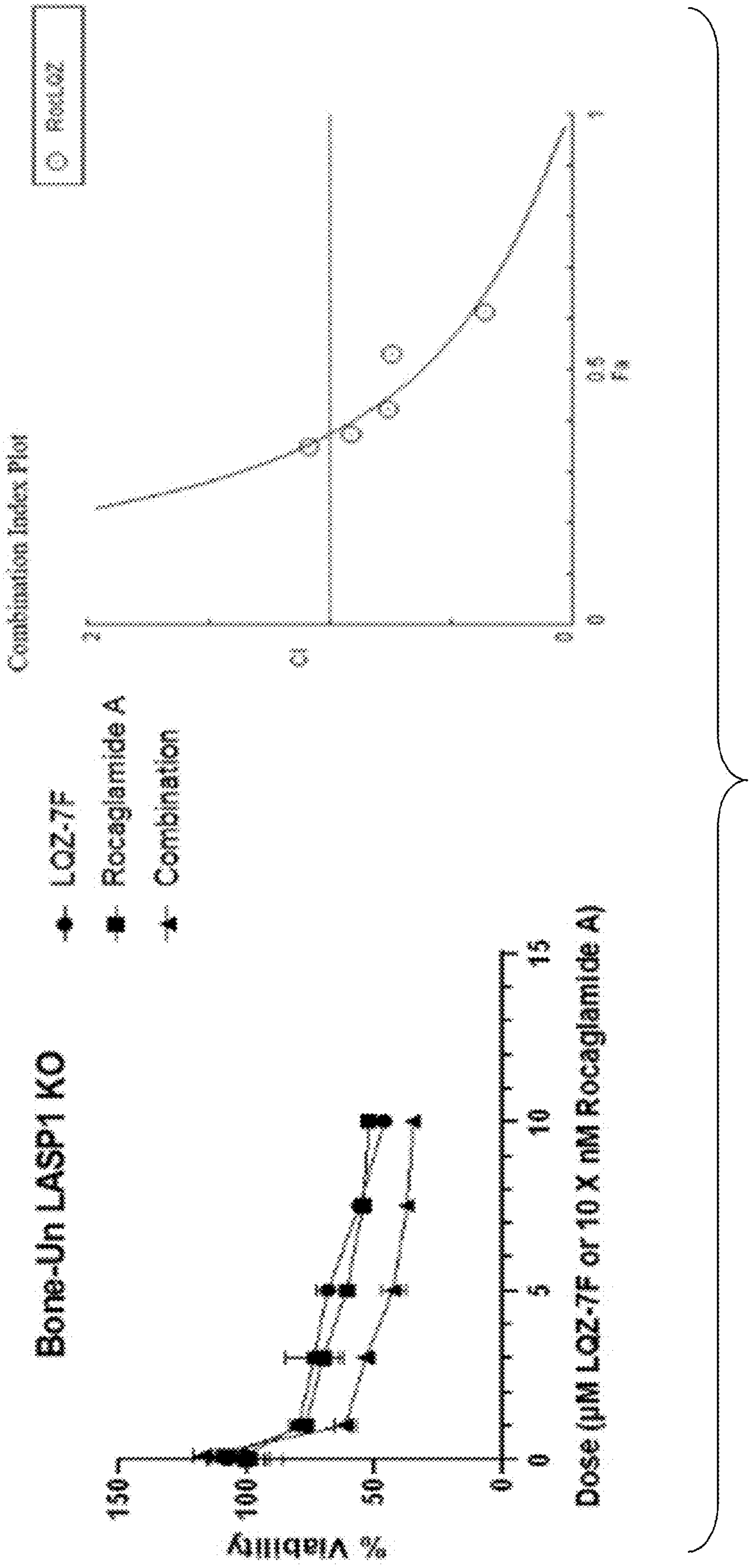
FIG. 34: LQZ-7F in combination with rocaglamide A is efficacious in affecting tumor cell viability. MDA-MB-231 triple-negative breast cancer cells that were originally isolated from the bone lesions were highly susceptible to cell death when eIF4A1 and survivin were inhibited pharmacologically by rocaglamide A and LQZ-7F, respectively, when LASP1 is knocked out.

It was observed that stable knockdown of LASP1 when combined with rocaglamide A effectively inhibited the proliferation in MDA-MB-231 cells (FIG. 32A). Furthermore, when LASP1 was knocked out by the CRISPR-Cas9 approach, it abolished the CXCL12-mediated matrigel-invasion. CXCL12 is the ligand for CXCR4 (FIG. 32B). Next, the LASP1-KO cells were treated with a combinatorial treatment of rocaglamide A and LQZ-7F. The combination was highly synergistic as indicated by the combination index of below 1 (FIG. 34). This efficacious treatment approach was tested in the subpopulation of breast tumor cells called breast cancer stem cells that are highly resistant to cytotoxic as well as targeted chemotherapy. As indicated in FIG. 35, a high synergy was observed between rocaglamide A and LQZ-7F targeting eIF4A1 and survivin, respectively.

Overall, this example demonstrates that the combinatorial treatment of triple-negative breast cancer cells with rocaglamide A and LQZ-7F targeting eIF4A1 and its downstream effector survivin is a useful therapeutic approach.

Example VI—AE-848, AT-2, and AN-465

The AN-465/41673523, AT-2 (CAST-2110) and AE-848/14270010 are available in the SPECS database and are commercially available compounds, however, they were synthesized and chemically characterized to ensure purity and integrity.

Figure 36A:
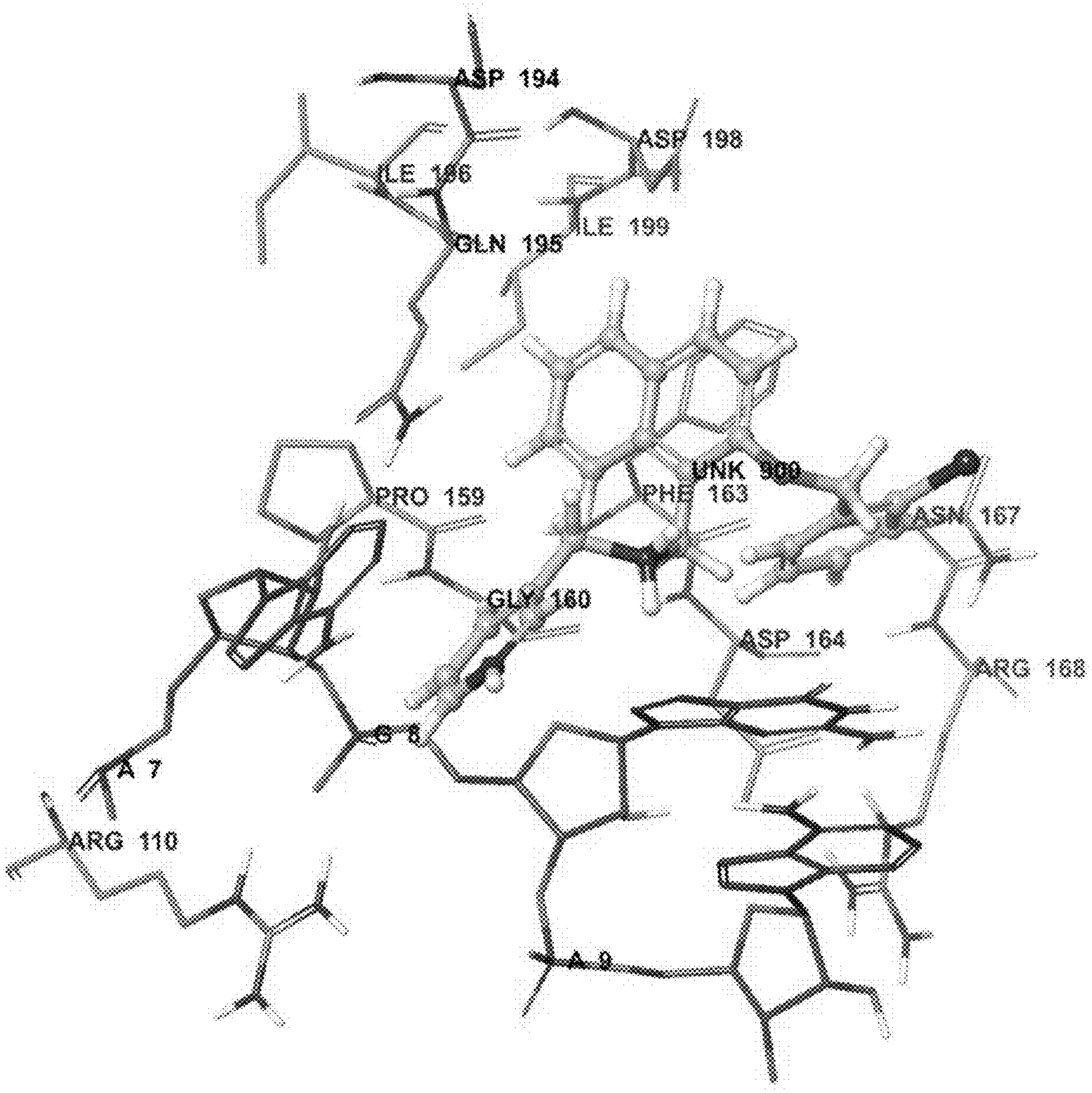
FIGS. 36A-36B.
Figure 36B:
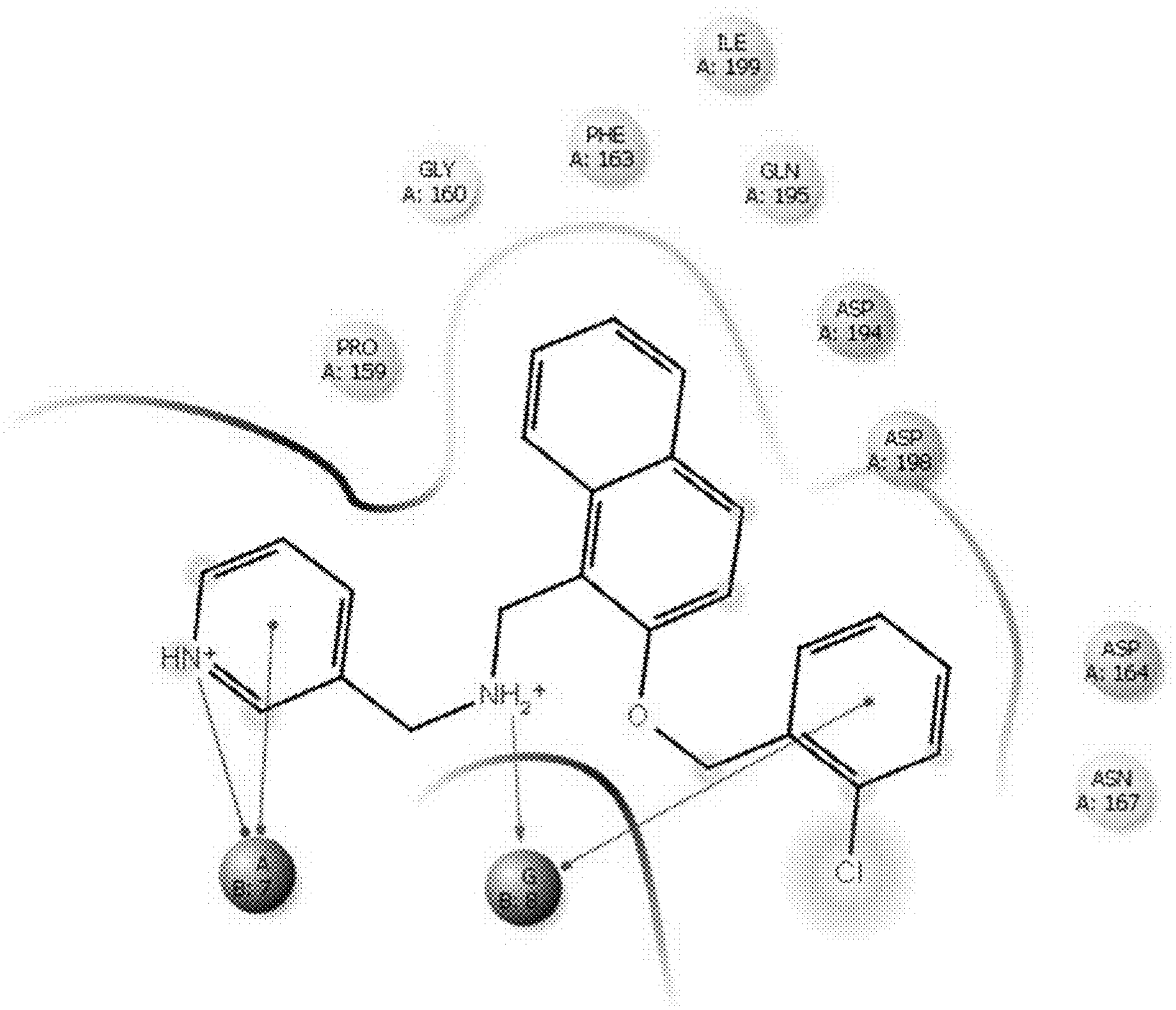
Figure 37A:
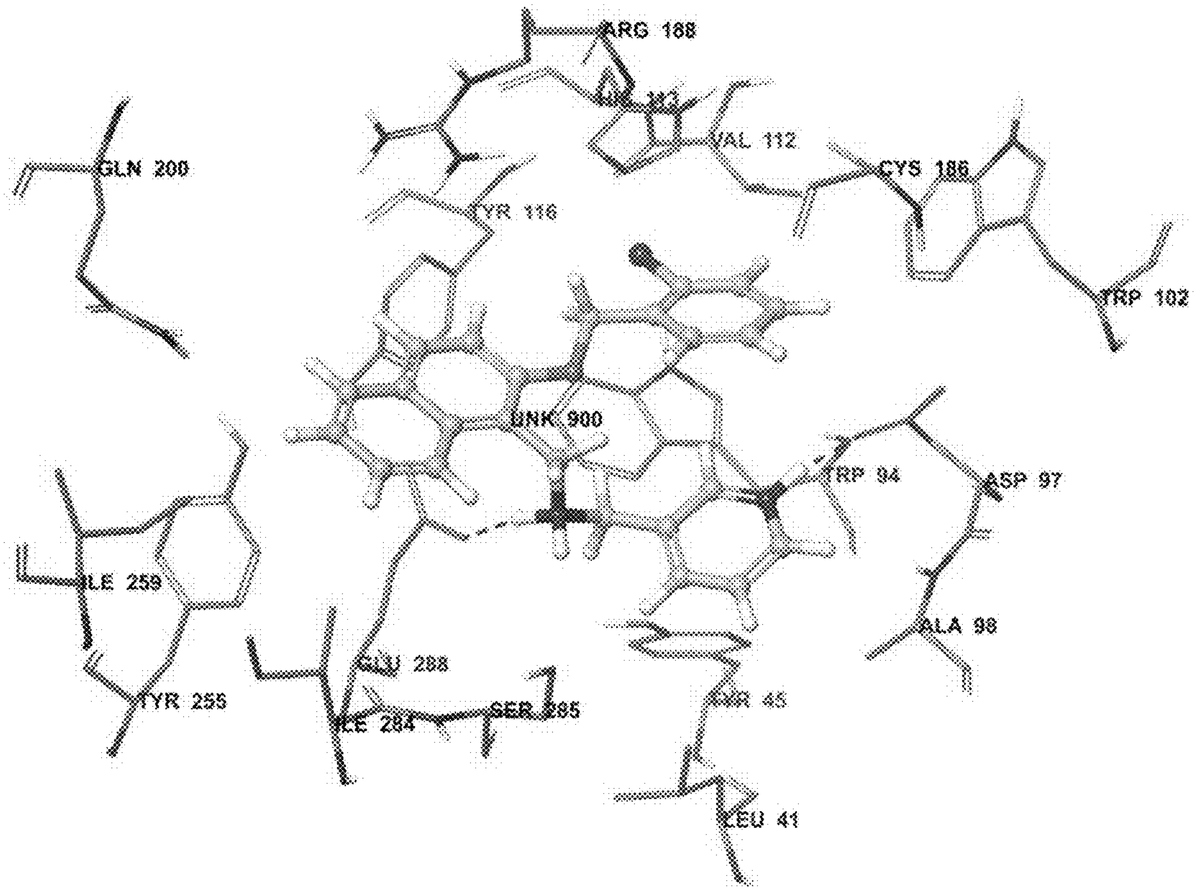
FIGS. 37A-37B.
Figure 37B:
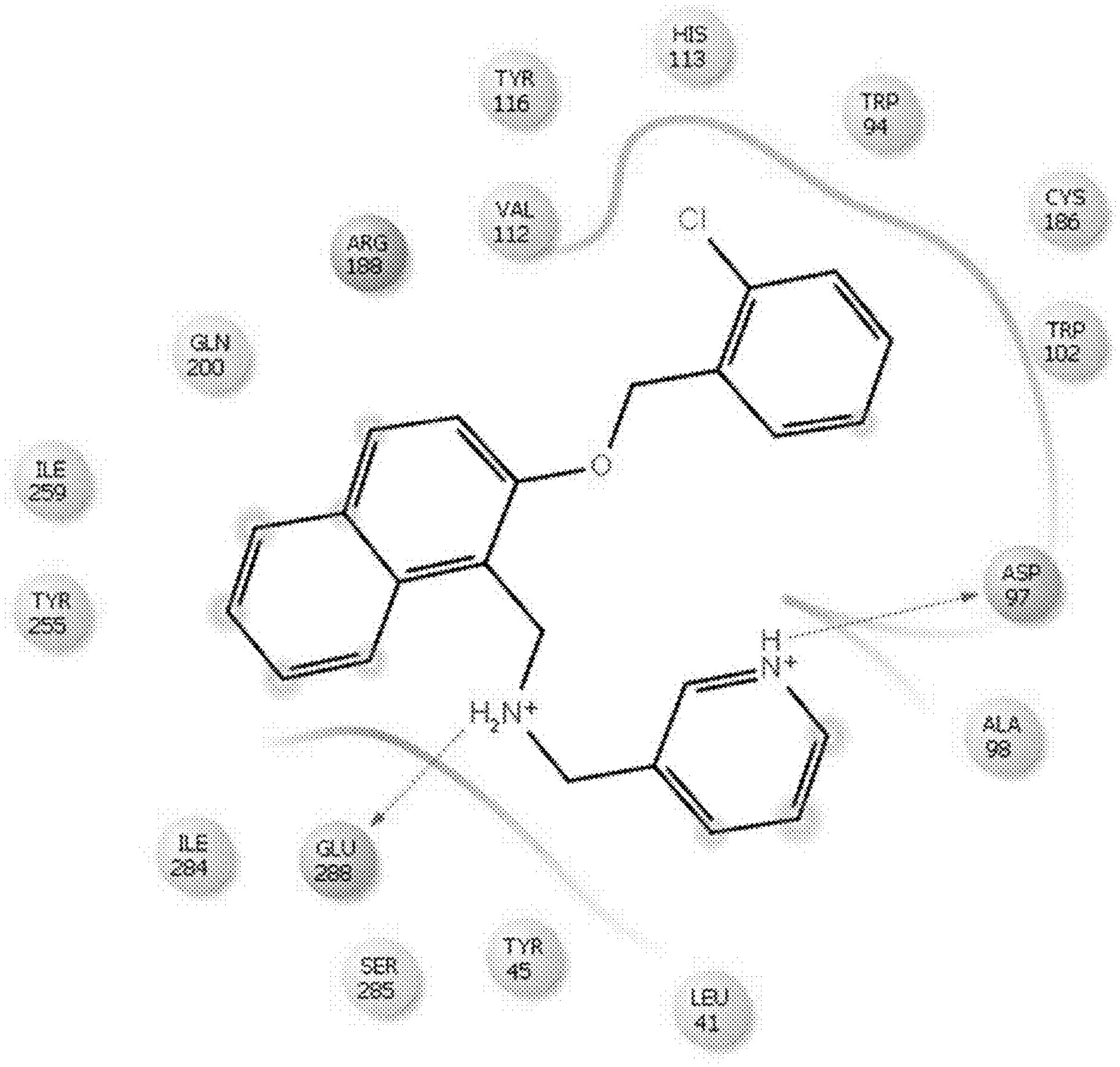

Docking studies were conducted, and revealed that AN-465/41673523 binds to eIF4A (FIGS. 36A-36B) and CXCR4 (FIGS. 37A-37B).

Figure 38:
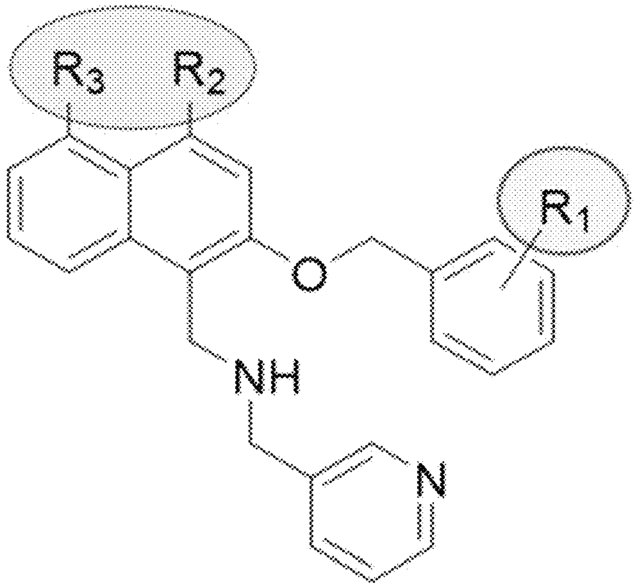
FIG. 38: Structure of the AN-465/41673523 pharmacophore.
Figure 39:
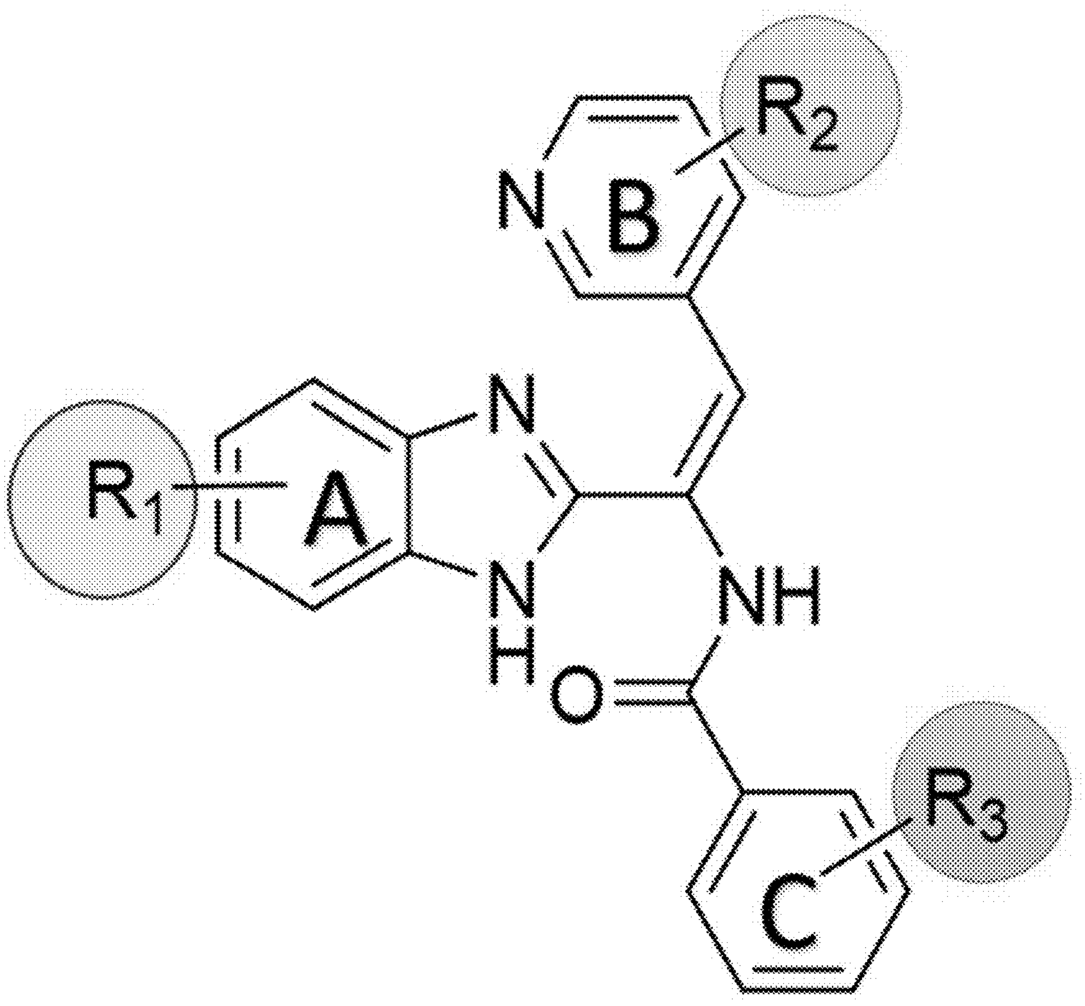
FIG. 39: Structure of the AT-2 and AE-848/14270010 pharmacophore.

The structures of the AN-465/41673523 (FIG. 38) and CAST-2110 (AT-2) and AE-848/14270010 (FIG. 39) pharmacophores are useful for inhibiting eIF4A, and have the advantage of being drug-like.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compounds, compositions, and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method for reducing breast cancer stemness, the method comprising: administering an effective amount of a eIF4A inhibitor to breast cancer stem cells to reduce stemness in the breast cancer cells, wherein the eIF4A inhibitor is a site-directed eIF4A inhibitor; wherein the method further comprises administering a survivin inhibitor to the breast cancer stem cells in combination with the eIF4A inhibitor, and wherein the eIF4A inhibitor comprises rocaglamide A and the survivin inhibitor comprises LQZ-7F.

2. The method of claim 1, wherein the method further reduces breast cancer stemness by: reducing expression in a stemness transcription factor by at least 2 hold, and wherein the stemness transcription factor comprises at least one of SOX2, OCT4 or NANOG.

* * * * *

SEQUENCE LISTING

```
<160> NUMBER OF SEQ ID NOS: 19

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

ctagctggat ccatgaaccc caactgcgcc                                        30


<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

ctagctctcg agtcagatgg cctccacgta                                        30


<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

aacatgctgc tggataaatc tgg                                               23


<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

tgtatcacat cgtaccatgc ct                                                22


<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

ccttcgtgag aattggcttc                                                   20


<210> SEQ ID NO 6
<211> LENGTH: 23
<212> TYPE: DNA
```

-continued

<213> ORGANISM: Artificial Sequence
<220> FEATURE:
<223> OTHER INFORMATION: Description of Artificial Sequence: Synthetic
primer

<400> SEQUENCE: 6
caacacatga ctctctggaa tca 23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7
atgttcgtgg cctctaagat ga 22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
caggttccac ttgagcttgt tc 22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
aagaactggc ccttcttgga 20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
caaccggacg aatgctttt 19

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
ttggccagat ctttagacca gacaac 26

<210> SEQ ID NO 12
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 12

ccgtaccaca tccaggacag aatc                                            24


<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

cggcggcggc gg                                                         12


<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

tttgtaggta ccgatgtacg ggccagatat ac                                   32


<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

tttgtactcg aggtattaat ttcgataagc                                      30


<210> SEQ ID NO 16
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

gatctctagg ttgaaagtac tttgacggcg gcggcggtca atcttacggc ggcggcggac     60

atagatacgg cggcggcggt agaaactacg gcggcggcgg attagaatag taaaa         115


<210> SEQ ID NO 17
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

agctttttac tattctaatc cgccgccgcc gtagtttcta ccgccgccgc cgtatctatg     60

tccgccgccg ccgtaagatt gaccgccgcc gccgtcaaag tactttcaac ctaga         115


<210> SEQ ID NO 18
```

-continued

```
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

gatctctagg gcgcacgtac ttcgacaacg tcagcgttca gcgttccaac gtcagcgtac     60

cagcgatcca acgtcagcgt tctgcgctac aacgtcagcg tatccgcgta gcacaa        116


<210> SEQ ID NO 19
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

agctttgtgc tacgcggata cgctgacgtt gtagcgcaga acgctgacgt tggatcgctg     60

tacgctgacg ttggaacgct gaacgctgac gttgtcgaag tacgtgcgcc ctaga         115
```